US011813049B2

(12) United States Patent
Mahfouz

(10) Patent No.: US 11,813,049 B2
(45) Date of Patent: Nov. 14, 2023

(54) BONE RECONSTRUCTION AND ORTHOPEDIC IMPLANTS

(71) Applicant: TechMah Medical, LLC, Knoxville, TN (US)

(72) Inventor: Mohamed Rashwan Mahfouz, Knoxville, TN (US)

(73) Assignee: TECHMAH MEDICAL LLC, Knoxville, TN (US)

(*) Notice: Subject to any disclaimer, the term of this patent is extended or adjusted under 35 U.S.C. 154(b) by 247 days.

(21) Appl. No.: 16/397,576

(22) Filed: Apr. 29, 2019

(65) Prior Publication Data
US 2019/0254561 A1 Aug. 22, 2019

Related U.S. Application Data

(63) Continuation of application No. 16/182,405, filed on Nov. 6, 2018, now Pat. No. 10,736,539, which is a (Continued)

(51) Int. Cl.
*A61B 5/00* (2006.01)
*A61B 5/06* (2006.01)
(Continued)

(52) U.S. Cl.
CPC .............. *A61B 5/062* (2013.01); *A61B 6/12* (2013.01); *A61B 6/466* (2013.01); *A61B 6/505* (2013.01);
(Continued)

(58) Field of Classification Search
CPC .......... A61B 5/62; A61B 34/10; A61B 34/20; A61B 6/12; A61B 6/466; A61B 6/505;
(Continued)

(56) References Cited

U.S. PATENT DOCUMENTS 5,008,679 A 4/1991 Effland
5,982,339 A 11/1999 Lalezari
(Continued)

FOREIGN PATENT DOCUMENTS

CA 2945266 2/2009
DE 102013219470 3/2015
(Continued)

OTHER PUBLICATIONS

Li_2015 (A modified ICP algorithm based on dynamic adjustment factor for registration and point cloud and CAD model, Pattern Recognition Letters 65 (2015) 88 - 94 (Year: 2015).*
(Continued)

*Primary Examiner* — Brian S Cook
(74) *Attorney, Agent, or Firm* — ALLEN, DYER, DOPPELT, GILCHRIST, P.A.

(57) ABSTRACT

A surgical navigation system comprising a signal receiver communicatively coupled to a primary processor, the primary processor programmed to utilize a sequential Monte Carlo algorithm to calculate changes in three dimensional position of an inertial measurement unit mounted to a surgical tool, the processor communicatively coupled to a first memory storing tool data unique to each of a plurality of surgical tools, and a second memory storing a model data sufficient to construct a three dimensional model of an anatomical feature, the primary processor communicatively coupled to a display providing visual feedback regarding the three dimensional position of the surgical tool with respect to the anatomical feature.

16 Claims, 161 Drawing Sheets

Related U.S. Application Data continuation of application No. 14/565,357, filed on Dec. 9, 2014, now Pat. No. 10,258,256.

(60) Provisional application No. 62/022,899, filed on Jul. 10, 2014, provisional application No. 61/977,984, filed on Apr. 10, 2014, provisional application No. 61/951,221, filed on Mar. 11, 2014, provisional application No. 61/913,608, filed on Dec. 9, 2013.

(51) Int. Cl.
| | | |
|---|---|---|
| *A61B 34/20* | (2016.01) | |
| *A61B 6/12* | (2006.01) | |
| *A61B 6/00* | (2006.01) | |
| *A61B 34/10* | (2016.01) | |
| A61B 5/055 | (2006.01) | |
| A61B 6/03 | (2006.01) | |

(52) U.S. Cl.
CPC .......... *A61B 6/5211* (2013.01); *A61B 6/5235* (2013.01); *A61B 34/10* (2016.02); *A61B 34/20* (2016.02); *A61B 5/055* (2013.01); *A61B 5/067* (2013.01); *A61B 6/032* (2013.01); *A61B 6/487* (2013.01); *A61B 2034/105* (2016.02); *A61B 2034/108* (2016.02); *A61B 2034/2048* (2016.02); *A61B 2576/00* (2013.01)

(58) Field of Classification Search
CPC ................ A61B 6/5211; A61B 6/5235; A61B 2034/105
USPC .......................................................... 703/2
See application file for complete search history.

(56) References Cited

U.S. PATENT DOCUMENTS

| | | | |
|---|---|---|---|
| 6,246,898 B1 | 6/2001 | Vesely | |
| 7,640,106 B1 | 12/2009 | Stokar et al. | |
| 8,203,487 B2 | 6/2012 | Hol | |
| 9,078,755 B2 | 7/2015 | Mahfouz | |
| 2003/0013146 A1 | 1/2003 | Werb | |
| 2004/0017313 A1 | 1/2004 | Menache | |
| 2004/0068187 A1* | 4/2004 | Krause | A61B 17/15 600/443 |
| 2006/0058616 A1 | 3/2006 | Marquart et al. | |
| 2006/0064005 A1 | 3/2006 | Triano et al. | |
| 2006/0074405 A1 | 4/2006 | Malackowski | |
| 2007/0078298 A1 | 4/2007 | Glukhovsky | |
| 2007/0105567 A1 | 5/2007 | Mohanty | |
| 2007/0197891 A1 | 8/2007 | Shachar et al. | |
| 2008/0012765 A1 | 1/2008 | Xu | |
| 2008/0169927 A1 | 7/2008 | Graves | |
| 2009/0112630 A1 | 4/2009 | Collins, Jr. | |
| 2009/0248014 A1 | 10/2009 | Shachar | |
| 2010/0063508 A1 | 3/2010 | Borja | |
| 2010/0310141 A1 | 12/2010 | Wilson | |
| 2011/0046915 A1 | 2/2011 | Hol | |
| 2011/0154569 A1 | 6/2011 | Wiggers | |
| 2011/0160572 A1 | 6/2011 | McIntosh | |
| 2011/0208093 A1 | 8/2011 | Gross et al. | |
| 2011/0275957 A1 | 11/2011 | Bhandari | |
| 2011/0305379 A1 | 12/2011 | Mahfouz | |
| 2011/0320153 A1* | 12/2011 | Lightcap | G01C 21/16 702/94 |
| 2012/0029345 A1 | 2/2012 | Mahfouz et al. | |
| 2012/0209117 A1 | 8/2012 | Mozes | |
| 2012/0319859 A1 | 12/2012 | Taub | |
| 2013/0122463 A1 | 5/2013 | Csillag | |
| 2013/0185018 A1 | 7/2013 | Sheng | |
| 2013/0217998 A1 | 8/2013 | Mahfouz et al. | |
| 2013/0218163 A1* | 8/2013 | Frey | A61B 34/10 606/87 |
| 2013/0261633 A1 | 10/2013 | Thornberry | |
| 2014/0005555 A1 | 1/2014 | Tesar | |
| 2014/0052149 A1* | 2/2014 | van der Walt | A61F 2/4609 606/130 |
| 2014/0136143 A1 | 5/2014 | Stein | |
| 2015/0157416 A1* | 6/2015 | Andersson | A61B 34/20 606/102 |
| 2015/0250597 A1 | 9/2015 | Lang | |
| 2015/0287598 A1 | 10/2015 | Wada et al. | |

FOREIGN PATENT DOCUMENTS

| | | | |
|---|---|---|---|
| EP | 2178011 A1 * | 4/2010 | ............ G06F 17/50 |
| GB | 2513245 | 10/2014 | |
| WO | 0056215 | 9/2000 | |
| WO | 0073815 | 12/2000 | |
| WO | 03090022 | 10/2003 | |
| WO | 2009102331 | 8/2009 | |
| WO | 2009117832 | 10/2009 | |
| WO | 2010088696 | 8/2010 | |
| WO | 2010099359 | 9/2010 | |
| WO | 2011060536 | 5/2011 | |
| WO | 2011162753 | 12/2011 | |
| WO | 2013013170 | 1/2013 | |
| WO | 2013049248 | 4/2013 | |
| WO | 2013056231 | 4/2013 | |
| WO | 2013126416 | 8/2013 | |
| WO | 2013181376 | 12/2013 | |
| WO | 2015089118 | 6/2015 | |
| WO | 2016007936 | 1/2016 | |

OTHER PUBLICATIONS

Besl_1992 (A Method of Registration of 3-D Shapes, IEEE Transactions on Pattern Analysis and Machine Intelligence, vol. 14, No. 2, Feb. 1992) (Year: 1992).*

AKCA_2007 (Least Squares 3D Surface Matching, Zurich 2007) (Year: 2007).*

Lowe_2004 (Distinctive Image Features from Scale-Invariant Keypoints, International Journal of Computer Vision 60(2), 91-110, 2004) (Year: 2004).*

Altuntas_2011 (An Experimental Study of Registration three-dimensional range Images Using Range and Intensity data, International Archives of Photogrammetry, Remote Sensing and Spatial Information Science 38 (3/W22)) (Year: 2011).*

Salamon, Accurate Tilt Estimation of a Rotating Platform Using Inertial Sensing, Drexel University, Jun. 2014.

STMicroelectronics NV, LSM303DLH Sensor module, 2009.

To, Quaternionic Attitude Estimation with Inertial Measuring Unit for Robotic and Human Body Motion Tracking using Sequential Monte Carlo Methods with Hyper-Dimensional Spherical Distributions, University of Tennessee, Dec. 2012.

Brodie et al., Fusion motion capture: a prototype system using inertial measurement units and GPS for the biomechanical analysis of ski racing, Sports Technology, 2008.

Cronskar, The Use of Additive Manufacturing in the Custom Design of Orthopedic Implants, Mid Sweden University, 2011.

Tsouknidas et al., ANSA as an Advanced Tool in Biomedical Modelling and Engineering, 4th ANSA & BETA International Conference, 2005.

Guillin et al., Sonographic assessment of orthopedic hardware impingement on soft tissues of the limbs, Journal of Ultrasound, 2012.

Daruwalla et al., An application of principal component analysis to the clavicle and clavicle fixation devices, Journal of Orthopaedic Surgery and Research, 2010.

Bancroft, Multiiple Inertial Measurement Unit Integration for Pedestrian Navigation, University of Calgary, Dec. 2010.

Ren et al., Multisensor Data Fusion in an Integrated Tracking System for Endoscopic Surgery, IEEE Transactions on Information Technology in Biomedicine, Jan. 2012.

To et al., Modular Wireless Inertial Trackers for Biomedical Applications, 2013 IEEE Topical Conference on Wireless Sensors and Sensor Networks (WiSNet), Jan. 2013.

(56) References Cited

OTHER PUBLICATIONS

IP Australia, Examination Report No. 1 in AU 2014363945, dated Nov. 16, 2018.
IP Australia, Examination Report No. 1 in AU 2019202571, dated Apr. 9, 2020.
IP Australia, Examination Report No. 2 in AU 2019202571, dated Aug. 13, 2020.
IP Australia, Examination Report No. 2 in AU 2014363945, dated Jan. 25, 2019.
IP Australia, Examination Report No. 1 in AU 2019202570, dated Apr. 8, 2020.
China National Intellectual Property Administration, Office Action in CN 201480073304.9, dated Dec. 25, 2018.
China National Intellectual Property Administration, Office Action in 201480073304.9, dated Jul. 22, 2019.
China National Intellectual Property Administration, Office Action in 201480073304.9, dated Feb. 3, 2020.
China National Intellectual Property Administration, Office Action in 201480073304.9, dated Aug. 12, 2020.
Canadian Intellectual Property Office, Official Letter in CA 2933235, dated Sep. 28, 2017.
Canadian Intellectual Property Office, Official Letter in CA 2933235, dated Dec. 14, 2018.
Canadian Intellectual Property Office, Official Letter in CA 2933235, dated Sep. 6, 2019.
Canadian Intellectual Property Office, Official Letter in CA 2998734, dated Jul. 30, 2019.
Canadian Intellectual Property Office, Official Letter in CA 3061807, dated Feb. 9, 2021.
European Patent Office, Extended European Search Report in EP 18166256.0, dated Oct. 1, 2018.
European Patent Office, Examination Report in EP 18166256.0, dated Aug. 26, 2019.
European Patent Office, Extended European Search Report in EP 19218532.0, dated Apr. 17, 2020.
European Patent Office, Extended European Search Report in EP 20210807.2, dated Feb. 17, 2021.
European Patent Office, Extended European Search Report in EP 14869434.2, dated Jul. 27, 2017.
ISA/US, International Search Report in PCT/US2014/069411, dated Apr. 23, 2015.
Japan Patent Office, Decision of Rejection in JP 2016-538056, dated Jul. 10, 2019.
Japan Patent Office, Notice of Reasons for Rejection in JP 2016-538056, dated Aug. 6, 2018.
Japan Patent Office, Notice of Reasons for Rejection in JP 2016-538056, dated Dec. 26, 2017.
Japan Patent Office, Notice of Reasons for Rejection in 2019-205398, dated Feb. 16, 2021.
Korean Intellectual Property Office, Notice of Preliminary Rejection in 10-2021-7004234, dated Mar. 31, 2021.
Korean Intellectual Property Office, Notice of Preliminary Rejection in KR 10-2021-7004235, dated Mar. 30, 2021.
Korean Intellectual Property Office, Notice of Preliminary Rejection in KR 10-2021-7004237, dated Mar. 30, 2021.
Mohamed R Mahfouz, Michael Kuhn, Gary To, Aly Fathy, "Integration of UWB and Wireless Pressure Mapping in Surgical Navigation," IEEE Transactions on Microwave Theory and Techniques 57(10), DOI:10.1109/TMTT.2009.2029721, Nov. 2009, pp. 2550-2564.
Mohamed R Mahfouz, Michael Kuhn, Gary To, "The Future of Ultra Wideband Systems in Medicine: Orthopedic Surgical Navigation," Novel Applications of the UWB Technologies, SN 978-953-307-324-8, pp. 265-316.
Alessio De Angelis, John Olof Nilsson, Isaac Skog, Peter Händel, Paolo Carbone, "Indoor Positioning by Ultrawide Band Radio Aided Inertial Navigation," Metrol. Meas. Syst., vol. XVII (2010), No. 3, pp. 447-460.
David Vissière, Alain Martin, Nicolas Petit, "Using Distributed Magnetometers to Increase IMU-based Velocity Estimation into Perturbed Area," Proceedings of the 46th IEEE Conference on Decision and Control, New Orleans, LA, USA, Dec. 12-14, 2007, pp. 4924-4931.

\* cited by examiner

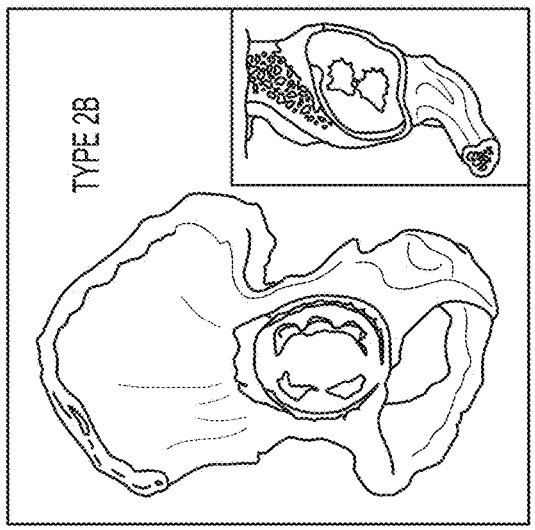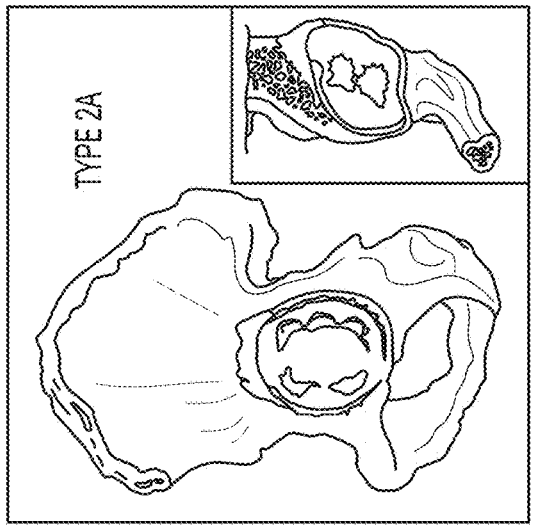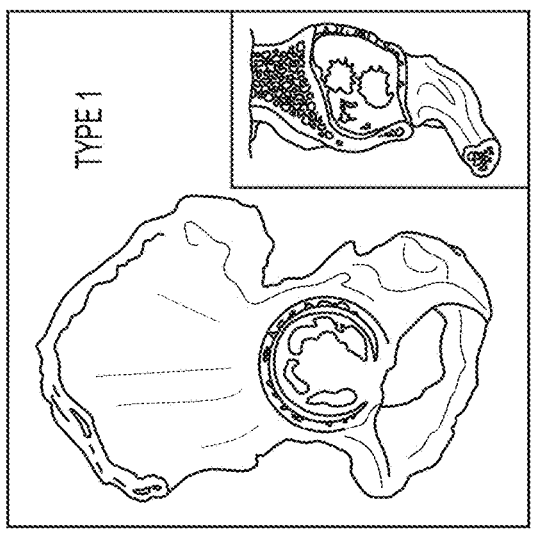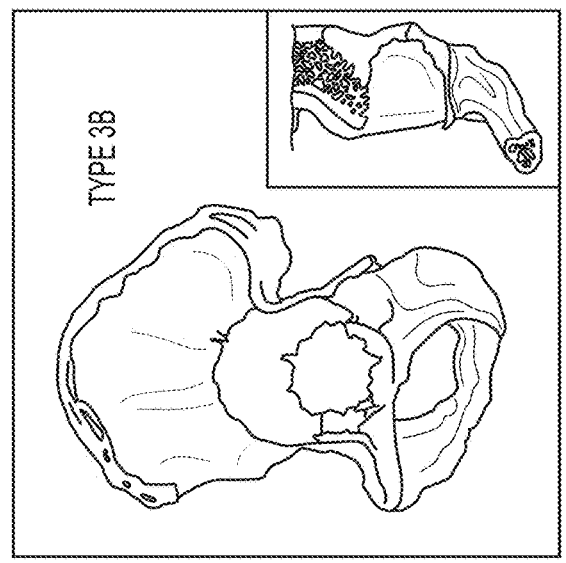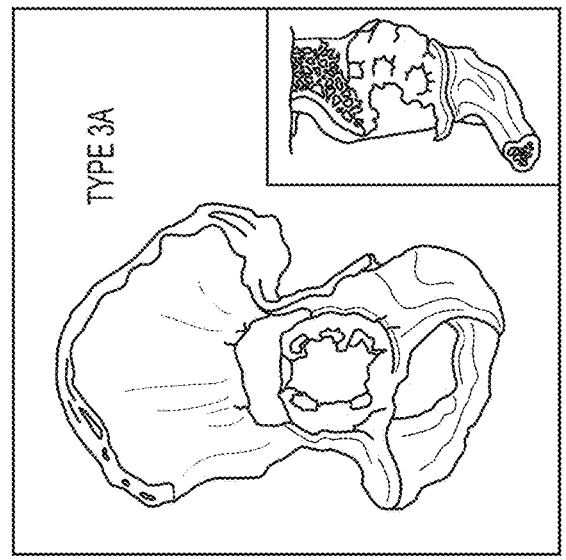
FIG. 11

| | ANTEVERSION TEA | | DIFF | ANTEVERSION PCA | | |
|---|---|---|---|---|---|---|
| | MEAN | STDEV | | MEAN | STDEV | |
| MALE | 4.31 | 7.47 | 0.23 | -1.47 | 2.84 | 8.62 |
| FEMALE | 10.84 | 8.40 | 0.13 | -2.03 | 8.80 | 9.12 |

*FIG. 71*

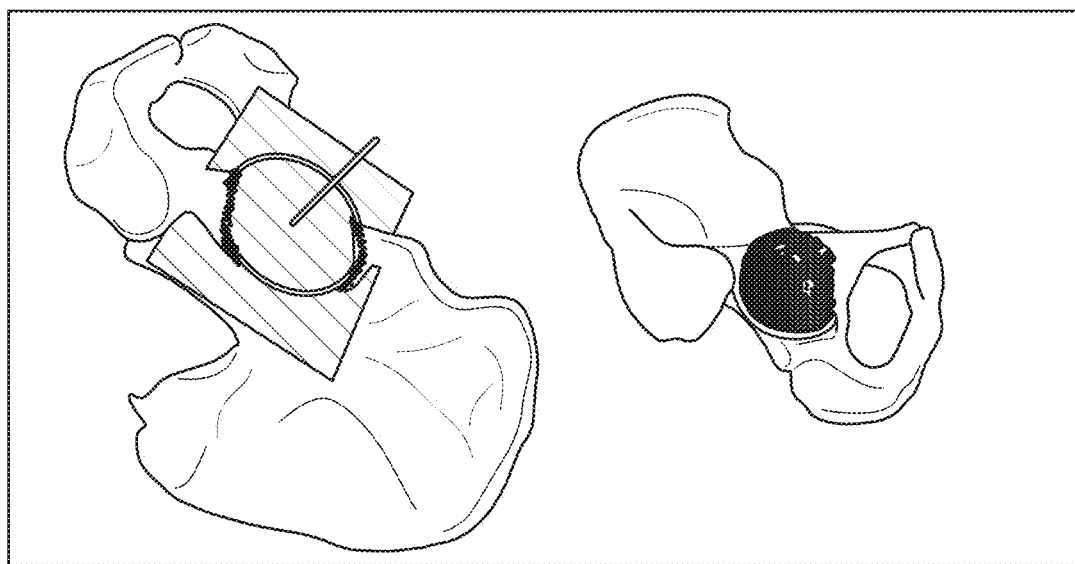
FIG. 78
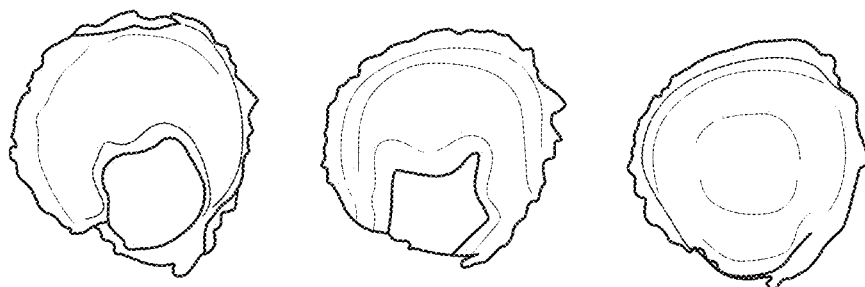
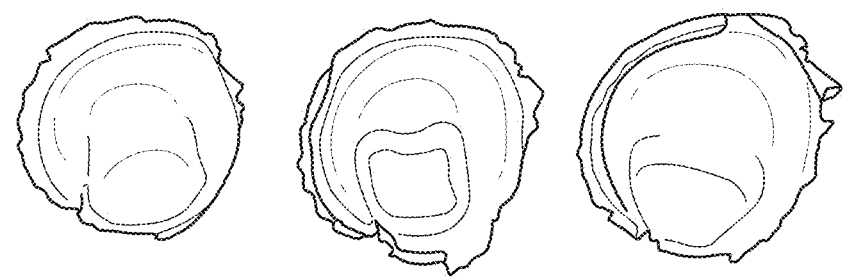
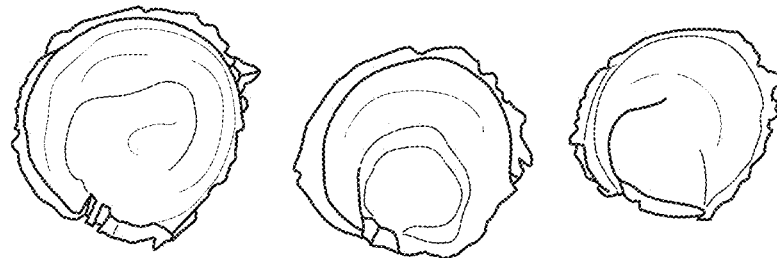
FIG. 79

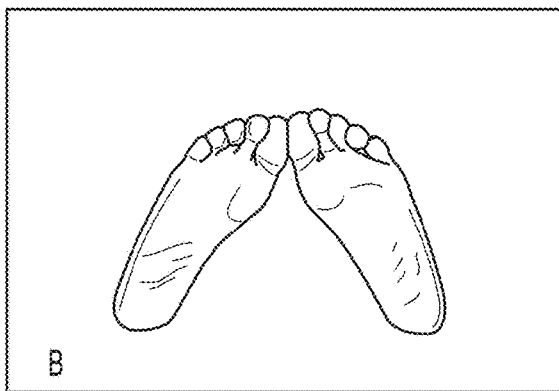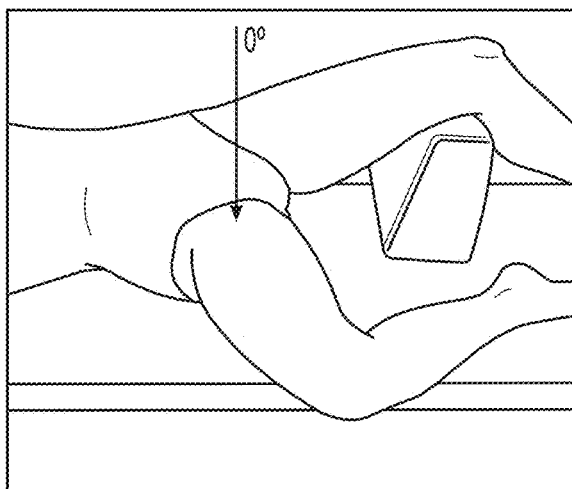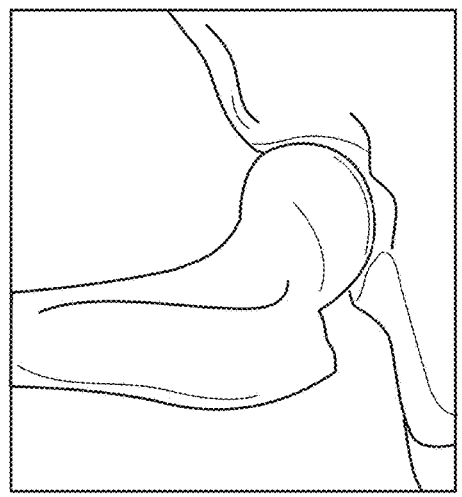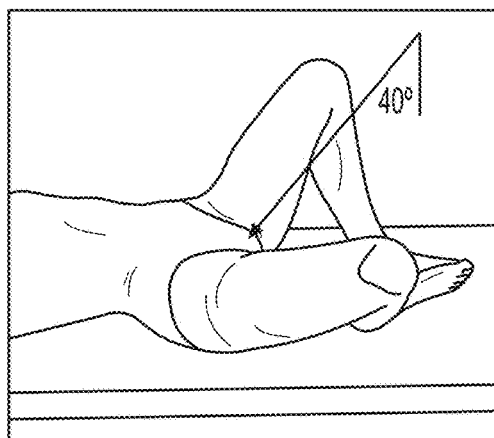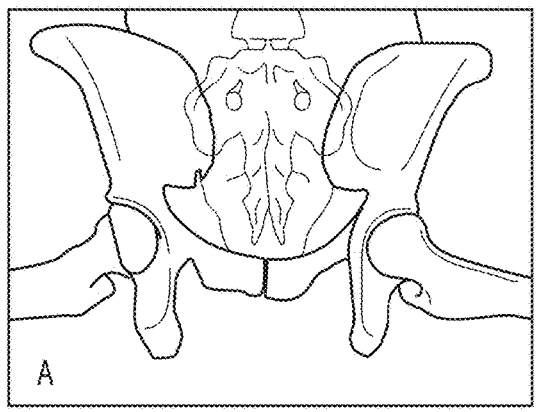
FIG. 89

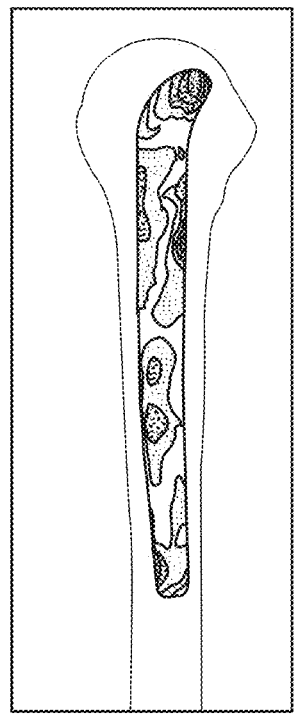
FIG. 124
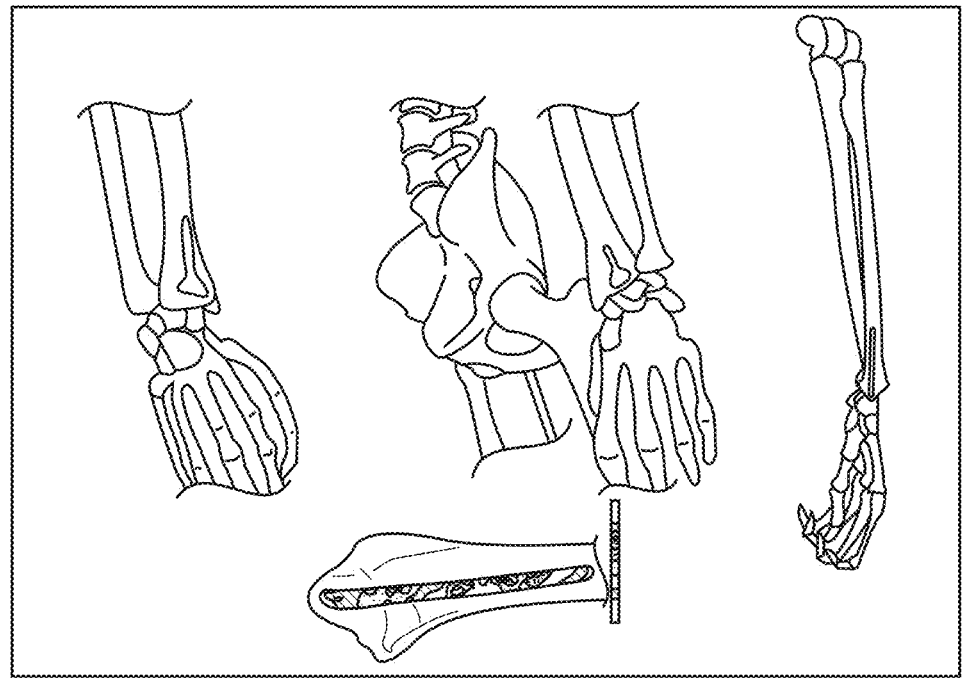
FIG. 125

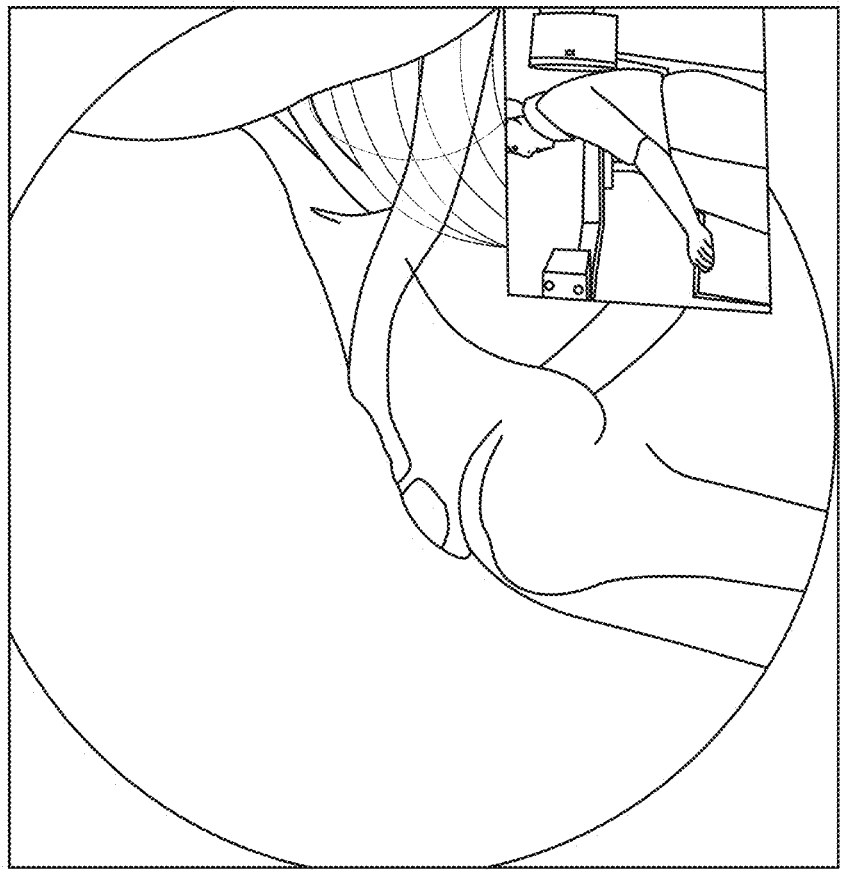
FIG. 129

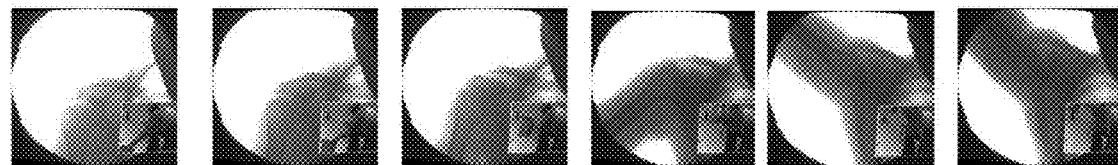
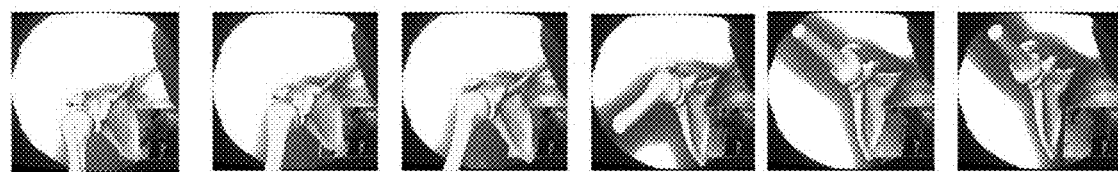
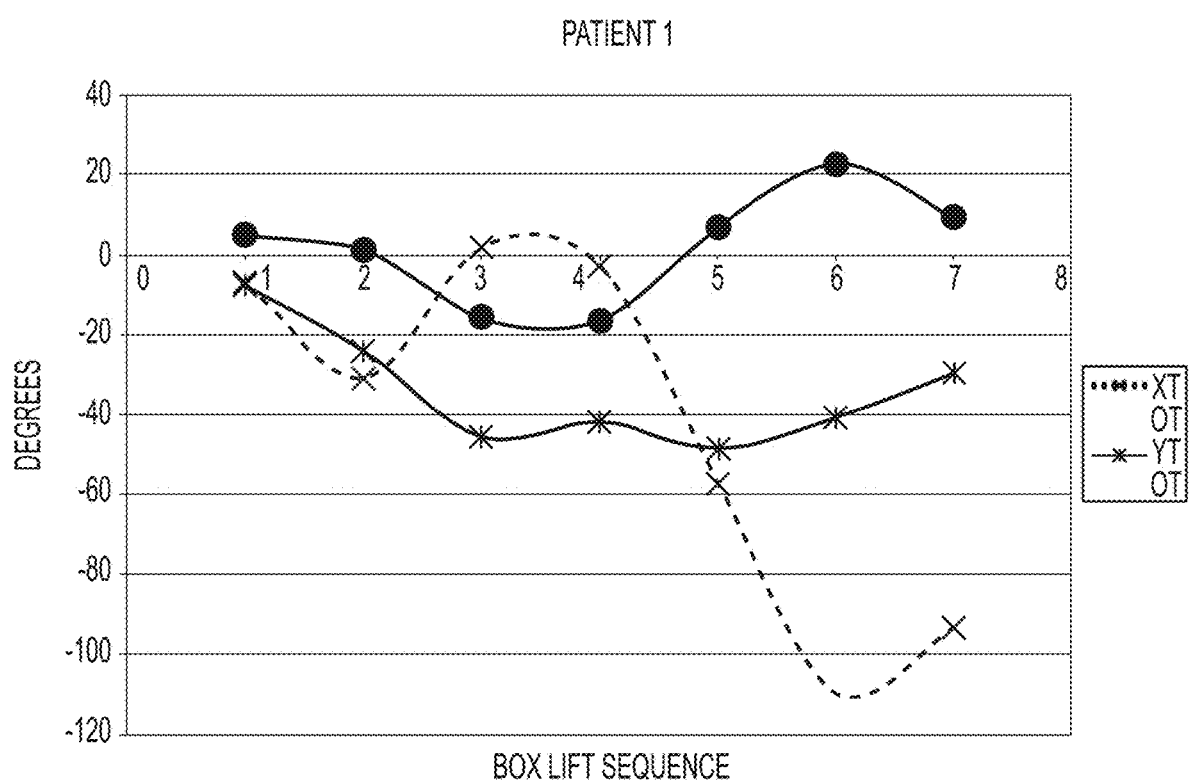
FIG. 131

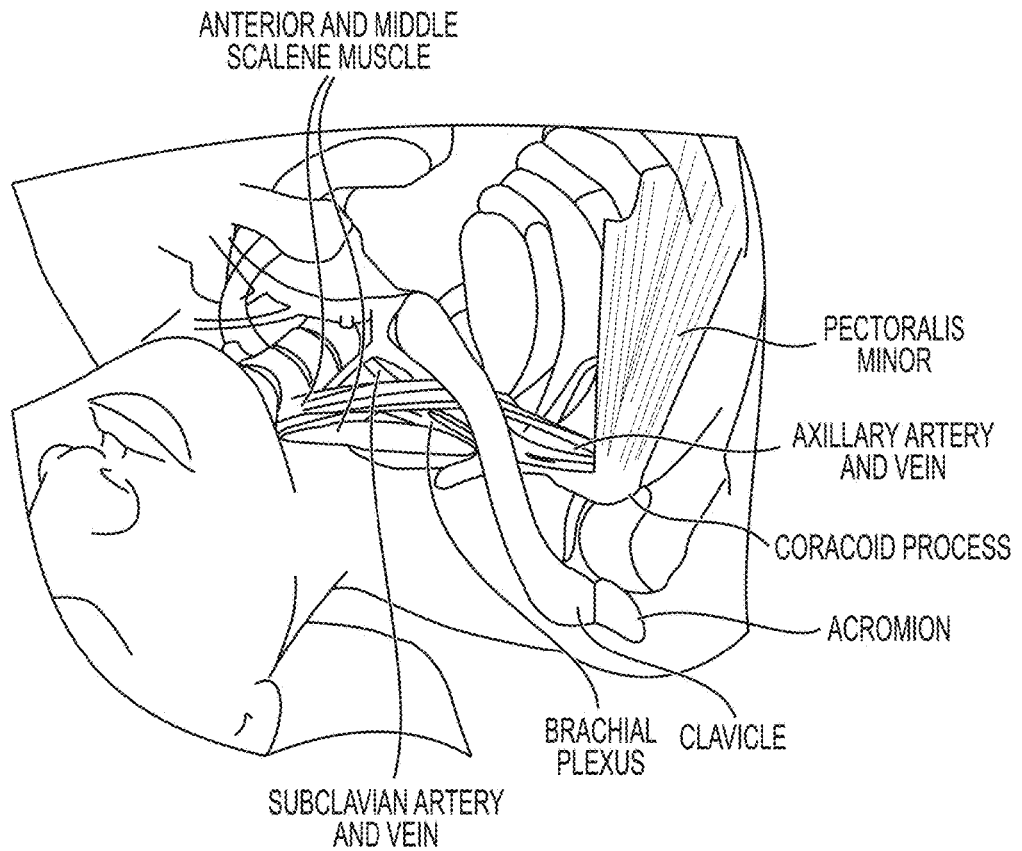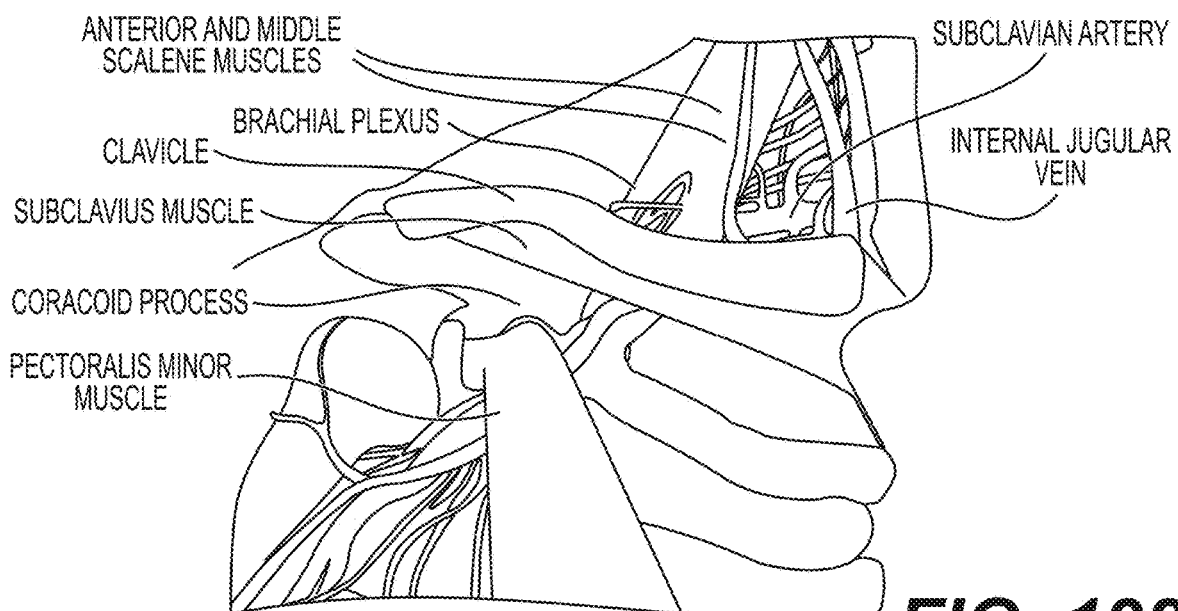
FIG. 132

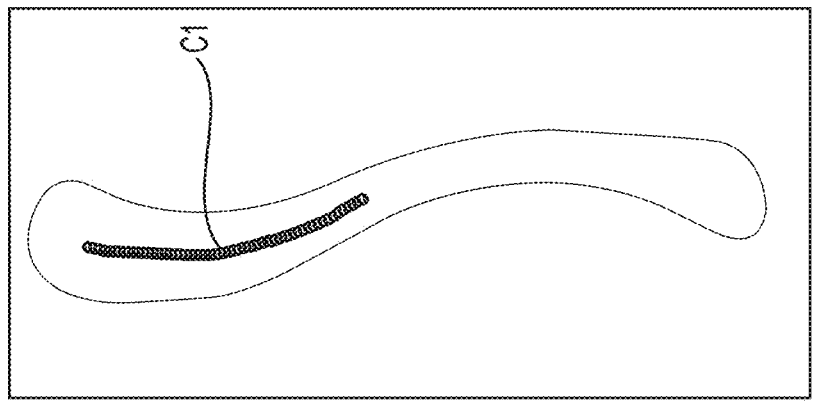
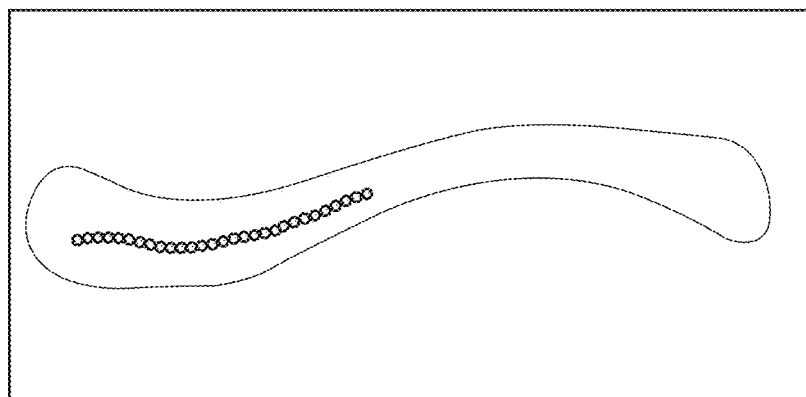
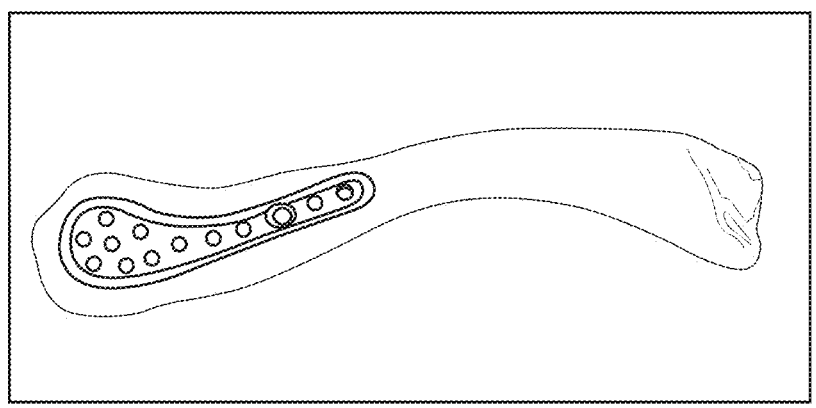
FIG. 140

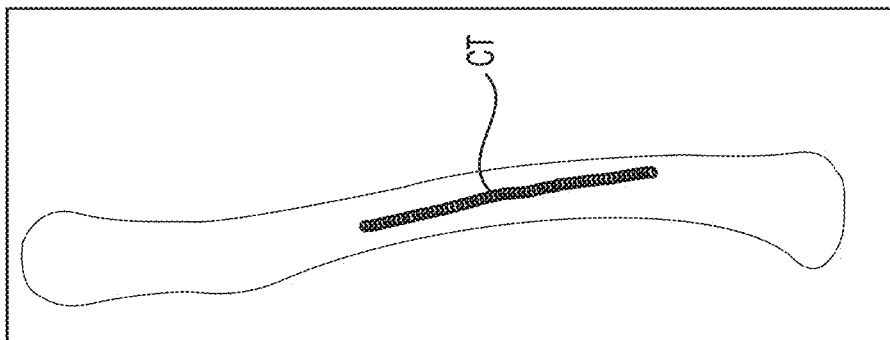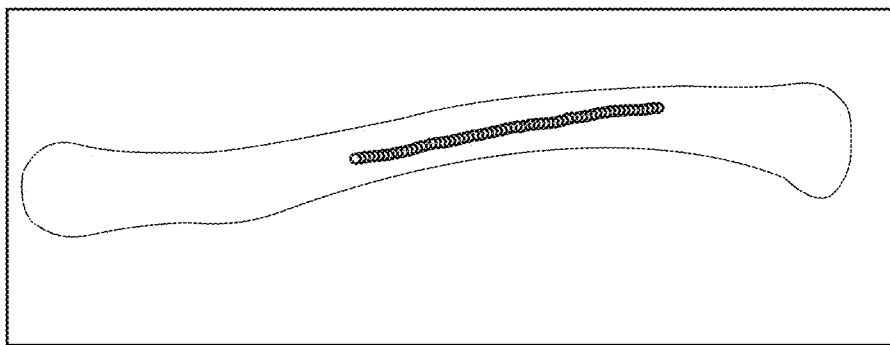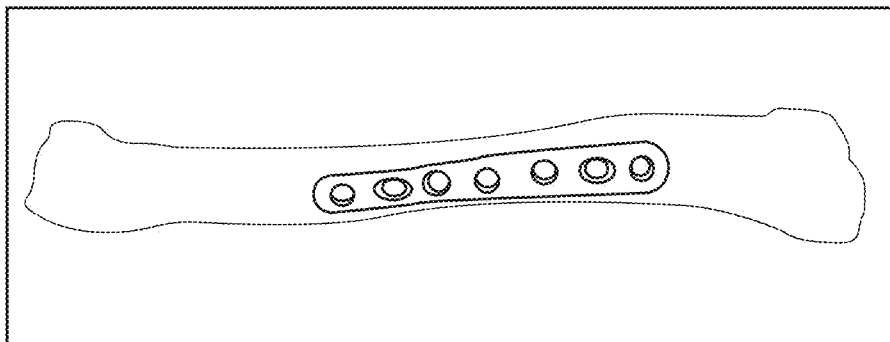
FIG. 142

TABLE 2 ANTERIOR MID-SHAFT 7H PLATE CLUSTER CENTERS.

| | PL_SMS7P | CSC50%_SMS7P | CSW50%_SMS7P | C1_SMS7P |
|---|---|---|---|---|
| CLUSTER 1 | 5.25 | 1.05 | 0.46 | 10.93 |
| CLUSTER 2 | 5.32 | 1.03 | 0.40 | 17.81 |
| CLUSTER 3 | 5.39 | 1.00 | 0.40 | 29.72 |

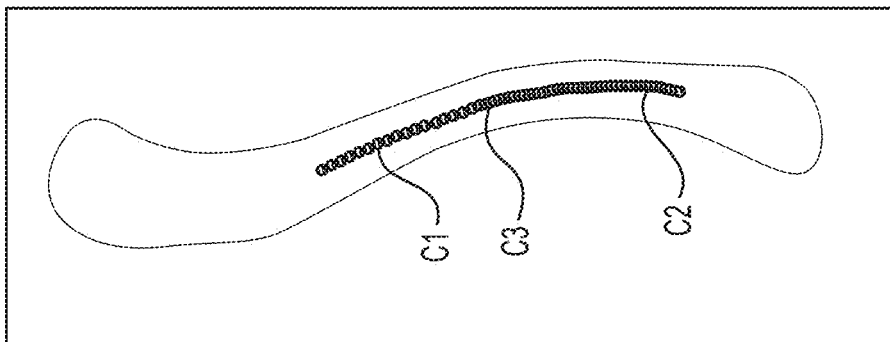
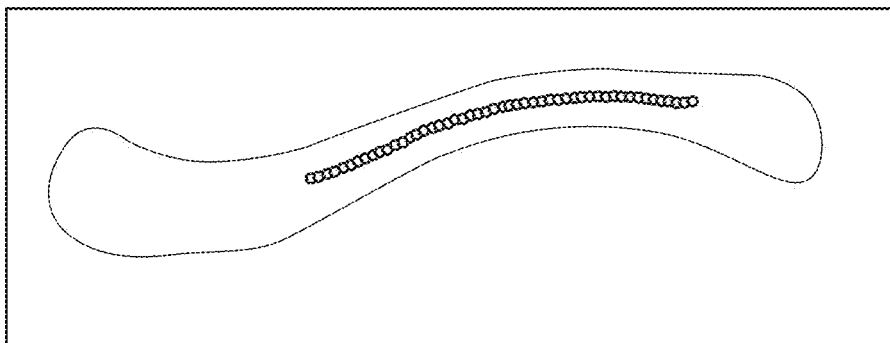
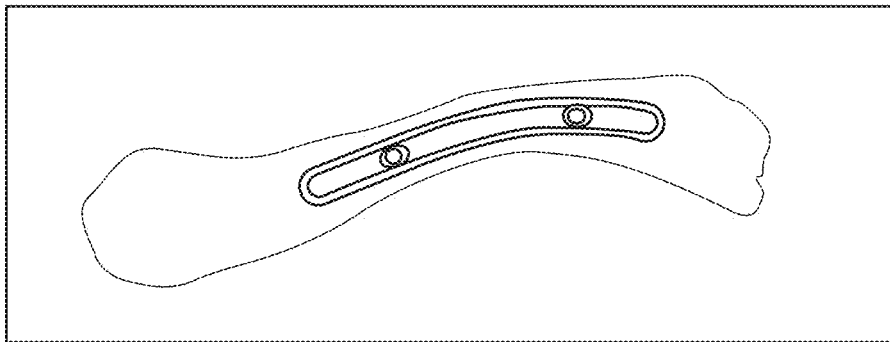
FIG. 144

TABLE 3 SUPERIOR MID-SHAFT PLATE CLUSTER CENTERS.

| | PL_SMSP | CSC50%_SMSP | CSW50%_SMSP | C1_SMSP | CS_SMSP | C3_SMSP |
|---|---|---|---|---|---|---|
| CLUSTER 1 | 8.01 | 0.87 | 0.72 | 32.64 | 9.77 | 6.01 |
| CLUSTER 2 | 7.69 | 0.88 | 0.62 | 21.04 | 8.83 | 5.91 |
| CLUSTER 3 | 7.48 | 0.85 | 0.57 | 13.17 | 8.23 | 6.03 |

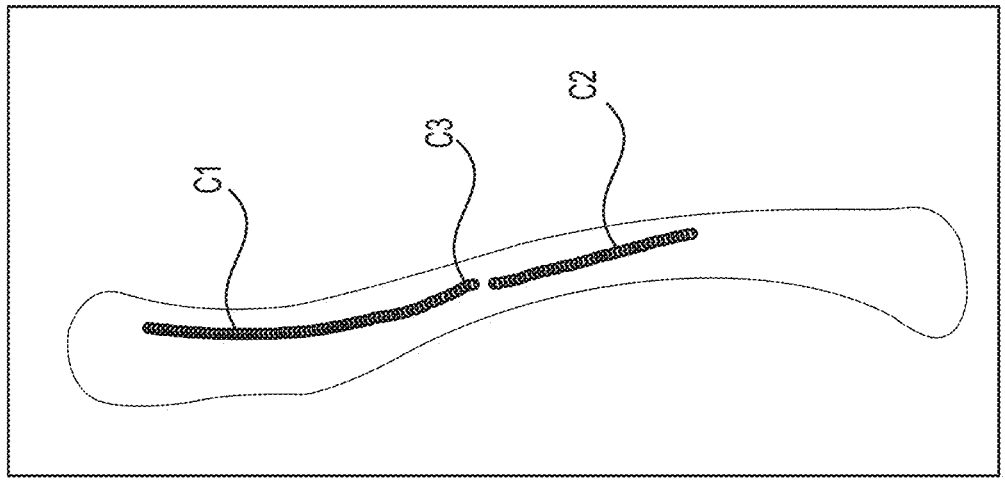
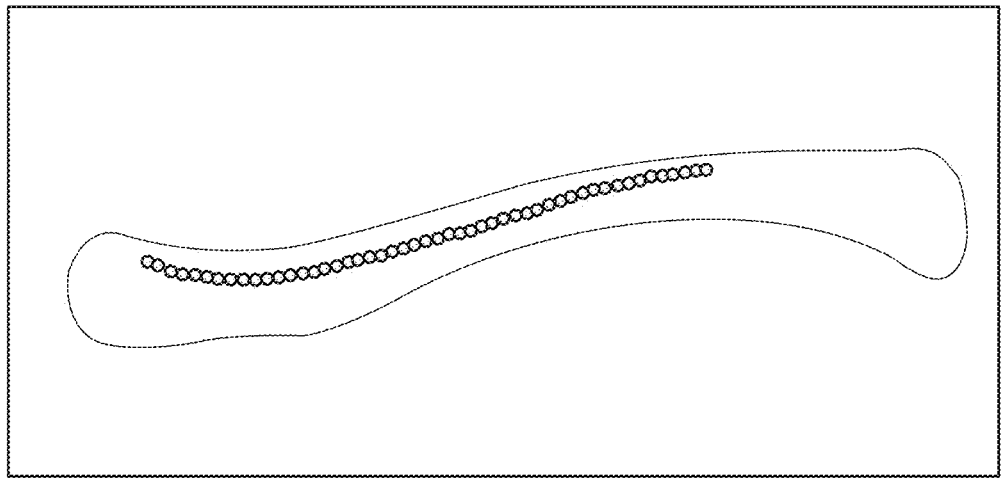
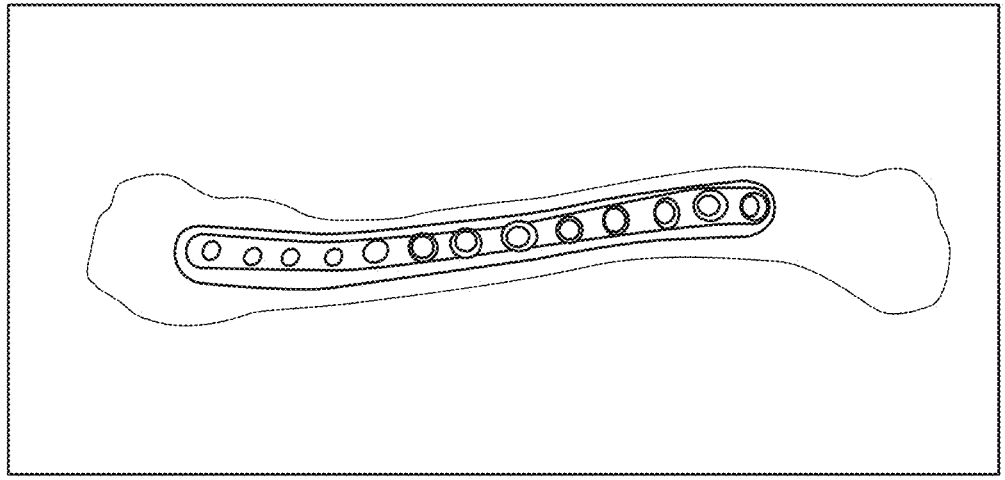
FIG. 146

TABLE 4 CLAVICLE ANTERIOR LATERAL PLATE CLUSTER CENTERS.

| | PL_ALP | CSW50%_ALP | C1_ALP | C2_ALP | C3_ALP |
|---|---|---|---|---|---|
| CLUSTER 1 | 8.92 | 0.27 | 28.51 | 3.55 | 10.67 |
| CLUSTER 2 | 9.06 | 0.36 | 5.45 | 9.73 | 16.06 |
| CLUSTER 3 | 8.84 | 0.32 | 13.55 | 3.46 | 8.43 |

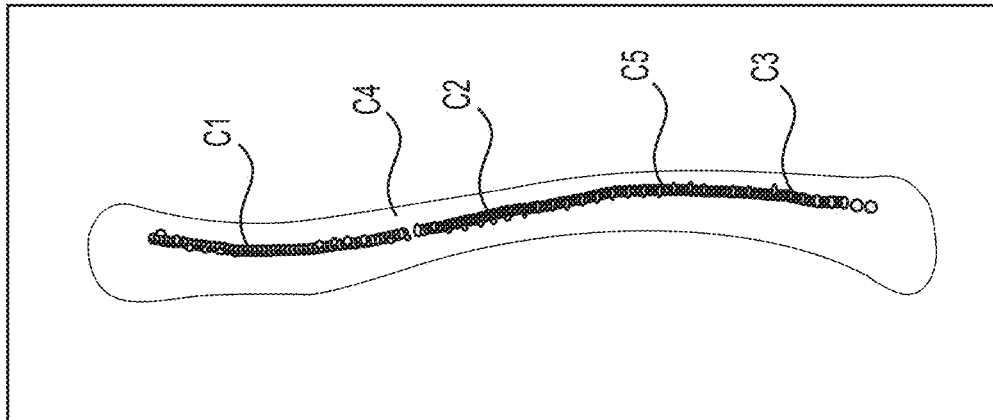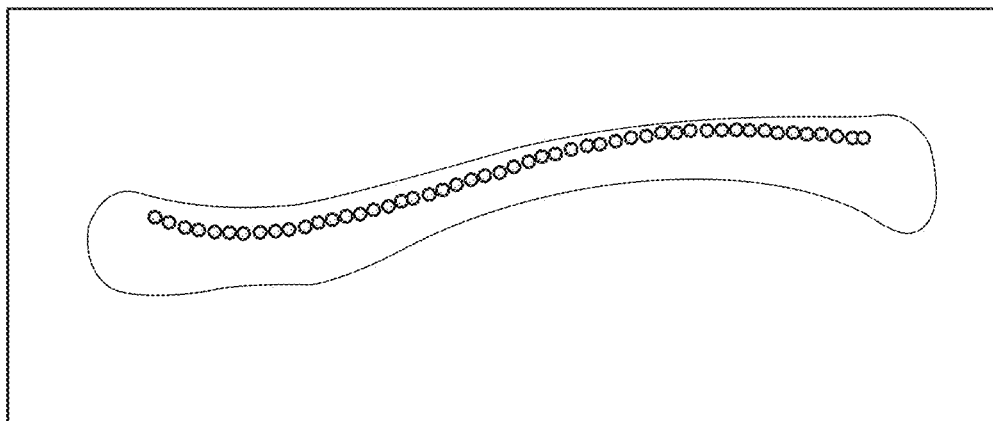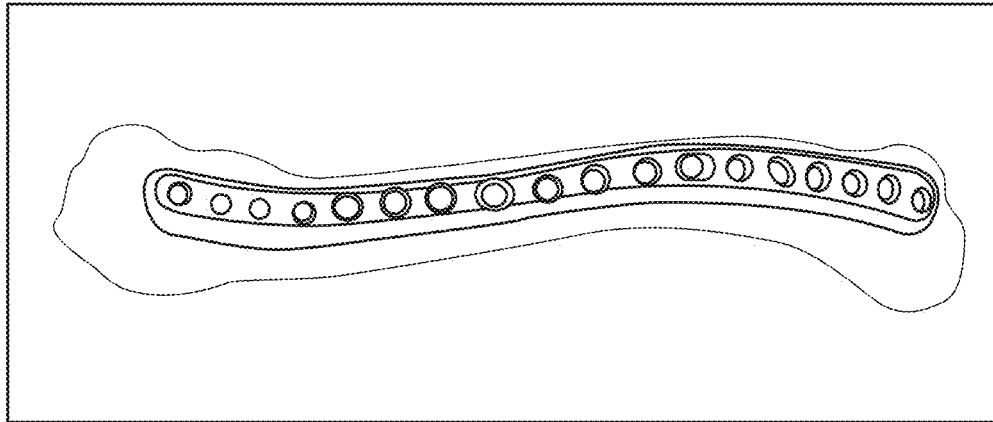
FIG. 148

TABLE 5 CLAVICLE ANTERIOR MID-SHAFT LONG PLATE CLUSTER CENTERS.

| | PL_AMSLP | CSW50%_AMSLP | C1 AMSLP | C2 AMSLP | C3 AMSLP | C4 AMSLP | C5 AMSLP |
|---|---|---|---|---|---|---|---|
| CLUSTER 1 | 12.20 | 0.35 | 4.02 | 11.71 | 13.55 | 14.44 | 11.97 |
| CLUSTER 2 | 12.22 | 0.30 | 18.43 | 33.41 | 3.01 | 8.86 | 3.67 |
| CLUSTER 3 | 12.63 | 0.35 | 4.05 | 11.38 | 23.24 | 19.39 | 12.65 |

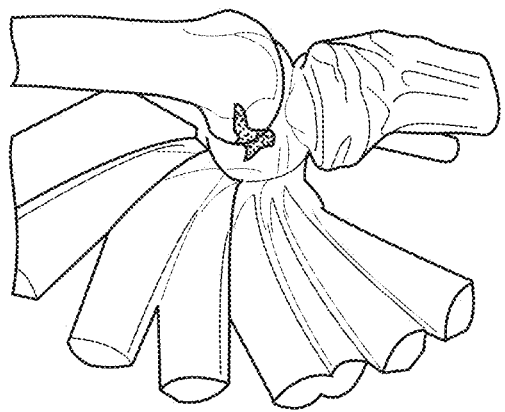
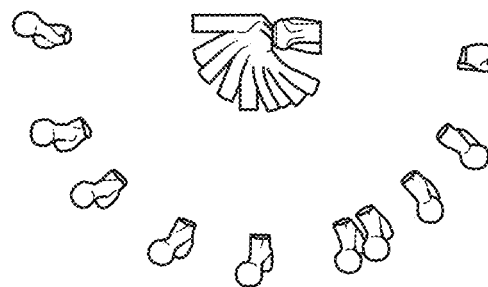
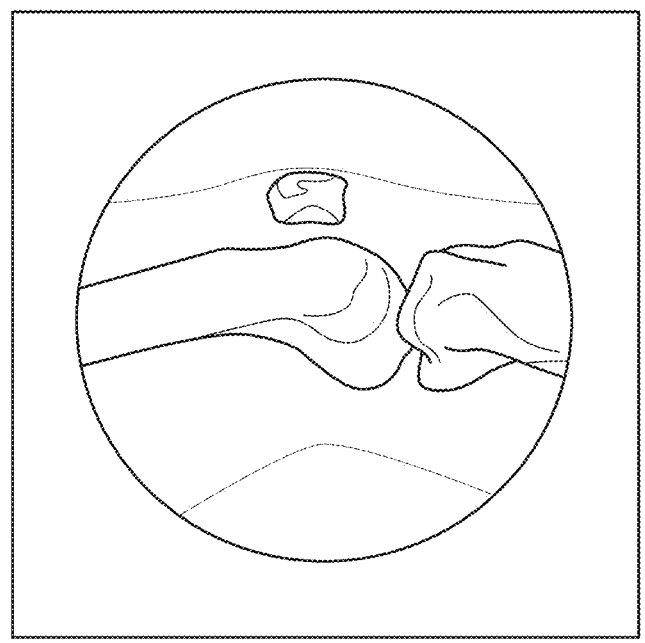
FIG. 160

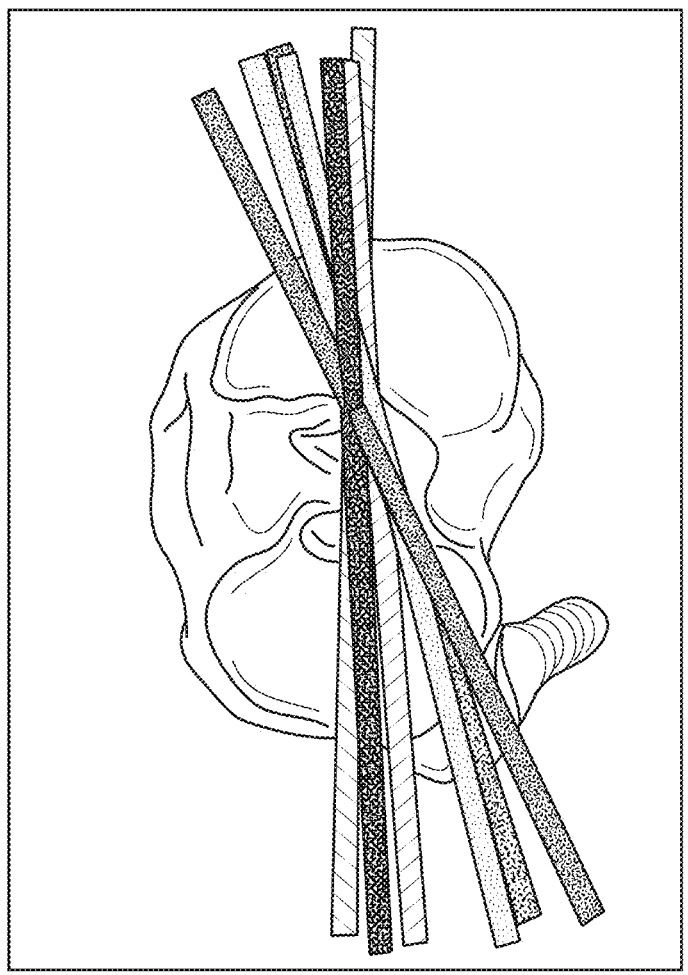
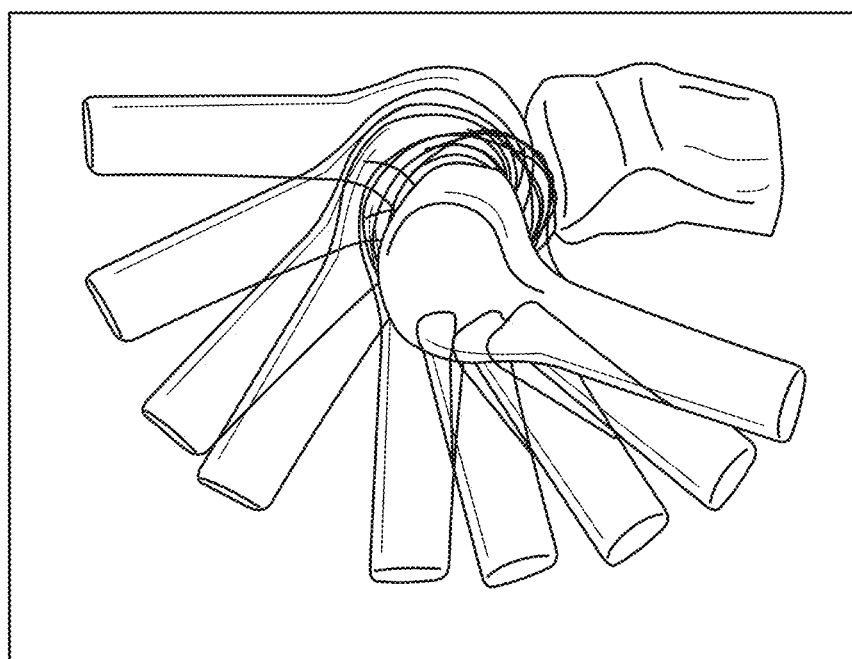
FIG. 162

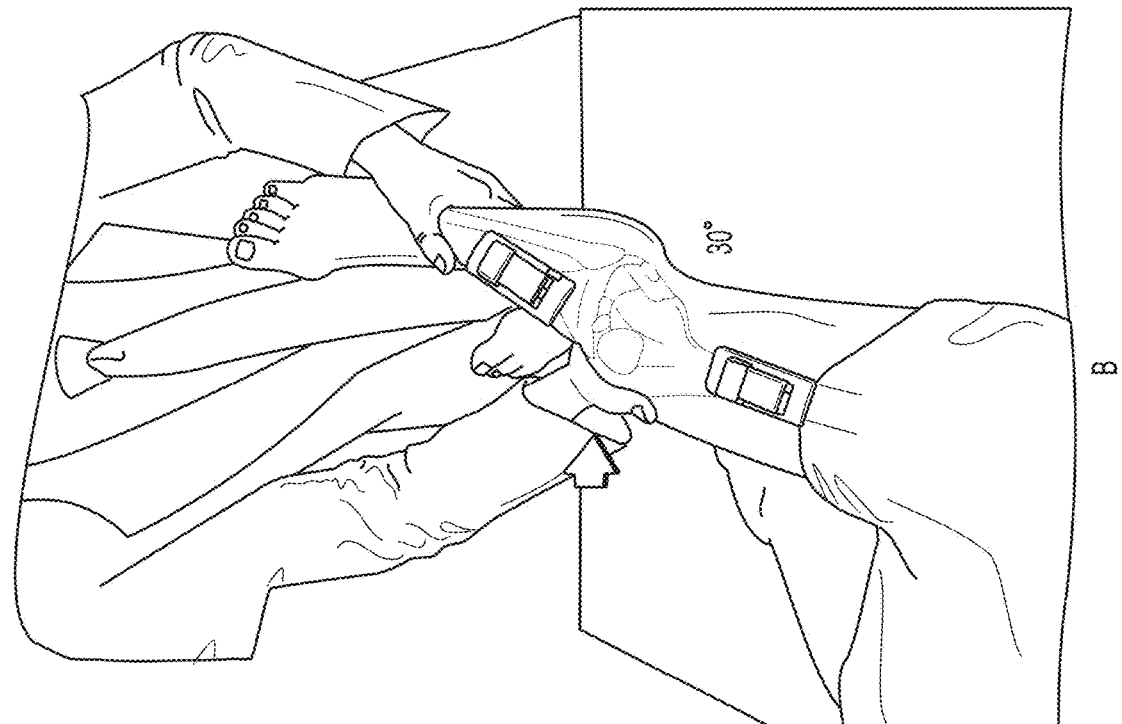
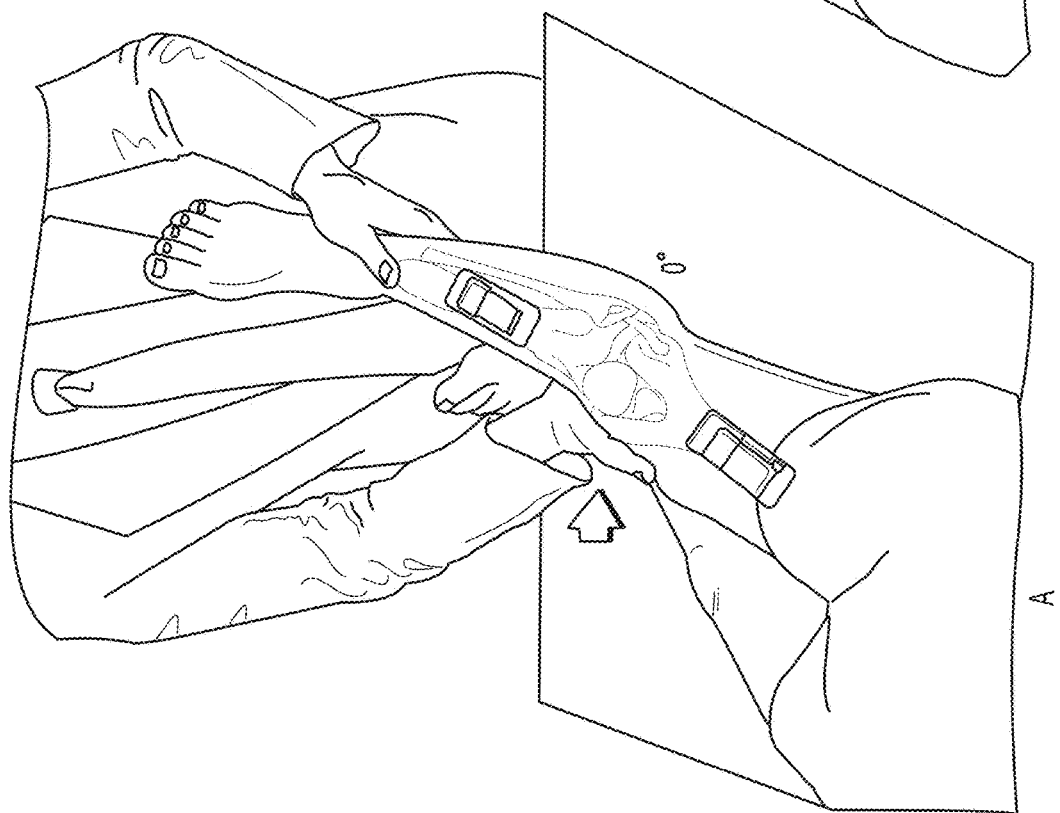
FIG. 165

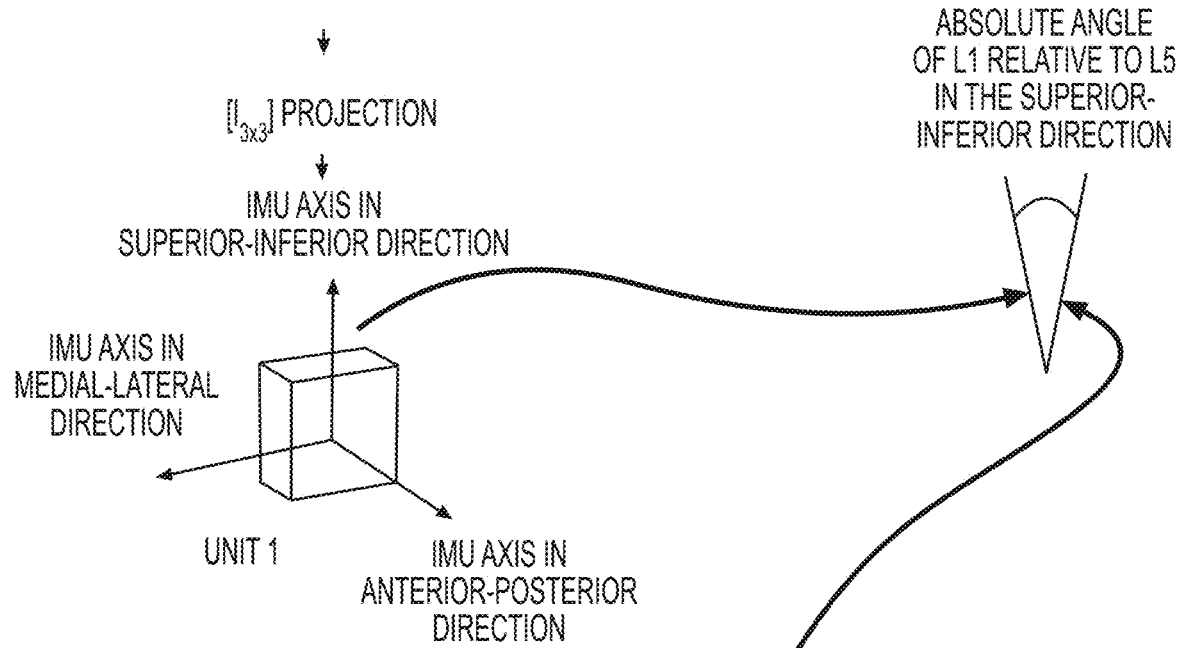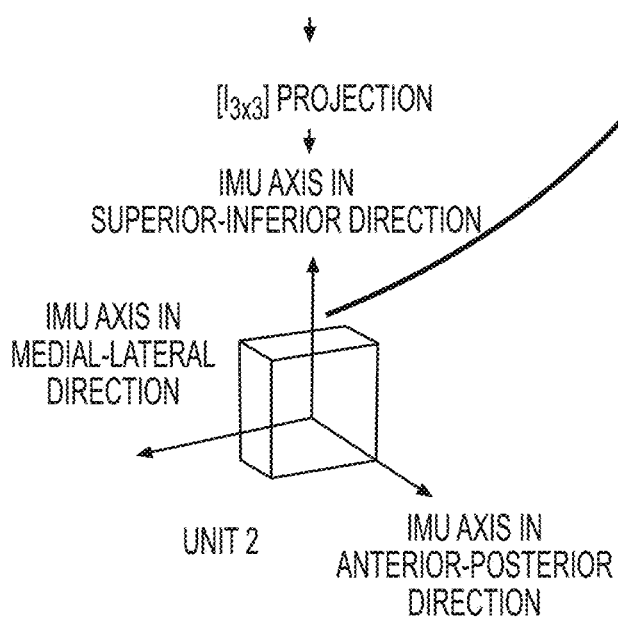
FIG. 177

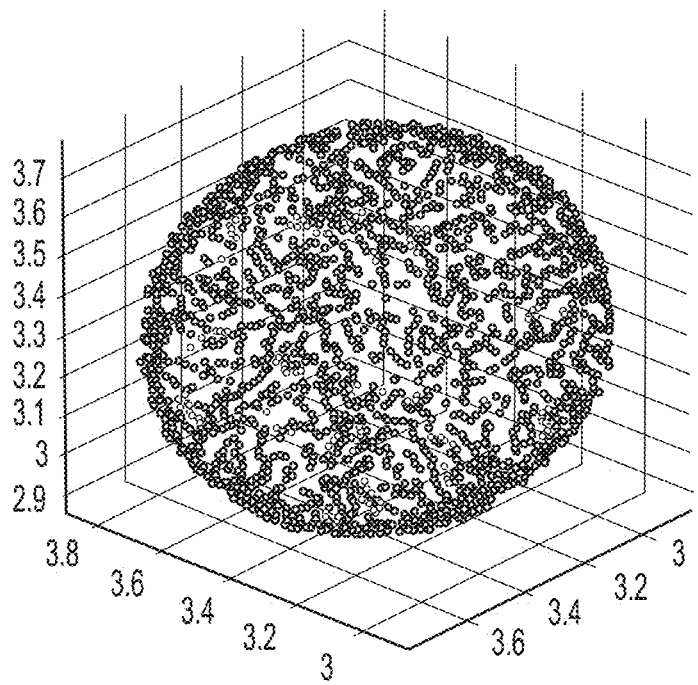
LOCAL MAGNETIC FIELD MAP
(RAW, ISOMETRIC VIEW)
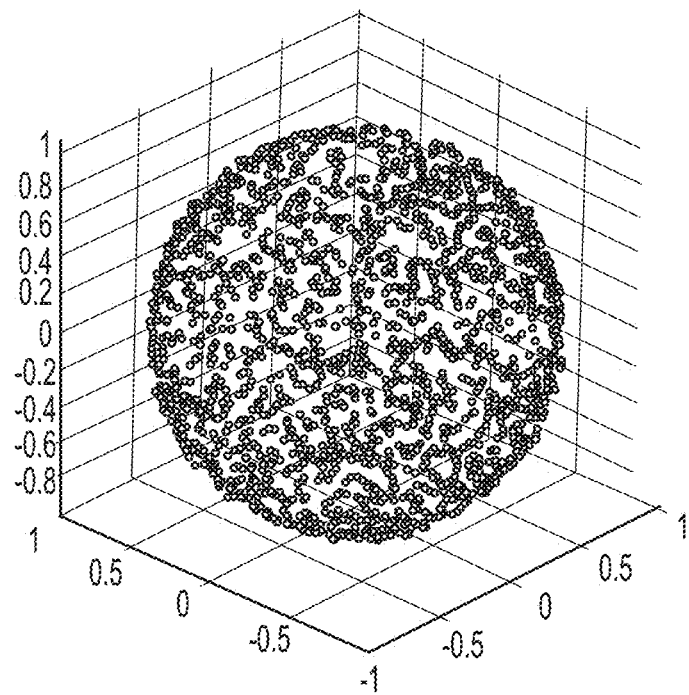
LOCAL MAGNETIC FIELD MAP
(CALIBRATED, ISOMETRIC VIEW)
*FIG. 181*

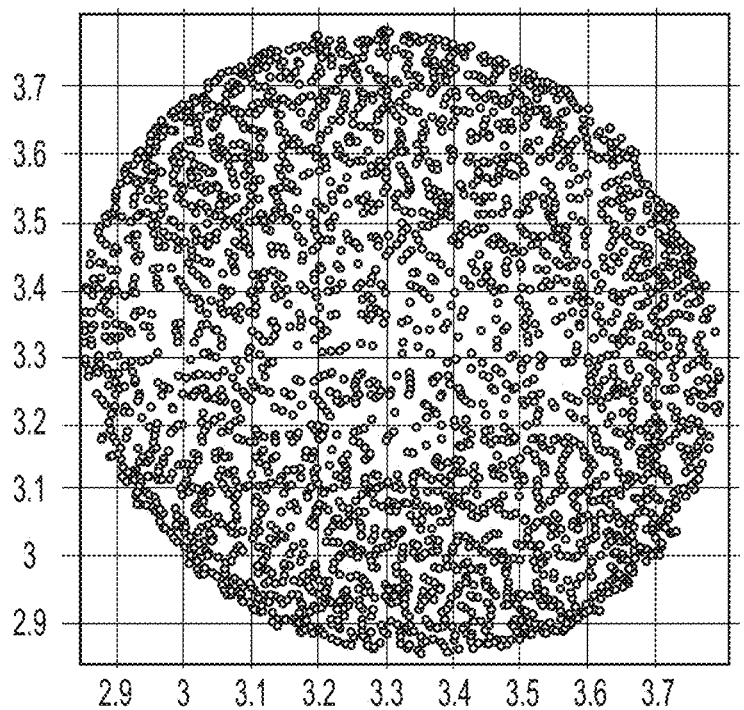
LOCAL MAGNETIC FIELD MAP
(RAW, FRONT VIEW)
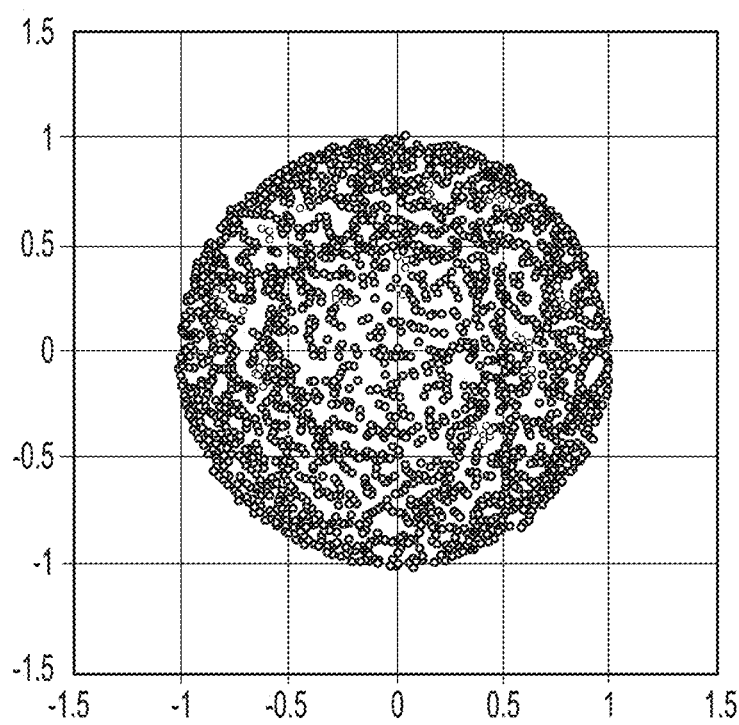
LOCAL MAGNETIC FIELD MAP
(CALIBRATED, FRONT VIEW)
*FIG. 181*
*(CONT. 1)*

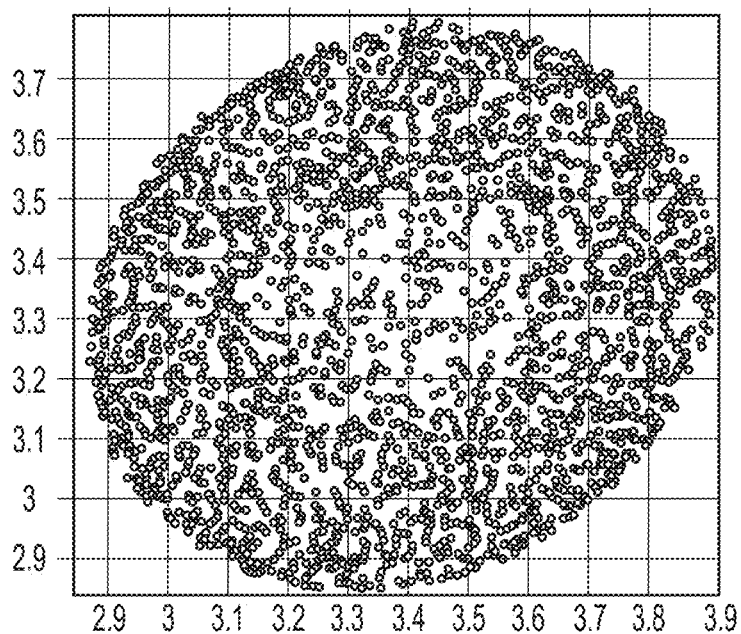
LOCAL MAGNETIC FIELD MAP
(RAW, TOP VIEW)
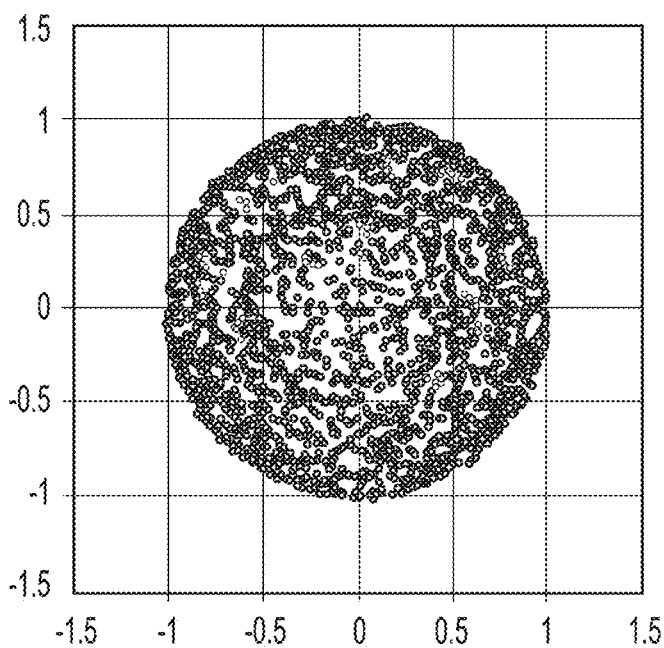
LOCAL MAGNETIC FIELD MAP
(CALIBRATED, TOP VIEW)
*FIG. 181*
*(CONT. 2)*

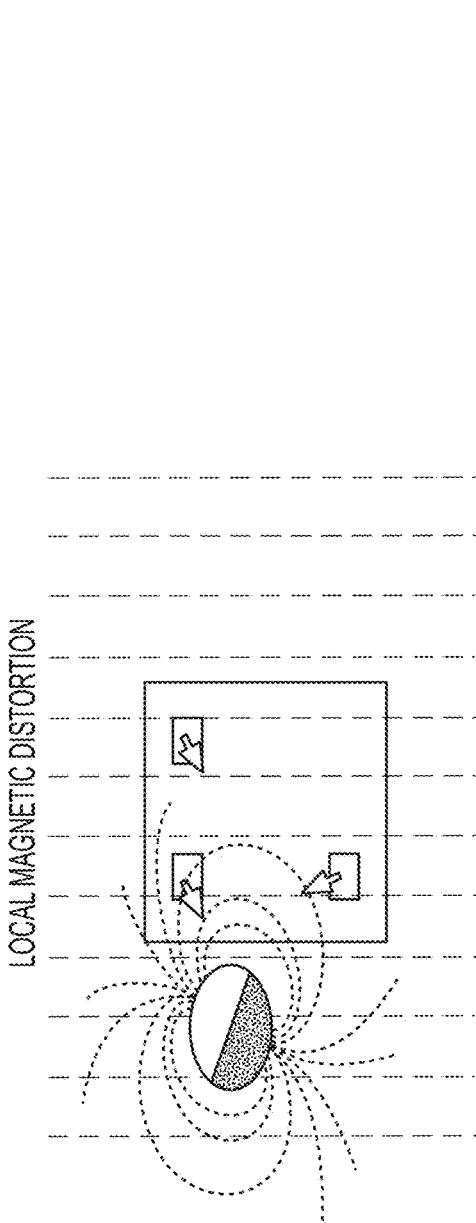
FIG. 182A
FIG. 182B
FIG. 182C

BONE RECONSTRUCTION AND ORTHOPEDIC IMPLANTS

CROSS REFERENCE TO RELATED APPLICATIONS

The present application is a continuation of U.S. Nonprovisional patent application Ser. No. 16/182,405, titled, "BONE RECONSTRUCTION AND ORTHOPEDIC IMPLANTS," filed Nov. 6, 2018, and a divisional of U.S. Nonprovisional patent application Ser. No. 14/565,357, titled, "BONE RECONSTRUCTION AND ORTHOPEDIC IMPLANTS," filed Dec. 9, 2014, now U.S. Pat. No. 10,258,256, which claimed the benefit of U.S. Provisional Patent Application Ser. No. 61/913,608, titled, "CRANIUM AND POSTCRANIAL BONE AND SOFT TISSUE RECONSTRUCTION," filed Dec. 9, 2013, and U.S. Provisional Patent Application Ser. No. 61/951,221, titled, "CRANIUM AND POSTCRANIAL BONE AND SOFT TISSUE RECONSTRUCTION," filed Mar. 11, 2014, and U.S. Provisional Patent Application Ser. No. 61/977,984, titled, "CRANIUM AND POSTCRANIAL BONE AND SOFT TISSUE RECONSTRUCTION," filed Apr. 10, 2014, and U.S. Provisional Patent Application Ser. No. 62/022,899, titled, "CRANIUM AND POSTCRANIAL BONE AND SOFT TISSUE RECONSTRUCTION," filed Jul. 10, 2014, the disclosure of each of which is incorporated herein by reference.

RELATED ART

Field of the Invention

The present disclosure is directed to various aspects of orthopedics including bone and tissue reconstruction, patient-specific and mass customized orthopedic implants, gender and ethnic specific orthopedic implants, cutting guides, trauma plates, bone graft cutting and placement guides, patient-specific instruments, utilization of inertial measurement units for anatomical tracking for kinematics and pathology, and utilization of inertial measurement units for navigation during orthopedic surgical procedures.

Introduction to the Invention

It is a first aspect of the present invention to provide a surgical navigation system comprising a signal receiver communicatively coupled to a primary processor, the primary processor programmed to utilize a sequential Monte Carlo algorithm to calculate changes in three dimensional position of an inertial measurement unit mounted to a surgical tool, the processor communicatively coupled to a first memory storing tool data unique to each of a plurality of surgical tools, and a second memory storing a model data sufficient to construct a three dimensional model of an anatomical feature, the primary processor communicatively coupled to a display providing visual feedback regarding the three dimensional position of the surgical tool with respect to the anatomical feature.

In a more detailed embodiment of the first aspect, the surgical navigation system further includes a reference inertial measurement unit communicatively coupled to a first on-board processor and a first wireless transmitter to transmit data to the primary processor, the reference inertial measurement unit configured to be attached to the anatomical feature, where the first on-board processor directs transmission of data from the reference inertial measurement unit to the first wireless transmitter, where the inertial measurement unit mounted to the surgical tool comprises a utility inertial measurement unit communicatively coupled to a second on-board processor and a second wireless transmitter, the second on-board processor configured to be mounted to one of the plurality of surgical tools, and where the primary processor is communicatively coupled to a primary received configured to receive data from the first wireless transmitter and data from the second wireless transmitter. In yet another more detailed embodiment, the second on-board processor directs communication via the second wireless transmitter of an identity of the surgical tool to which the utility inertial measurement unit is mounted. In a further detailed embodiment, the inertial measurement unit includes at least three accelerometers and three magnetometers, each of the at least three accelerometers outputs data relative to three axes for a total of no less than nine accelerometer data streams, each of at least three magnetometers outputs data relative to three axes for a total of no less than nine magnetometer data streams, the primary processor utilizes the nine accelerometer data streams and the nine magnetometer data streams to calculate changes in three dimensional position of the inertial measurement unit mounted to the surgical tool. In still a further detailed embodiment, the model data stored in the second memory includes a three dimensional virtual model of the anatomical feature, the tool data stored in the first memory includes three dimensional virtual models of the plurality of surgical tools, the display displays the three dimensional virtual model of the anatomical feature, the display displays a three dimensional virtual model of the surgical tool, the primary processor is operative to utilize data from the reference inertial measurement unit to reposition the three dimensional virtual model of the anatomical feature, and the primary processor is operative to utilize data from the utility inertial measurement unit to reposition the three dimensional virtual model of the surgical tool. In a more detailed embodiment, the primary processor is operative to utilize data from the inertial measurement unit to reposition the three dimensional virtual model of the surgical tool with respect to a three dimensional virtual model of the anatomical feature in real-time. In a more detailed embodiment, the sequential Monte Carlo algorithm includes a von Mises-Fisher density algorithm component. In another more detailed embodiment, the tool data stored in the first memory includes positional data indicating the relative distances between an end effector of the surgical tool and a mounting location on the surgical device for the inertial measurement unit, and the surgical tool includes at least one of a reamer, a cup positioned, an impacter, a drill, a saw, and a cutting guide. In yet another more detailed embodiment, the inertial measurement unit includes at least three magnetometers, and the display is at least one of coupled to the surgical tool or coupled to the primary processor.

It is a second aspect of the present invention to provide a calibration system, for an inertial measurement unit including a magnetometer and an accelerometer, comprising: (a) a primary platform rotationally repositionable with respect to an intermediate platform along a first axis; (b) a final platform rotationally repositionable with respect to the intermediate platform along a second axis, the second axis being perpendicular to the first axis, the final platform including a retainer configured to mount to an inertial measurement unit; and, (c) a processor and associated software configured to communicatively couple to the inertial measurement unit, the software operative to utilize data output from a magnetometer associated with the inertial measurement unit while the primary platform is rotated with respect to the intermediate platform and while the final platform is rotated with respect to the intermediate platform and record a data set resembling an ellipsoid, the software operative to fit a sphere to the data set and generate magnetometer correction calculations to account for distortions in a local magnetic field, thereby normalizing future data output from the magnetometer.

In a more detailed embodiment of the second aspect, the primary platform is stationary. In yet another more detailed embodiment, the primary platform at least partially houses a motor configured to cause rotation of the intermediate platform with respect to the primary platform. In a further detailed embodiment, the software is operative to utilize a first set of data output from an accelerometer associated with the inertial measurement unit while the inertial measurement unit is at a first stationary position and operative to utilize a second set of data output from the accelerometer at a second stationary position different from the first stationary position to generate accelerometer correction calculations to normalizing future data output from the accelerometer. In still a further detailed embodiment, the first stationary position corresponds to the primary platform being at a first fixed position with respect to the intermediate platform and the final platform is at a second fixed position with respect to the intermediate platform, and the second stationary position corresponds to at least one of the primary platform being at a third fixed position with respect to the intermediate platform and the final platform is at a fourth fixed position with respect to the intermediate platform. In a more detailed embodiment, the final platform includes a plurality of retainers, where each of the plurality of retainers is configured to mount to at least one of a plurality of inertial measurement units.

It is a third aspect of the present invention to provide a method of calibrating an inertial measurement unit including a magnetometer, the method comprising: (a) rotating a first inertial measurement unit, which includes a first inertial measurement unit, about a first rotational axis and a second rotational axis, the first rotational axis being perpendicular to the second rotational axis, while concurrently receiving raw local magnetic field data from the first magnetometer; (b) applying a uniform calculation to the raw local magnetic field data to calculate a distortion in a local magnetic field; and, (c) normalizing the raw local magnetic field data received from the magnetometer by accounting for a calculated distortion in the local magnetic field to provide refined local magnetic field data.

In a more detailed embodiment of the third aspect, the first inertial measurement unit includes a first accelerometer, the method further comprises: (i) holding stationary the first inertial measurement unit in a first three dimensional position while concurrently receiving raw accelerometer data from the first accelerometer; (ii) holding stationary the first inertial measurement unit in a second three dimensional position while concurrently receiving raw accelerometer data from the first accelerometer, the second three dimensional position being different than the first three dimensional position; and, (iii) normalizing data received from the first accelerometer to reflect zero acceleration when the first accelerometer is stationary. In yet another more detailed embodiment, the first inertial measurement unit includes a second accelerometer, the method further comprises: (i) holding stationary the second inertial measurement unit, as the first accelerometer is held stationary, in a third three dimensional position while concurrently receiving raw accelerometer data from the second accelerometer; (ii) holding stationary the second inertial measurement unit, as the first accelerometer is held stationary, in a fourth three dimensional position while concurrently receiving raw accelerometer data from the second accelerometer, the fourth three dimensional position being different than the third three dimensional position; and, (iii) normalizing data received from the second accelerometer to reflect zero acceleration when the second accelerometer is stationary. In a further detailed embodiment, the raw local magnetic field data is representative of an ellipsoid in three dimensions, and the refined local magnetic field data is representative of a sphere in three dimensions. In still a further detailed embodiment, the uniform calculation includes fitting a sphere to the raw local magnetic field data, and normalizing the raw local magnetic field data includes subtracting the calculated distortion from the raw local magnetic field data to provide refined local magnetic field data. In a more detailed embodiment, the method further comprises a second inertial measurement unit having its own first accelerometer. In a more detailed embodiment, the second inertial measurement unit has its own first accelerometer.

It is a fourth aspect of the present invention to provide a method of identifying a surgical tool when coupled to an inertial measurement unit, the method comprising: (a) mounting an inertial measurement unit to one of a plurality of surgical tools, each of the plurality of surgical tools having a unique interface; and, (b) reading the unique interface to transmit a signal to a processor communicatively coupled to the inertial measurement unit to identify one of the plurality of surgical tools responsive to reading the unique interface.

In a more detailed embodiment of the fourth aspect, the inertial measurement unit is operatively coupled to a plurality of switches, the unique interface engages at least one of the plurality of switches, and the step of reading the unique interface includes a determination by the processor as to which of the plurality of switches have been engaged by the unique interface. In yet another more detailed embodiment, the processor is coupled to the inertial measurement unit, and the processor and inertial measurement unit are housed within a common housing. In a further detailed embodiment, the processor is remote from the inertial measurement unit, and the processor and inertial measurement unit are not housed within a common housing.

It is a fifth aspect of the present invention to provide a method of conducting surgical navigation comprising: (a) utilizing a plurality of inertial measurement units to generate acceleration data and magnetic data; (b) calibrating the plurality of inertial measurement units in proximity to a surgical procedure location; (c) registering relative locations of a first and second inertial measurement units comprising the plurality of inertial measurement units, where registering relative locations includes mounting the first inertial measurement unit to a registration tool that uniquely engages a patient's anatomy in a particular location and orientation, and where registering the relative locations includes mounting the second inertial measurement unit to the patient; (d) attaching the first inertial measurement unit to a surgical tool post registration; (e) repositioning the surgical tool and the first inertial measurement unit toward a surgical site associated with the patient's anatomy; and, (f) providing visual feedback regarding at least one of a location and an orientation of the surgical tool when at least one of the patient's anatomy is not visible or an operative end of the surgical tool is not visible.

It is a sixth aspect of the present invention to provide a method of conducting surgical navigation comprising: (a)

utilizing a plurality of inertial measurement units to generate acceleration data and magnetic data; (b) calibrating the plurality of inertial measurement units in proximity to a surgical procedure location; (c) registering relative locations of a first and second inertial measurement units comprising the plurality of inertial measurement units, where registering relative locations includes mounting the first inertial measurement unit to a registration tool that uniquely engages a patient's anatomy in a particular location and orientation, and where registering the relative locations includes mounting the second inertial measurement unit to the patient; (d) attaching the first inertial measurement unit to a surgical tool post registration; (e) repositioning the surgical tool and the first inertial measurement unit toward a surgical site associated with the patient's anatomy; and, (f) providing visual feedback regarding a location and an orientation of the surgical tool with respect to a predetermined surgical plan, where the predetermined surgical plan identifies at least one of a permissible range of locations and a permissible range of orientations the surgical tool may occupy.

It is a seventh aspect of the present invention to provide a method of generating a trauma plate for a particular bone, the method comprising: (a) accessing a database comprising a plurality of three dimensional bone models of a particular bone; (b) assessing features comprising at least one of longitudinal contours and cross-sectional contours for each of the plurality of three dimensional bone models, where the longitudinal contours are taken along a dominant dimension of the plurality of three dimensional bone models; (c) clustering the plurality of three dimensional bone models based upon the assessed features to generate a plurality of clusters, where the plurality of clusters is numerically less than ten percent of the plurality of three dimensional bone models; and, (d) generating a trauma plate for each of the plurality of clusters.

In a more detailed embodiment of the seventh aspect, generating a trauma plate for each of the plurality of clusters includes selection of fixation locations to avoid soft tissue attachments to the particular bone. In yet another more detailed embodiment, the plurality of three dimensional bone models include at least one commonality, wherein the commonality comprises at least one of sex, ethnicity, age range, and height range. In a further detailed embodiment, generating the trauma plate for each of the plurality of clusters includes incorporating at least one of a mean longitudinal contour and a mean cross-sectional contour for that particular cluster.

It is an eighth aspect of the present invention to provide a method of generating a patient-specific trauma plate for a particular bone, the method comprising: (a) obtaining patient-specific image data for a particular bone having been injured or degenerated; (b) using the patient-specific image data to analyze at least one of those portions of the particular bone absent and those portions of the particular bone present; (c) generating a patient-specific virtual bone model of the particular bone in a unified state that includes bone not visible in the patient-specific image data; (d) assessing the contours of the patient-specific virtual bone model; and, (e) generating a patient-specific trauma plate using the patient-specific virtual bone model.

It is a ninth aspect of the present invention to provide a method of kinematically tracking motion of a patient's anatomy using inertial measurement units, the method comprising: (a) mounting a first inertial measurement unit to an exterior of a patient's first anatomical feature of interest; (b) mounting a second inertial measurement unit to an exterior of a patient's second anatomical feature of interest; (c) registering a position of the patient's first anatomical feature with a virtual model of the patient's first anatomical feature of interest using the first inertial measurement unit; (d) registering a position of the patient's second anatomical feature with a virtual model of the patient's second anatomical feature of interest using the second inertial measurement unit; (e) dynamically correlating the position of the patient's first anatomical feature of interest with a virtual model of the first anatomical feature using the first inertial measurement unit; and, (f) dynamically correlating the position of the patient's second anatomical feature of interest with a virtual model of the second anatomical feature using the second inertial measurement unit.

BRIEF DESCRIPTION OF THE DRAWINGS

FIG. 11 is a graphical example of existing Paprosky acetabular defect subclassifications.

FIG. 71 is a table reflecting anteversion angle measurements for males and females.

FIG. 75. Mass custom implant shape parameters for a femoral stem component extracted from clustering.

FIG. 78 is a graphical representation of surface points and utilization of a plane to isolate an acetabular cup geometry in accordance with the instant disclosure.

FIG. 79 graphically depicts a plurality of virtual, 3D acetabular cup anatomical templates created in accordance with the instant disclosure.

FIG. 89 are pictures and multiple X-ray views used for reconstruction of pelvis and proximal femur in accordance with the instant disclosure.

Figure 120:
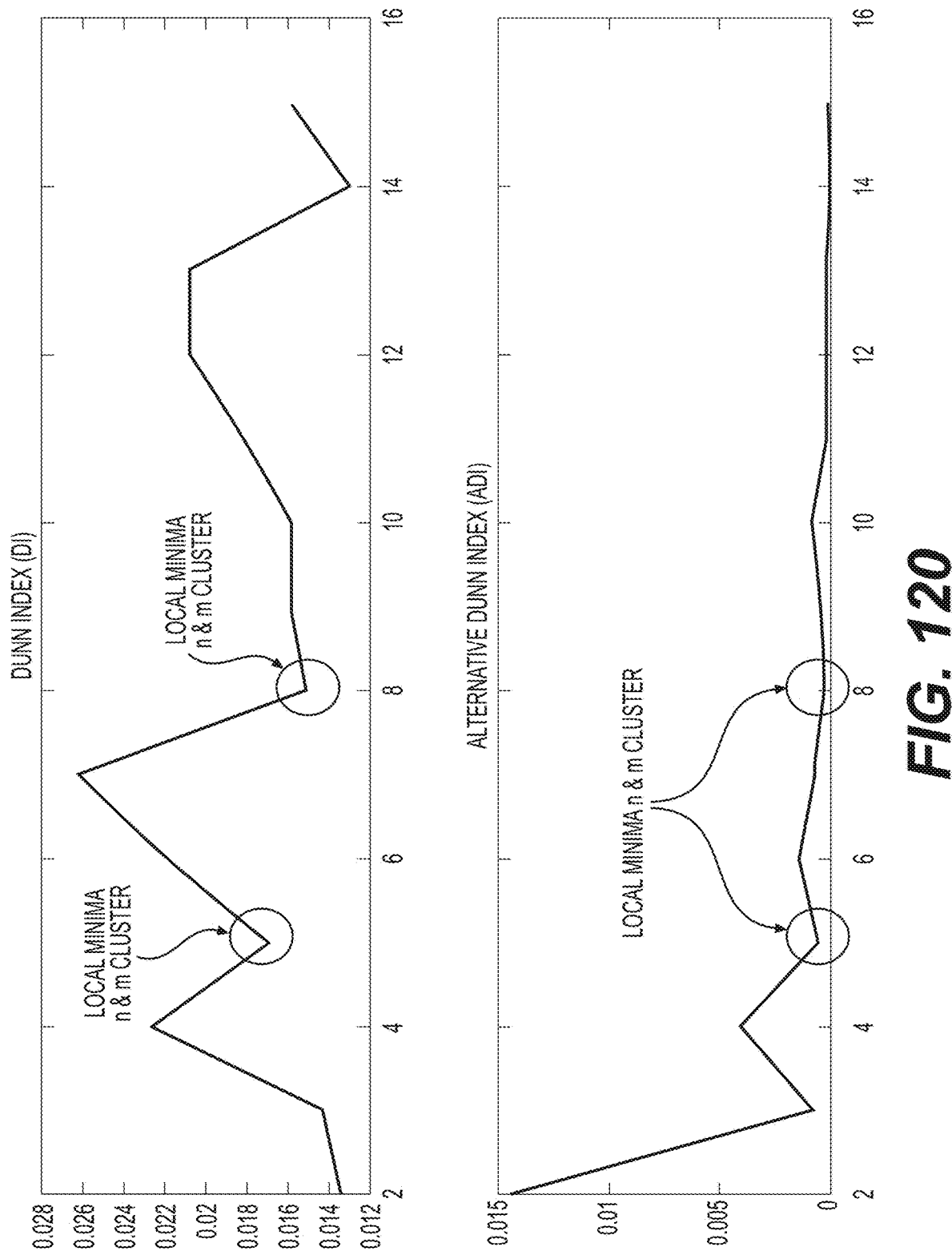

FIG. 120 showing plots of plate size data utilized to determine the optimal number of clusters.

Figure 111:
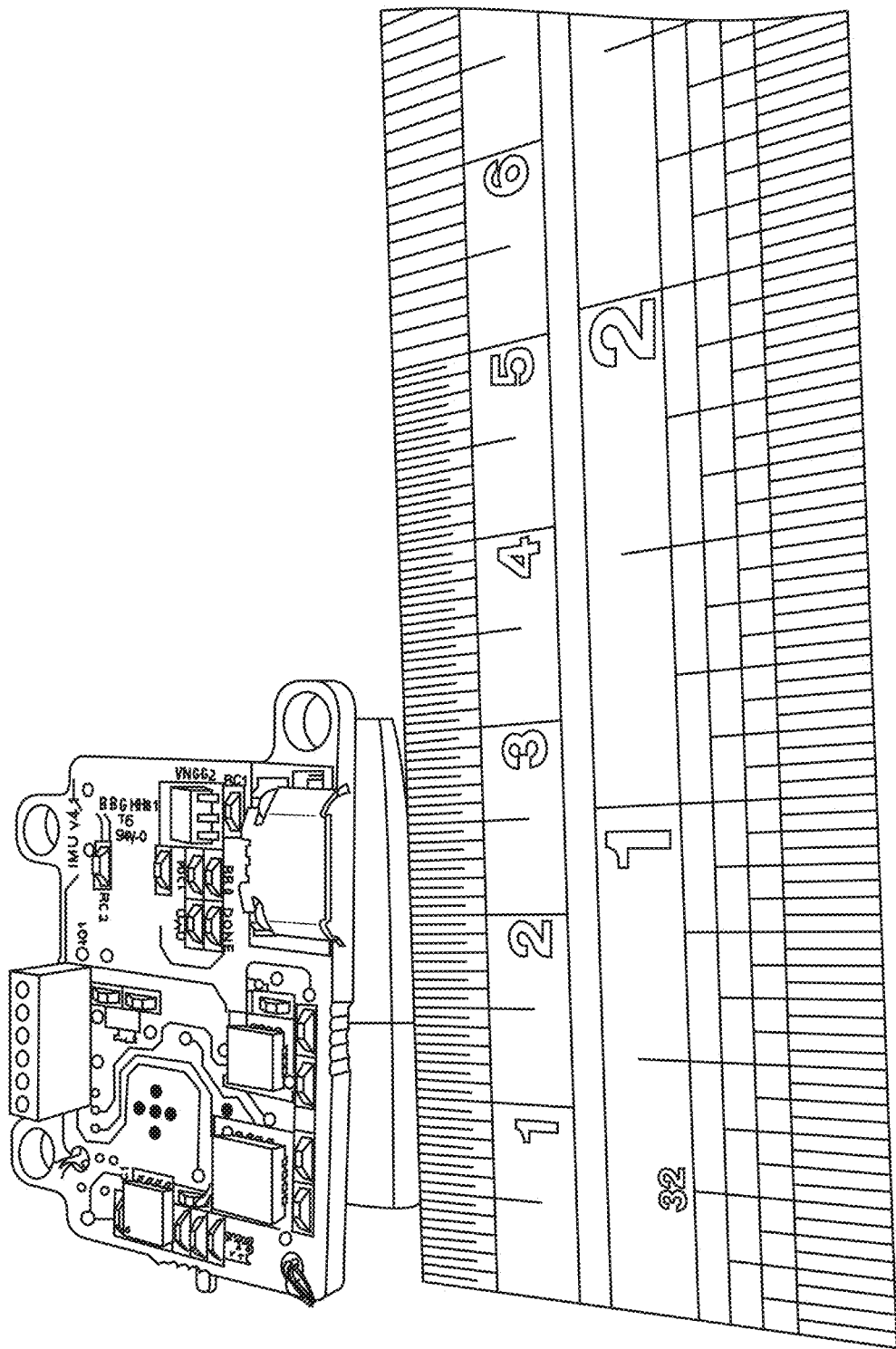
FIG. 111 is a picture of an IMU utilized in accordance with the instant disclosure along with a reference ruler for characterizing the relative dimensions of the IMU.
Figure 112:
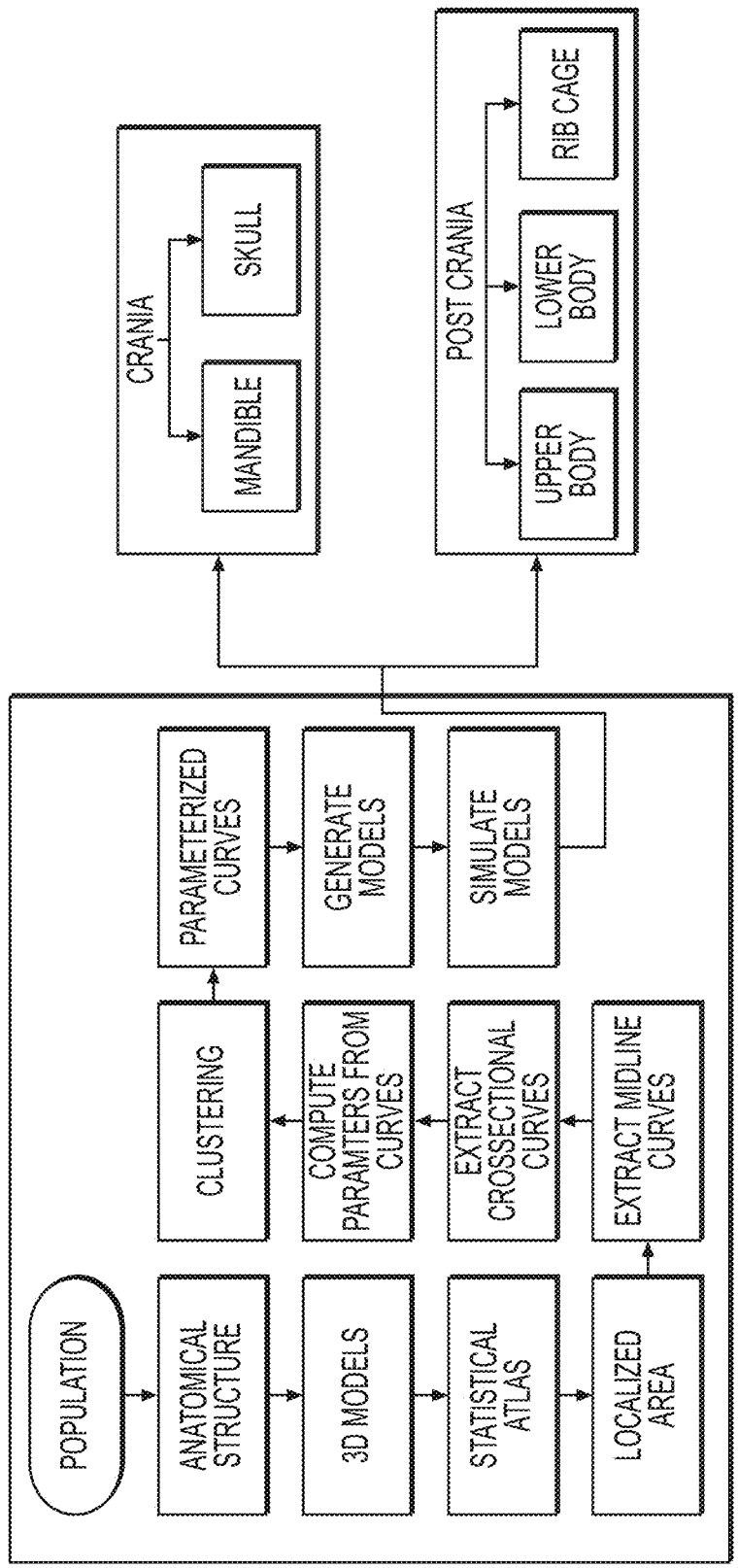
FIG. 112 is an exemplary process flow diagram for creating trauma plates and fixation devices for a given population in accordance with the instant disclosure.
Figure 113:
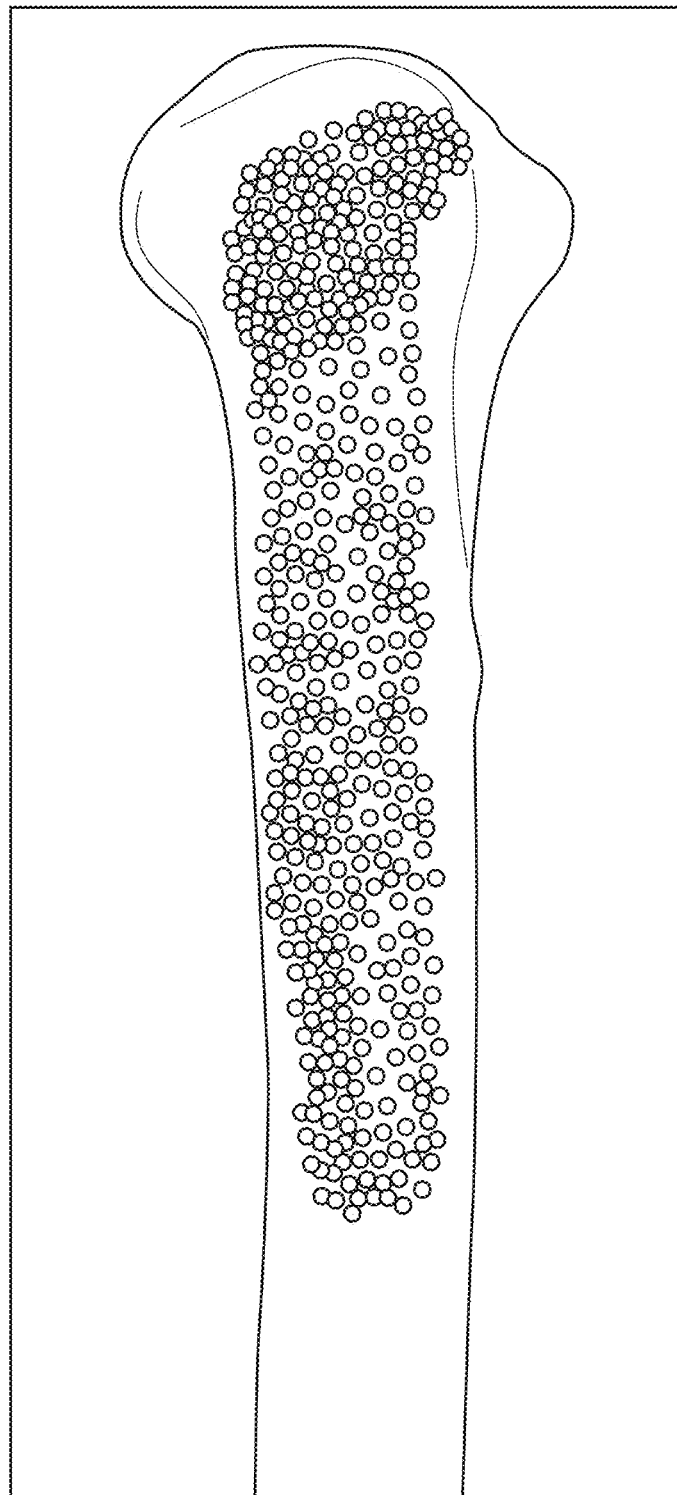
FIG. 113 is a graphical image from a mean bone showing localized points on the bone surface that are localized across a population of bones in a statistical atlas in order to define the shape of a bone or trauma plate.
Figure 114:
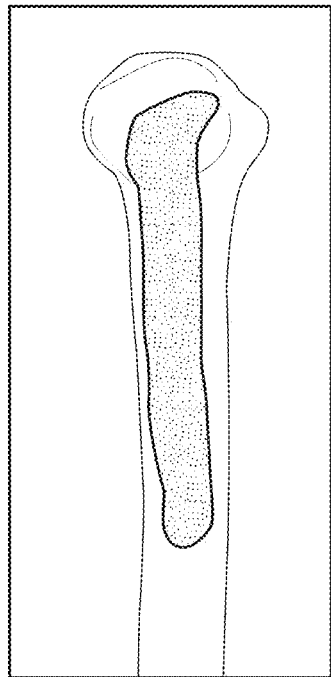
FIG. 114 is a graphical image of a bone showing propagation of plate loci on an entire population, here shown on a single instance.
Figure 115:
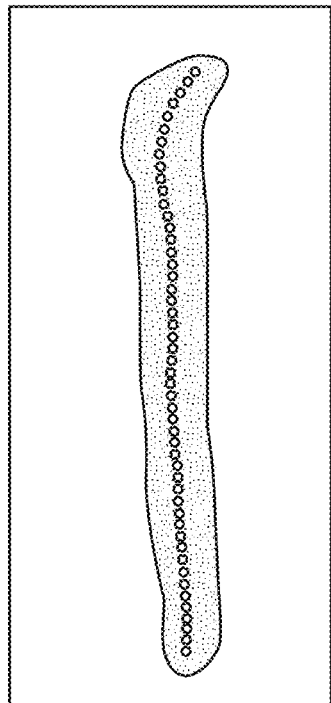
FIG. 115 is a graphical image showing extraction of bone/trauma plate midline curve post propagation of plate loci.
Figure 116:
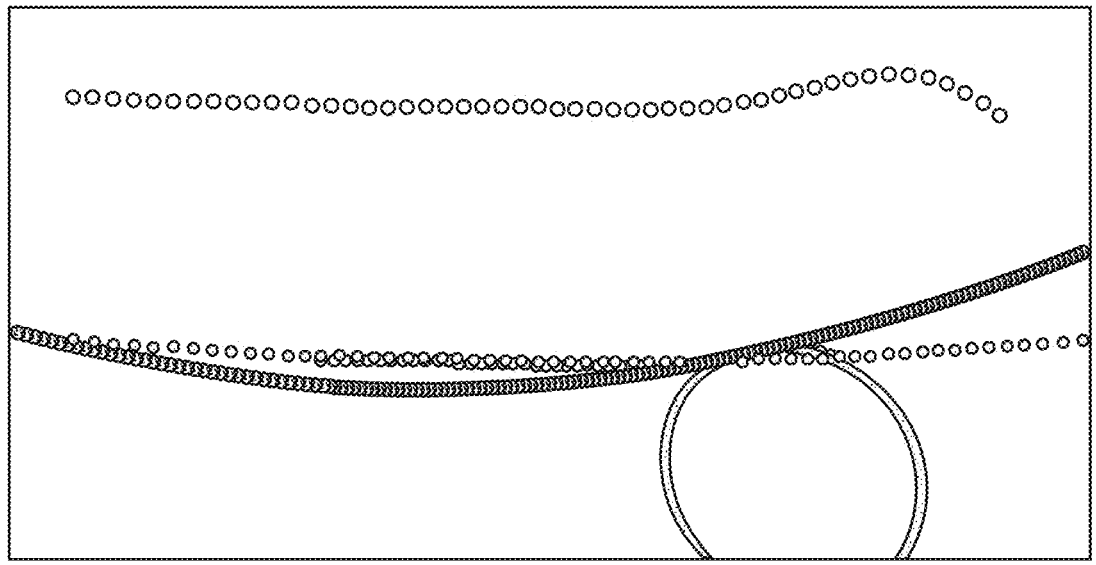
FIG. 116 is a graphical depiction of the results of computing 3D radii of curvature (parameters) for a trauma plate midline curve.
Figure 117:
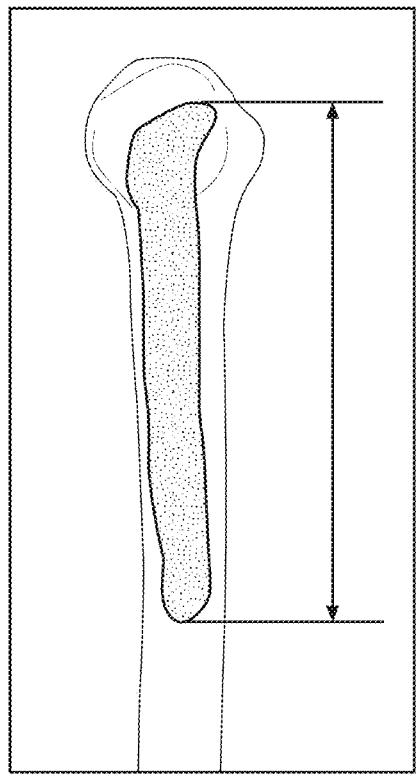
FIG. 117 is a graphical depiction showing how the length of the trauma plate is calculated post propagation of plate loci.
Figure 118:
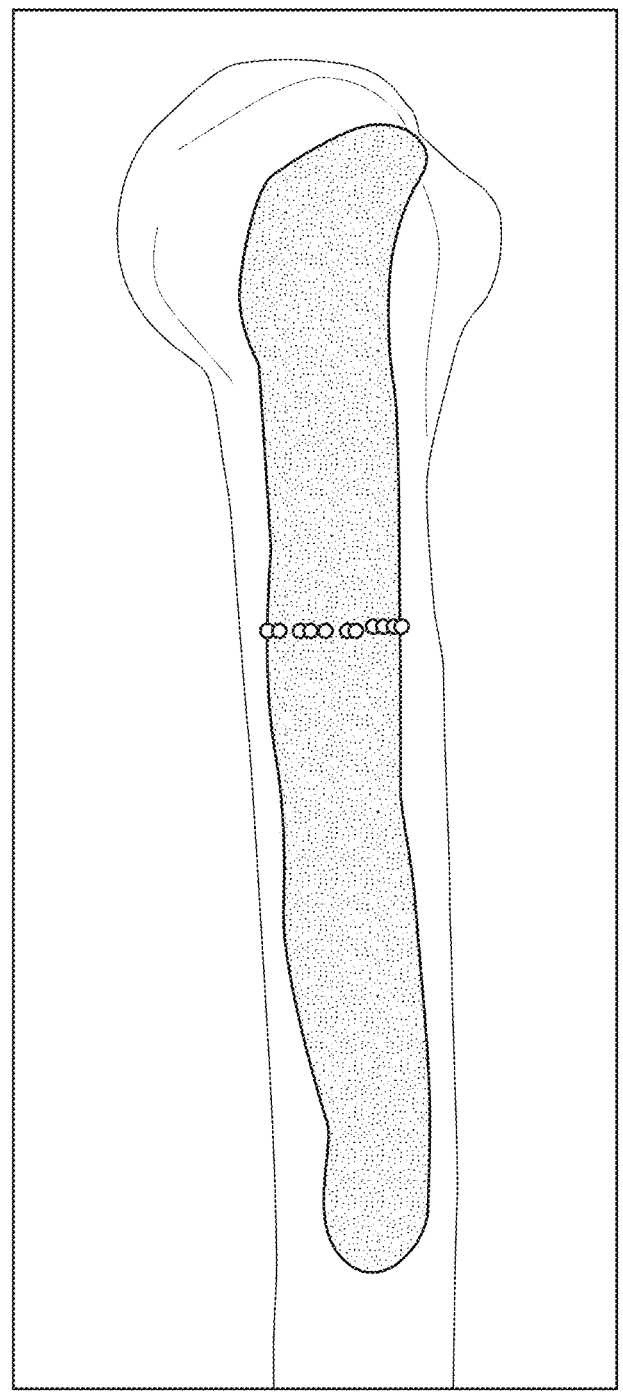
FIG. 118 is a graphical depiction showing how the mid-plate width of the trauma plate is calculated post propagation of plate loci.
Figure 119:
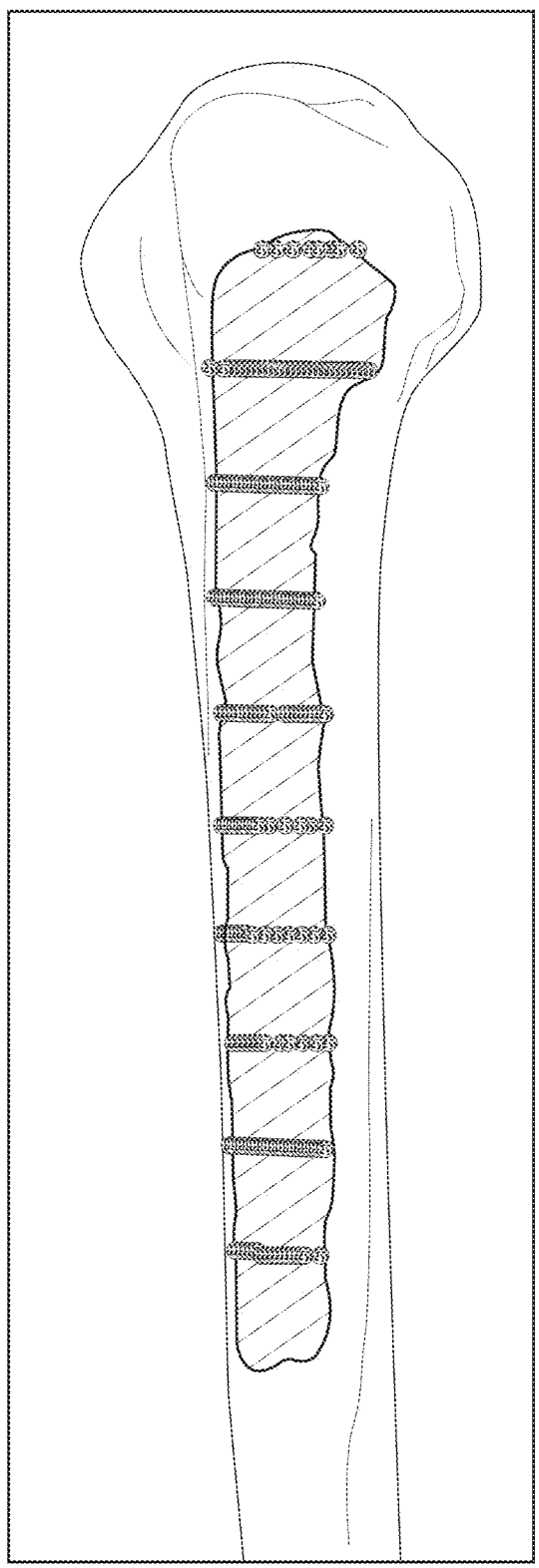
FIG. 119 is a graphical depiction showing how the plate cross sectional radii of the trauma plate is calculated post propagation of plate loci . . . .
Figure 121:
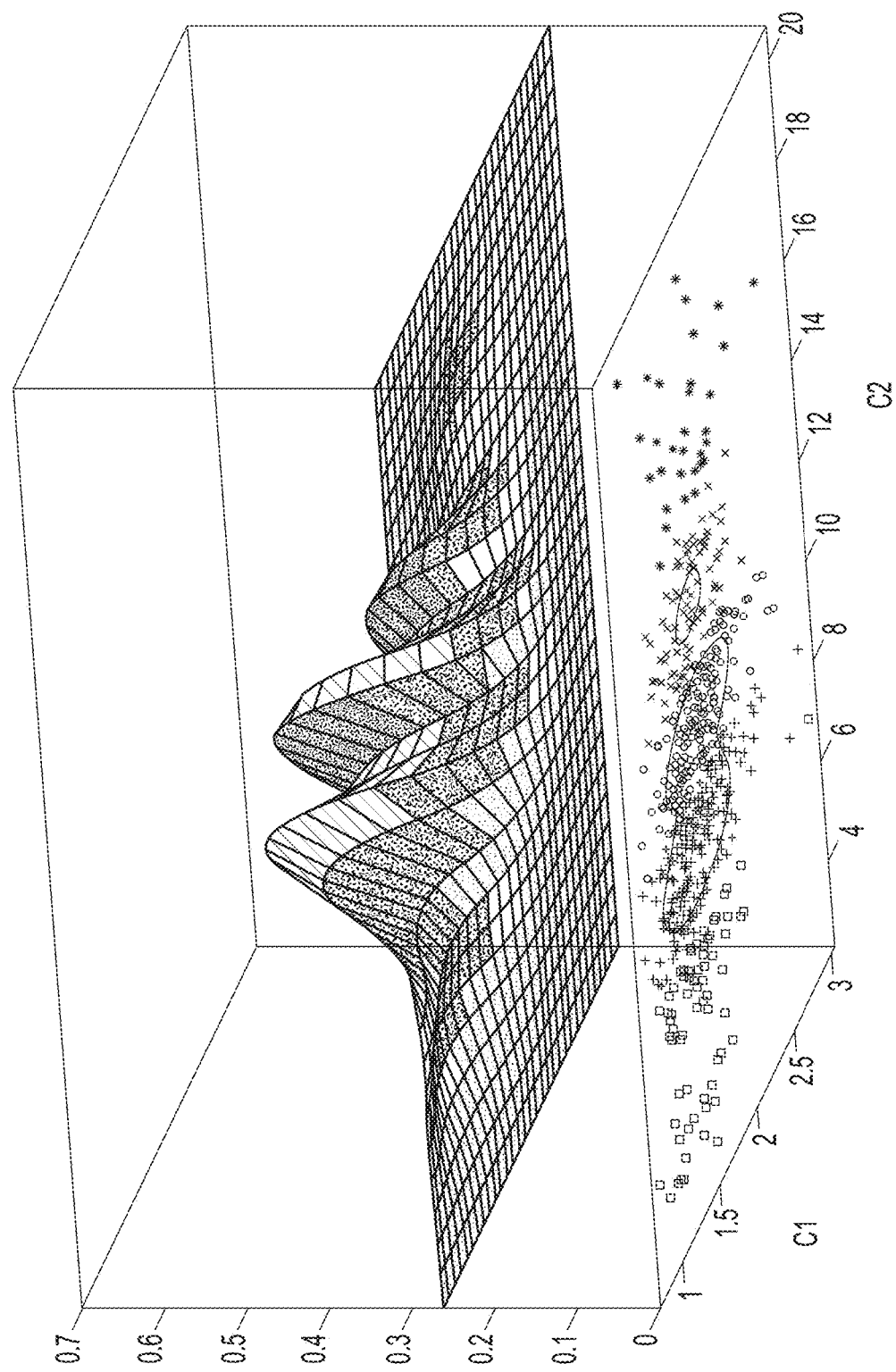

FIG. 121 includes 2D and 3D plots of plate size data utilized to generate clusters (identified in FIG. 111 as "Clustering").

Figure 122:
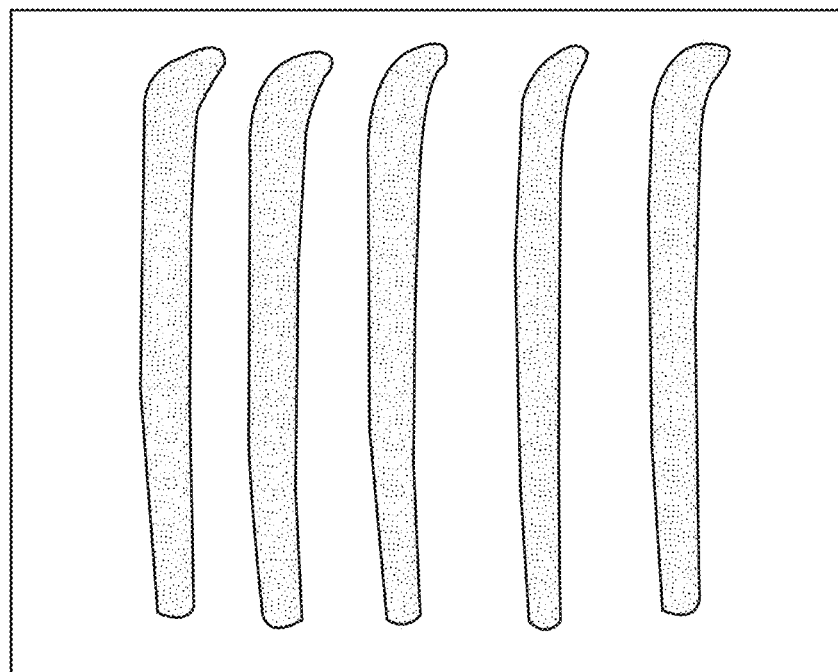

FIG. 122 depicts numerous images reflecting parameterization of plate sizes (identified in FIG. 111 as "Parameterized Curves" and "Generate Models").

Figure 123:
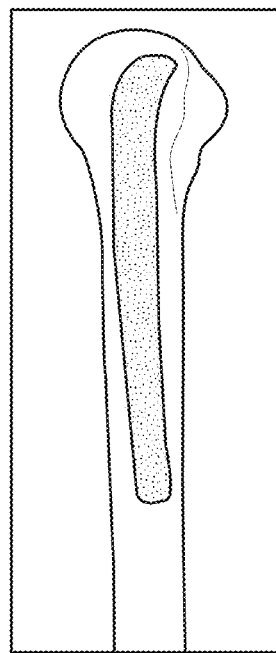

FIG. 123 is an exemplary image showing a bone/trauma plate for a particular cluster being fit to one of the bone models from the cluster to evaluate conformity/fitting to the population.

FIG. 124 is a 3D surface distance map reflecting the spacing between the underside of the bone/trauma plate surface and the surface of the bone model selected for evaluating plate fit.

FIG. 125 depicts validation of designed plate on cadaver to avoid muscle and ligament impingement.

Figure 126:
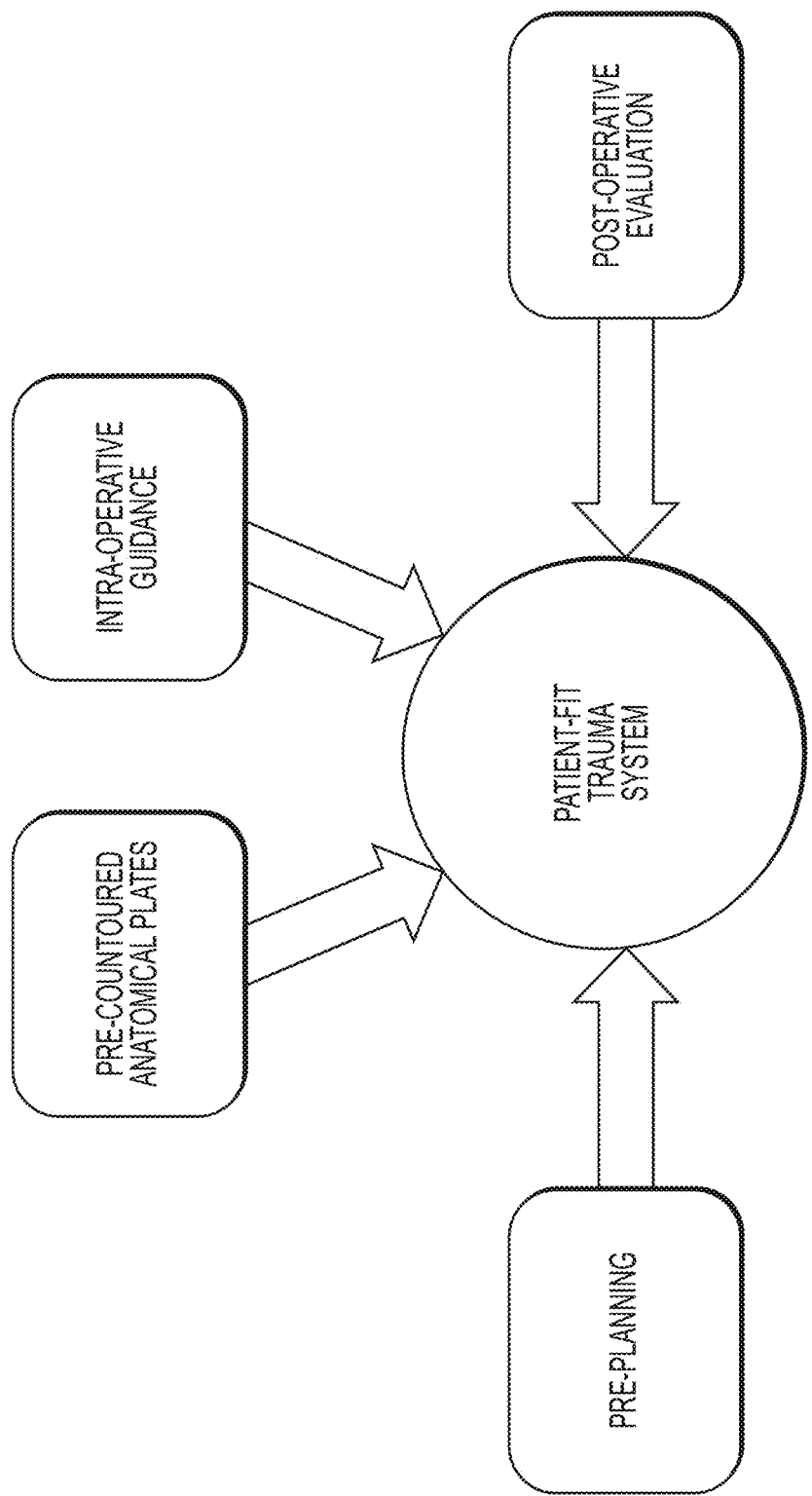

FIG. 126 is an exemplary diagram reflecting the interaction between elements of an exemplary patient-fit clavicle trauma system in accordance with the instant disclosure.

Figure 127:
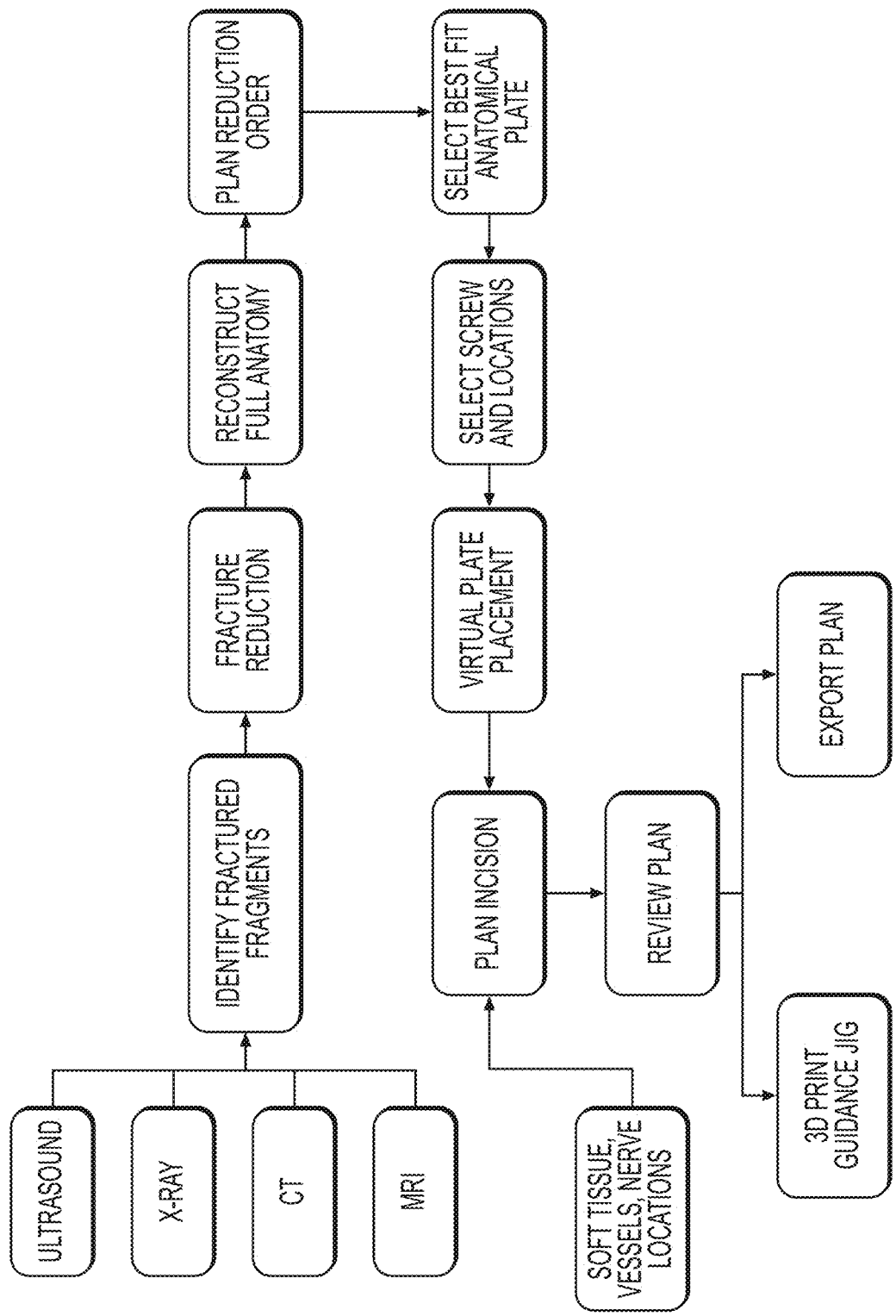

FIG. 127 is an exemplary process flow diagram for the pre-planning element depicted in FIG. 126.

Figure 128:
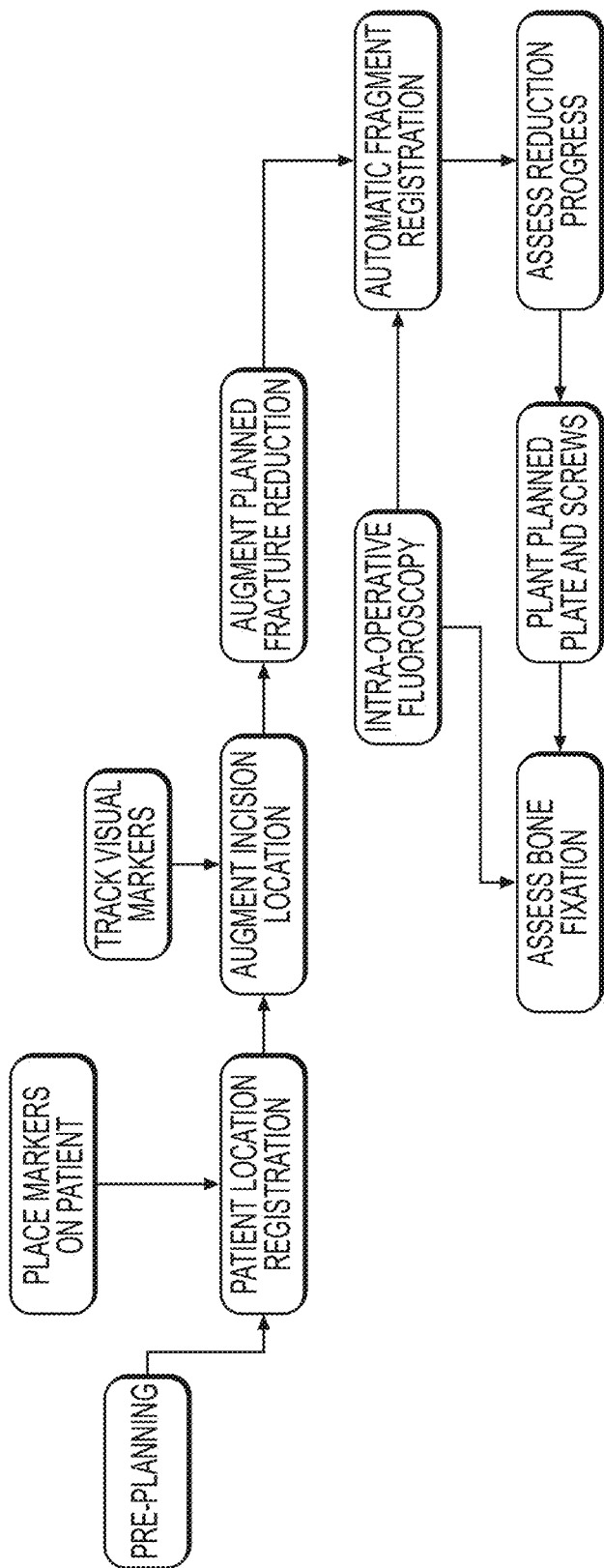

FIG. 128 is an exemplary process flow diagram for the intra-operative guidance depicted in FIG. 126, in this case using fluoroscopy.

FIG. 129 is a fluoroscopic image of a clavicle adjacent to an illustration of a clavicle from a top view with partial surrounding anatomy.

Figure 130:
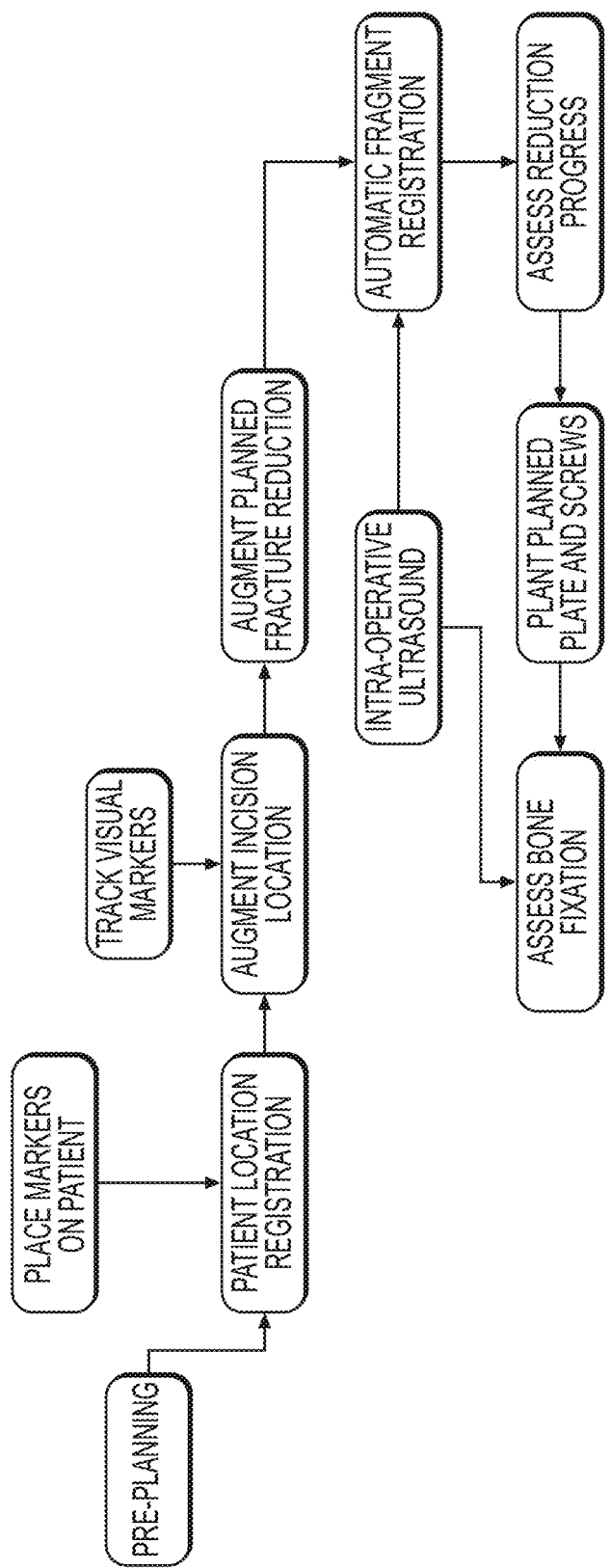

FIG. 130 is an exemplary process flow diagram for the intra-operative guidance depicted in FIG. 126, in this case using ultrasound.

FIG. 131 is a graphical representation matched to X-rays or fluoroscopic images taken during a range of motion, as well as a plot showing a post-operative evaluation of shoulder kinematics using one or more inertial measurement units.

FIG. 132 is a pair of three dimensional illustrations of a clavicle with surrounding anatomy.

Figure 133:
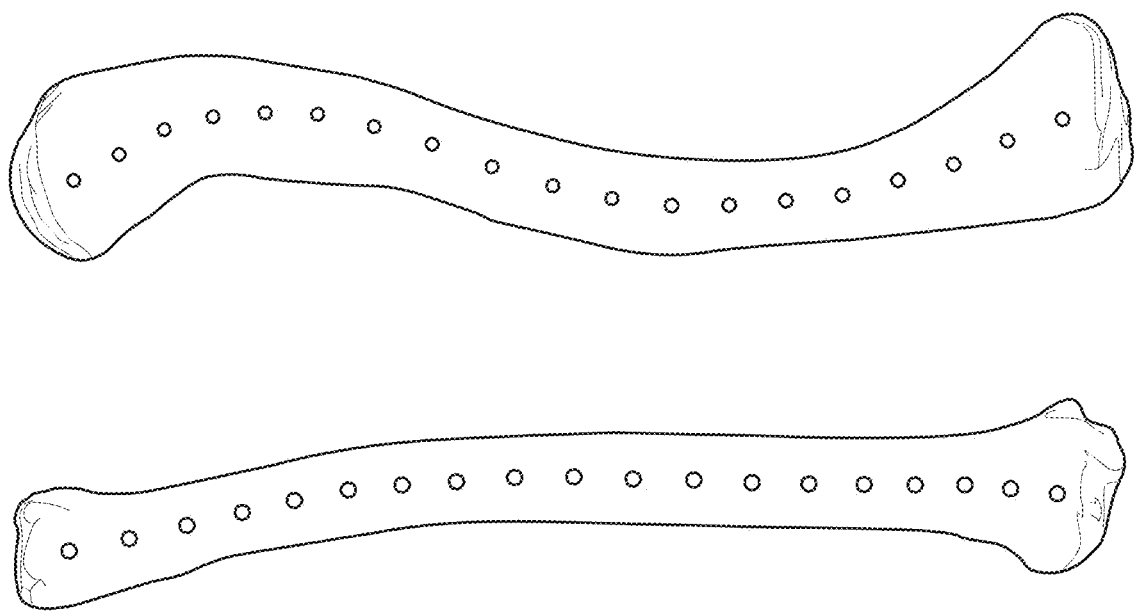

FIG. 133 depicts two different views of a clavicle bone model and points along the bone model utilized to identify the clavicle midline curvature.

Figure 134:
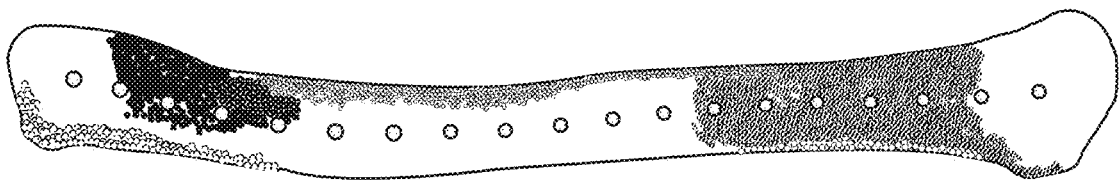

FIG. 134 is depicts a clavicle bone model and locations on the bone model where muscle is attached.

Figure 135:
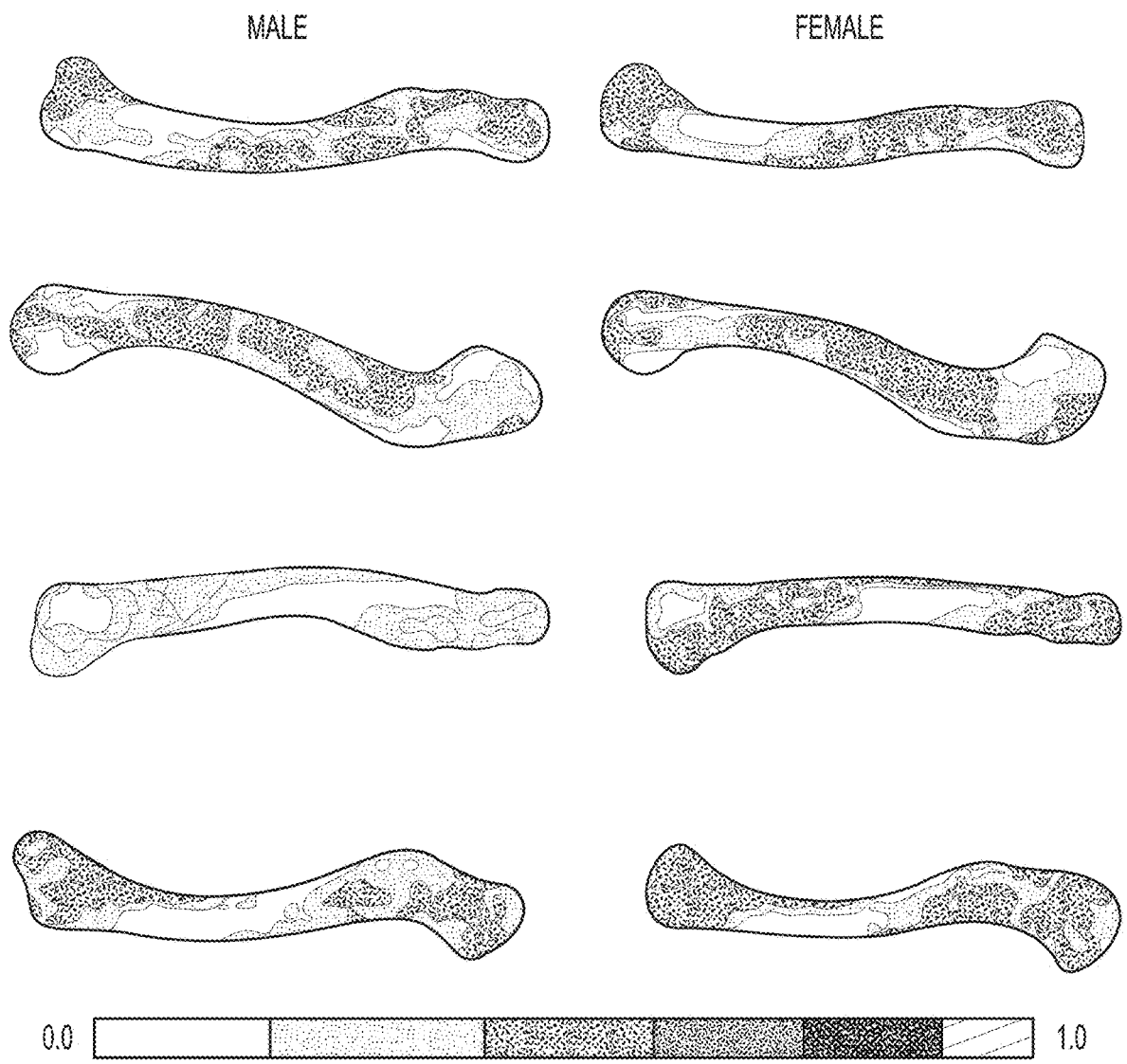

FIG. 135 depicts a series of surfaces maps of male and female mean clavicle models across a given population and the degree of shape differences across each population.

Figure 136:
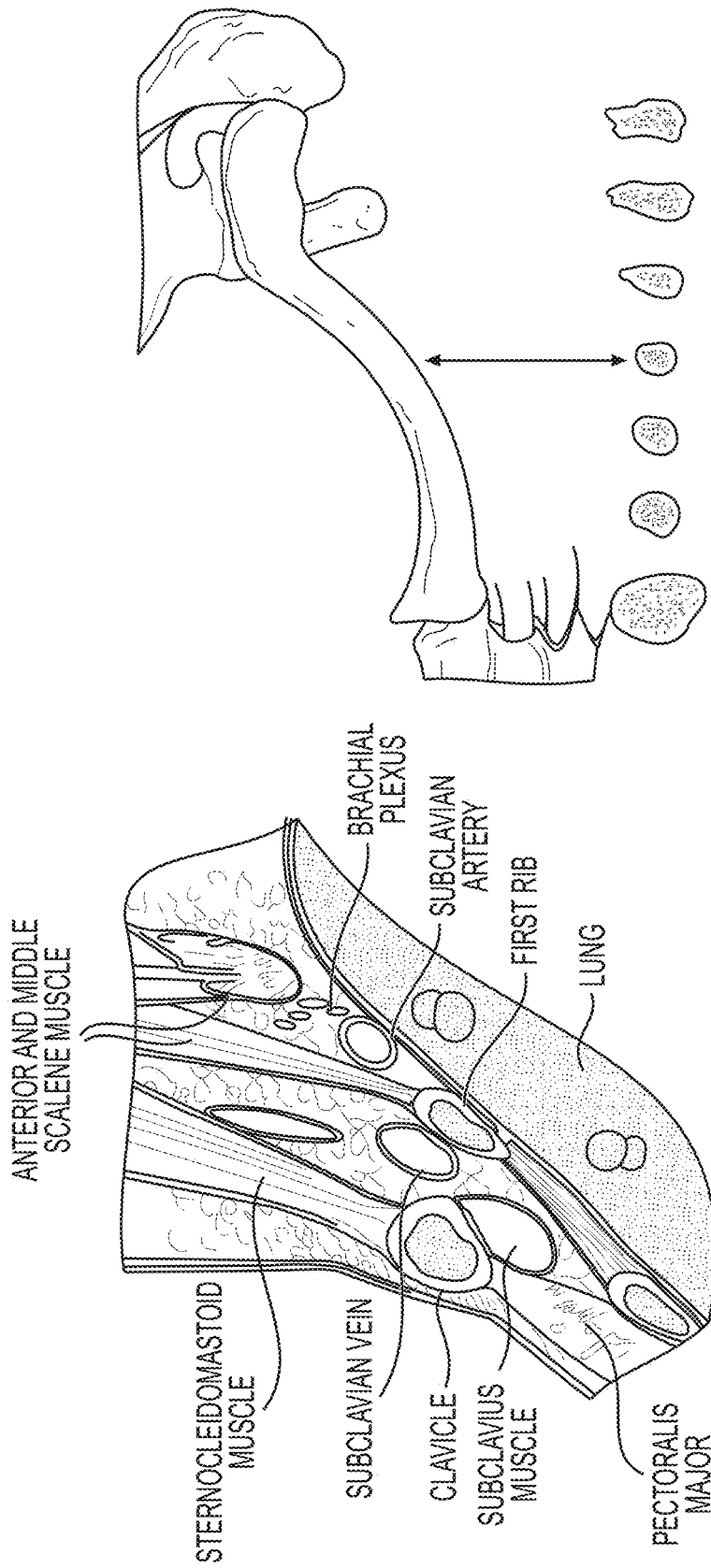

FIG. 136 is a pair of three dimensional illustrations of a clavicle correlating contour differences with the muscle attachment sites.

Figure 137:
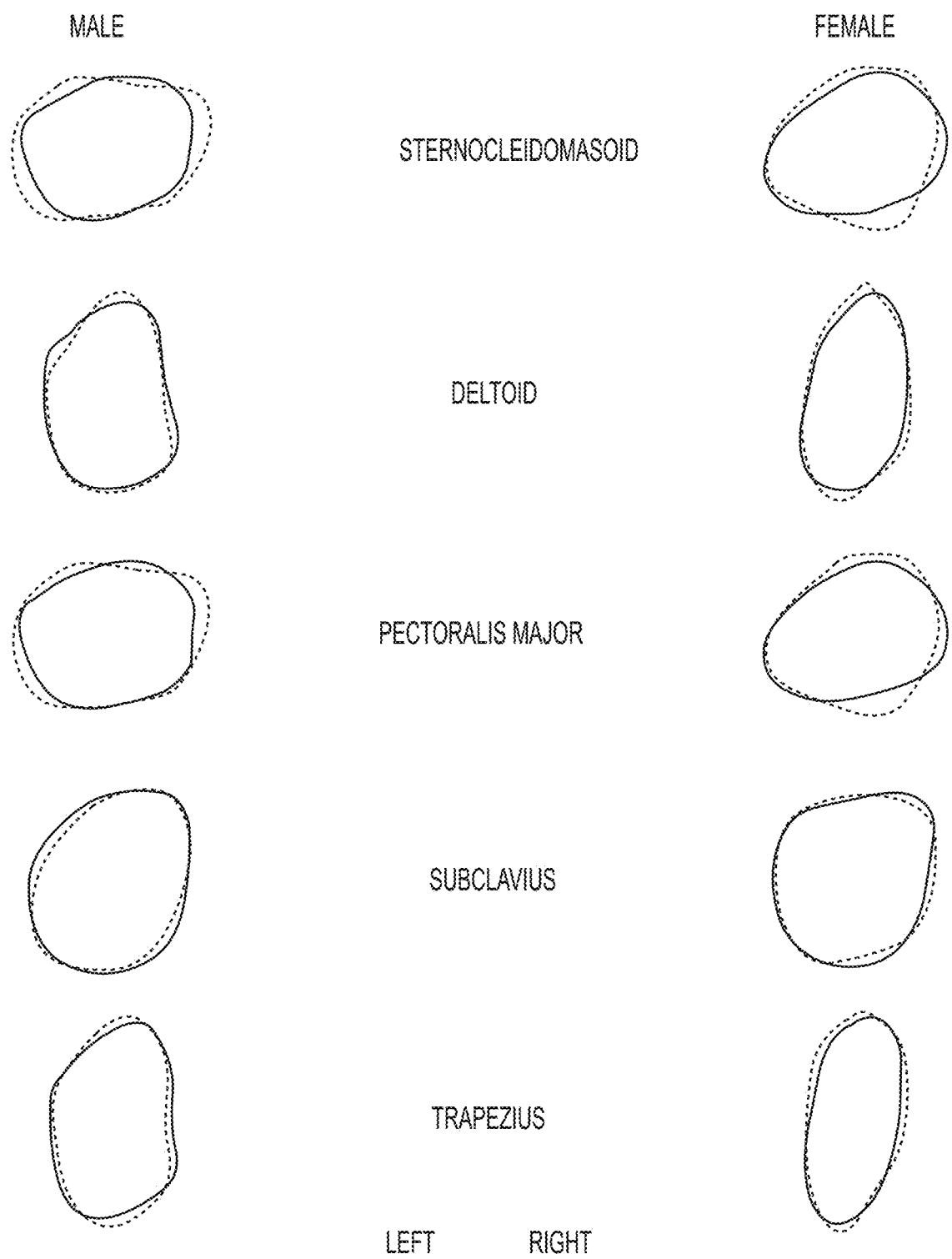

FIG. 137 is a series of cross-sections of a clavicles taken across male and female populations that shows the contour differences in the clavicle at the various muscle attachment sites.

Figure 138:
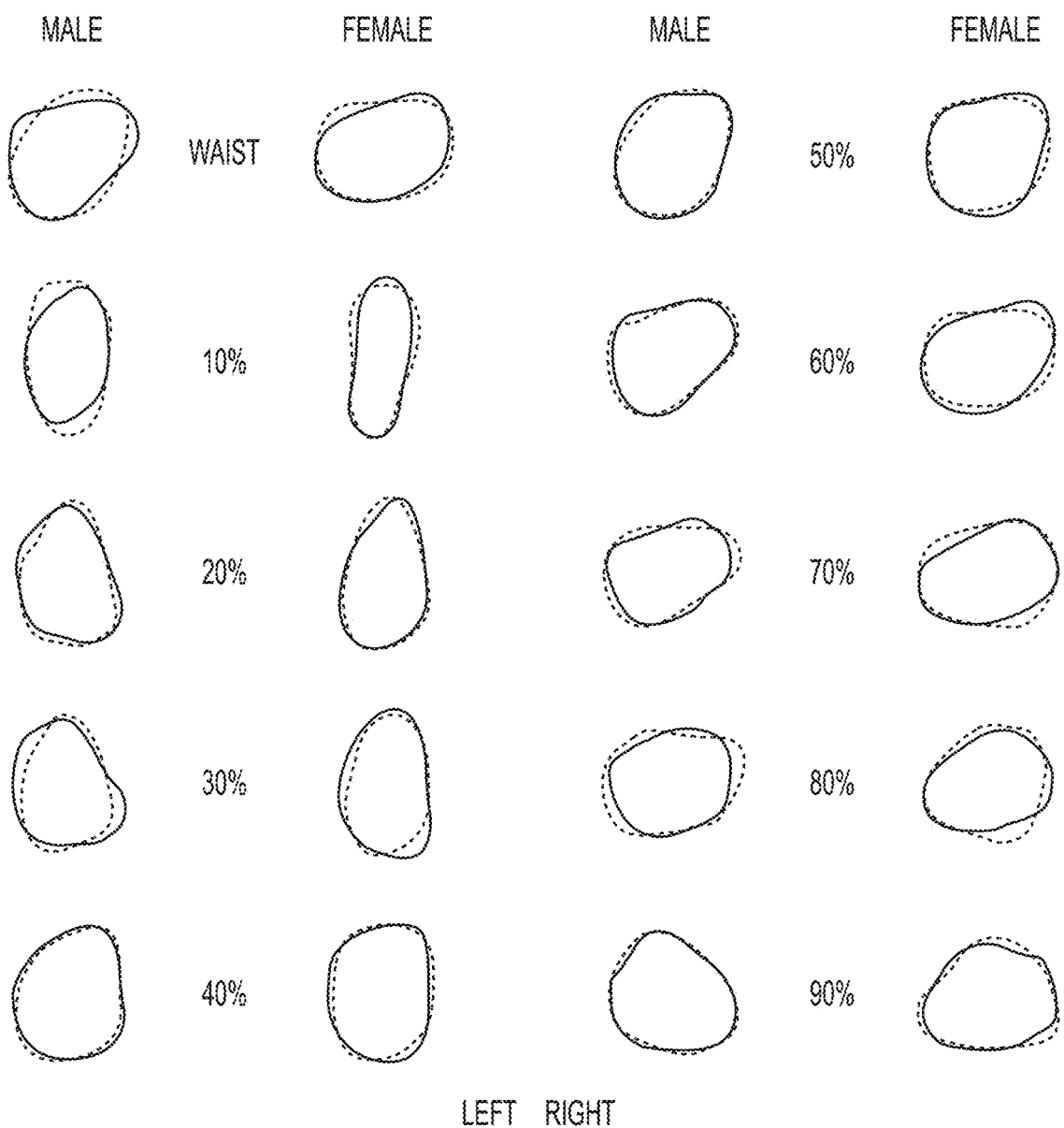

FIG. 138 is a series of cross-sections of a clavicles taken across male and female populations that shows the contour differences in the clavicle along the length of the clavicle.

Figure 139:
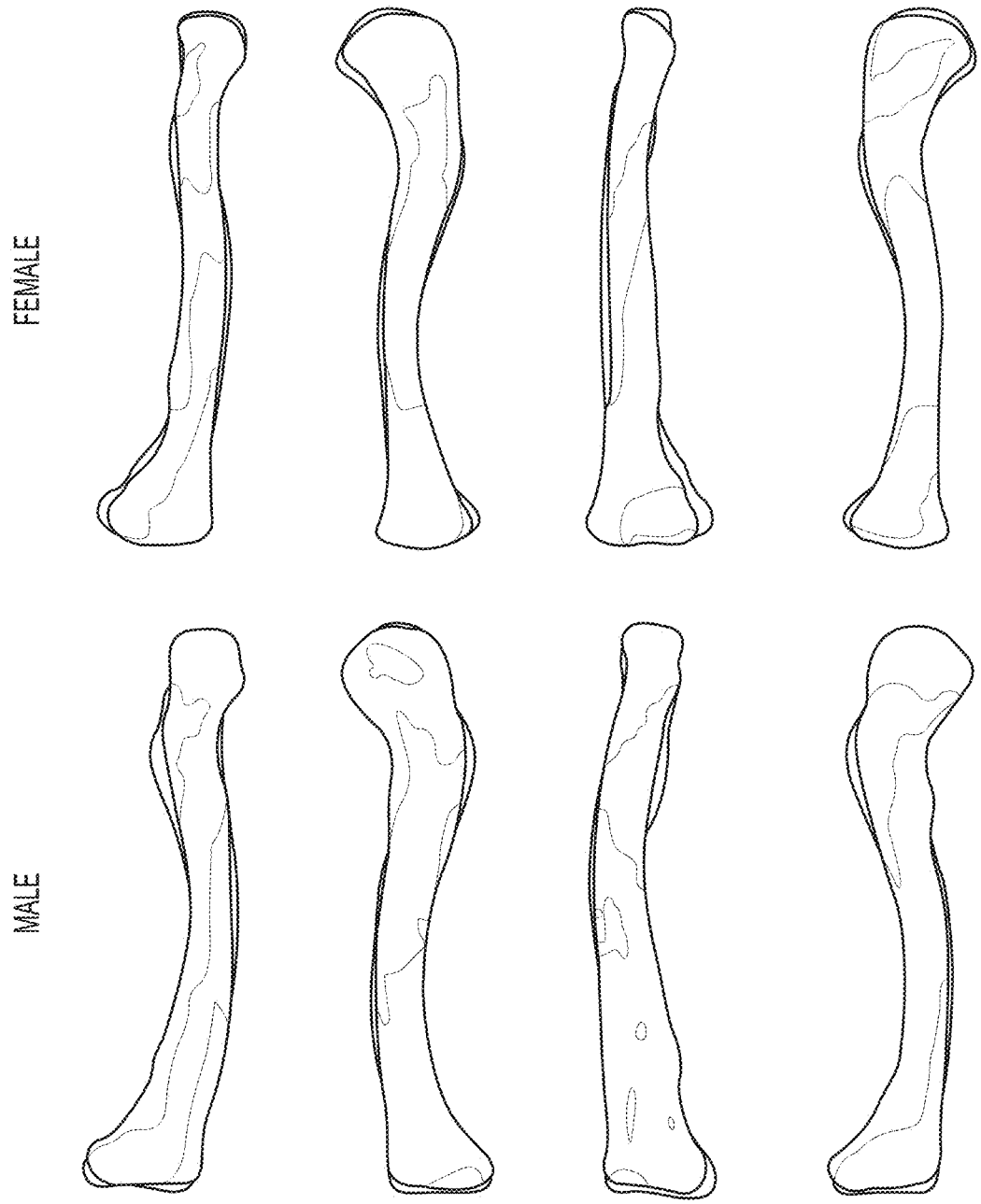

FIG. 139 depicts left and right clavicle models generated responsive to population data in a statistical atlas reflecting morphological differences between left and right clavicles.

FIG. 140 depicts a clavicle bone model to which is fit a superior lateral plate (left), plate midline curve (center), and midline plate curvature showing radius of curvature (right) in accordance with the instant disclosure.

Figure 141:
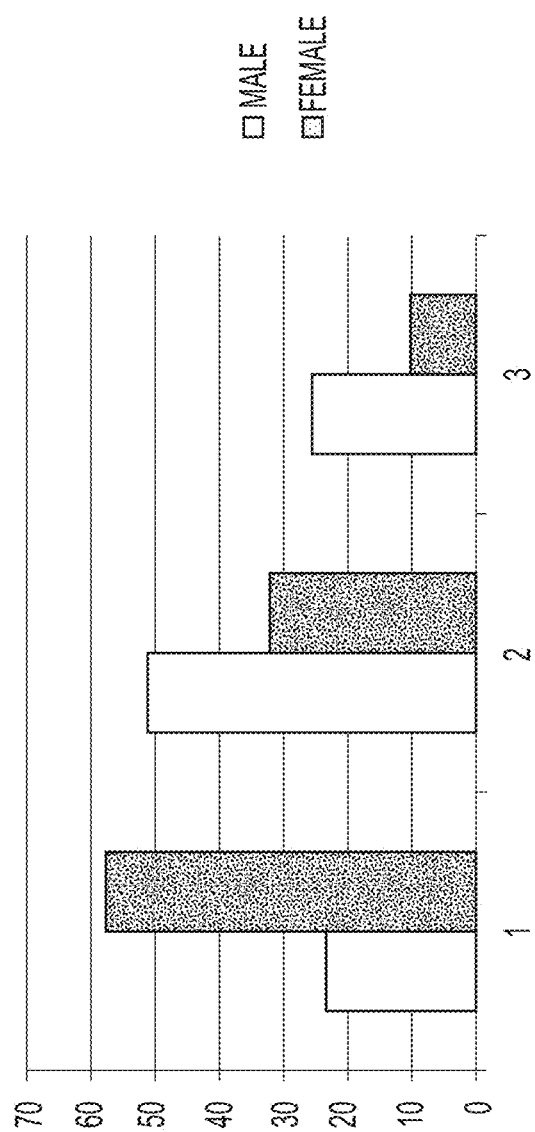

FIG. 141 is a chart depicting superior lateral plate clusters for clavicle male and female populations and Table 1 includes data relating to the same.

FIG. 142 depicts a clavicle bone model to which is fit an anterior mid-shaft $7h$ plate (left), plate midline curve (center), and midline plate curvature showing single radius of curvature (right) in accordance with the instant disclosure.

Figure 143:
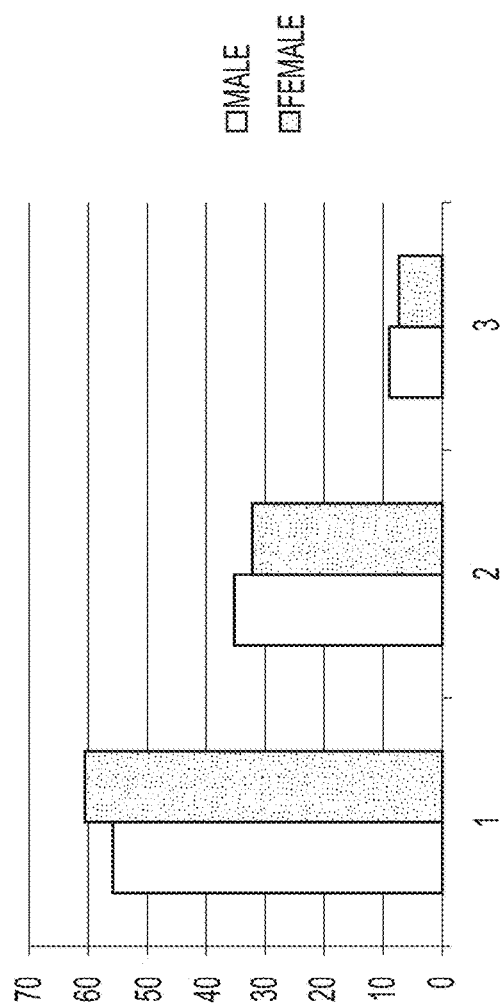

FIG. 143 is a chart depicting anterior mid-shaft $7h$ plate clusters for clavicle male and female populations and Table 2 includes data relating to the same.

FIG. 144 depicts a clavicle bone model to which is fit a superior mid-shaft plate (left), plate midline curve (center), and midline plate curvature showing differing radii of curvature (right) in accordance with the instant disclosure.

Figure 145:
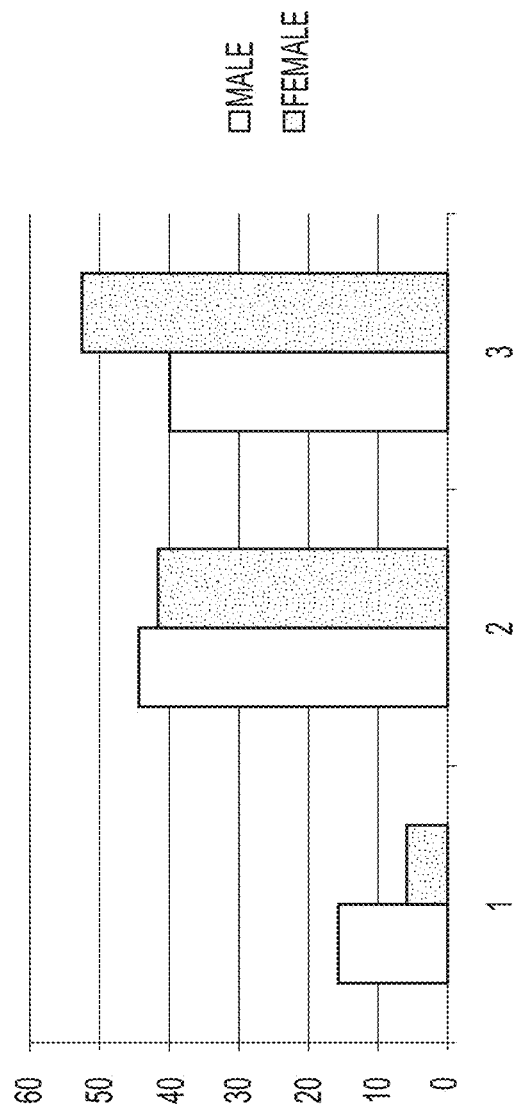

FIG. 145 is a chart depicting superior mid-shaft plate clusters for clavicle male and female populations and Table 3 includes data relating to the same.

FIG. 146 depicts a clavicle bone model to which is fit an anterior lateral plate (left), plate midline curve (center), and midline plate curvature showing differing radii of curvature (right) in accordance with the instant disclosure.

Figure 147:
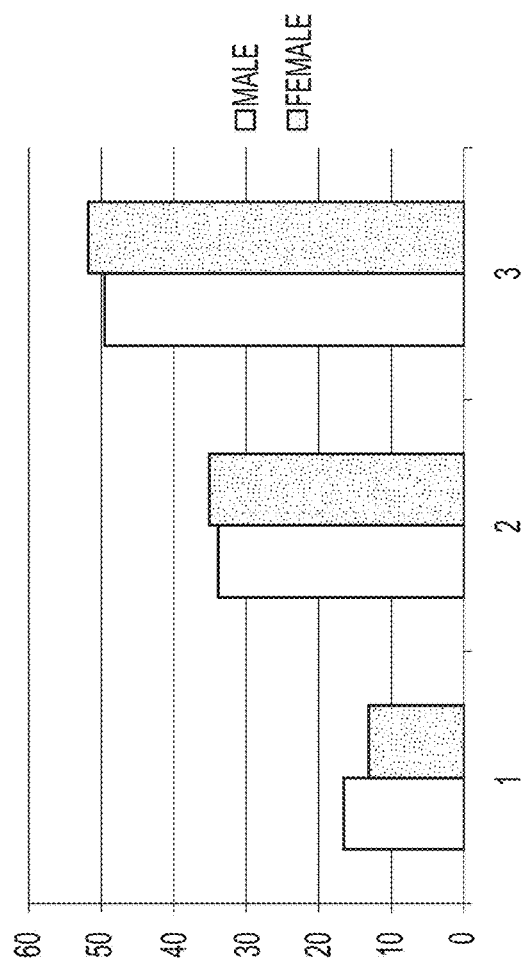

FIG. 147 is a chart depicting anterior lateral plate clusters for clavicle male and female populations and Table 4 includes data relating to the same.

FIG. 148 depicts a clavicle bone model to which is fit an anterior mid-shaft long plate (left), plate midline curve (center), and midline plate curvature showing differing radii of curvature (right) in accordance with the instant disclosure.

Figure 149:
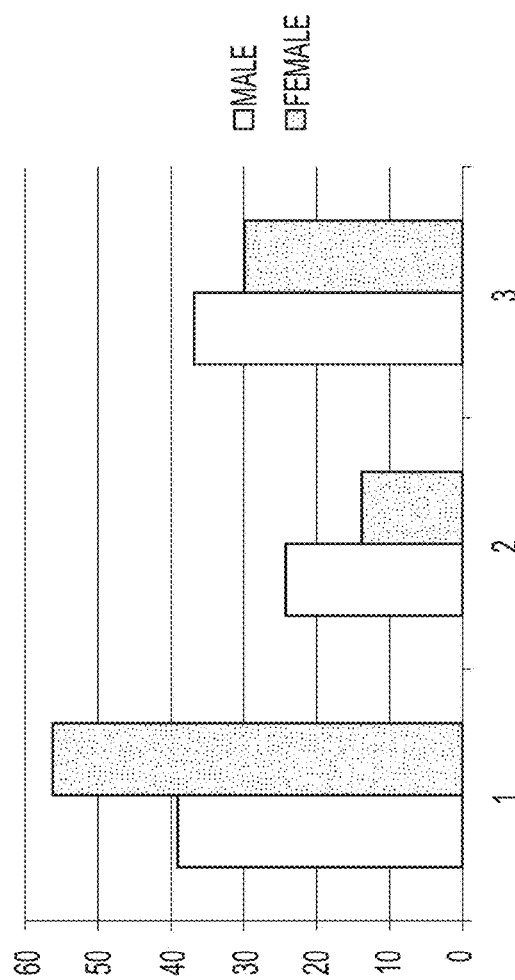

FIG. 149 is a chart depicting anterior mid-shaft plate clusters for clavicle male and female populations and Table 5 includes data relating to the same.

Figure 150:
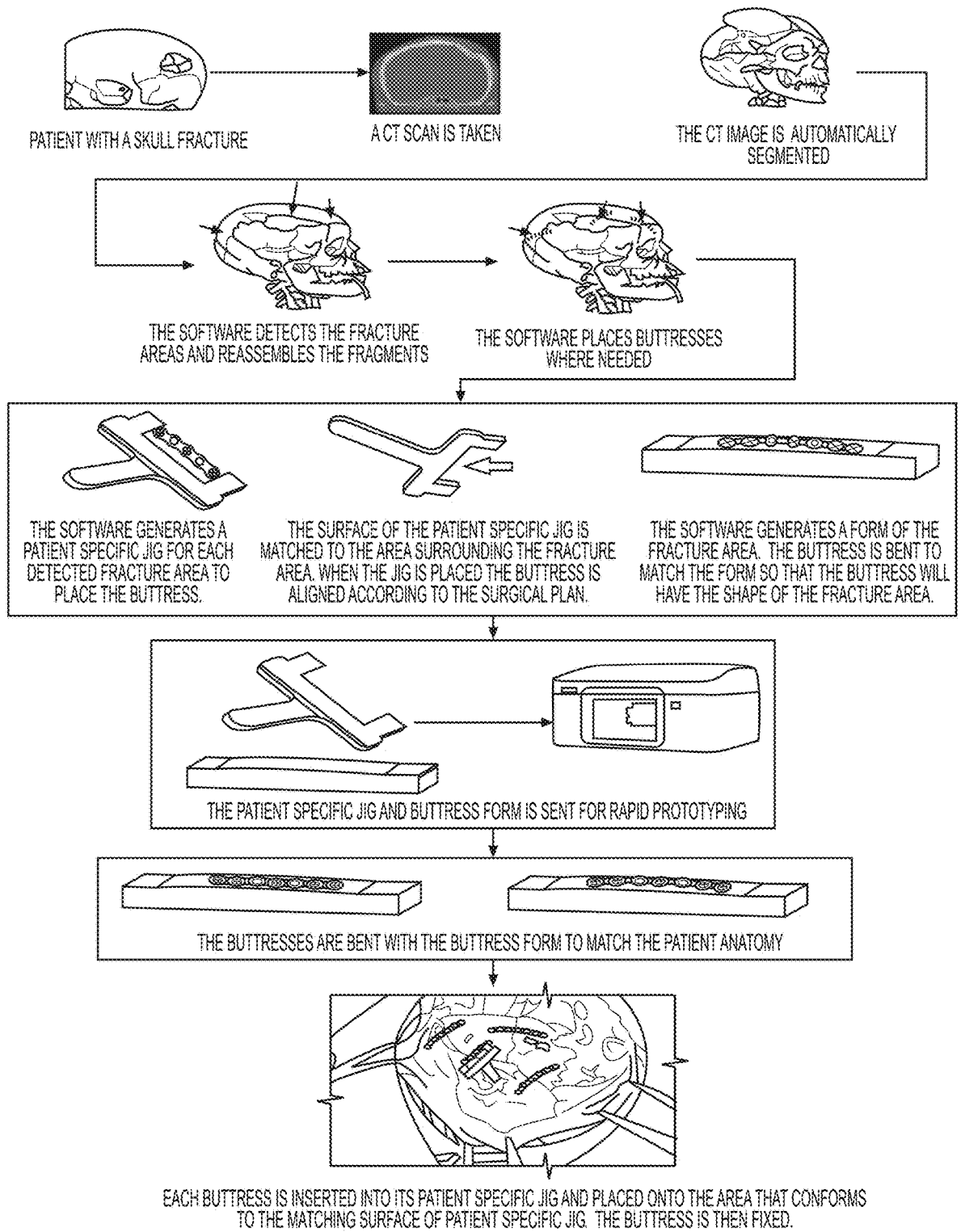

FIG. 150 is an exemplary process flow diagram for generating customized plate placement guides for trauma reconstructive surgeries in accordance with the instant disclosure.

Figure 151:
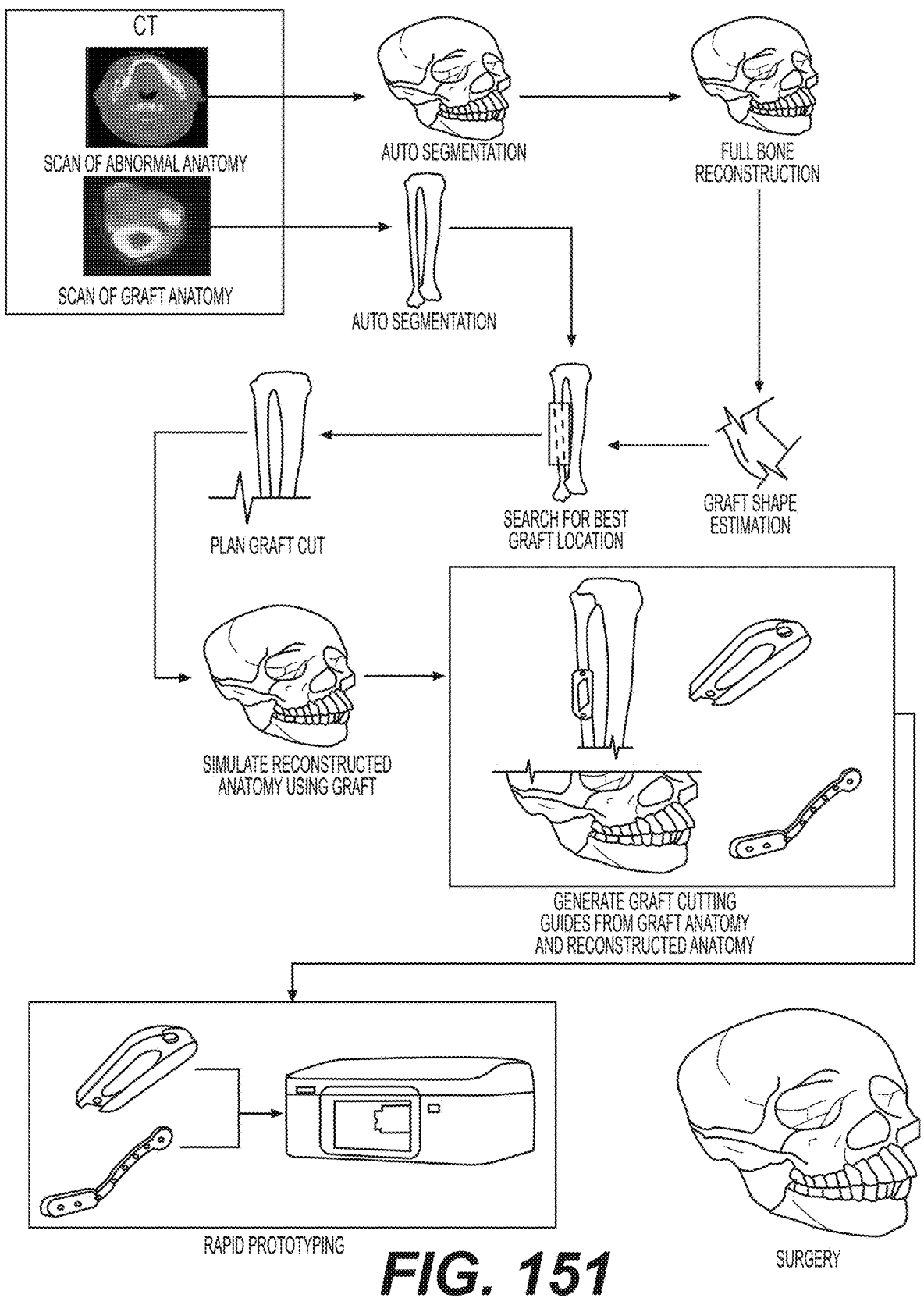

FIG. 151 is an exemplary process flow diagram for generating customized cutting and placement guide for reconstructive surgeries using bone grafts in accordance with the instant disclosure.

Figure 152:
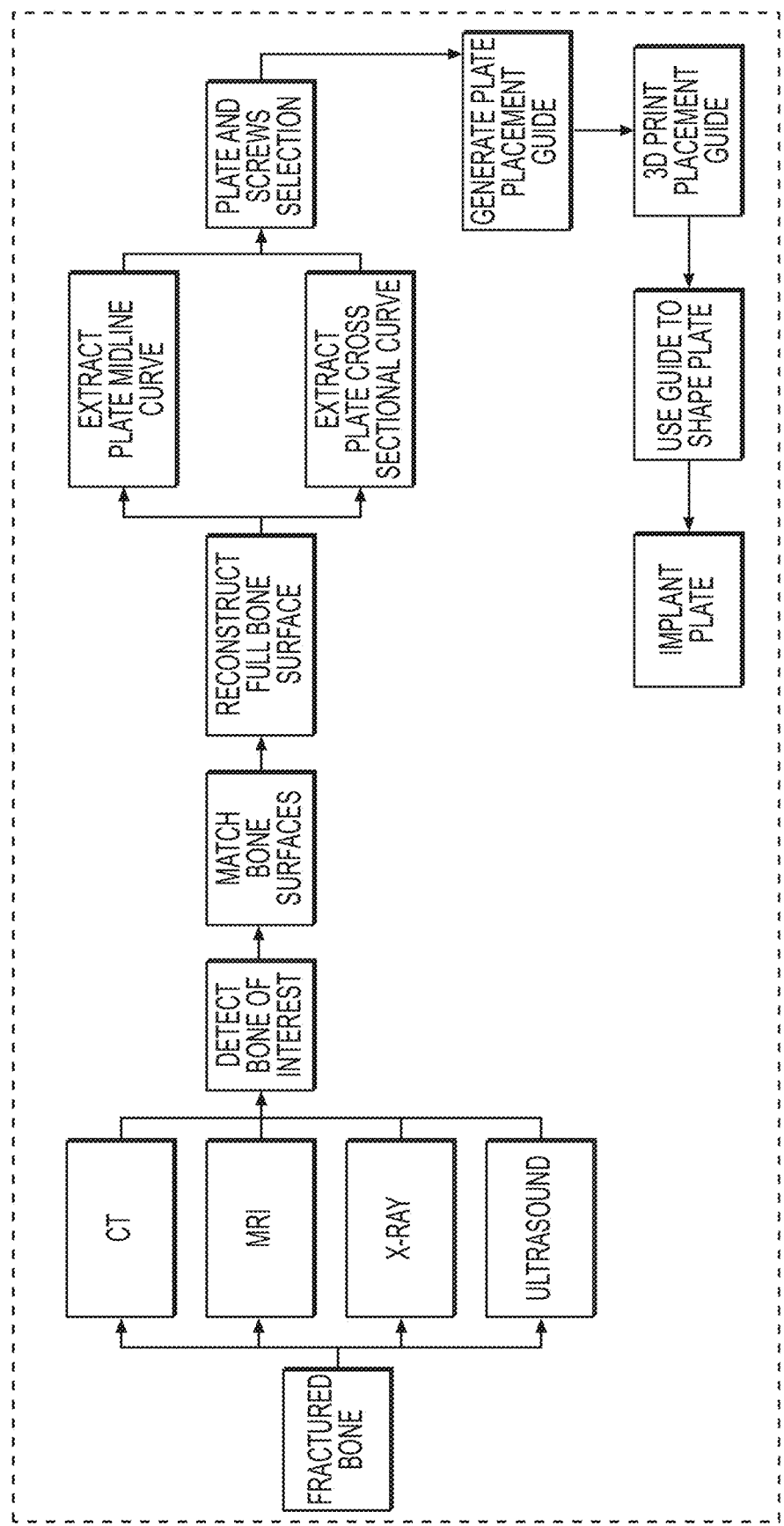

FIG. 152 is an exemplary process flow diagram for generating trauma plate templates and placement tools in accordance with the instant disclosure.

Figure 153:
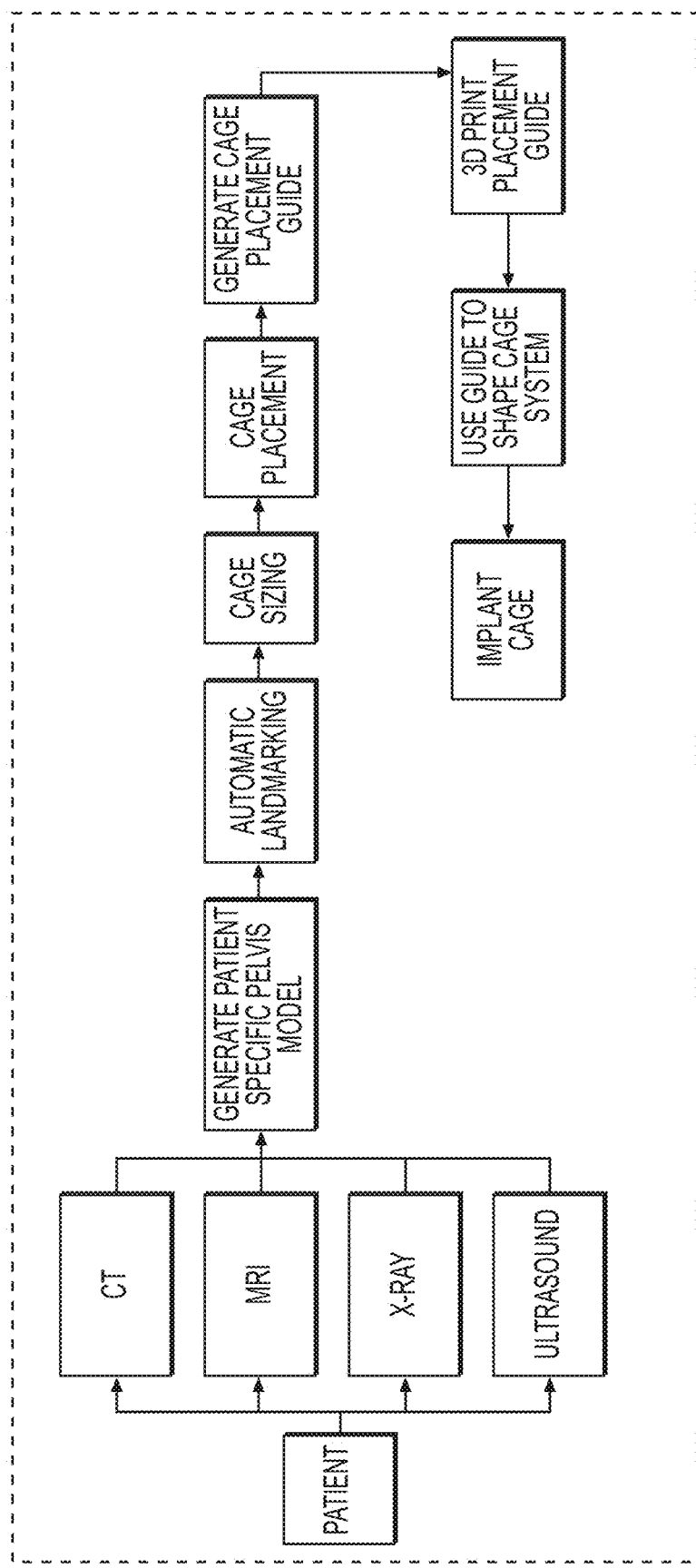

FIG. 153 is an exemplary process flow diagram for generating hip revision cage templates and placement tools in accordance with the instant disclosure.

Figure 154:
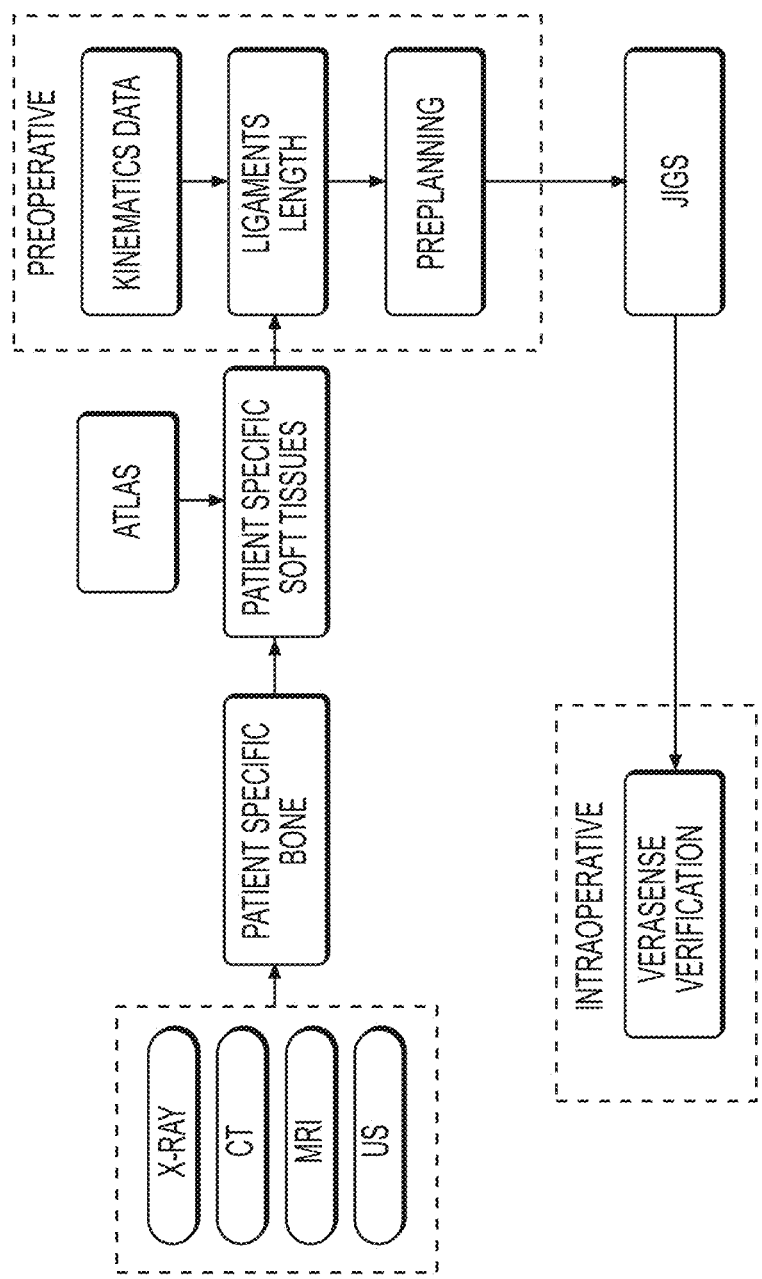

FIG. 154 is an exemplary process flow diagram for soft tissue and kinematic tracking of body anatomy using inertial measurement units in accordance with the instant disclosure.

Figure 155:
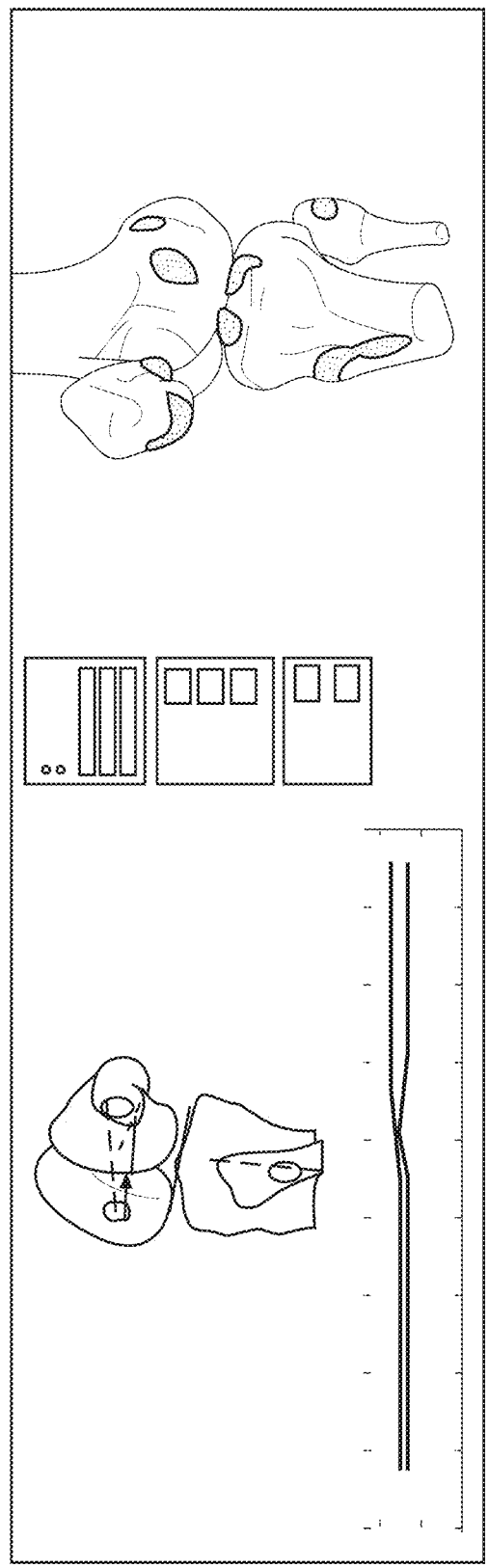

FIG. 155 comprises a pair of screen shots showing a kinematic software interface that identifies soft tissue locations on bone models and tracks soft tissue deformity in accordance with the instant disclosure.

Figure 156:
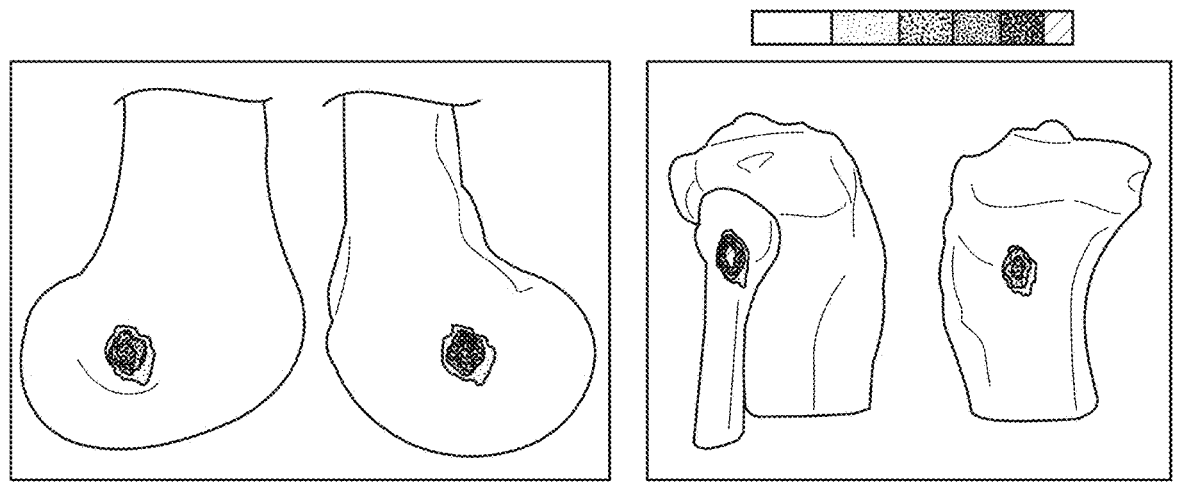

FIG. 156 comprises bone models of the femur, tibia, and fibula depicting points on the respective bone models where ligaments (MCL, LCL) are attached, where the points are color coded to identify points of higher or lower likelihood of ligament attachment.

Figure 157:
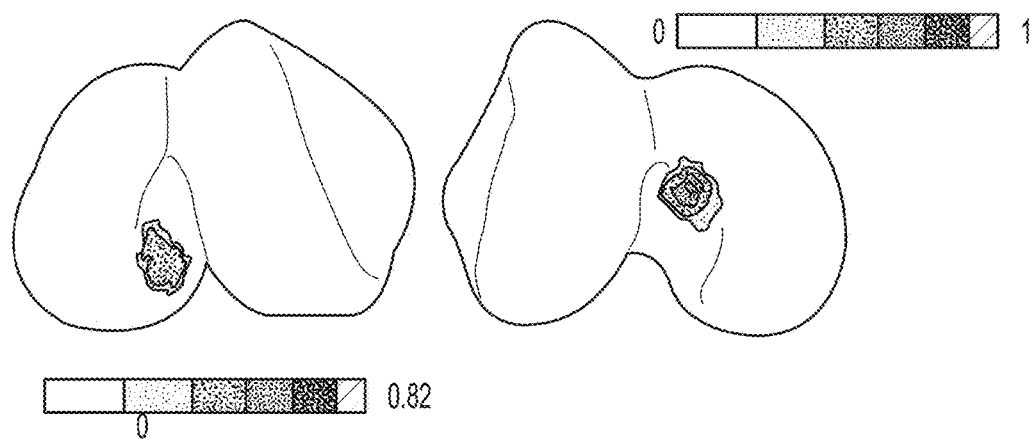

FIG. 157 comprises a bone model of the distal femur depicting points on the respective bone models where ligaments (ACL, PCL) are attached, where the points are color coded to identify points of higher or lower likelihood of ligament attachment.

Figure 158:
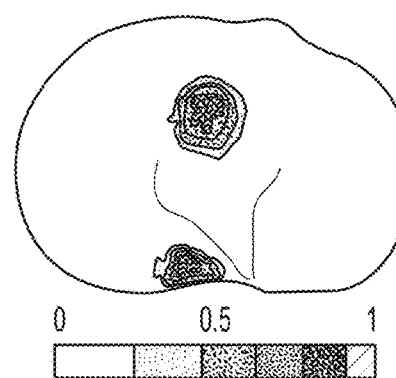

FIG. 158 comprises a bone model of the proximal tibia depicting points on the respective bone models where ligaments (ACL, PCL) are attached, where the points are color coded to identify points of higher or lower likelihood of ligament attachment.

Figure 159:
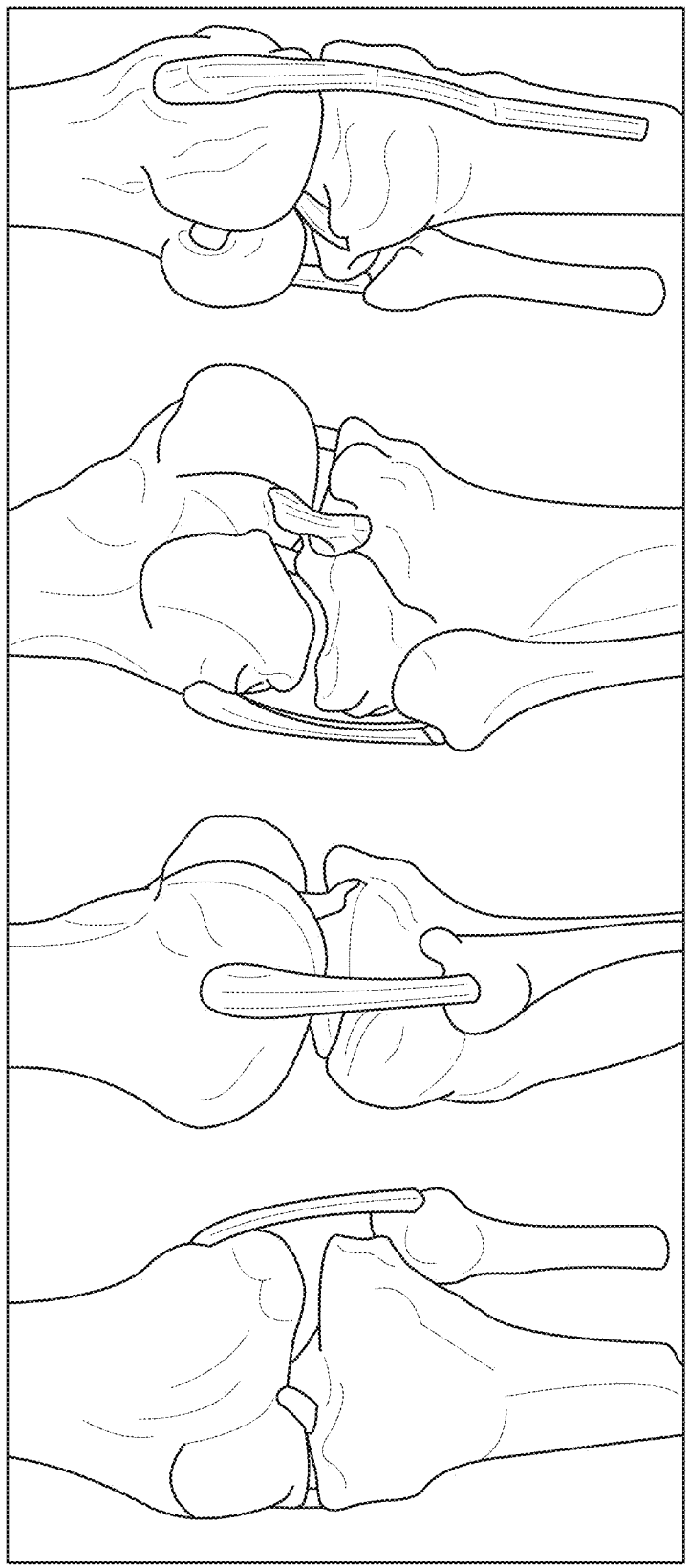

FIG. 159 depicts front, rear, and two side views of a 3D virtual model of a knee joint that includes ligament attachment in accordance with the instant disclosure.

FIG. 160 depicts utilizing fluoroscopic images to model kinematic motion of the fully assembled knee joint model of FIG. 159.

Figure 161:
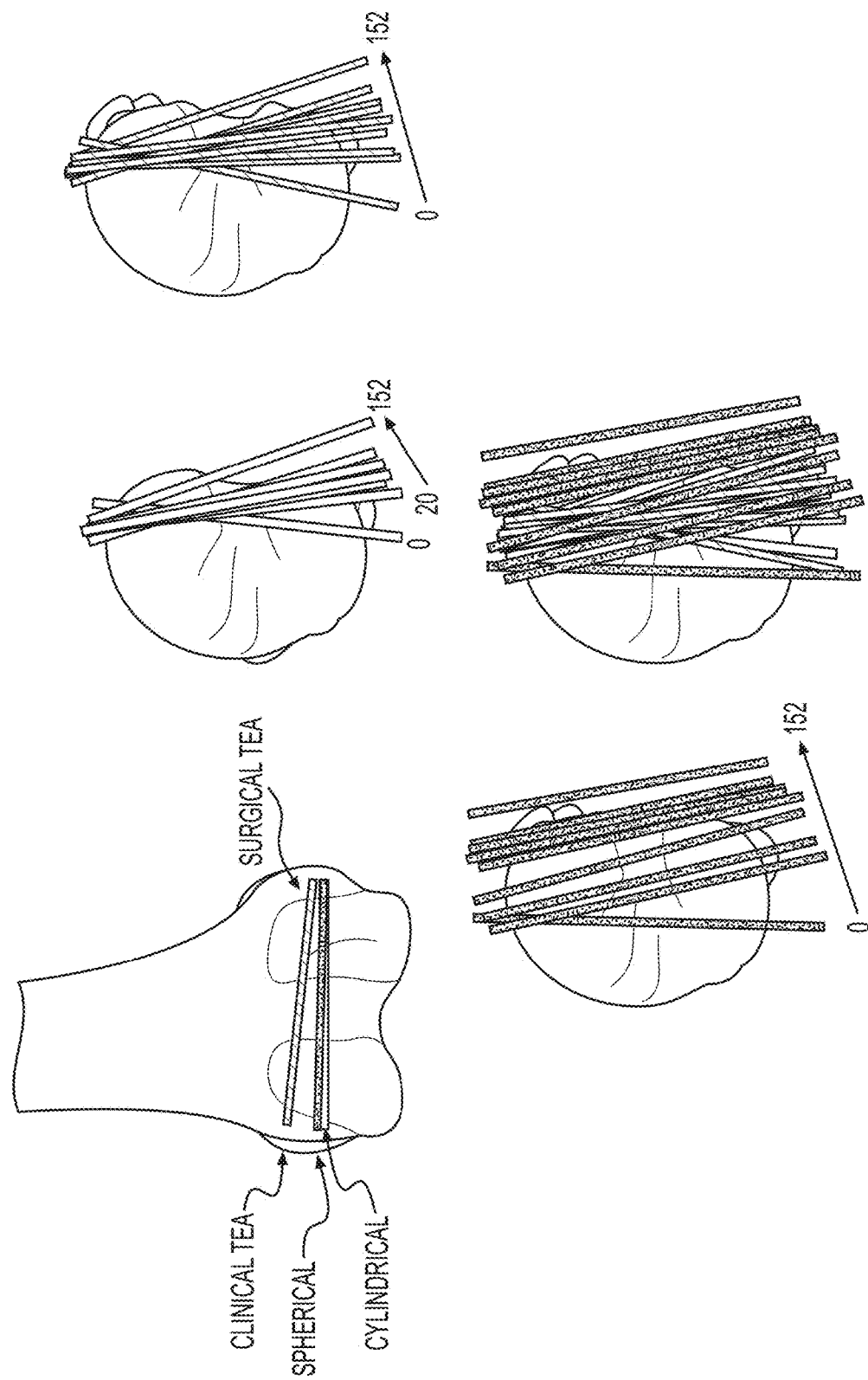

FIG. 161 includes a depiction of a distal femur bone model and a proximal tibia bone model reflecting real-time tracking of anatomical axes in accordance with the instant disclosure.

FIG. 162 includes a knee joint model through a range of motion and reconstructing the helical axes.

Figure 163:
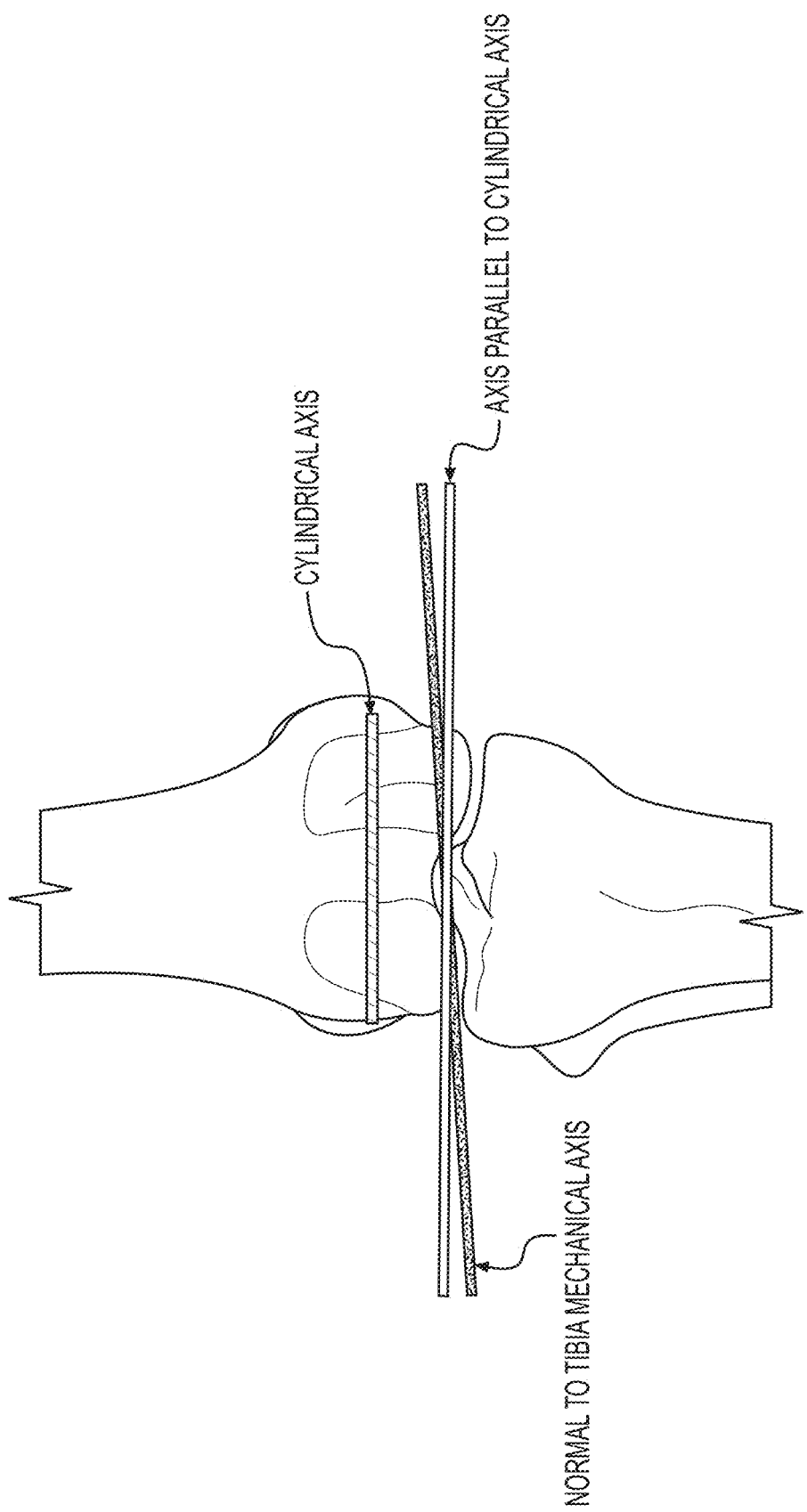

FIG. 163 includes a knee joint bone model depicting the anatomical axes in the coronal plane.

Figure 164:
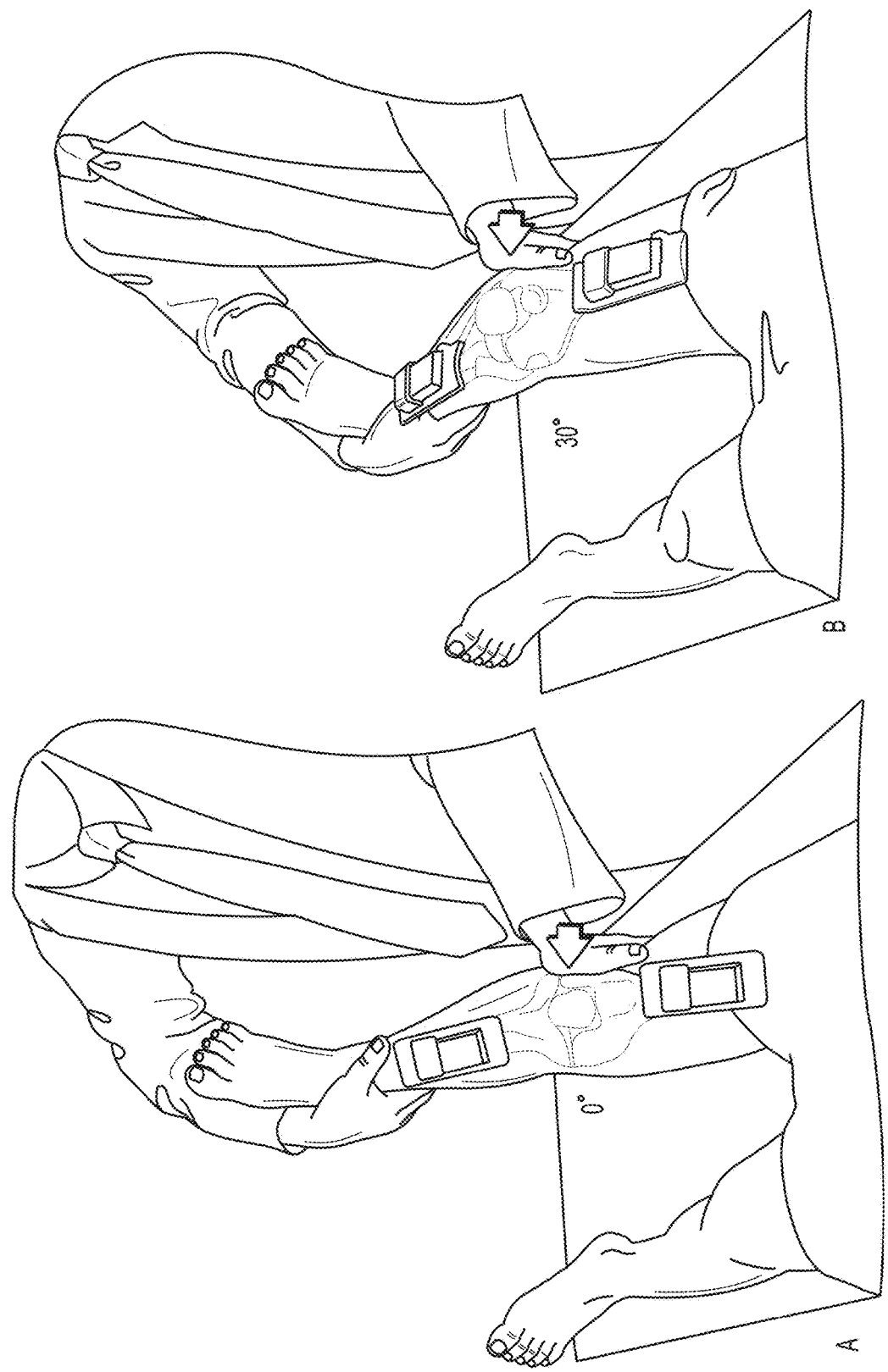

FIG. 164 is an exemplary illustration of a clinical examination of a knee joint using inertial measurement units to record motion data in accordance with the instant disclosure.

FIG. 165 is an exemplary illustration of a clinical examination of a knee joint using inertial measurement units to record motion data in accordance with the instant disclosure.

Figure 166:
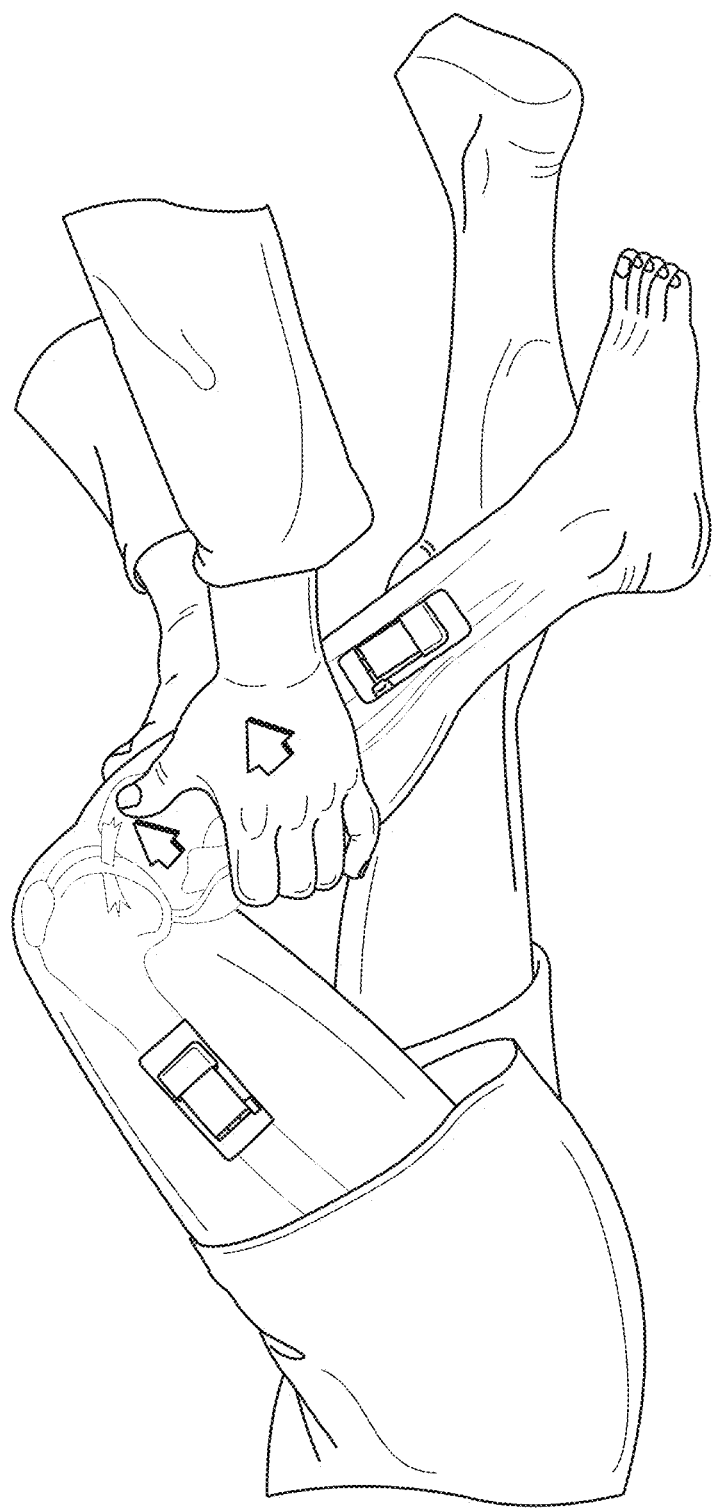

FIG. 166 is an exemplary illustration of a clinical examination of a knee joint using inertial measurement units to record motion data in accordance with the instant disclosure.

Figure 167:
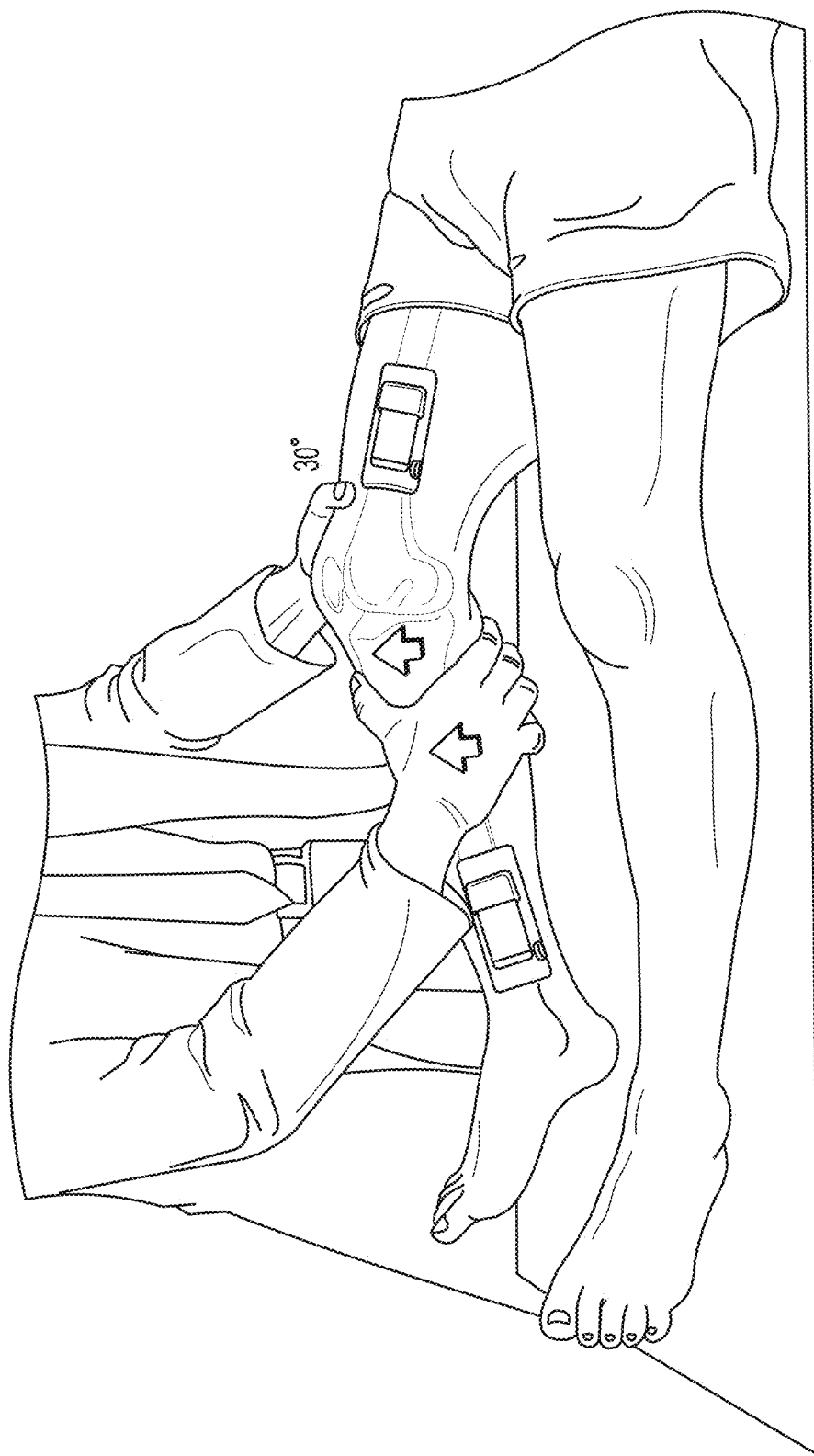

FIG. 167 is an exemplary illustration of a clinical examination of a knee joint using inertial measurement units to record motion data in accordance with the instant disclosure.

Figure 168:
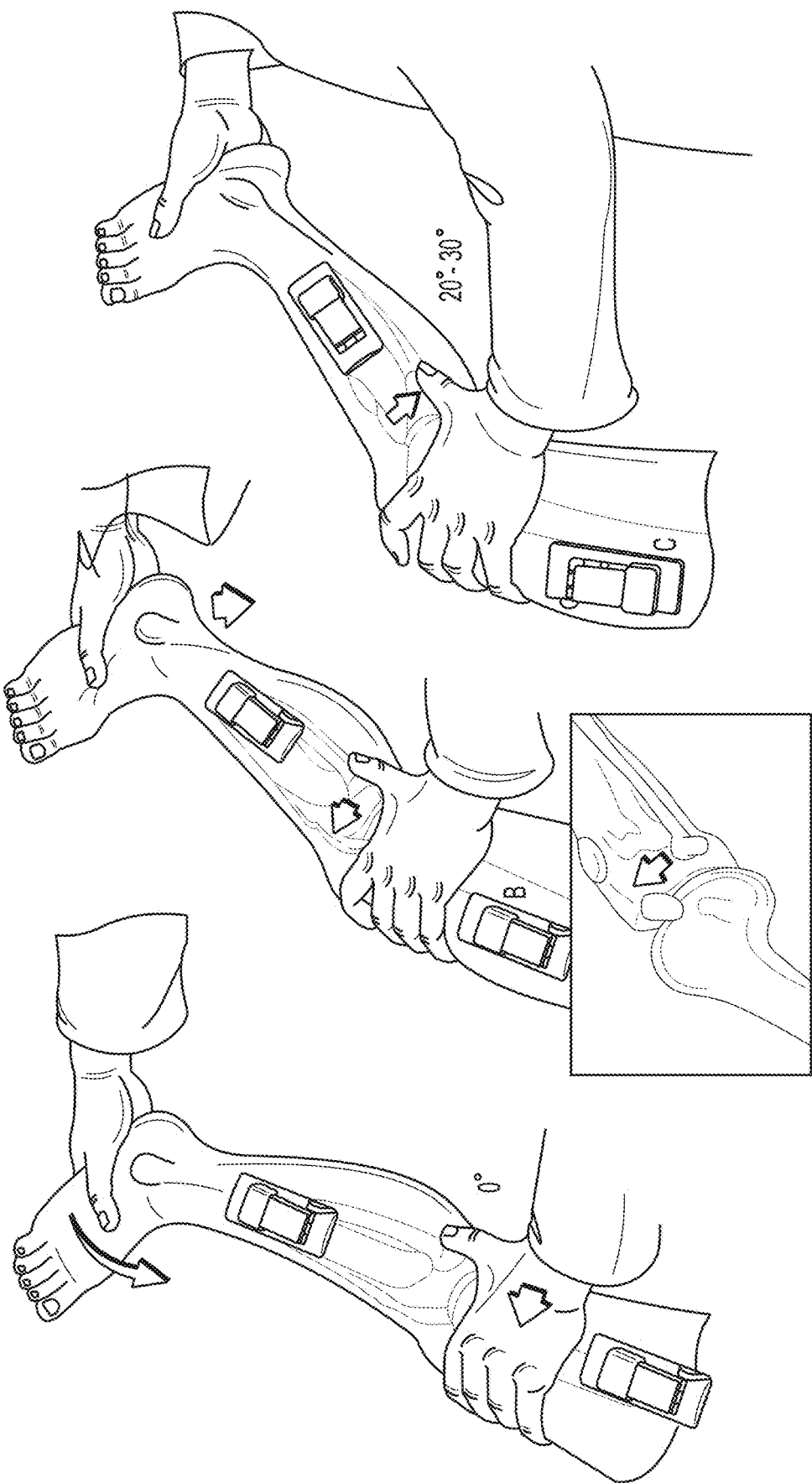

FIG. 168 is an exemplary illustration of a clinical examination of a knee joint using inertial measurement units to record motion data in accordance with the instant disclosure.

Figure 169:
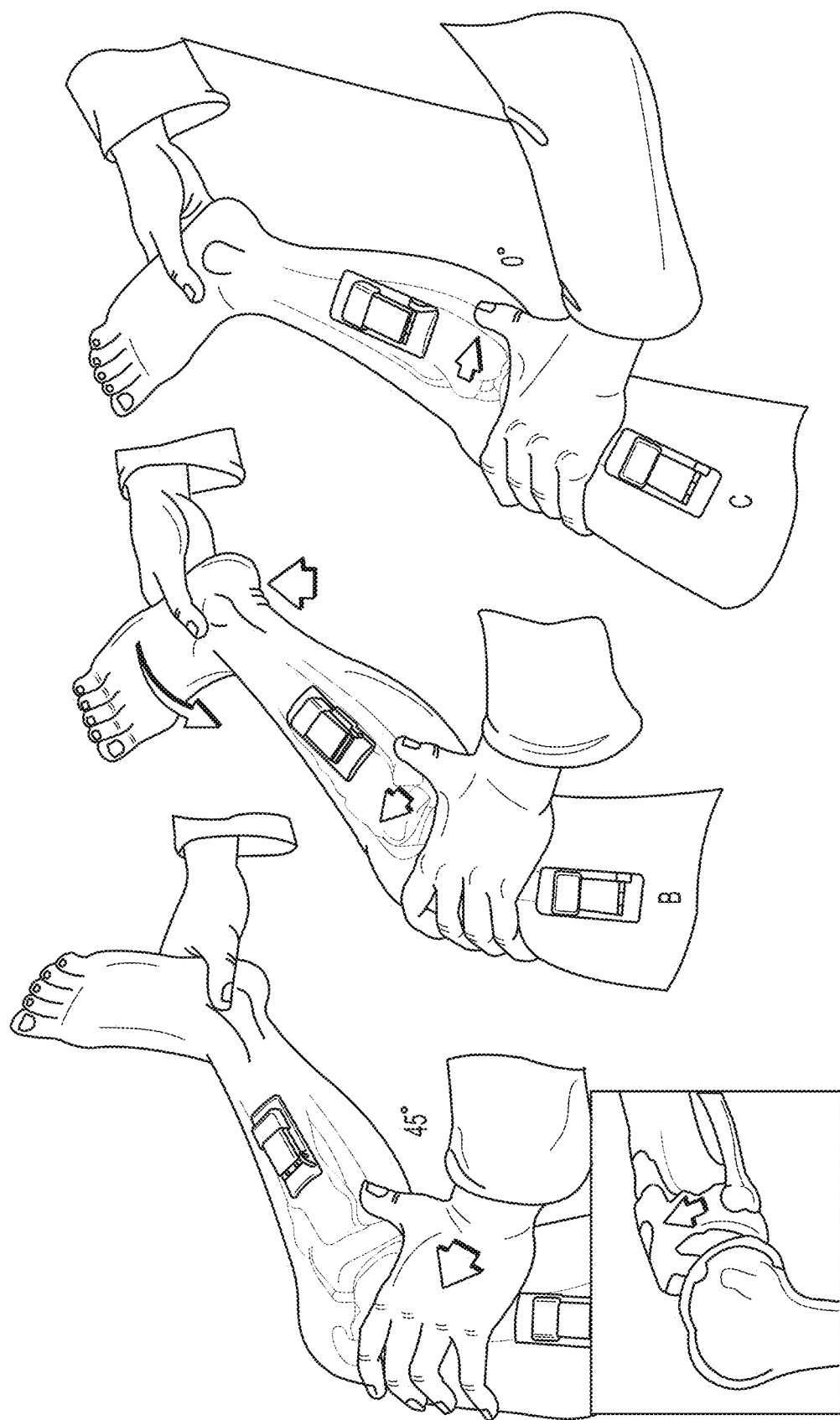

FIG. 169 is an exemplary illustration of a clinical examination of a knee joint using inertial measurement units to record motion data in accordance with the instant disclosure.

Figure 170:

FIG. 170 is an exemplary illustration of a clinical examination of a knee joint using inertial measurement units to record motion data in accordance with the instant disclosure.

Figure 171:
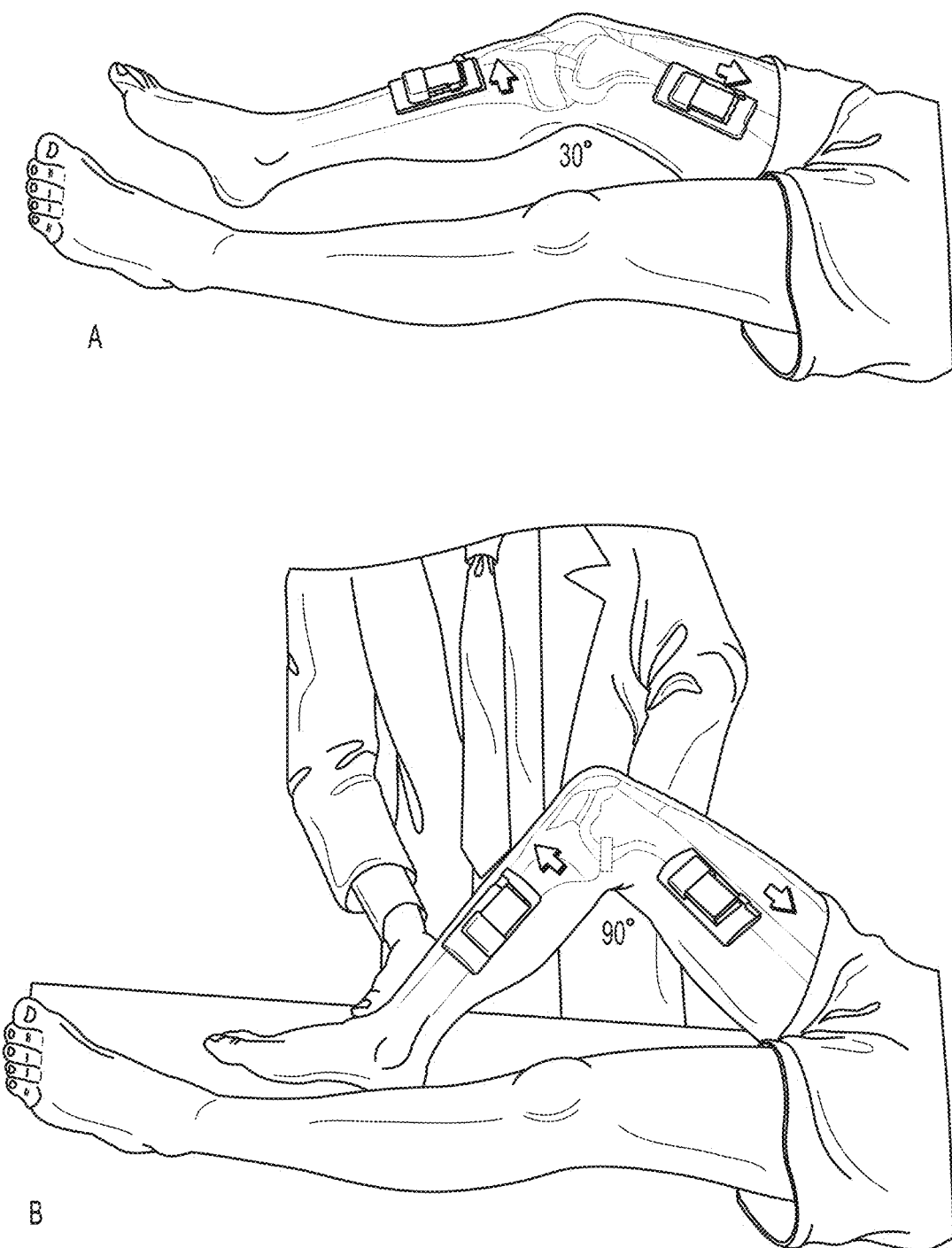

FIG. 171 is an exemplary illustration of a clinical examination of a knee joint using inertial measurement units to record motion data in accordance with the instant disclosure.

Figure 172:
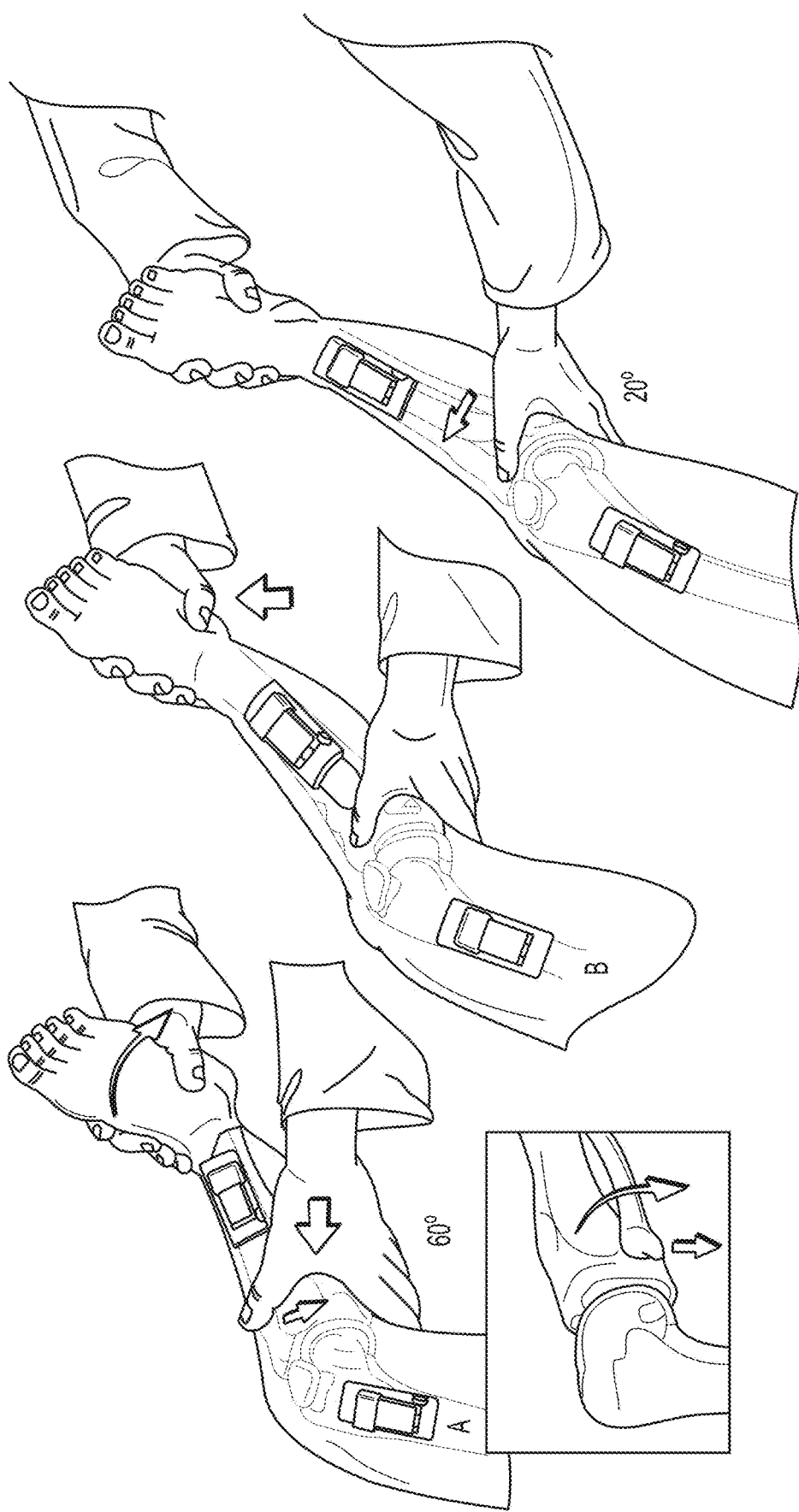

FIG. 172 is an exemplary illustration of a clinical examination of a knee joint using inertial measurement units to record motion data in accordance with the instant disclosure.

Figure 173:
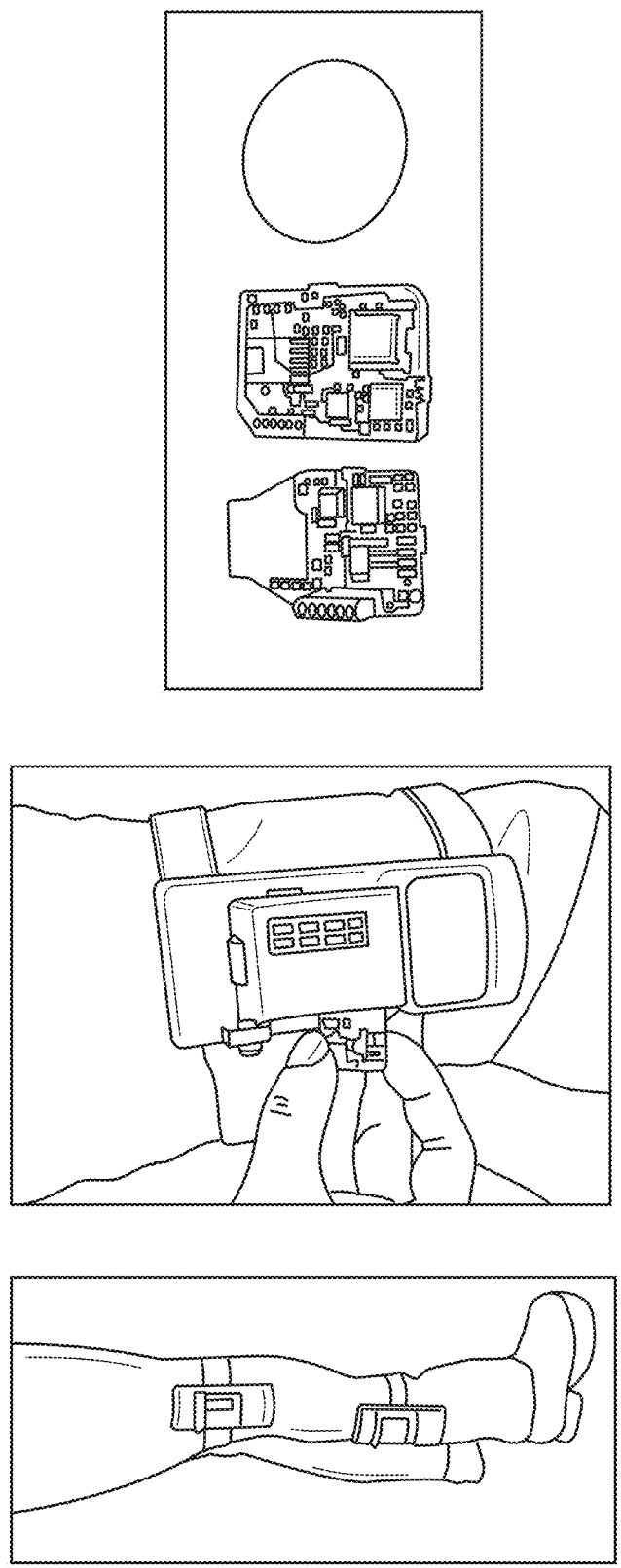

FIG. 173 includes a series of photographs, a first of which shows a patient donning a pair of inertial measurement unit (IMU) packages, a second of which shows the relative size of the IMU package to an individual IMU, and the third of which shows the relative size of an individual IMU to a U.S. currency quarter.

Figure 174:
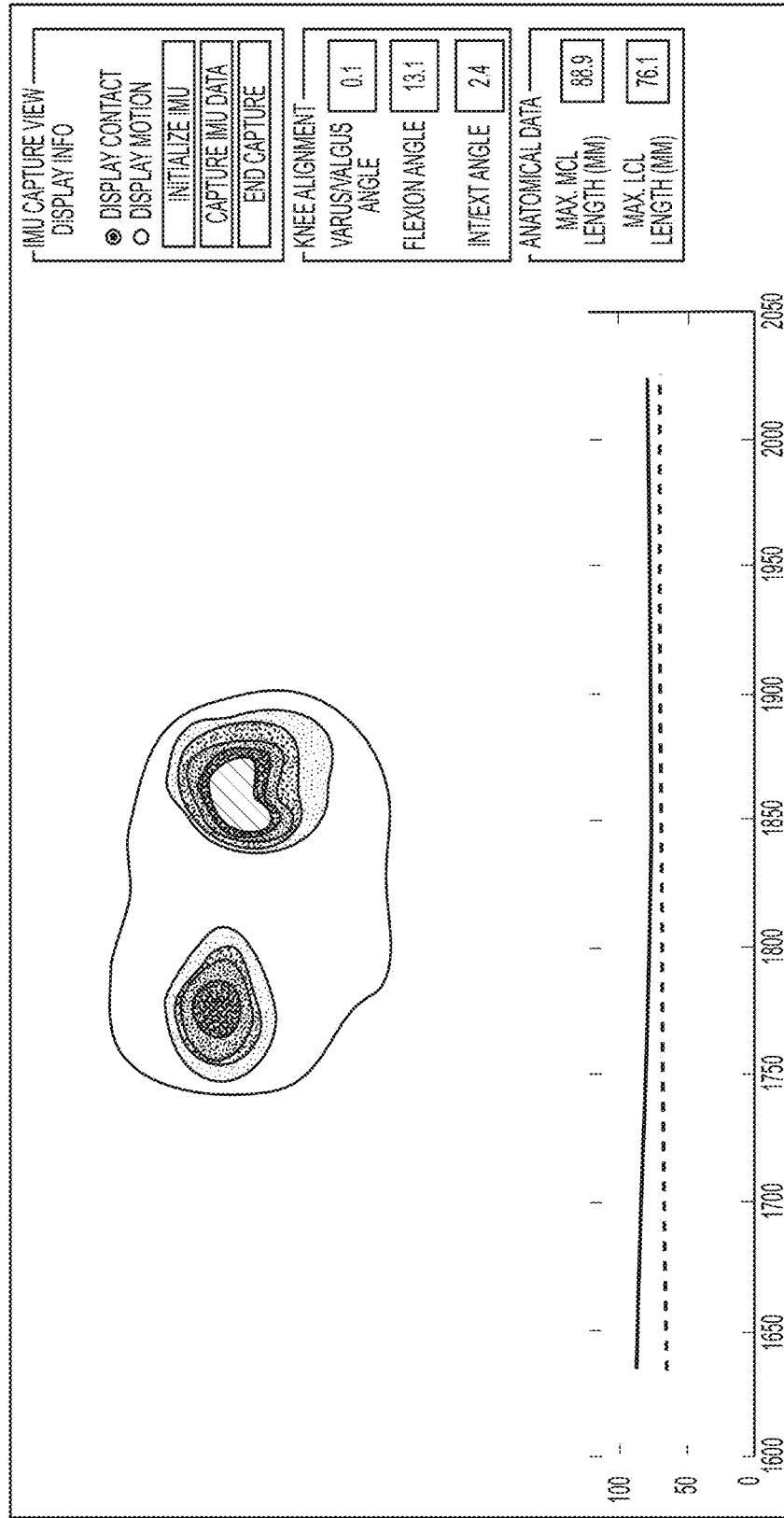

FIG. 174 is a screenshot of a user interface in accordance with the instant disclosure that is depicting a proximal tibia model that is dynamically updated based upon input received from an inertial measurement unit in order to provide feedback on load distribution when the patient's knee joint is taken through a range of motion.

Figure 175:
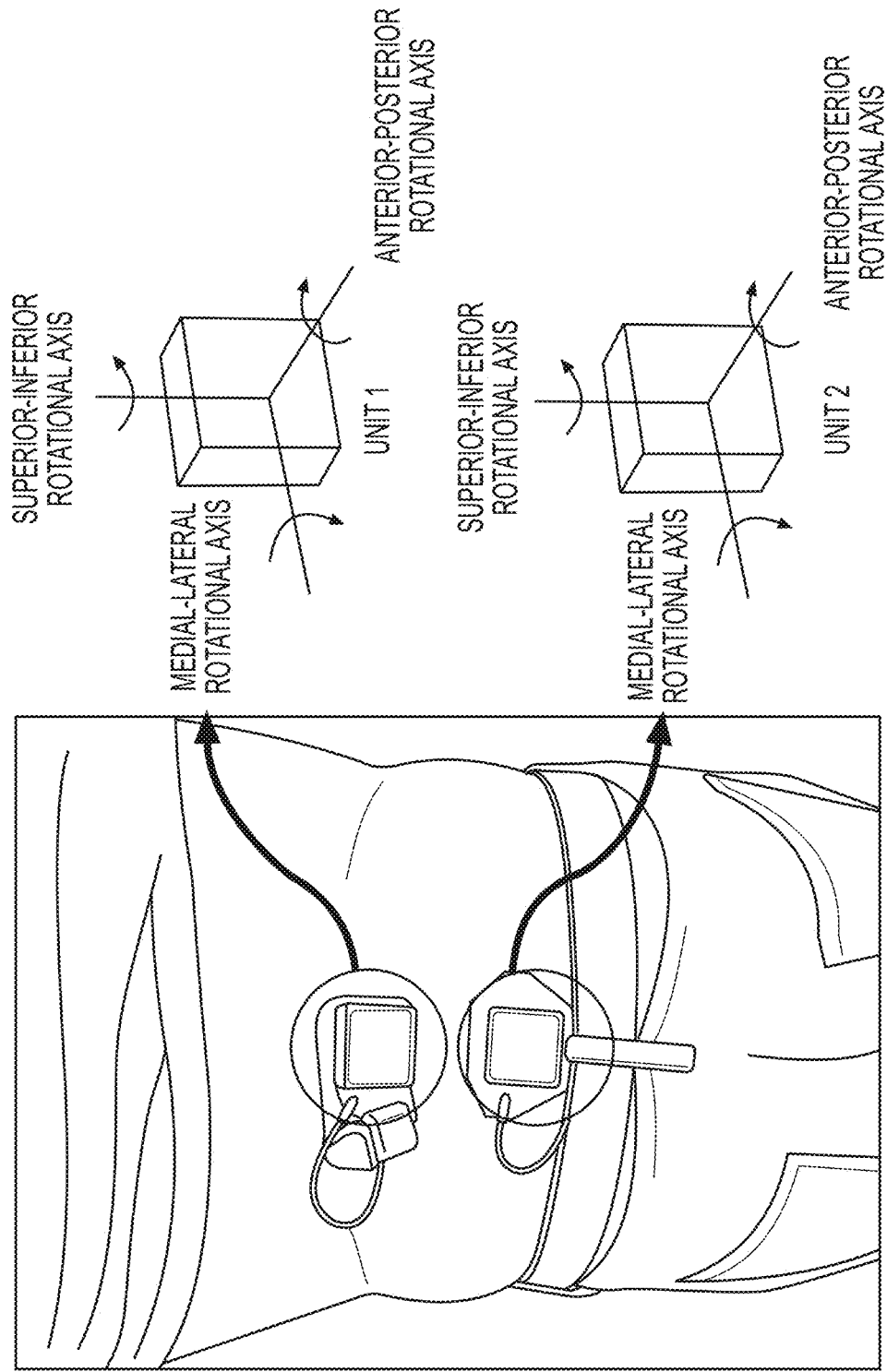

FIG. 175 is a photograph of the rear, lower back of a patient showing separate inertial measurement units (IMU) placed over the L1 and L5 vertebrae for tracking relative motion of each vertebra through a range of motion, as well as an ancillary diagram showing that each IMU is able to output data indicative of motion across three axes.

Figure 176:
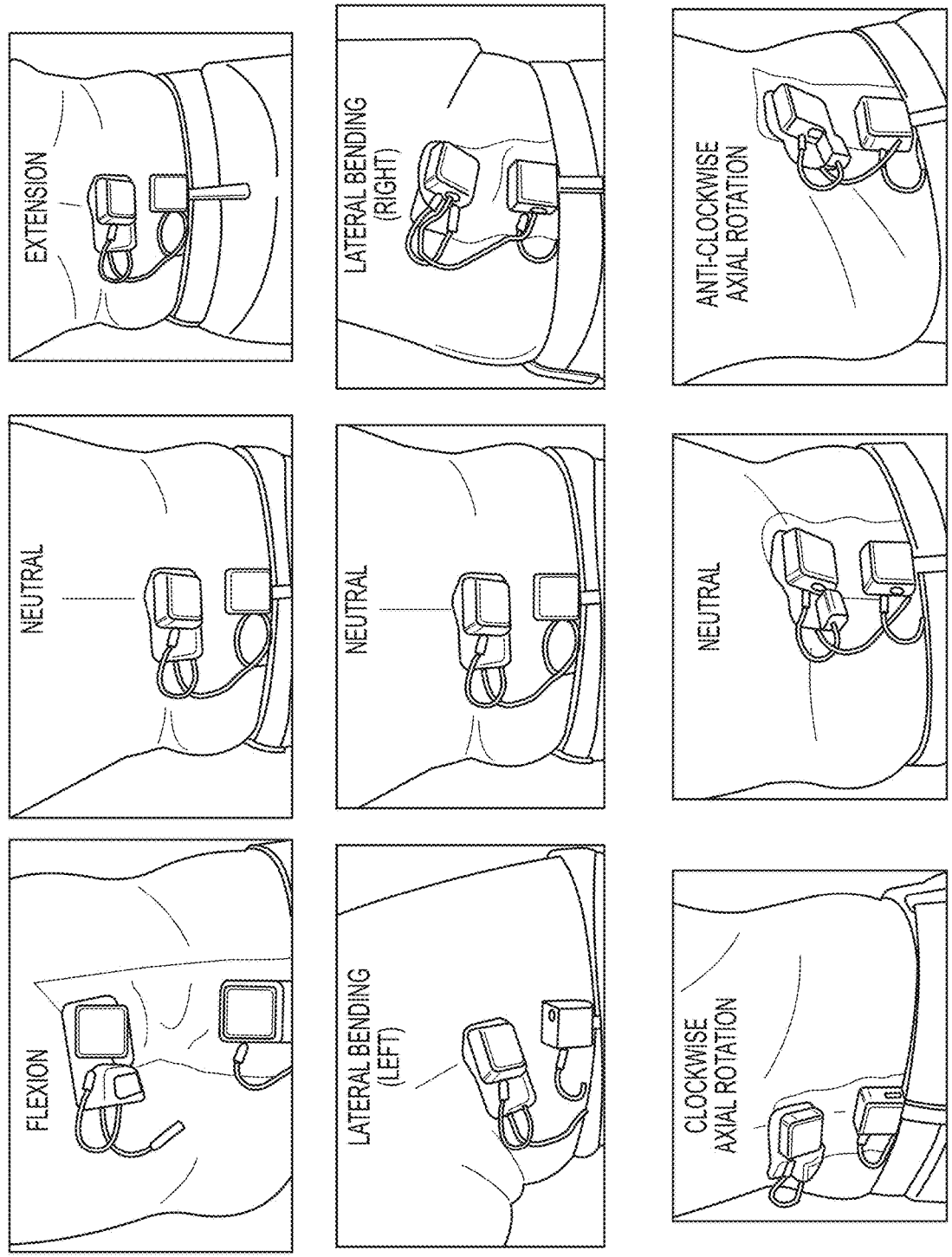

FIG. 176 comprises a series of photographs showing the patient and IMUs of FIG. 175 while the patient is moving through a range of motion.

FIG. 177 is a graphical depiction representative of a process for determining the relative orientation of at least two bodies using inertial measurement unit data in accordance with the instant disclosure.

Figures 178A, 178B:
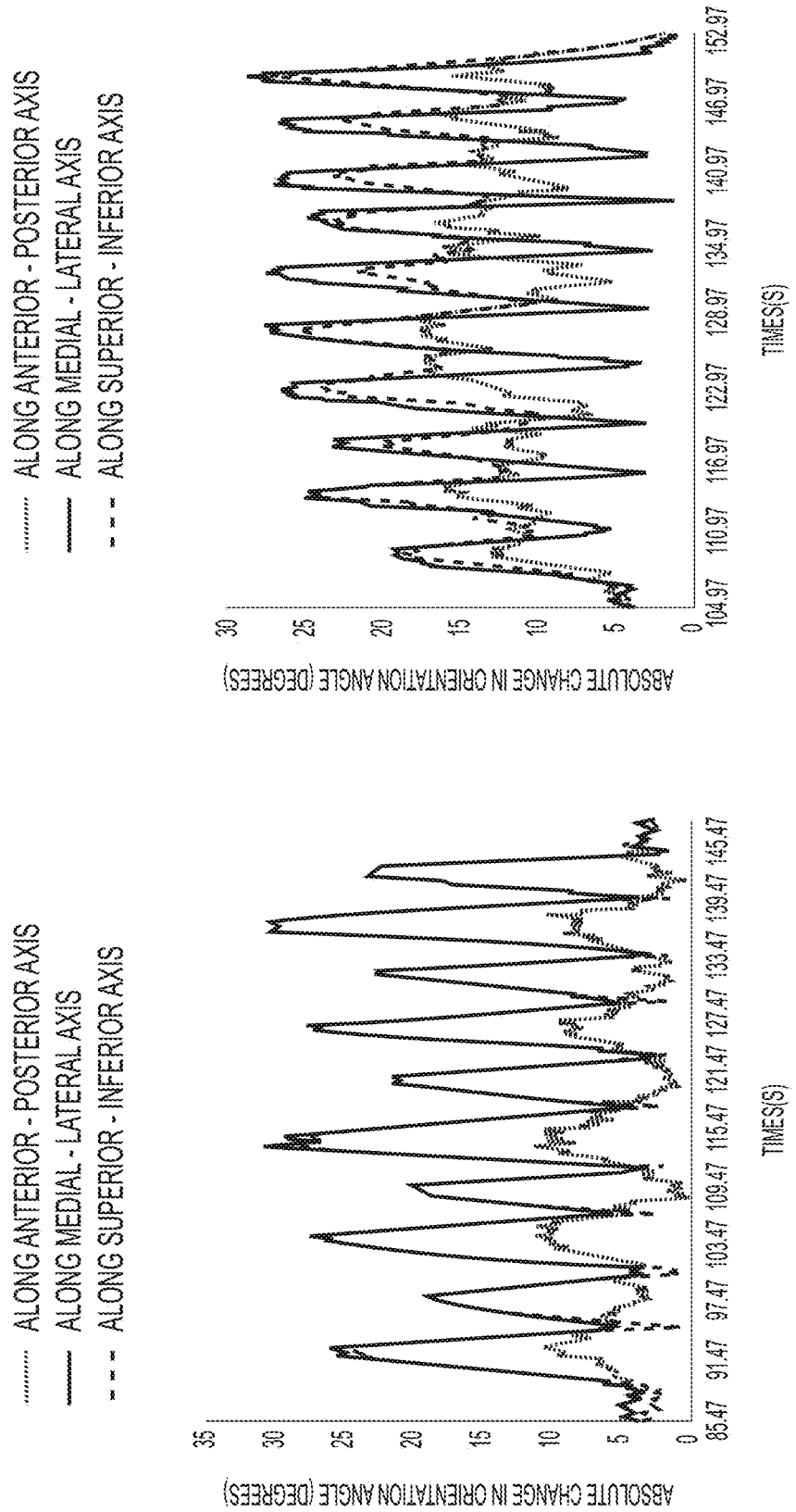

FIG. 178A comprises plot showing the absolute change in orientation of anatomical axes relevant to the spine (in particular L1, L5) during lateral bending activities of a patient, where the data plot is representative of a healthy patient.

FIG. 178B comprises a plot showing the absolute change in orientation of anatomical axes relevant to the spine (in particular L1, L5) during lateral bending activities of a patient, where the data plot is representative of a patient exhibiting spinal degeneration.

Figure 179:
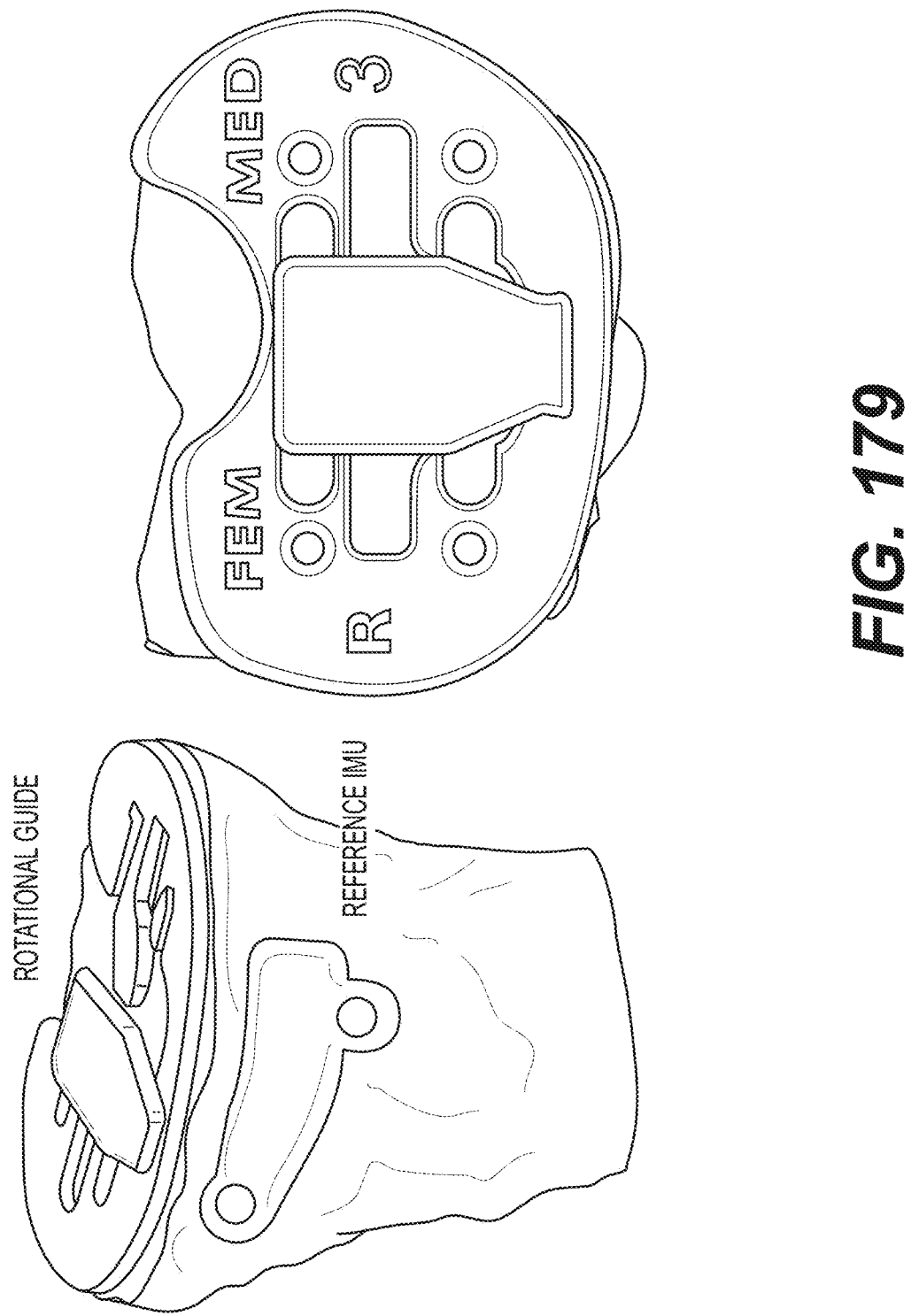

FIG. 179 comprises a pair of images, one a tope view of a proximal tibia, and the second an elevated perspective view of the proximal tibia, shown with a surgical navigation tool utilized to normalize IMUs to ensure proper orientation and location of a tibial implant component.

Figure 180:
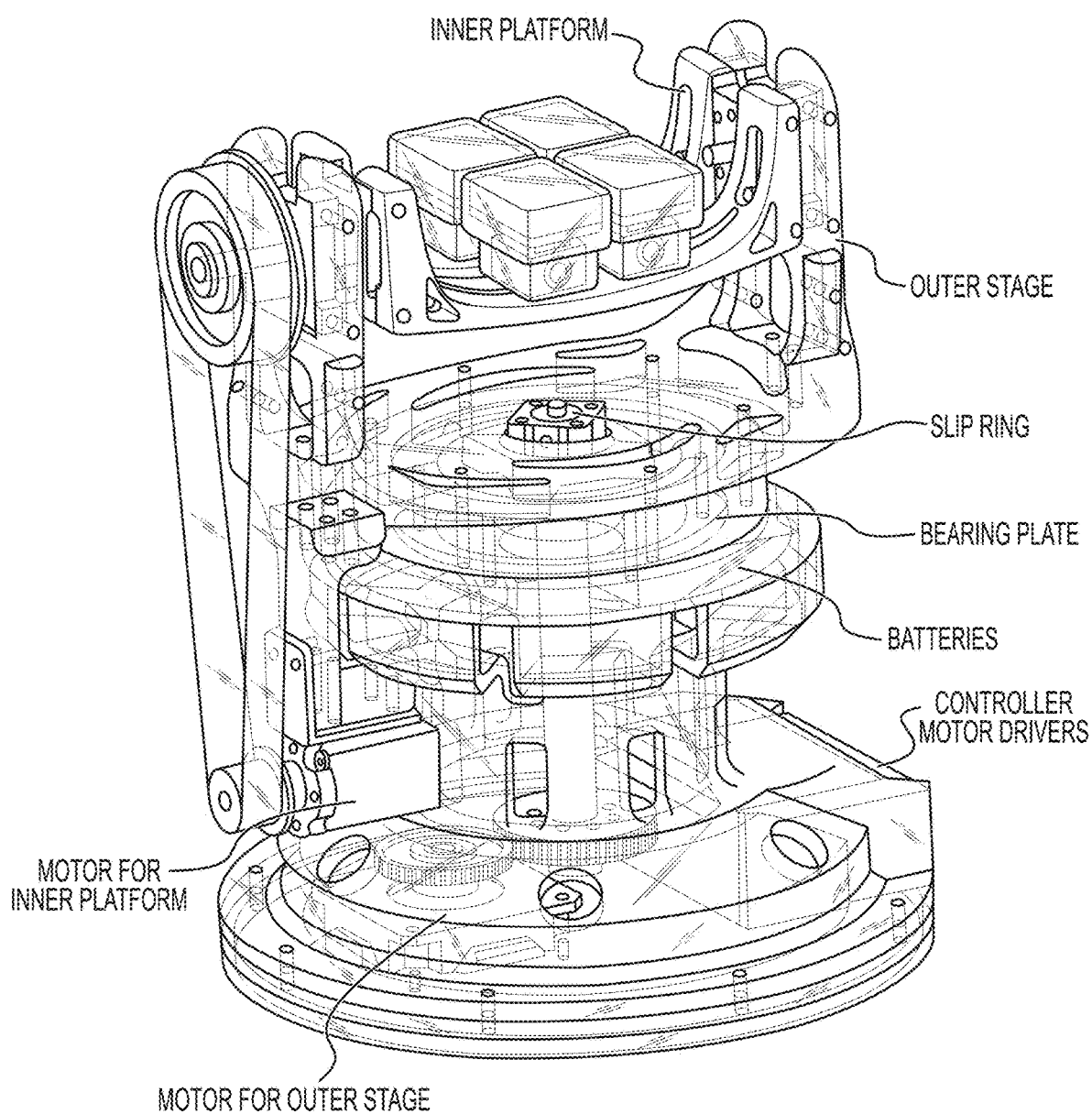

FIG. 180 is an elevated perspective view of an exemplary inertial measurement unit calibration device in accordance with the instant disclosure.

FIG. 181 shows local magnetic field maps (isometric, front, and top views) generated from data output from an inertial measurement unit before calibration (top series of three plots resembling an ellipsoid), and local magnetic field maps (isometric, front, and top views) generated from data output from an inertial measurement unit after calibration (bottom series of three plots resembling a sphere).

FIG. 182A comprises a diagram showing exemplary locations of magnetometers associated with an inertial measurement unit.

FIG. 182B comprises a diagram showing what the detected magnetic field from the magnetometers of FIG. 182A should reflect if normalized to account for distortions.

FIG. 182C comprises a diagram showing the result of a local distortion in the magnetic field upon the magnetometers of FIG. 182A if no normalization is carried out.

Figure 183:
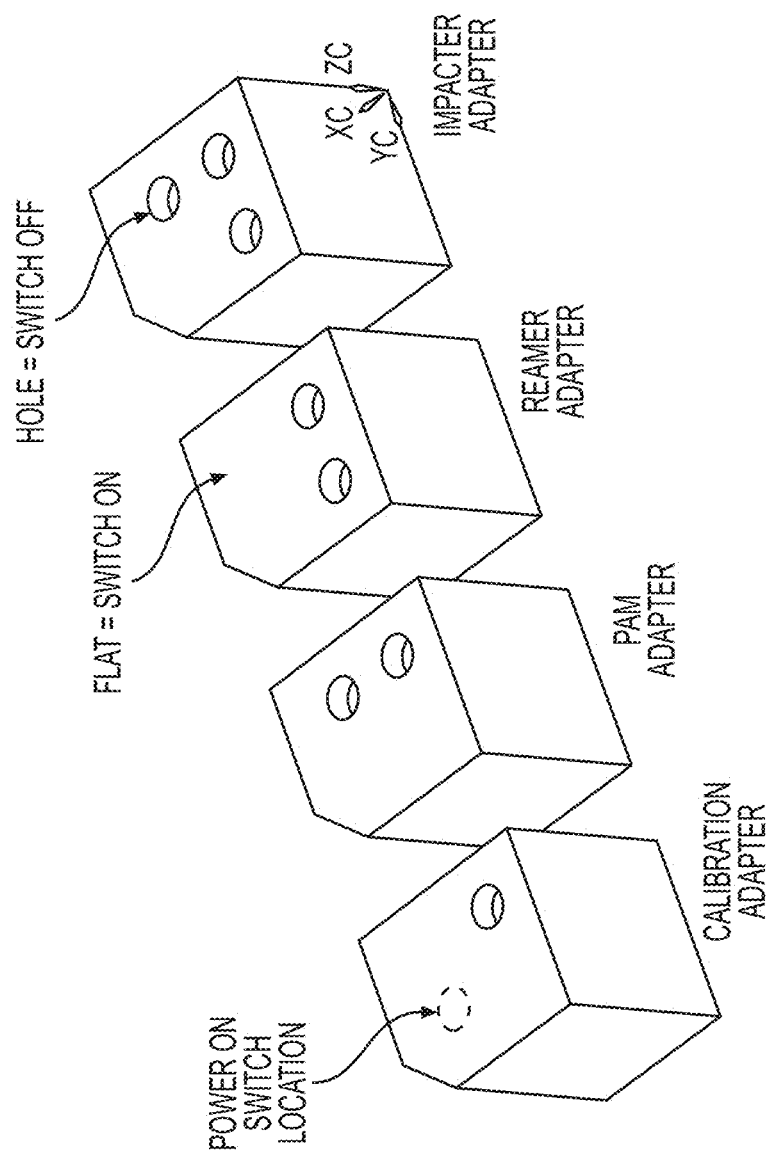

FIG. 183 is a series of projections for varied surgical tools each having a unique top surface in order to allow an inertial measurement unit processor to intelligently identify the surgical tool to which the IMU is mounted.

Figure 184:
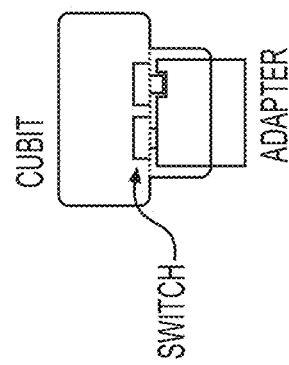
Figure 185:
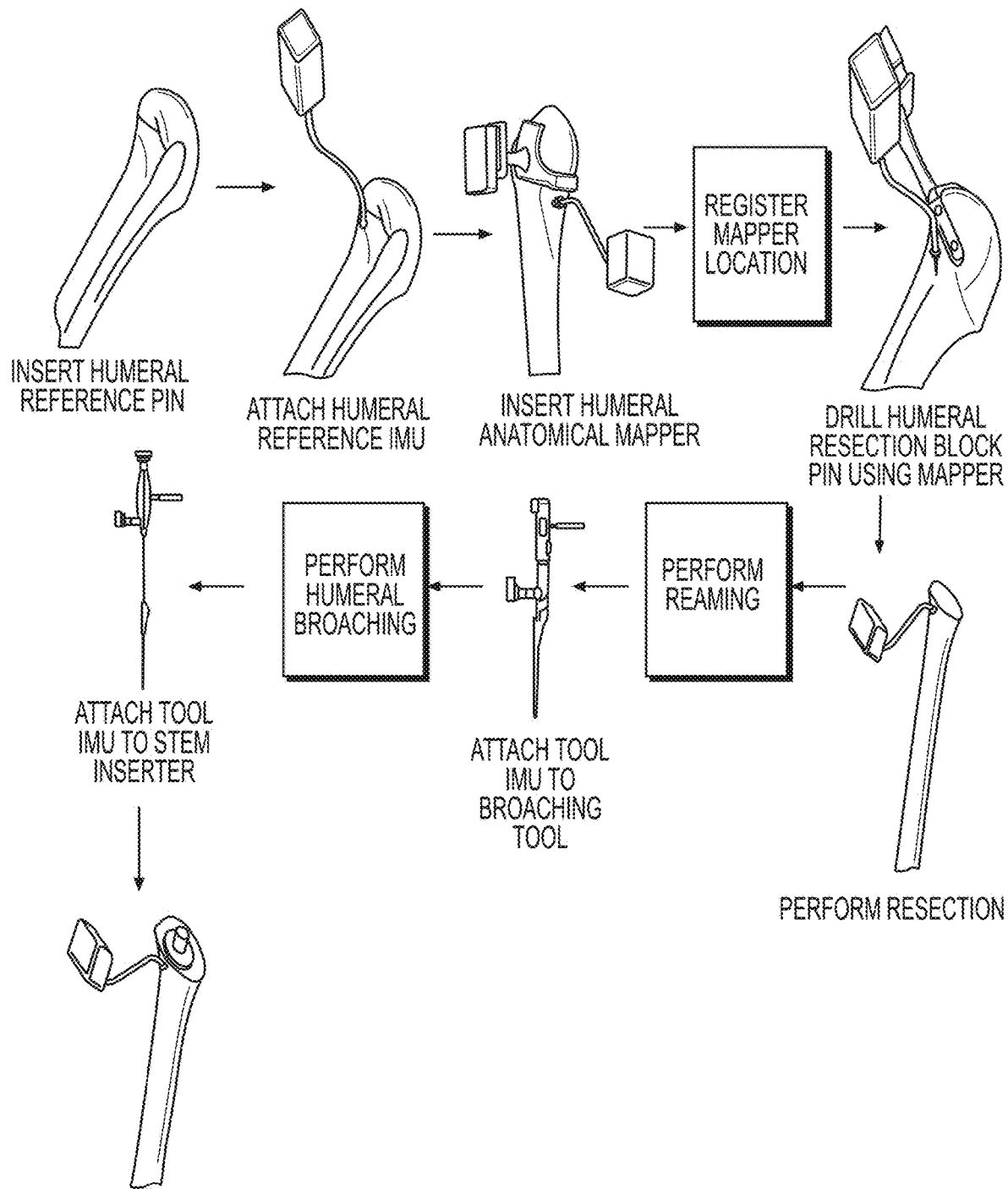

FIG. 184 is an outline drawings representative of a IMU housing and depicting the interaction between one of the projections of FIG. 185 and a bottom cavity of the IMU housing.

FIG. 185 is an exemplary process flow diagram for preparing a proximal humerus and implanting a humeral component as part of a shoulder replacement procedure by using inertial measurement units in accordance with the instant disclosure.

Figure 186:
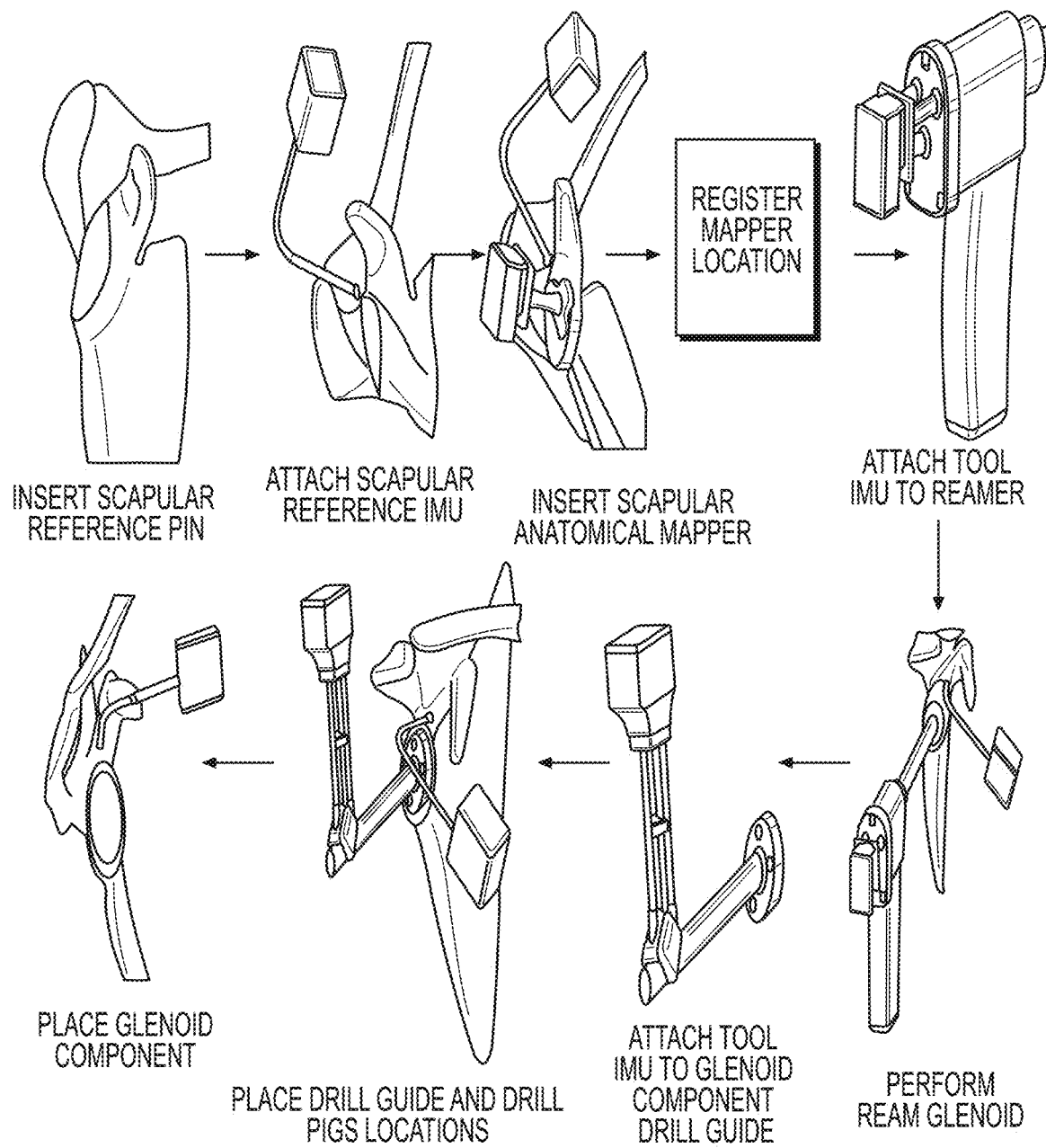

FIG. 186 is an exemplary process flow diagram for preparing a scapular socket and implanting a glenoid cavity cup as part of a shoulder replacement procedure by using inertial measurement units in accordance with the instant disclosure.

Figure 187:
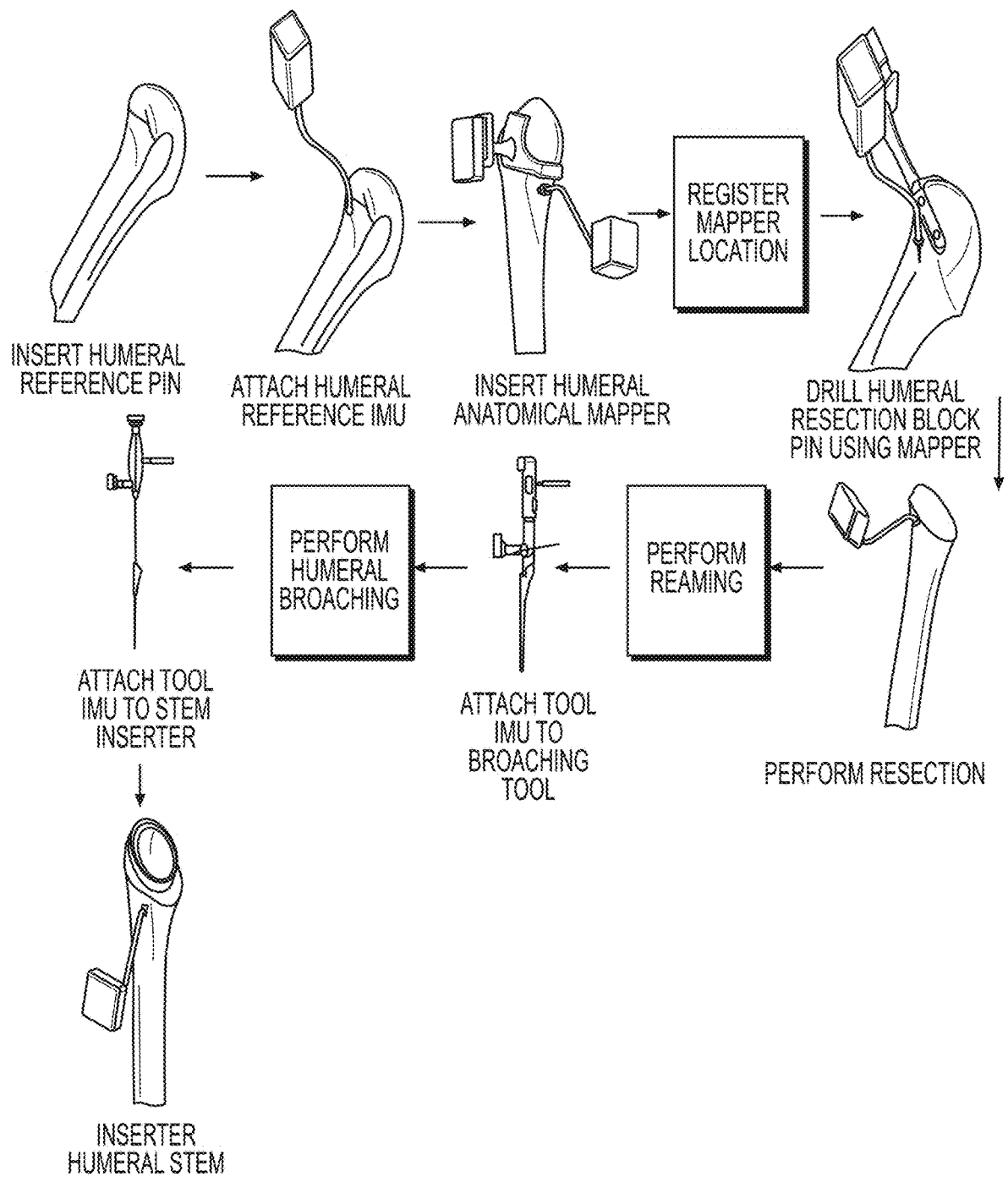

FIG. 187 is an exemplary process flow diagram for preparing a proximal humerus and implanting a humeral component as part of a reverse shoulder replacement procedure by using inertial measurement units in accordance with the instant disclosure.

Figure 188:
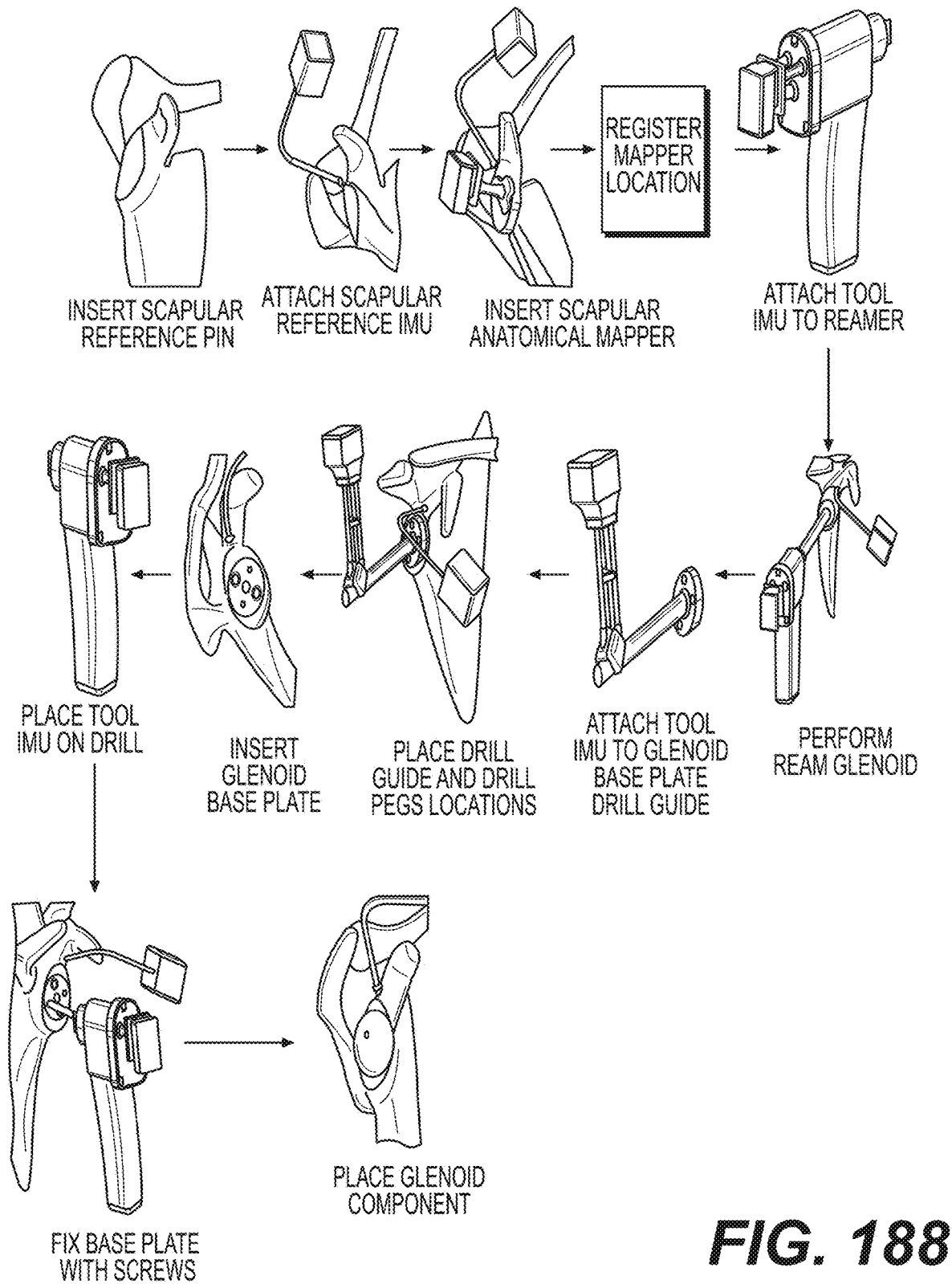

FIG. 188 is an exemplary process flow diagram for preparing a scapular socket and implanting a glenoid ball as part of a reverse shoulder replacement procedure by using inertial measurement units in accordance with the instant disclosure.

DETAILED DESCRIPTION

The exemplary embodiments of the present disclosure are described and illustrated below to encompass various aspects of orthopedics including bone and tissue reconstruction, patient-specific and mass customized orthopedic implants, gender and ethnic specific orthopedic implants, cutting guides, trauma plates, bone graft cutting and placement guides, and patient-specific instruments. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Full Anatomy Reconstruction

Referring to FIGS. 1-8, reconstruction of a deformed anatomy or a partial anatomy is one of the complex problems facing healthcare providers. Loss of anatomy may be the result of birth conditions, tumors, diseases, personal injuries, or failure of previous surgeries. As part of providing treatment for various ailments, healthcare providers may find it advantageous to reconstruct an anatomy or construct an anatomy to facilitate treatment for various conditions that may include, without limitation, broken/shattered bones, bone degeneration, orthopedic implant revision, joint degeneration, and custom instrumentation design. For example, prior art hip reconstruction solution requires mirroring of the healthy patient anatomy which may not be an accurate reflection of the healthy anatomy due to naturally occurring asymmetry, as shown in FIG. 15-19.

The present disclosure provides a system and methods for bone and tissue reconstruction. In order to carry out this reconstruction, the system and associated methods utilizes anatomical images representative of one or more persons. These images are processed to create a virtual three dimensional (3D) tissue model or a series of virtual 3D tissue models mimicking the proper anatomy in question. Thereafter, the system and associated methods are utilized to create a mold and/or other devices (e.g., fixation devices, grafting devices, patient-specific implants, patient-specific surgical guides) for use with reconstructive surgery.

Figure 1:
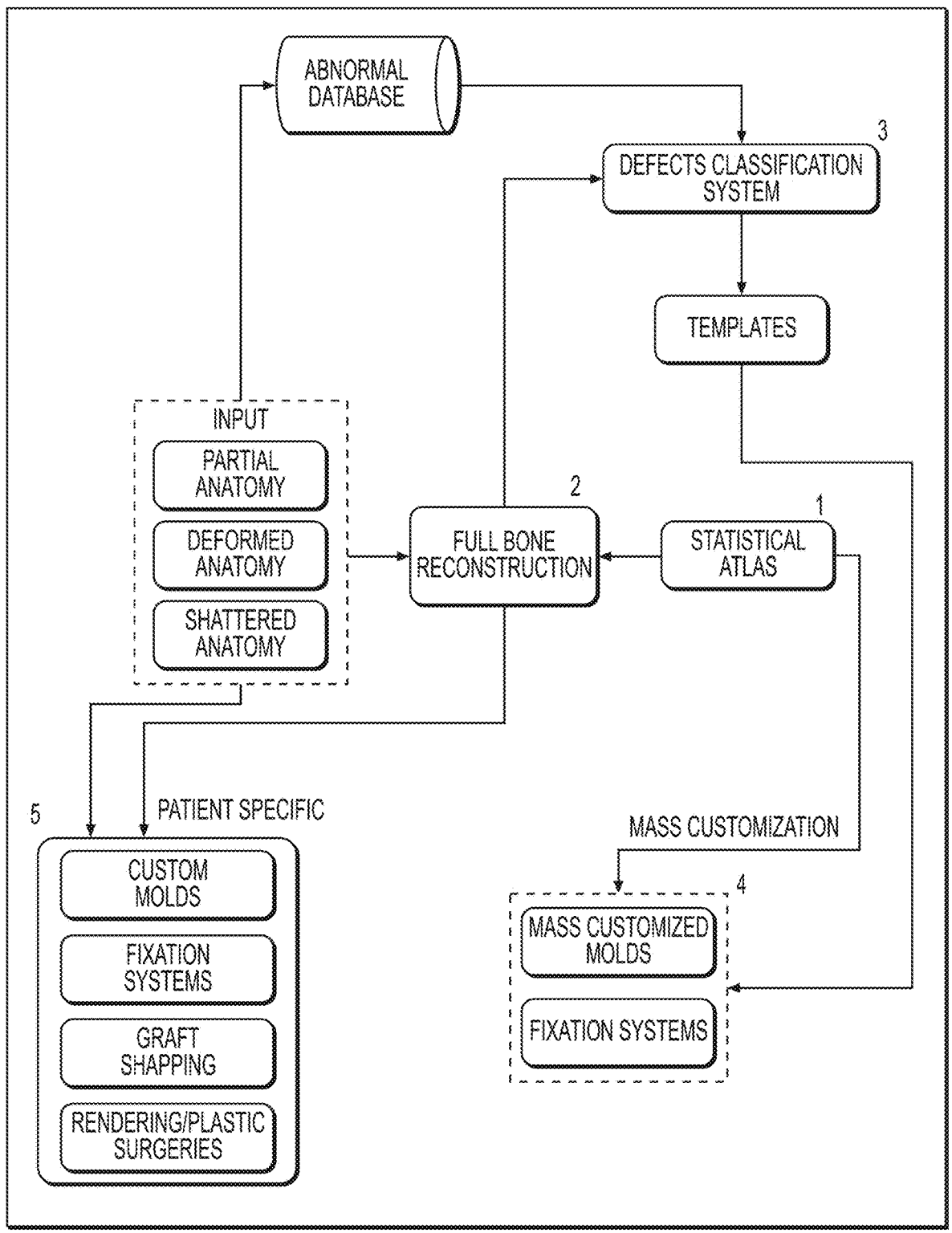
FIG. 1 is a schematic diagram of an overall process of generating mass customized and patient-specific molds from a partial anatomy.

As represented in FIG. 1, an overview of the exemplary system flow begins with receiving input data representative of an anatomy. This anatomy may comprise a partial anatomy in the case of tissue degeneration or tissue absence resulting from genetics, or this anatomy may comprise a deformed anatomy resulting from genetics or environmental conditions, or this anatomy may comprise a shattered tissue resulting from one or more anatomy breaks. Input anatomical data comprises two dimensional (2D) images or three dimensional (3D) surface representations of the anatomy in question that may, for example, be in the form of a surface model or point cloud. In circumstances where 2D images are utilized, these 2D images are utilized to construct a 3D virtual surface representation of the anatomy in question. Those skilled in the art are familiar with utilizing 2D images of anatomy to construct a 3D surface representation. Accordingly, a detailed explanation of this process has been omitted in furtherance of brevity. By way of example, input anatomical data may comprise one or more of X-rays, computed tomography (CT) scans, magnetic resonance images (Mills), or any other imaging data from which a 3D surface representation of the tissue in question may be generated.

Figure 50:
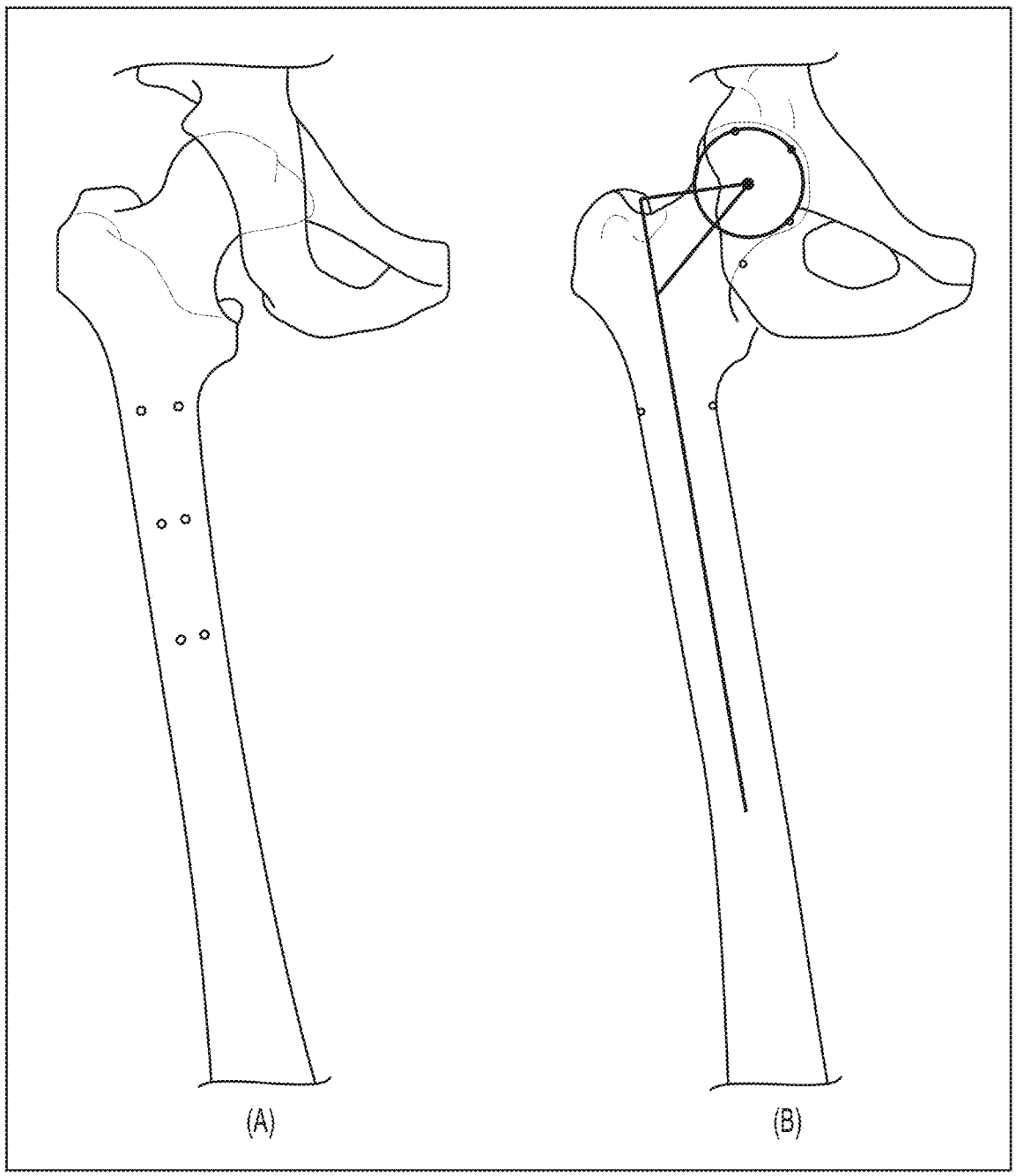
FIG. 50 is an X-ray depiction shown the IM width at 3 levels, and the proximal axis, head offset and femur head.
Figure 51:
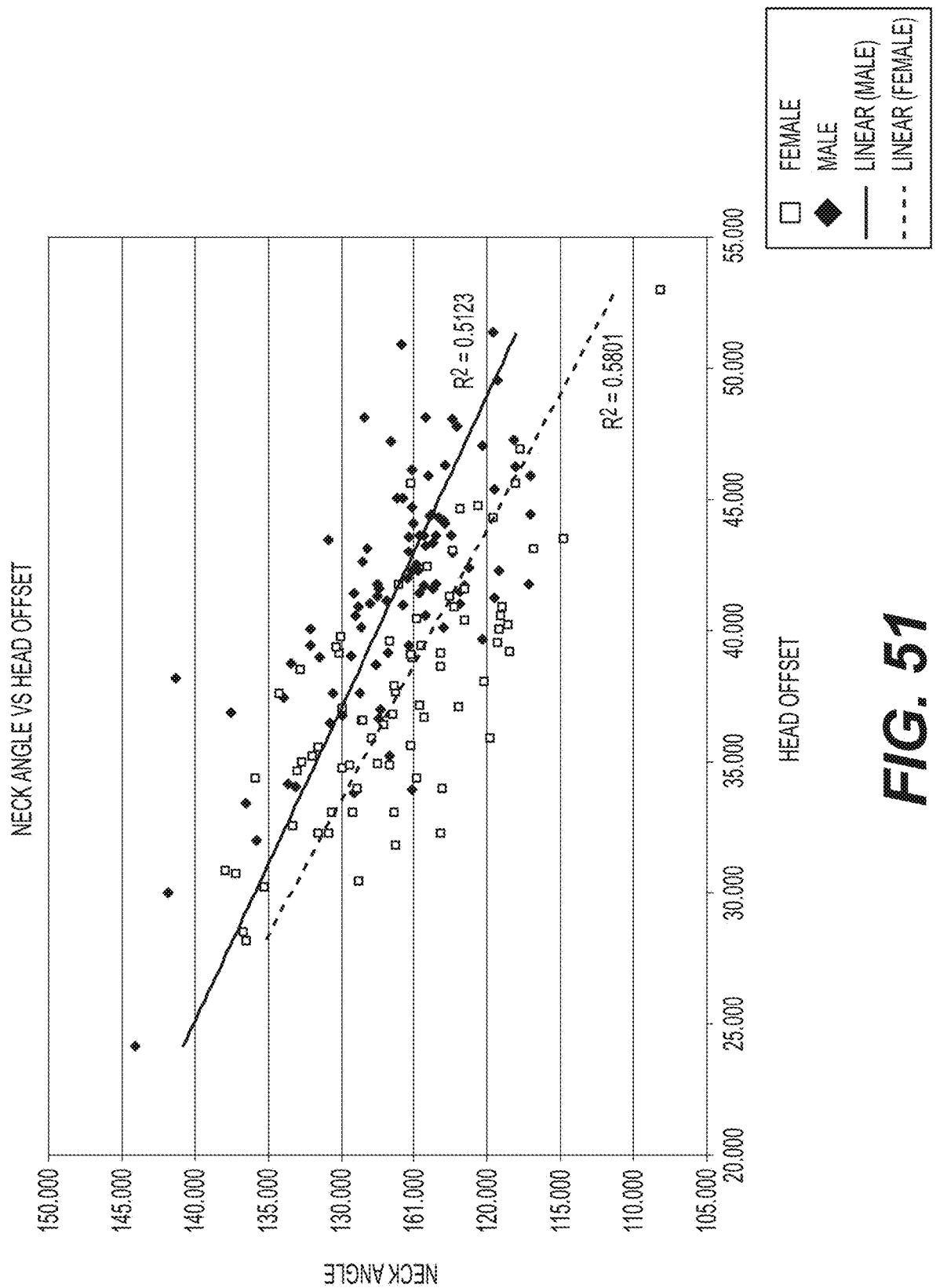
FIG. 51 is a plot of proximal angle versus head offset.
Figure 52:
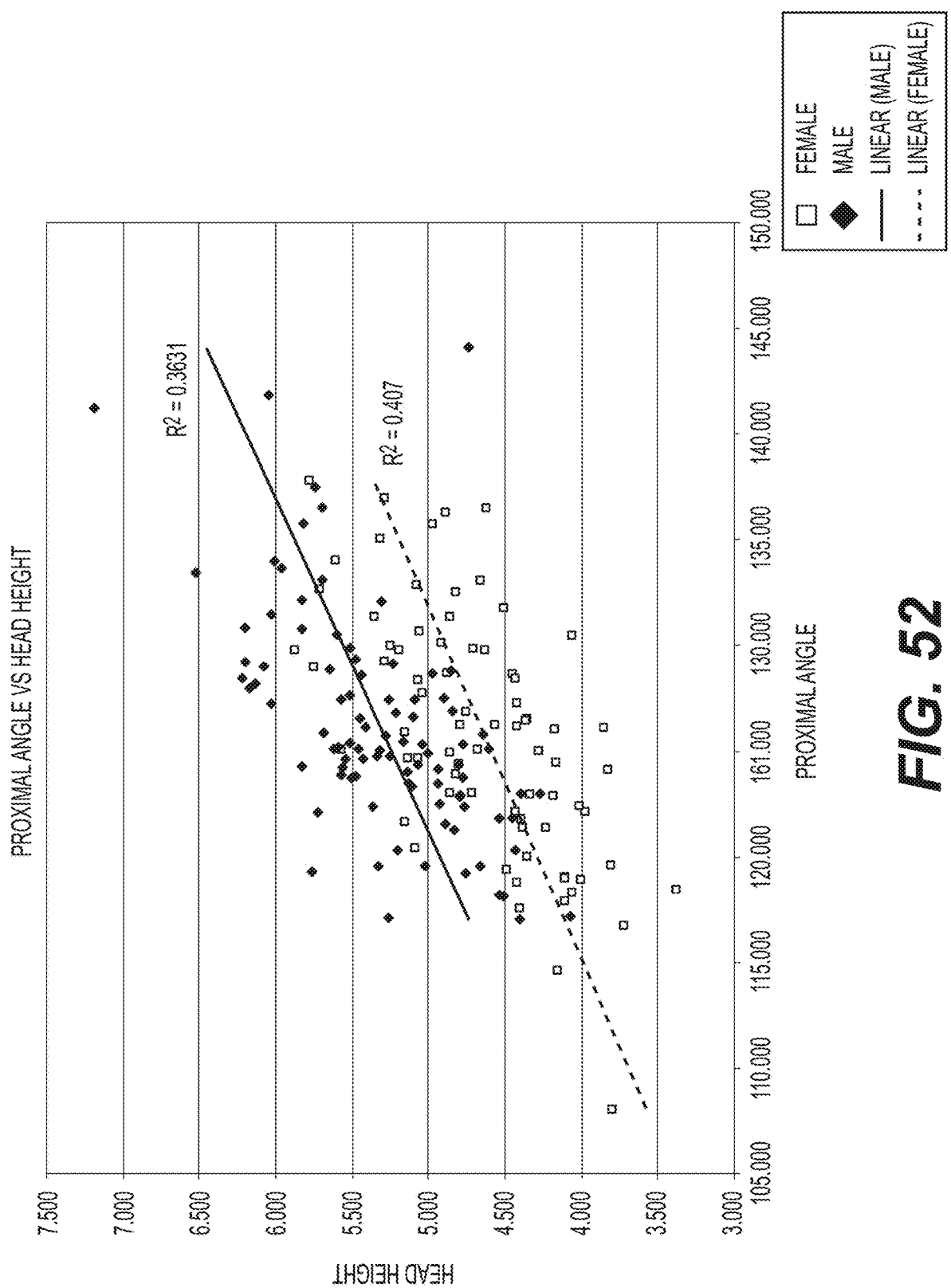
FIG. 52 is a plot of proximal angle versus head height.
Figure 53:
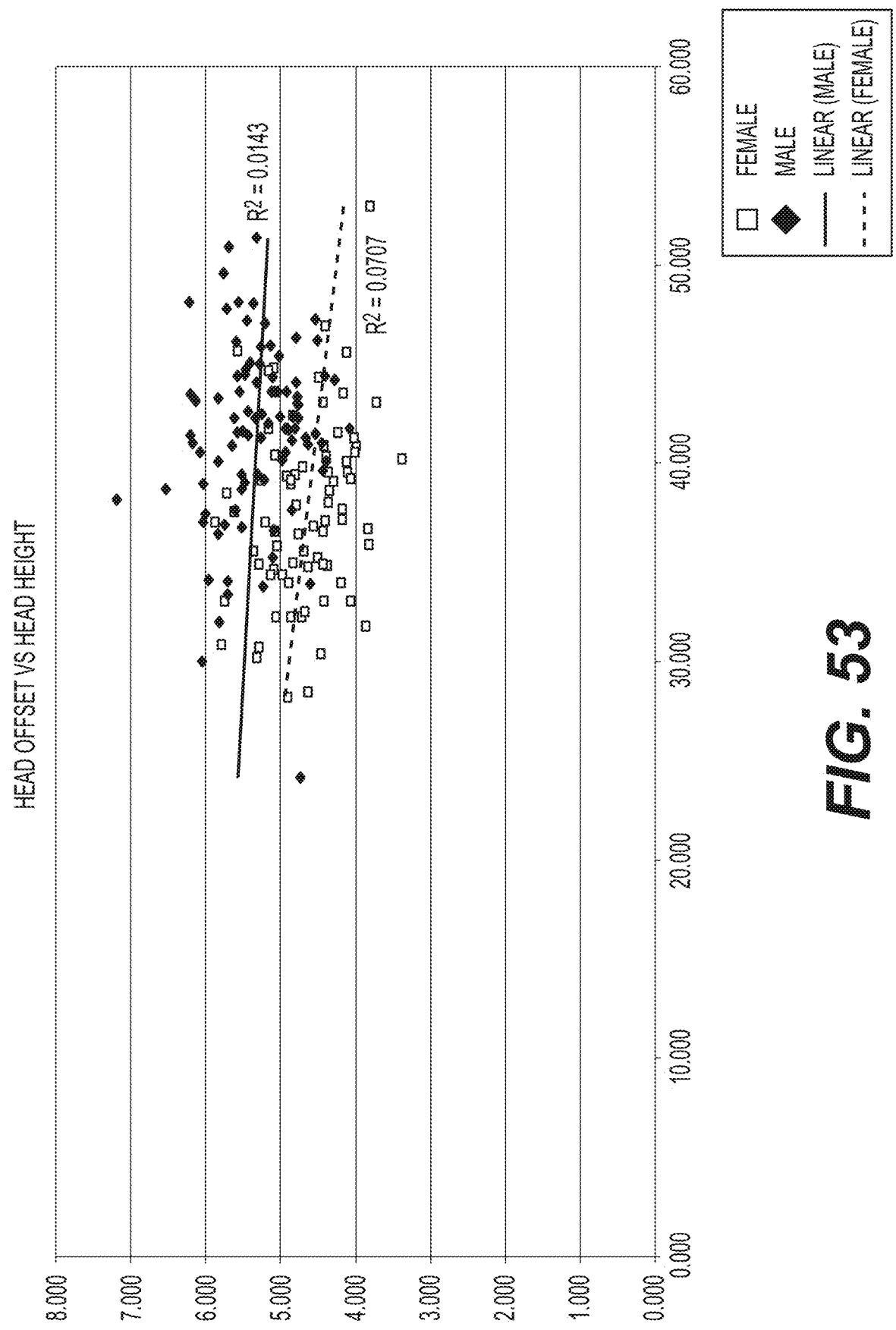
FIG. 53 is a plot of head offset versus head height.
Figure 54:
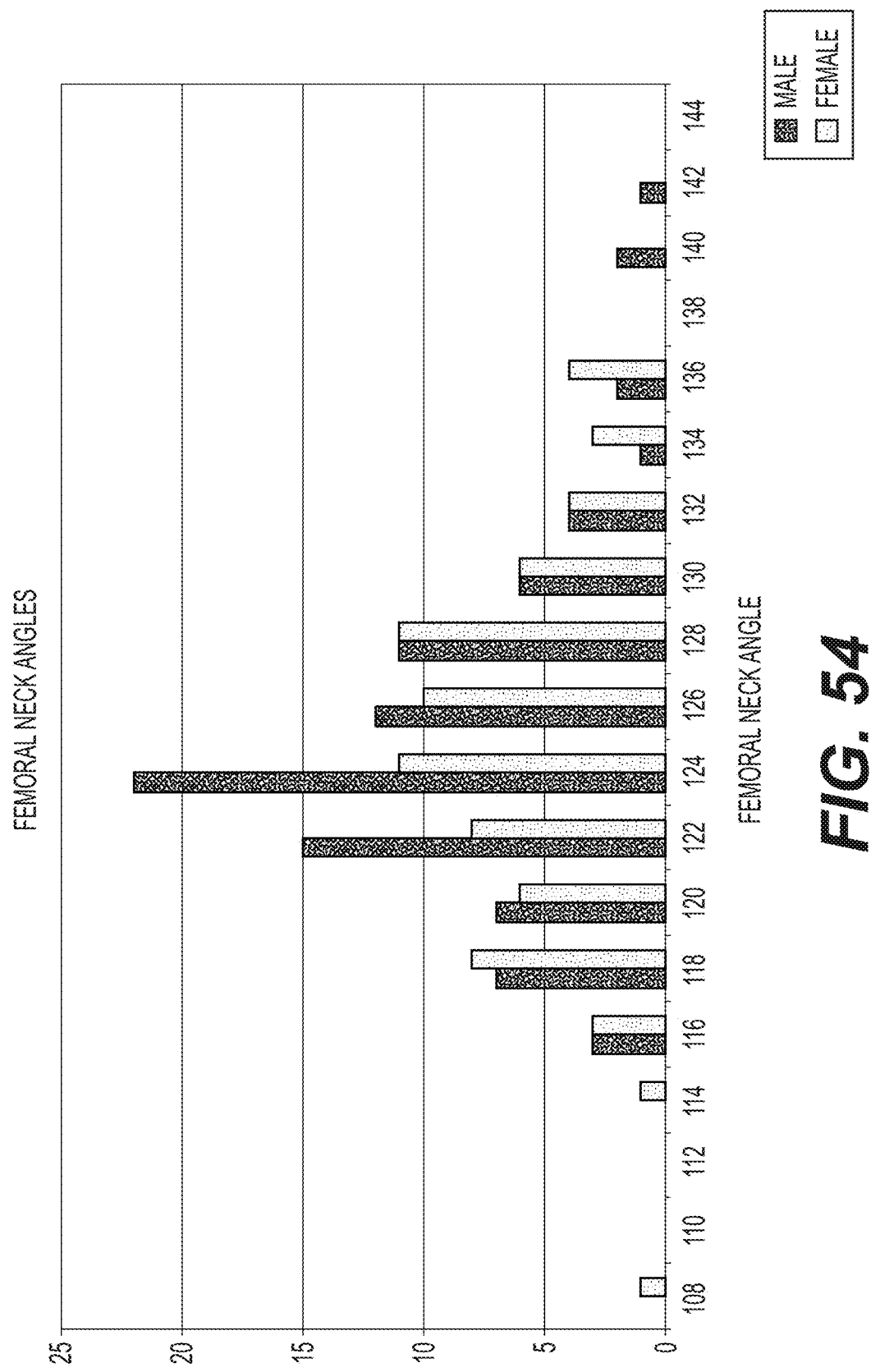
FIG. 54 is a proximal angle histogram.
Figure 55:
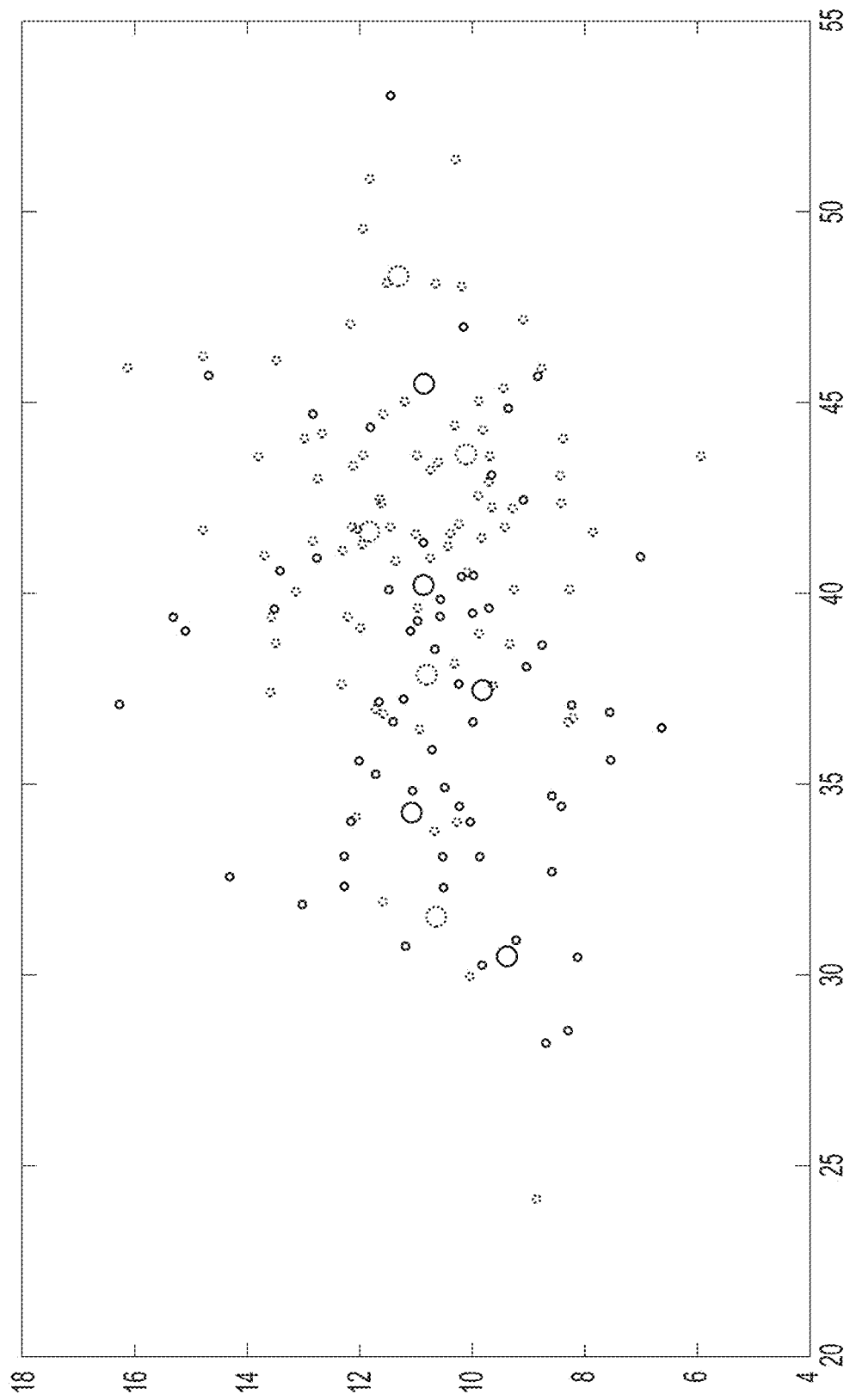
FIG. 55 is a plot depicting clusters of females and males for head offset and calcar diameter.
Figure 56:
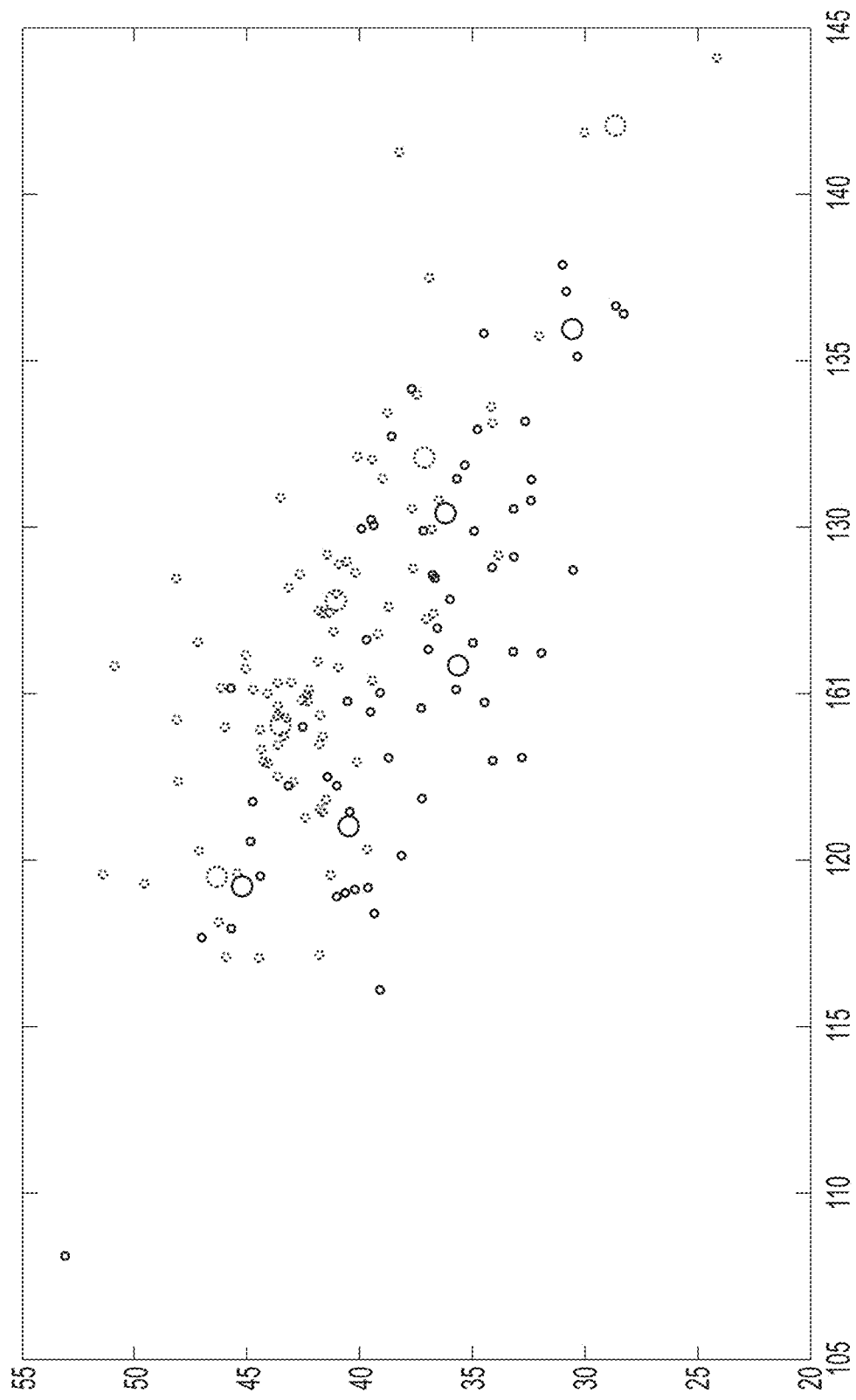
FIG. 56 is a plot depicting clusters of females and males for head offset and proximal angle.
Figure 57:
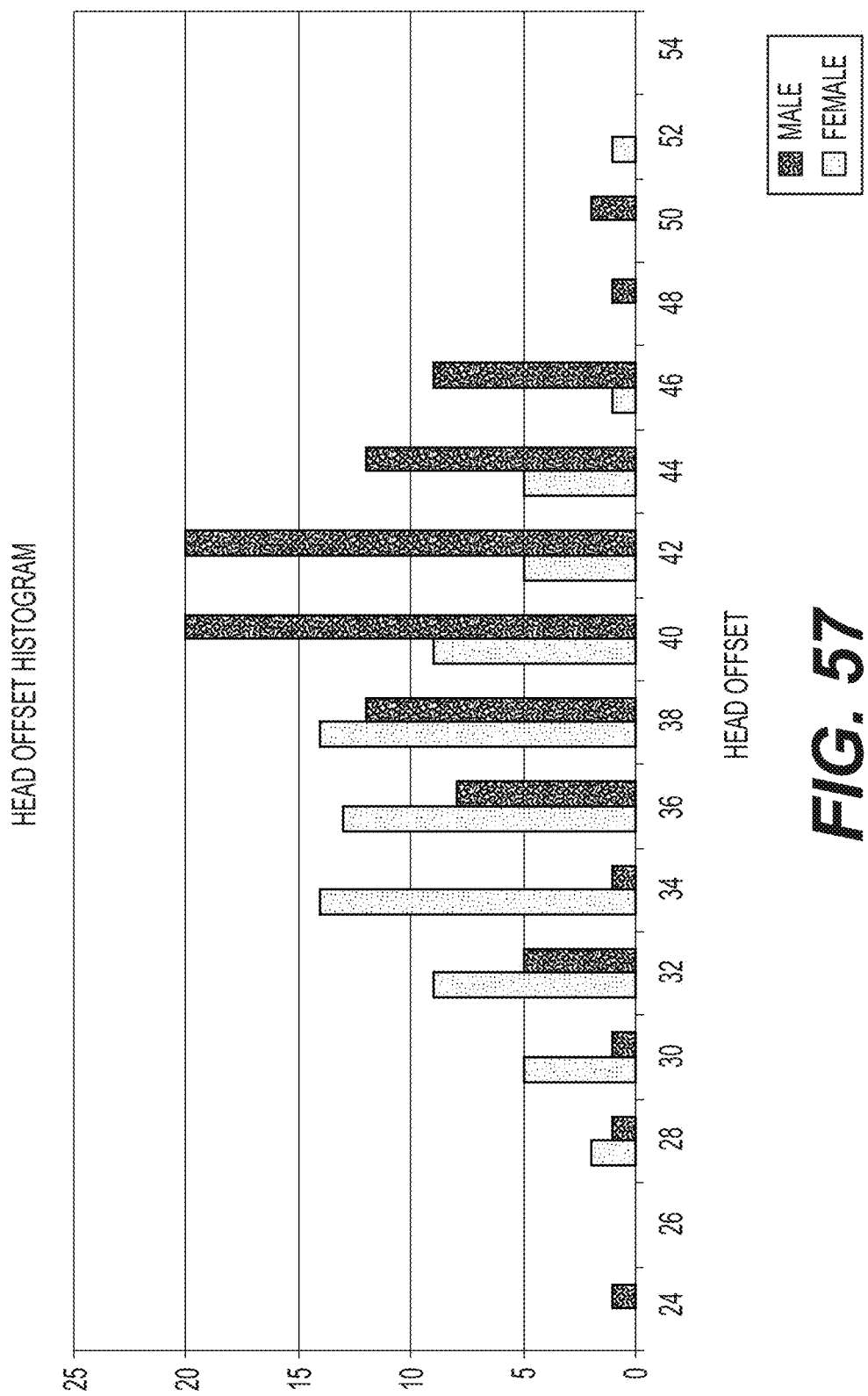
FIG. 57 is a head offset histogram.
Figure 58:
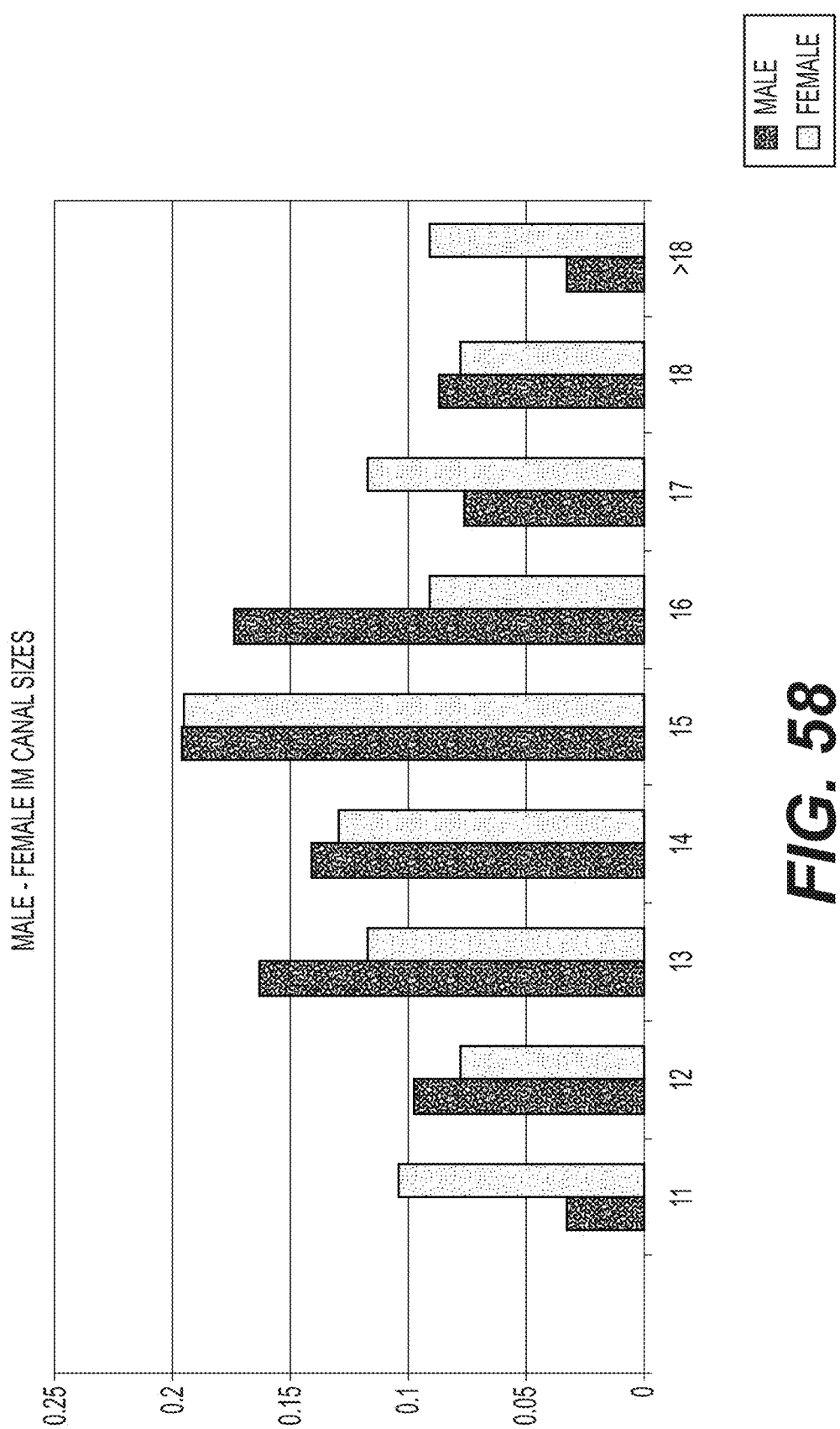
FIG. 58 is an IM sizes histogram.

Referring to FIG. 50 and Table I, in the context of X-ray images used to construct a virtual 3D bone model, it has been discovered that bone rotation during imaging plays an important role in correctly constructing the model. In other words, if one attempts to compile X-ray images in circumstances where bone rotation has occurred between images, the X-ray images need to be normalized to account for this bone rotation.

By way of example, in the context of a proximal femur, it has been discovered that bone rotation of six and fifteen degrees results in significant changes to the measurements extracted from X-ray images. By way of example, these measurements include, without limitation, proximal angle, head offset, and intramedullary canal width. As reflected in Table I, for the same femur, that was X-ray imaged at zero degrees (i.e., a starting point established by the initial X-ray), six degrees of rotation, and fifteen degrees of rotation exhibited differences proximal angle, head offset, and intramedullary canal width as measured using pixels, where each pixel size was approximately 0.29 millimeters. In particular, proximal angle increased with increasing rotation, as did head offset, but the same was not true for intramedullary width. In this exemplary table, three transverse planes were spaced apart along the longitudinal axis, where each plane corresponded to a location where the width of the intramedullary canal was measured. As reflected in Table I, the widths of the intramedullary canal for the same location change depending upon the angle of rotation. Consequently, as will be discussed in more detail hereafter, when constructing a 3D virtual model of a bone using X-rays, one must account for rotational deviation to the extent bone rotation occurs during imaging.

It should be understood, however, that the foregoing is an exemplary description of anatomies that may be used with the exemplary system and methods and, therefore, is in no way intended to limit other anatomies from being used with the present system pursuant to the disclosed methods. As used herein, tissue includes bone, muscle, ligaments, tendons, and any other definite kind of structural material with a specific function in a multicellular organism. Consequently, when the exemplary system and methods are discussed in the context of bone, those skilled in the art should realize the applicability of the system and methods to other tissue.

Referring back to FIG. 1, the anatomy data input to the system is directed to three modules, two of which involve processing of the anatomy data (full bone reconstruction module, patient-specific module), while a third (abnormal database module) catalogues the anatomy data as part of a database. A first of the processing modules, the full bone reconstruction module, processes the input anatomy data with data received from the statistical atlas module to generate a virtual, 3D model of the bone(s) in question. This 3D model is a full, normal reconstruction of the bone(s) in question. A second of the processing modules, the patient-specific module, processes the input anatomy data with data received from the full bone reconstruction module to generate one or more molds, fixation systems, graft shaping tools, and renderings, in addition to one or more final orthopedic implants. A rendering refers to visualization of reconstructed anatomy for feedback regarding expected surgical outcome. More specifically, the patient-specific module is adapted to generate fully customized devices, designed to precisely fit patient-specific anatomy, despite severe deviation of the patient's anatomy from normal. Moreover, the patient-specific module utilizes the virtual 3D reconstructed bone model from the full bone reconstruction module to automatically identify anatomical regions and features for device design parameters (e.g., fitting region and/or shape). In this fashion, patient-specific data is used to define design parameters so that the output instrument and any implant precisely fits the specific anatomy of the patient. Exemplary utilizations of the patient-specific module will be discussed in greater detail hereafter. In order to understand the functions and processes of the system in further detail, the following is an explanation of the modules of the system starting with the statistical atlas module.

Figure 2:
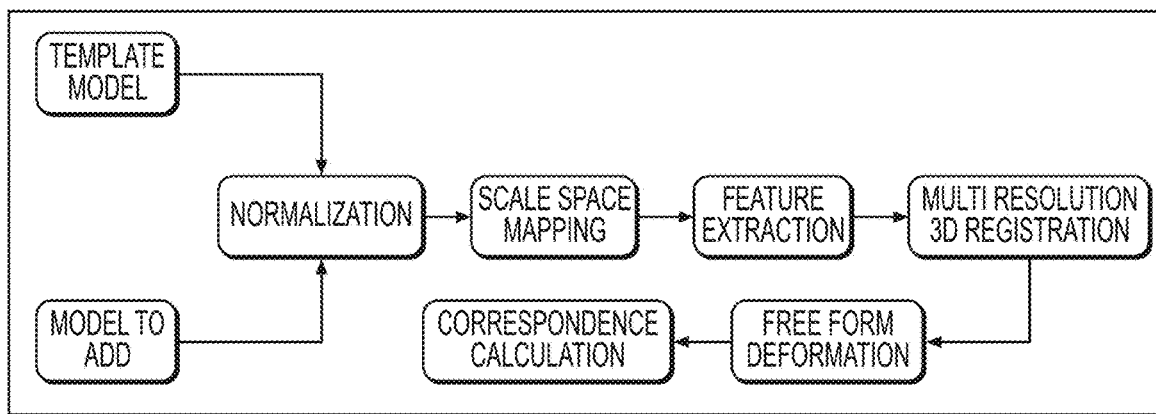
FIG. 2 is a schematic diagram detailing how to add a new anatomical structure to a statistical atlas in order to generate correspondence.

As shown in FIGS. 1 and 2, the statistical atlas module logs virtual, 3D models of one or more anatomies (e.g., bones) to capture the inherent anatomical variability in a given population. In exemplary form, the atlas logs mathematical representations of anatomical features of the one or more anatomies represented as a mean representation and variations about the mean representation. By representing the anatomical features as mathematical representations, the statistical atlas allows automated measurements of anatomies and, as will be discussed in more detail hereafter, reconstruction of missing anatomies.

In order to extract anatomical variations across a common anatomy, input anatomy data is compared to a common frame of reference across a population, commonly referred to as a template 3D model or anatomical 3D template model. This template 3D model is visually represented on a graphic display as a 3D model that can be rotated and otherwise visually manipulated, but comprises a mathematical representation of anatomical surface features/representations for all anatomies across the statistical atlas for the tissue in question (i.e., for a given bone all properties of the bone are shared across the population of the statistical atlas, which is generated from the template 3D model). The template 3D model can be a combination of multiple anatomical representations or a single representative instance and may represent the lowest entropy state of the statistical atlas. For each anatomy to be added to the statistical atlas (i.e., input anatomy data), an anatomical 3D model is created and both the anatomical 3D model and the template 3D model are subjected to a normalization process.

During the normalization process, the anatomical 3D model is normalized relative to the scale of the template 3D model. The normalization process may involve scaling one or both of the anatomical 3D model and the template 3D model to have a common unit scale. After normalization of the anatomical 3D model and the template 3D model, the normalized anatomical 3D model and template 3D model are rendered scale invariant, so that shape features can be utilized independent of scale (meaning size in this case). After normalization is complete, both 3D models are processed via a scale space mapping and feature extraction sequence.

Scale space mapping and feature extraction is essentially a multi-resolution feature extraction process. In particular, this process extracts shape-specific features at multiple feature scales. Initially, a plurality of anatomical features is selected, each representing features present at a different scale space. Thereafter, for each scale space representation of the selected anatomical feature, model specific features are extracted. These extracted features are used to draw out robust (as to noise) registration parameters between the template 3D model and the anatomical 3D model. Subsequent to this multi-resolution feature extraction process, the extracted data is processed via a multi-resolution 3D registration process.

Figure 5:
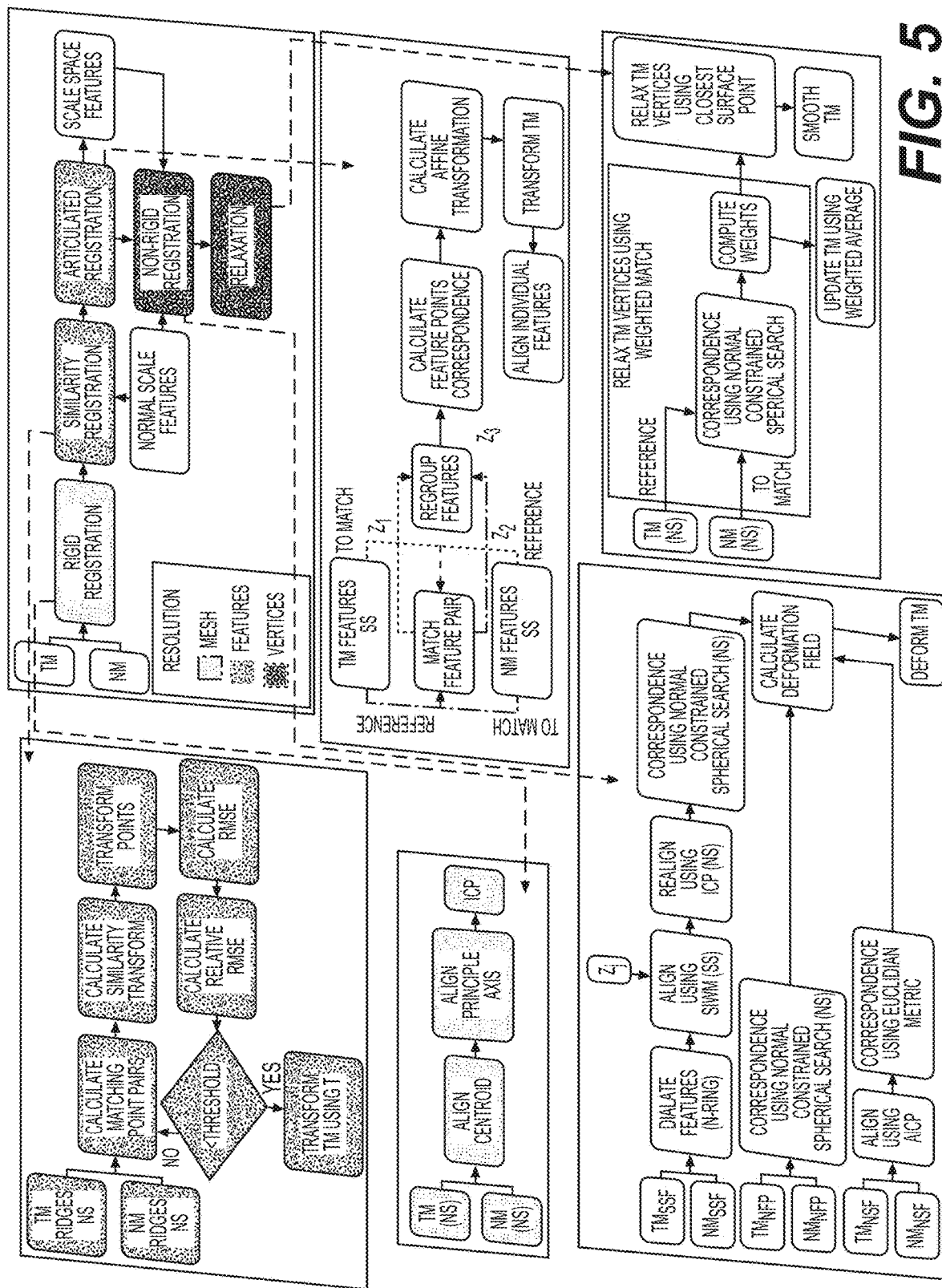
FIG. 5 is a low level break down of multi-resolution registration as outlined in FIG. 3.

Referring to FIGS. 2-5, the multi-resolution 3D registration process uses the scale space extracted features to carry out an affine registration calculation between the anatomical 3D model and template 3D model in order to register the two models. In particular, the anatomical 3D model and template 3D model are processed via a rigid registration process. As represented in FIG. 5, this rigid registration process is operative to align the anatomical 3D model and template 3D model to ensure both models are in the same space and with no pose singularity. In order to align the 3D models, the centroids associated with each model are aligned. In addition, the principle axes for each 3D model are aligned so that the major direction of both 3D models is the same. Finally, the pose difference between the 3D models is minimized by carrying out an iterative closest point calculation.

Post rigid registration, the 3D models are registered using a similarity registration process. This process involves aligning the template 3D model and the anatomical 3D model in normal scale iteratively by calculating a similarity transform that best aligns the normal scale features (i.e., ridges) for both the template 3D model and the anatomical 3D model. The iterative similarity alignment algorithm is a variant of iterative closest point. Within each iteration rotation, translation and scale are calculated between point pairs until convergence. Pair matching or correspondence between the two set of points is evaluated using distance query calculated using Kd-tree, or some other space partitioning data structure. In particular, the ridges for both models are utilized to carry out a calculate matching point pairs process. In this exemplary description, ridges refers to points on a 3D model where a single principle curvature has extrema along its curvature lines. As part of the calculate matching point pairs process, points are identified on ridges of the 3D models that match one another. Next, the ridges of both 3D models are subjected to a similarity transformation calculation process where rotation, translation, and scale are calculated that best align the ridges of both models. A transform points process follows, which is operative to apply the calculated rotation, translation, and scale to the template 3D model ridges. Thereafter, the root mean square error or distance error between each matched point set is calculated, followed by calculation of the change in relative root mean square error or distance error from the previous process. If the change in relative root mean square error or distance error is within a predetermined threshold, then a transformation process occurs to apply the final rotation, translation, and scale to the template 3D model.

An articulated registration process follows the similarity registration process and receives input data from a scale space features process. In the scale space feature process, feature are extracted from the template 3D model and the anatomical 3D model in different scale spaces. Each scale space is defined by convolving the original anatomical 3D model with Gaussian smoothing function.

The purpose of the articulated registration process is to match "n" scale space features of the template 3D model with "m" scale space features calculated on the anatomical 3D model. The difference between the number of detected features on the template 3D model and the anatomical 3D model is due to anatomical variation. This difference in a number of detected features may result in many relationships between the template 3D model and the anatomical 3D model. Therefore, a two-way, mutual feature matching is performed to accommodate such variation and achieve accurate matching between all mutual features. Specifically, feature sets are computed on the template 3D model in scale space. In this exemplary process, feature sets are connected sets of points that represent a prominent anatomical structure (e.g., acetabular cup in the pelvis, spine process in the lumbar). Likewise, feature sets are computed on the anatomical 3D model in scale space. A matching feature pair process matches the feature sets computed on the template 3D model to the feature sets on the anatomical 3D model using shape descriptors (e.g., curvature, shape index, etc.). The result of this process is an "n-m" mapping of feature sets between the template 3D model and the anatomical 3D model. If necessary, a regrouping process is carried out to regroup the matched feature sets into a single feature set (e.g., if acetabular cup was detected as two pieces, this process would regroup the two pieces into one single feature set). Thereafter, a calculation process is carried out to calculate the correspondence between each point in matched feature sets on the template 3D model and the anatomical 3D model. An affine calculation transformation process follows in order to calculate the rotation, translation, and shear that transform each matched feature set on the template 3D model to its corresponding feature set on the anatomical 3D model. Thereafter, the template 3D model is transformed using the calculated affine transformation parameters (i.e., rotation, translation, and shear). Finally, a rigid alignment process is carried out to align each matched feature set on the template 3D model and the anatomical 3D model.

A non-rigid registration process, occurring after the articulated registration process and the normal scale features process, involves matching all surface vertices on the template 3D model to vertices on the anatomical 3D model and calculating initial correspondence. This correspondence is then used to calculate deformation fields that move each vertex on the template 3D model to the matched point on the anatomical 3D model. Matching is done between vertices within the same class (i.e., scale space feature vertex; normal scale feature vertex, or non-feature vertex). In the context of the normal scale features process, shape features are calculated on the template 3D model and the anatomical 3D model in the original scale space (ridges), meaning the original input model.

Specifically, as part of the non-rigid registration process, the scale space features are calculated on the template 3D model (TMssf) and on the anatomical 3D model (NMssf). Each set of features on the template 3D model and on the anatomical 3D model are grown using "k" neighbor points. An alignment process is applied to the template 3D model scale space features to match its corresponding feature on the anatomical 3D model. Given two point clouds, reference (X) and moving (Y), the goal is to iteratively align the two point clouds to minimize overall error metric, under constraint of a minimum relative root mean squared error and maximum angle threshold. A realignment process is carried out to align feature sets on the template 3D model with the matching sets on the anatomical 3D model using iterative closest point in normal scale. Post realignment, the point correspondence between points in each feature set on the template 3D model with the matched feature set on the anatomical 3D model is calculated. The matched point on the anatomical 3D model should have a surface normal direction close to the template 3D model point. The output is forwarded to the calculate deformation fields step.

Parallel to the scale space features calculation course, template 3D model (TMnfp) and anatomical 3D model (NMnfp) non-feature points or the remaining set of points on the template 3D model surface that does not belong to either scale space features or normal scale features are processed pursuant to a correspondence calculation to calculate the point correspondence between non-feature points on the template 3D model and non-feature points on the anatomical 3D model. The matched point(s) on the new model should have a surface normal direction close to the template model point. The output is forwarded to the calculate deformation fields step.

Also parallel to the scale space features calculation course, normal scale features (i.e., ridges) on the template 3D model (TM nsf) are aligned with the normal scale features (i.e., ridges) on the anatomical 3D model (NM nsf) using AICP. AICP is a variant of the iterative closest point calculation where in each iteration translation, rotation, and scale are calculated between matched point sets. After the alignment process, a correspondence process is carried out.

The outputs from scale space features calculation course, the correspondence course, and the alignment course are subjected to a deformation process where the deformation field is calculated to move each point on the template 3D model to its matched point on the anatomical 3D model.

The output of the non-rigid registration process is a subjected to a relaxation process in order to move the vertices of the template 3D model mesh closer to surface of the anatomical 3D model after the multi-resolution registration step and smooth the output model. In particular, the template 3D model in normal space (TM ns) and the anatomical 3D model in normal space (NM ns) are processed via a correspondence calculation to compute the closest vertices on template 3D model to the anatomical 3D model using a normal constrained spherical search algorithm. This calculation, using the closest vertices for both models, generates a correspondence vector from each vertex in the template 3D model and its matched vertices in anatomical 3D model, which may result in more than one match point from the anatomical 3D model. Using the matched points for each vertex on the template 3D model, the weighted mean of the matched points on the anatomical 3D model is calculated based on the Euclidian distance from the point and matched points. At this point, the template 3D model is updated using the weighted average so as to move each point on template 3D model using the calculated weighted average distance. After the computed weights process, a relaxation process is carried out for every point on template model in order to find the closest point on the anatomical 3D model surface and move it to that point. Finally, a smoothing operation is performed on the deformed template 3D model to remove noise. The resultant registered 3D models (i.e., template and anatomical 3D models) are then subjected to a free form deformation process.

The free form deformation process morphs the surface of the template 3D model with the surface of the anatomical 3D model. More specifically, the surface of the template 3D model is iteratively moved on a weighted point-to-point basis using mutually matched points on both the template 3D model surface and the anatomical 3D model surface.

Figure 6:
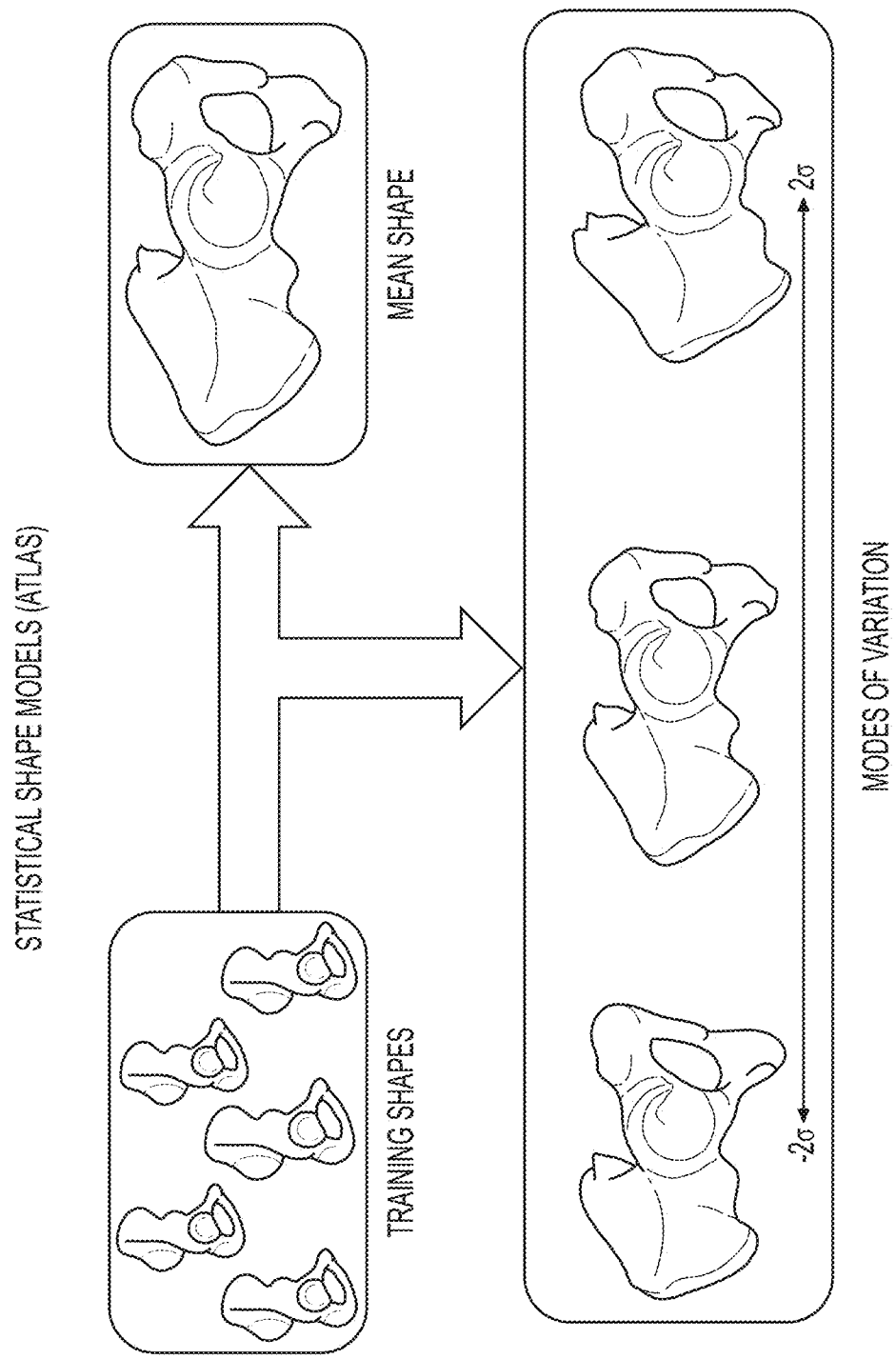
FIG. 6 is a graphical representation of capturing variation in population upon generation of correspondence

Referencing FIGS. 2 and 6, after the free form deformation process, the anatomical 3D model is subjected to a correspondence calculation process to determine the deviation between the anatomical 3D model and the morphed template 3D model. This correspondence calculation process refines the template 3D model from the free form deformation step to perform a final match of the selected landmark locations on the template deformed 3D model and the deformed anatomical 3D model. In this fashion, the correspondence calculation process calculates and records the variation in size and shape between the 3D models, which is recorded as deviation about the mean model. The output of this correspondence calculation process is the addition of a normalized anatomical 3D model and a revised template 3D model having been updated to account for the variations in the anatomical 3D model. In other words, the output of the process outlined in FIG. 2 is the normalized anatomical 3D model having been modified to have properties (e.g., point correspondence) consistent with the revised template 3D model to facilitate full anatomical reconstruction (e.g., full bone reconstruction).

Figure 7:
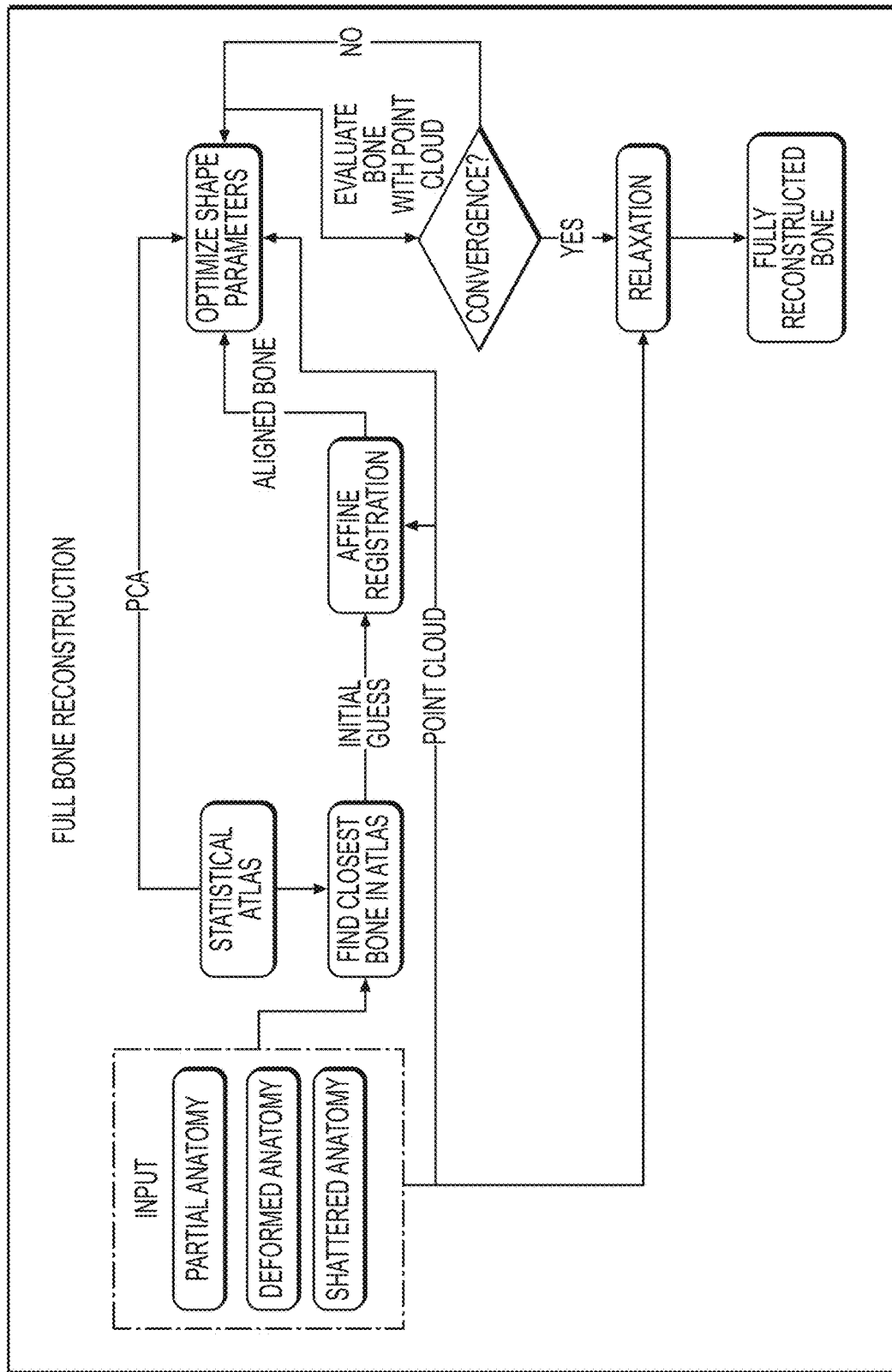
FIG. 7 is a schematic diagram of a full bone reconstruction process using partial, deformed or shattered anatomy.

Referring to FIGS. 1 and 7, inputs from the statistical atlas module and anatomy data are directed to a full anatomy reconstruction module. By way of example, the anatomy in question may be a bone or multiple bones. It should be noted, however, that anatomies other than bone may be reconstructed using the exemplary hardware, processes, and techniques described herein. In exemplary form, the full anatomy reconstruction module may receive input data as to a partial, deformed, or shattered pelvis. Input anatomical data comprises two dimensional (2D) images or three dimensional (3D) surface representations of the anatomy in question that may, for example, be in the form of a surface model or point cloud. In circumstances where 2D images are utilized, these 2D images are utilized to construct a 3D surface representation of the anatomy in question. Those skilled in the art are familiar with utilizing 2D images of anatomy to construct a 3D surface representation. Accordingly, a detailed explanation of this process has been omitted in furtherance of brevity. By way of example, input anatomical data may comprise one or more of X-rays, computed tomography (CT) scans, magnetic resonance images (MRIs), or any other imaging data from which a 3D surface representation may be generated. As will be discussed in more detail hereafter, this input anatomical data may be used, without limitation, for: (1) a starting point for identifying the closest statistical atlas 3D bone model; (2) registration using a set of 3D surface vertices; and, (3) a final relaxation step of reconstruction output.

Figure 3:
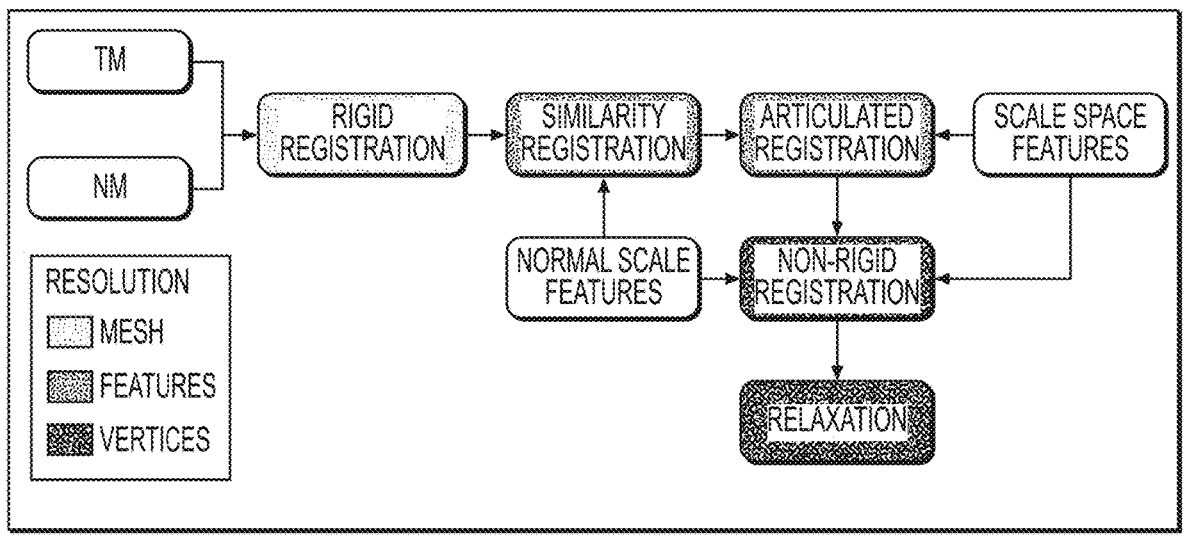
FIG. 3 is a multi-resolution 3D registration algorithm overview corresponding to the multi-resolution 3D registration in FIG. 2.
Figure 4:
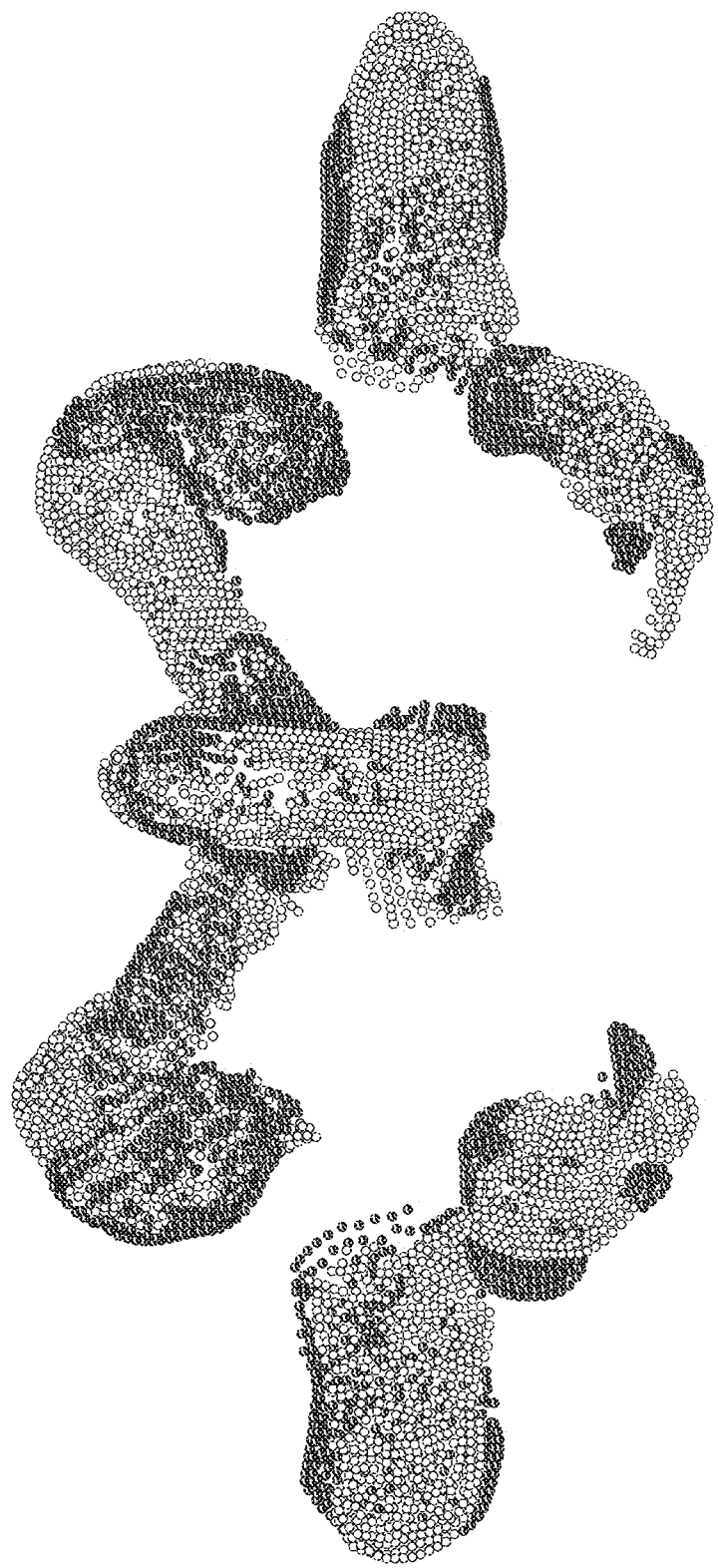
FIG. 4 is a multi-scale registration of feature points using multi-scale features.

As depicted in FIG. 7, the input anatomical data (e.g., bone model of the patient) is utilized to identify the anatomical model (e.g., bone model) in the statistical atlas that most closely resembles the anatomy of the patient in question. This step is depicted in FIG. 3 as finding the closest bone in the atlas. In order to initially identify a bone model in the statistical atlas that most closely resembles the patient's bone model, the patient's bone model is compared to the bone models in the statistical atlas using one or more similarity metrics. The result of the initial similarity metric(s) is the selection of a bone model from the statistical atlas that is used as an "initial guess" for a subsequent registration step. The registration step registers the patient bone model with the selected atlas bone model (i.e., the initial guess bone model) so that the output is a patient bone model that is aligned with the atlas bone model. Subsequent to the registration step, the shape parameters for aligned "initial guess" are optimized so that the shape matches the patient bone shape.

Shape parameters, in this case from the statistical atlas, are optimized so that the region of non-deformed or existing bone is used to minimize the error between the reconstruction and patient bone model. Changing shape parameter values allows for representation of different anatomical shapes. This process is repeated, at different scale spaces, until convergence of the reconstructed shape is achieved (possibly measured as relative surface change between iterations or as a maximum number of allowed iterations).

A relaxation step is performed to morph the optimized tissue to best match the original patient 3D tissue model. Consistent with the exemplary case, the missing anatomy from the reconstructed pelvis model that is output from the convergence step is applied to the patient-specific 3D pelvis model, thereby creating a patient-specific 3D model of the patient's reconstructed pelvis. More specifically, surface points on the reconstructed pelvis model are relaxed (i.e., morphed) directly onto the patient-specific 3D pelvis model to best match the reconstructed shape to the patient-specific shape. The output of this step is a fully reconstructed, patient-specific 3D tissue model representing what should be the normal/complete anatomy of the patient.

Referencing FIG. 1, the abnormal database is utilized as a data input and training for the defect classification module. In particular, the abnormal database contains data specific to an abnormal anatomical feature that includes an anatomical surface representation and related clinical and demographic data.

Figure 8:
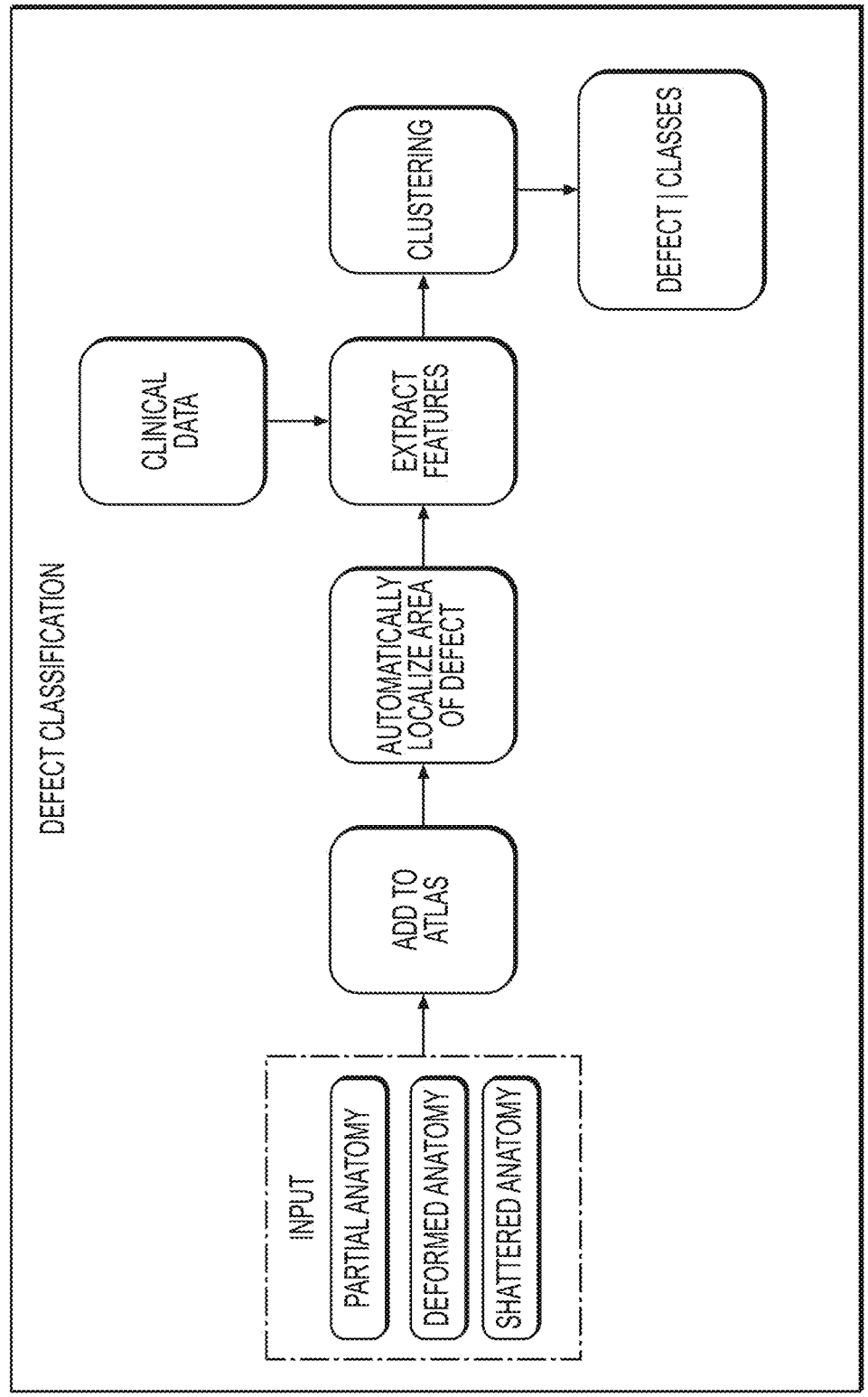
FIG. 8 is a schematic diagram of a defect classification process for generation of defect templates.
Figure 9:
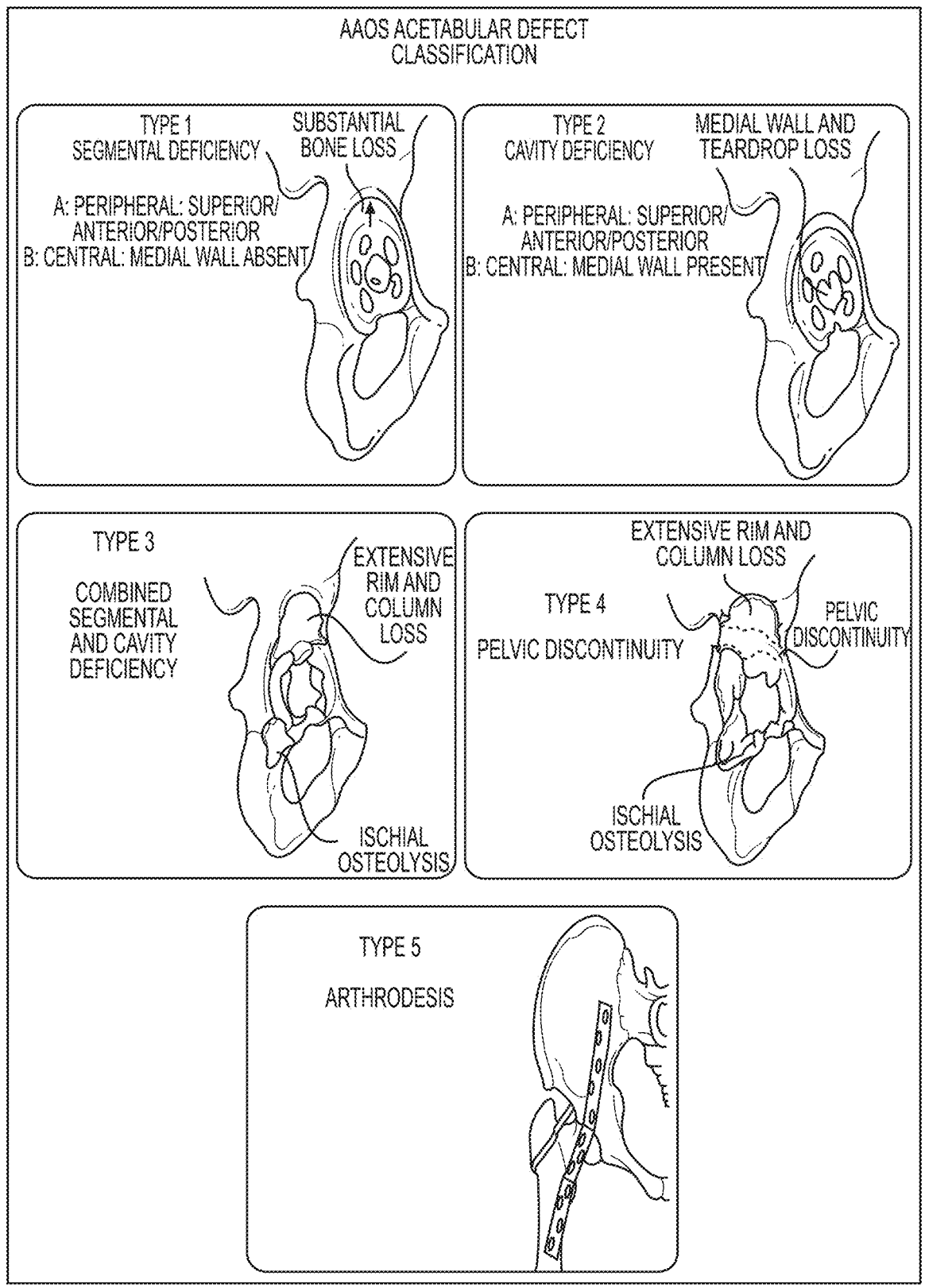
FIG. 9 is a graphical example of existing AAOS classifications for acetabular defects.

Referencing FIGS. 1 and 8, the fully reconstructed, patient-specific 3D tissue model representing the normal/complete tissue and input anatomical data (i.e., 3D surface representation or data from which a 3D surface representation may be generated) representing abnormal/incomplete tissue from the abnormal database are input to the defect classification module. This anatomical data from the abnormal database may be a partial anatomy in the case of tissue degeneration or tissue absence resulting from genetics, or this anatomy may be a deformed anatomy resulting from genetics or environmental conditions (e.g., surgical revisions, diseases, etc.), or this anatomy may be a shattered tissue resulting from one or more anatomy breaks. By way of example, input anatomical data may comprise one or more of X-rays, computed tomography (CT) scans, magnetic resonance images (MRIs), or any other imaging data from which a 3D surface representation may be generated.

The defect classification module pulls a plurality of abnormal 3D surface representations from abnormal database coupled with the normal 3D representation of the anatomy in question to create a quantitative defect classification system. This defect classification system is used to create "templates" of each defect class or cluster. More generally, the defect classification module classifies the anatomical deficiency into classes which consist of closely related deficiencies (referring to those with similar shape, clinical, appearance, or other characteristics) to facilitate the generation of healthcare solutions which address these deficiencies. The instant defect classification module uses software and hardware to classify the defects automatically as a means to eliminate or reduce discrepancies between pre-operative data and intra-operative observer visualization. Traditionally, pre-operative radiographs have been taken as a means to qualitatively analyze the extent of anatomical reconstruction necessary, but this resulted in pre-operative planning that was hit-or-miss at best. Currently, intra-operative observers make the final determination of the extent of anatomy deficiency and many times conclude that the pre-operative planning relying on radiographs was defective or incomplete. As a result, the instant defect classification module improves upon current classification systems by reducing interobserver and intraobserver variation related to defect classification and providing quantitative metrics for classifying new defect instances.

Figure 10:
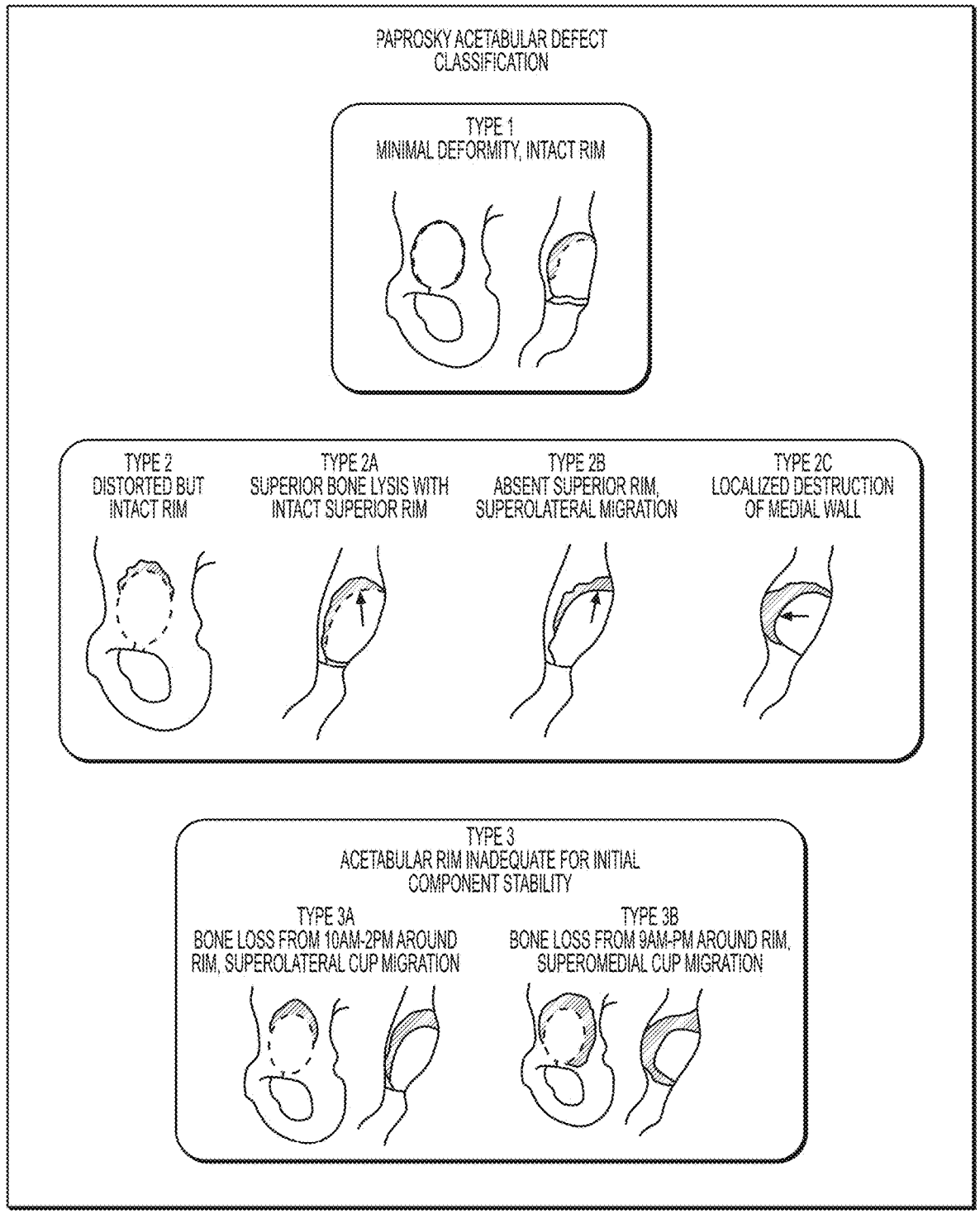
FIG. 10 is a graphical example of existing Paprosky acetabular defect classifications.
Figure 12:
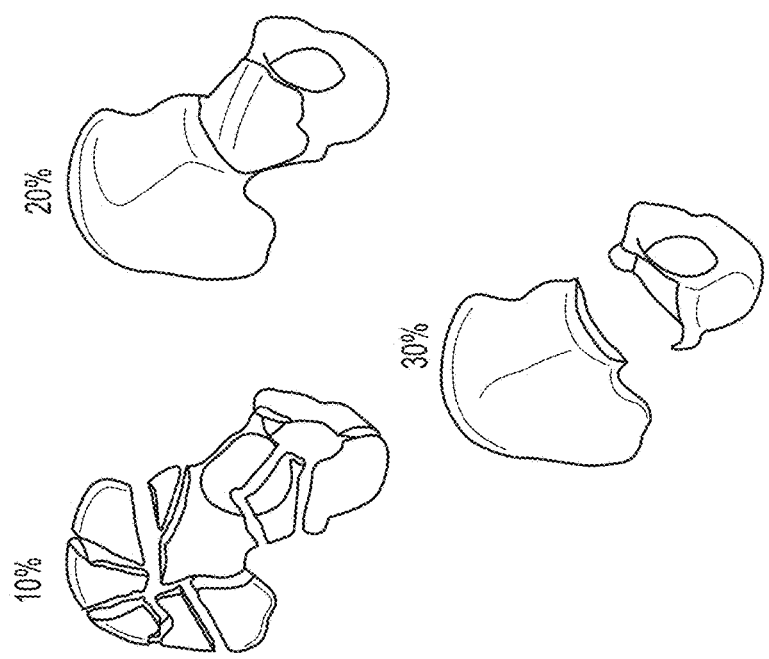
FIG. 12 is a table and associated drawings showing the results of reconstruction on a pelvis for different defects, which is an exemplary application and validation of the full bone reconstruction depicted in FIG. 7.
Figure 13:
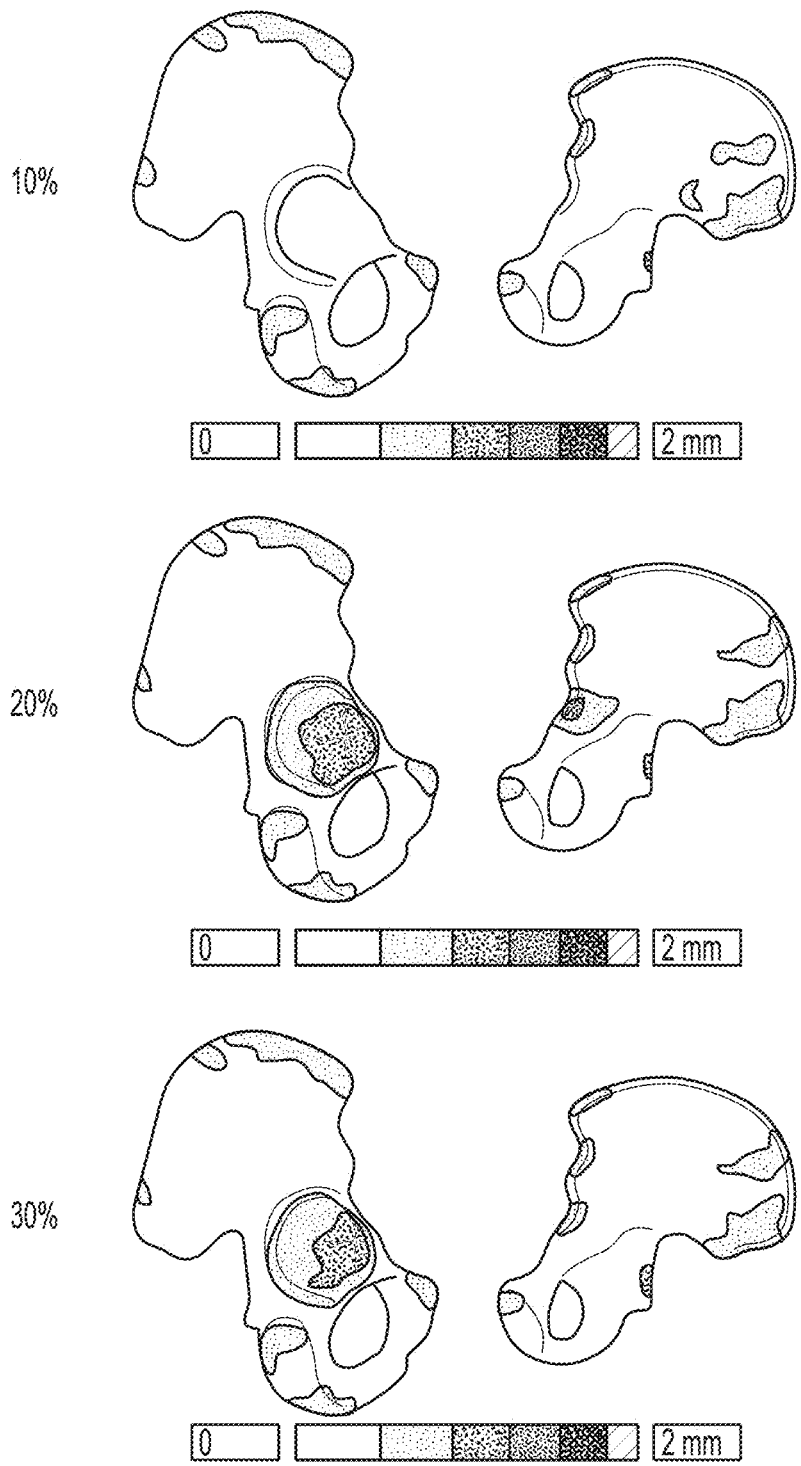
FIG. 13 is a distance map for the mean RMS error of reconstruction on a pelvis for different defects, which validates the accuracy of the full bone reconstruction depicted in FIG. 7.
Figure 14:
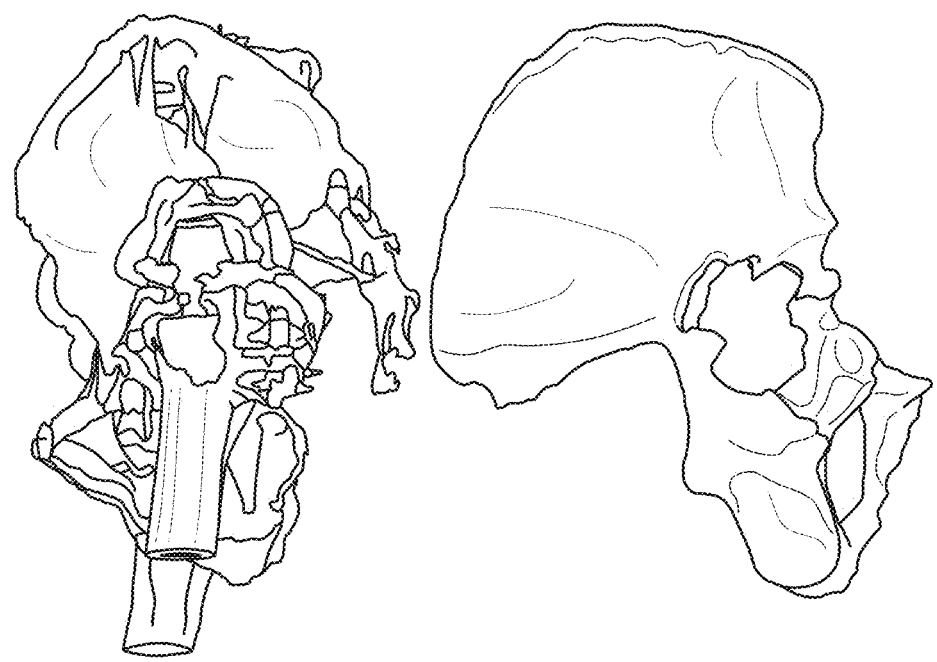
FIG. 14 is a three dimensional model representation of a patient with severe pelvis discontinuity on the left. On the right is an example of the three dimensional model of the patient's pelvis shown on the left.
Figure 15:
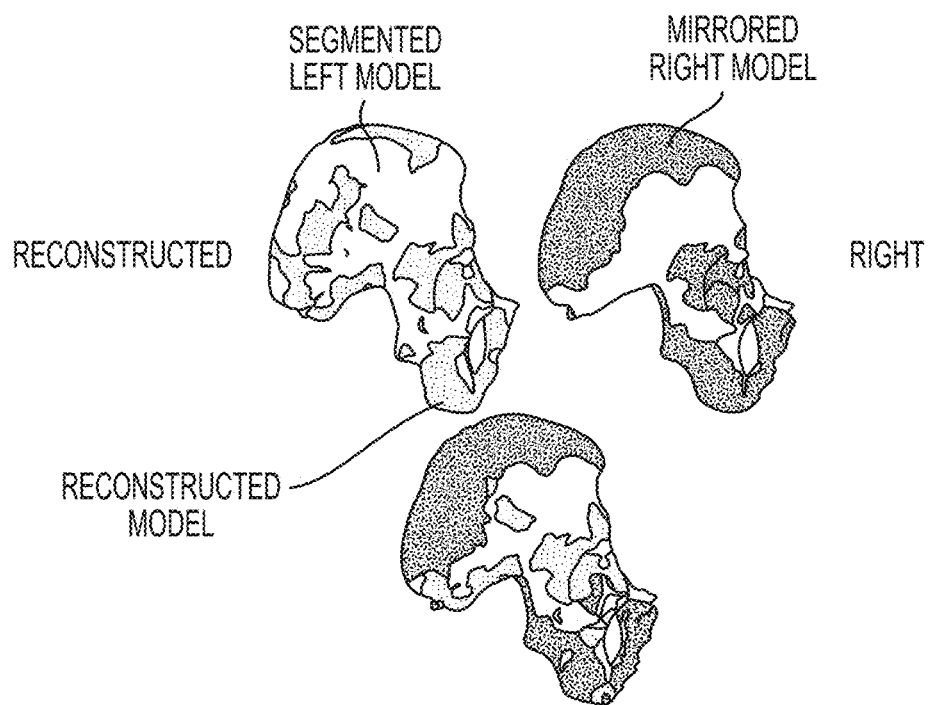
FIG. 15 is a comparison of the reconstructed left model and the original patient model, as well as right and left anatomy.
Figure 16:
FIG. 16 is a distance map between a reconstructed model and a mirror image of the pelvis model reconstructed.
Figure 17:
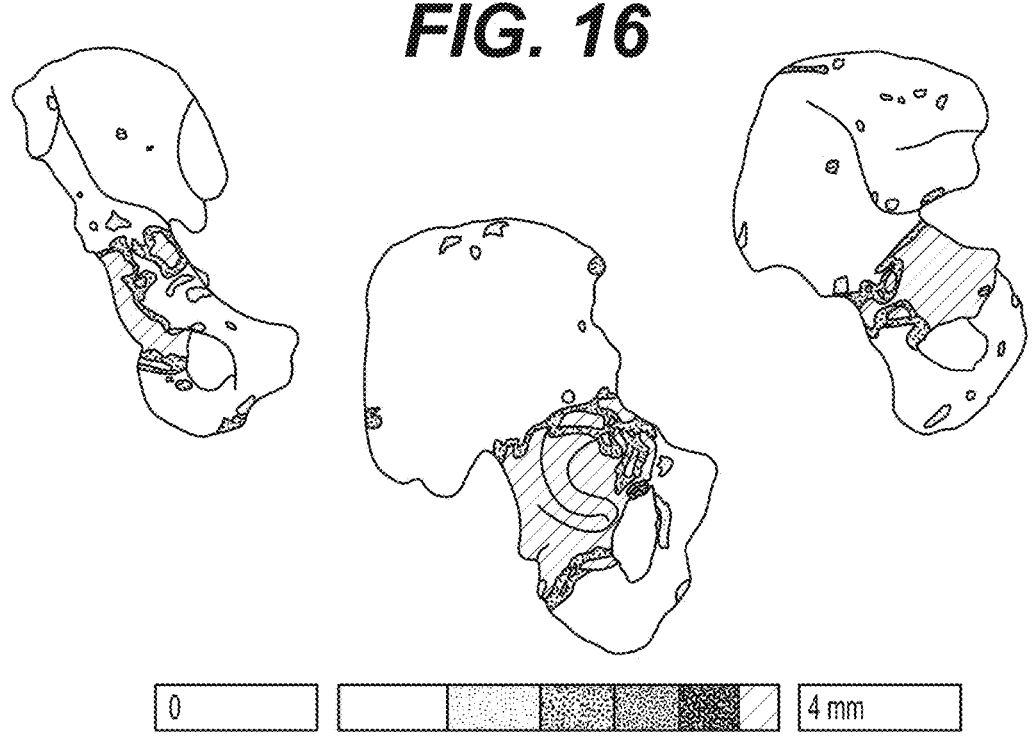
FIG. 17 is a patient with complete pelvis discontinuity and results of reconstruction with RMS error of 1.8 mm.
Figure 18:
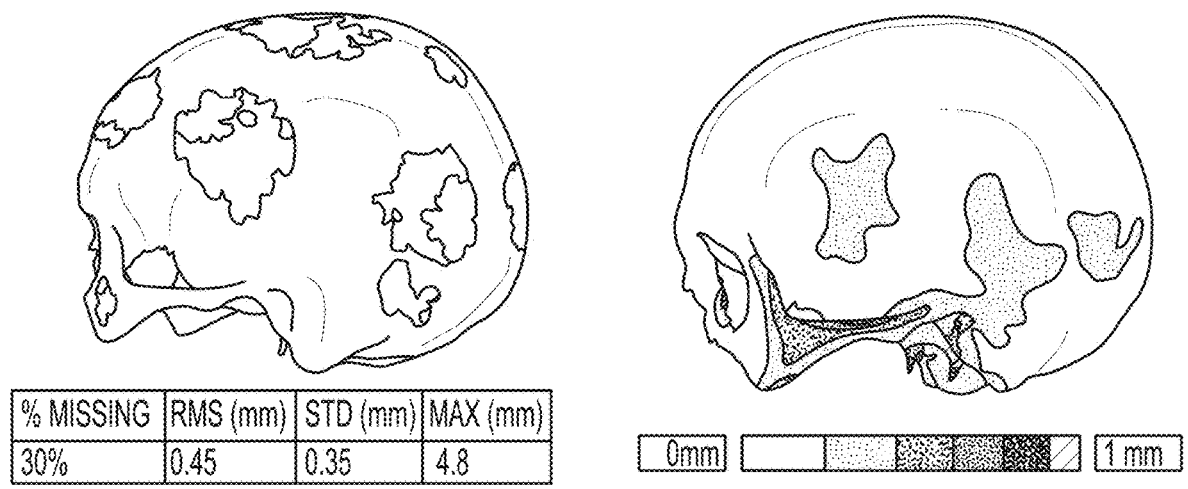
FIG. 18 are the results of reconstruction on partial skulls and mean distance map for reconstruction error.
Figure 19:
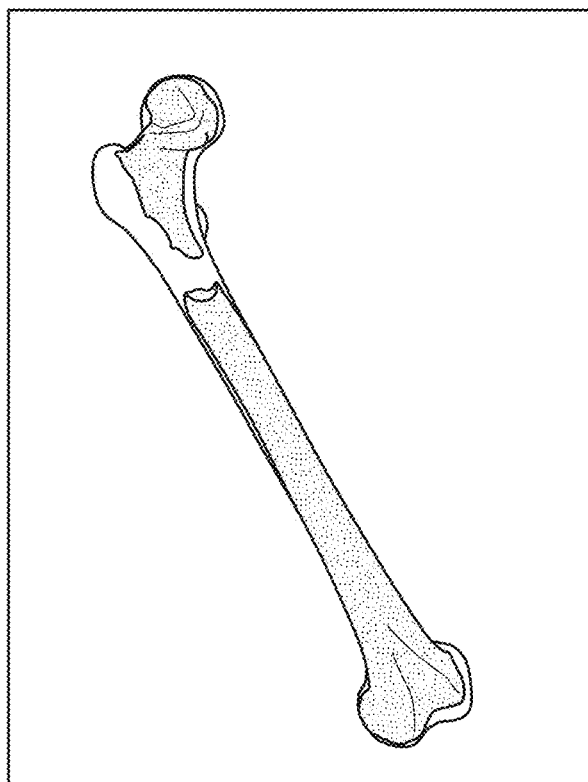
FIG. 19 are the results of reconstruction of a shattered femur.

As part of the defect classification module, the module may take as an input one or more classification types to be used as an initial state. For example, in the context of a pelvis, the defect classification module may use as input defect features corresponding to the American Academy of Orthopaedic Surgeons (AAOS) D'Antonio et al. bone defect classification structure. This structure includes four different classes as follows: (1) Type I, corresponding to segmental bone loss; (2) Type II, corresponding to cavitary bone loss; (3) Type III, corresponding to combined segmental and cavitary bone loss; and, (4) Type IV, corresponding to pelvis discontinuity. Alternatively, the defect classification module may be programmed with the Paprosky bone defect classification structure, depicted graphically for the pelvis in FIG. 10. This structure includes three different classes as follows: (1) Type I, corresponding to supportive rim with no bone lysis; (2) Type II, corresponding to distorted hemispheres with intact supportive columns and less than two centimeters of superomedial or lateral migration; and, (3) Type III, corresponding to superior migration greater than two centimeters and sever ischial lysis with Kohler's line broken or intact. Moreover, the defect classification module may be programmed with the Modified Paprosky bone defect classification structure. This structure includes six different classes as follows: (1) Type 1, corresponding to supportive rim with no component migration; (2) Type 2A, corresponding to distorted hemisphere but superior migration less than three centimeters; (3) Type 2B, corresponding to greater hemisphere distortion having less than ⅓ rim circumference and the dome remaining supportive; (4) Type 2C, corresponding to an intact rim, migration medial to Kohler's line, and the dome remains supportive; (5) Type 3A, corresponding to superior migration, greater than three centimeters and severe ischial lysis with intact Kohler's line; and, (6) Type 3B, corresponding to superior migration, greater than three centimeters and severe ischial lysis with broken Kohler's line and rim defect greater than half the circumference. Using the output classification types and parameters, the defect classification module compares the anatomical data to that of the reconstructed data to discern which of the classification types the anatomical data most closely resembles, thereby corresponding to the resulting assigned classification.

As an initial step, the add to statistical atlas step involves generating correspondence between normal atlas 3D bone model and the abnormal 3D bone model. More specifically, the 3D bone models are compared to discern what bone in the normal 3D model is not present in the abnormal 3D model. In exemplary form, the missing/abnormal bone is identified by comparing points on the surface of each 3D bone model and generating a list of the discrete points on the surface of the normal 3D bone model that are not present on the abnormal 3D bone model. The system may also record and list (i.e., identify) those surface points in common between the two models or summarily note that unless recorded as points being absent on the abnormal 3D bone model, all other points are present in common in both bone models (i.e., on both the normal and abnormal bone models). Accordingly, the output of this step is the abnormal 3D bone model with statistical atlas correspondence and a list of features (points) from the normal atlas 3D bone model indicating if that feature (point) is present or missing in the abnormal 3D bone model.

After generating correspondence between the normal atlas 3D bone model (generated from the full bone reconstruction module) and the abnormal 3D bone model (generated from the input anatomical data), the missing/abnormal regions from the abnormal 3D bone model are localized on the normal atlas 3D bone model. In other words, the normal atlas 3D bone model is compared to the abnormal 3D bone model to identify and record bone missing from the abnormal 3D bone model that is present in the normal atlas 3D bone model. Localization may be carried out in a multitude of fashions including, without limitation, curvature comparison, surface area comparisons, and point cloud area comparisons. Ultimately, in exemplary form, the missing/abnormal bone is localized as a set of bounding points identifying the geometrical bounds of the missing/abnormal region(s).

Using the bounding points, the defect classification module extracts features from the missing/abnormal region(s) using input clinical data. In exemplary form, the extracted features may include shape information, volumetric information, or any other information used to describe the overall characteristics of the defective (i.e., missing or abnormal) area. These features may be refined based on existing clinical data, such as on-going defect classification data or patient clinical information not necessarily related to the anatomical feature (demographics, disease history, etc.). The output of this step is a mathematical descriptor representative of the defective area(s) that are used in a subsequent step to group similar tissue (e.g., bone) deformities.

The mathematical descriptor is clustered or grouped based upon a statistical analysis. In particular, the descriptor is statistically analyzed and compared to other descriptors from other patients/cadavers to identify unique defect classes within a given population. Obviously, this classification is premised upon multiple descriptors from multiple patients/cadavers that refine the classifications and identifications of discrete groups as the number of patients/cadavers grows. The output from this statistical analysis is a set of defect classes that are used to classify new input anatomical data and determines the number of templates.

The output of the defect classification module is directed to a template module. In exemplary form, the template module includes data that is specific as to each of the defect classifications identified by the defect classification module. By way of example, each template for a given defect classification includes surface representations of the defective bone, location(s) of the defect(s), and measurements relating to the defective bone. This template data may be in the form of surface shape data, point cloud representations, one or more curvature profiles, dimensional data, and physical quantity data. Outputs from the template module and the statistical atlas are utilized by a mass customization module to design, test, and allow fabrication of mass customized implants, fixation devices, instruments or molds. Exemplary utilizations of the mass customization module will be discussed in greater detail hereafter.

Patient-Specific Reconstruction Implants

Figure 20:
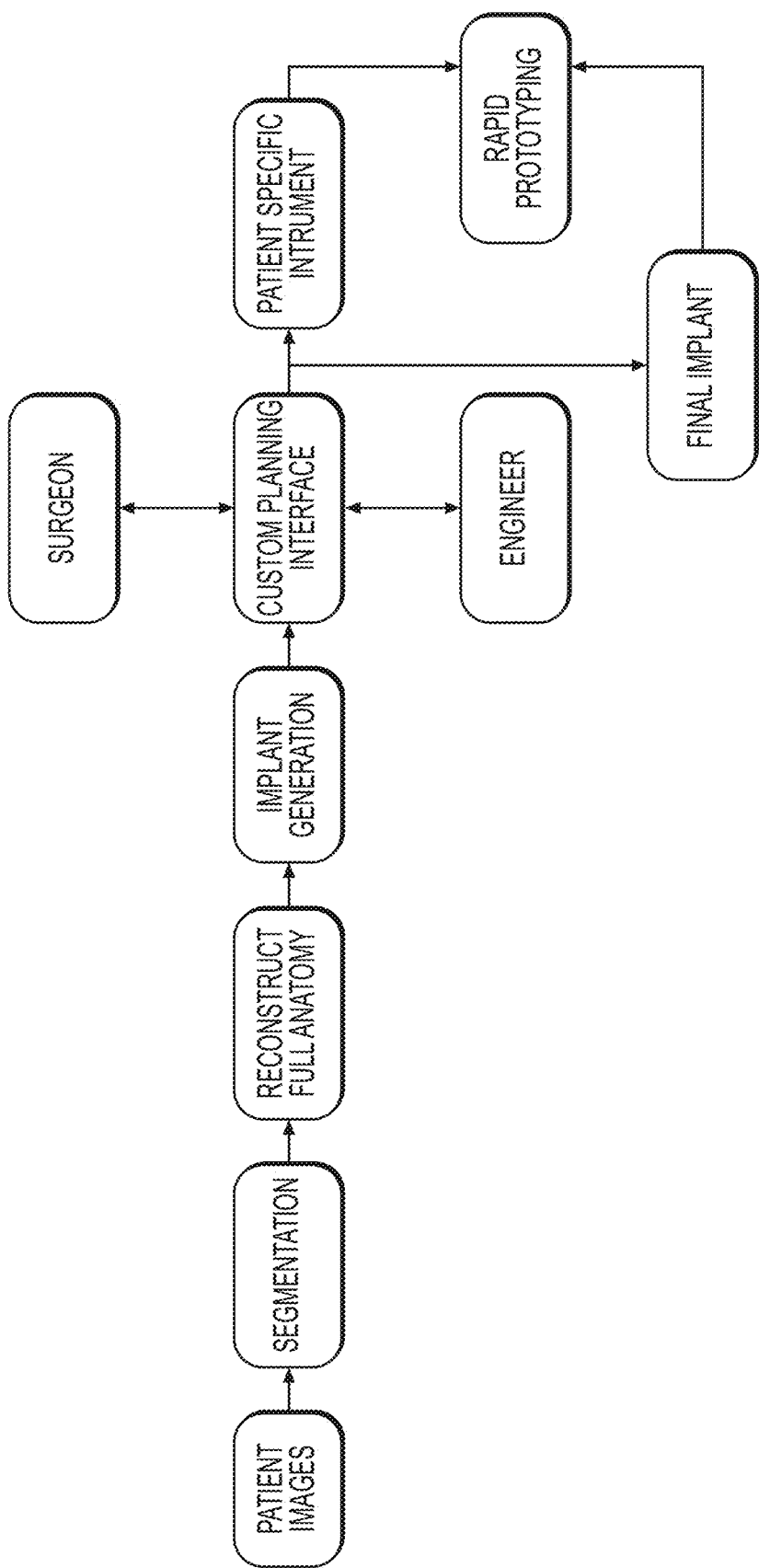
FIG. 20 is a schematic diagram of the process of creating a patient-specific reconstructive implant.

Referring to FIGS. 1 and 20, an exemplary process and system are described for generating patient-specific orthopedic implant guides and associated patient-specific orthopedic implants for patients afflicted with partial, deformed, and/or shattered anatomies. For purposes of the exemplary discussion, a total hip arthroplasty procedure will be described for a patient with a partial anatomy. It should be understood, however, that the exemplary process and system are applicable to any orthopedic implant amenable to patient-specific customization in instances where incomplete or deformed anatomy is present. For example, the exemplary process and system are applicable to shoulder replacements and knee replacements where bone degeneration (partial anatomy), bone deformation, or shattered bones are present. Consequently, though a hip implant is discussed hereafter, those skilled in the art will understand the applicability of the system and process to other orthopedic implants, guides, tools, etc. for use with original orthopedic or orthopedic revision surgeries.

Pelvis discontinuity is a distinct form of bone loss most often associated with total hip arthroplasty (THA), in which osteolysis or acetabular fractures can cause the superior aspect of the pelvis to become separated from the inferior portion. The amount and severity of bone loss and the potential for biological in-growth of the implant are some of the factors that can affect the choice of treatment for a particular patient. In the case of severe bone loss and loss of pelvic integrity, a custom tri-flange cup may be used. First introduced in 1992, this implant has several advantages over existing cages. It can provide stability to pelvic discontinuity, eliminate the need for structural grafting and intraoperative contouring of cages, and promote osseointegration of the construct to the surrounding bone.

Regardless of the context, whether partial, deformed, and/or shattered anatomies of the patient are at issue, the exemplary system and process for generating patient-specific implants and/or guides utilizes the foregoing exemplary process and system of 3D bone model reconstruction (see FIGS. 1-7 and the foregoing exemplary discussion of the same) to generate a three dimensional model of the patient's reconstructed anatomy. More specifically, in the context of total hip arthroplasty where pelvis discontinuity is involved, the exemplary patient-specific system utilizes the patient pelvis data to generate a 3D model of the patient's complete pelvis, which is side specific (right or left). Consequently, a discussion of the system and process for utilizing patient anatomy data for a partial anatomy and generating a 3D reconstructed model of the patient's anatomy is omitted in furtherance of brevity. Accordingly, a description of the process and system for generating patient-specific orthopedic implant guides and associated patient-specific orthopedic implants for patients afflicted with partial, deformed, and/or shattered anatomies will be described post formation of the three dimensional reconstructed model.

Referring specifically to FIGS. 20-22 and 27, after the patient-specific reconstructed 3D bone model of the pelvis and femur are generated, both the incomplete patient-specific 3D bone model (for pelvis and femur) and the reconstructed 3D bone model (for pelvis and femur) are utilized to create the patient-specific orthopedic implant and a patient-specific placement guide for the implant and/or its fasteners. In particular, the extract defect shape step includes generating correspondence between the patient-specific 3D model and the reconstructed 3D model (correspondence between pelvis models, and correspondence between femur models, but not between one femur model and a pelvis model). More specifically, the 3D models are compared to discern what bone in the reconstructed 3D model is not present in the patient-specific 3D model. In exemplary form, the missing/abnormal bone is identified by comparing points on the surface of each 3D model and generating a list of the discrete points on the surface of the reconstructed 3D model that are not present on the patient-specific 3D model. The system may also record and list (i.e., identify) those surface points in common between the two models or summarily note that unless recorded as points being absent on the patient-specific 3D model, all other points are present in common in both models (i.e., on both the reconstructed and patient-specific 3D models).

Figure 21:
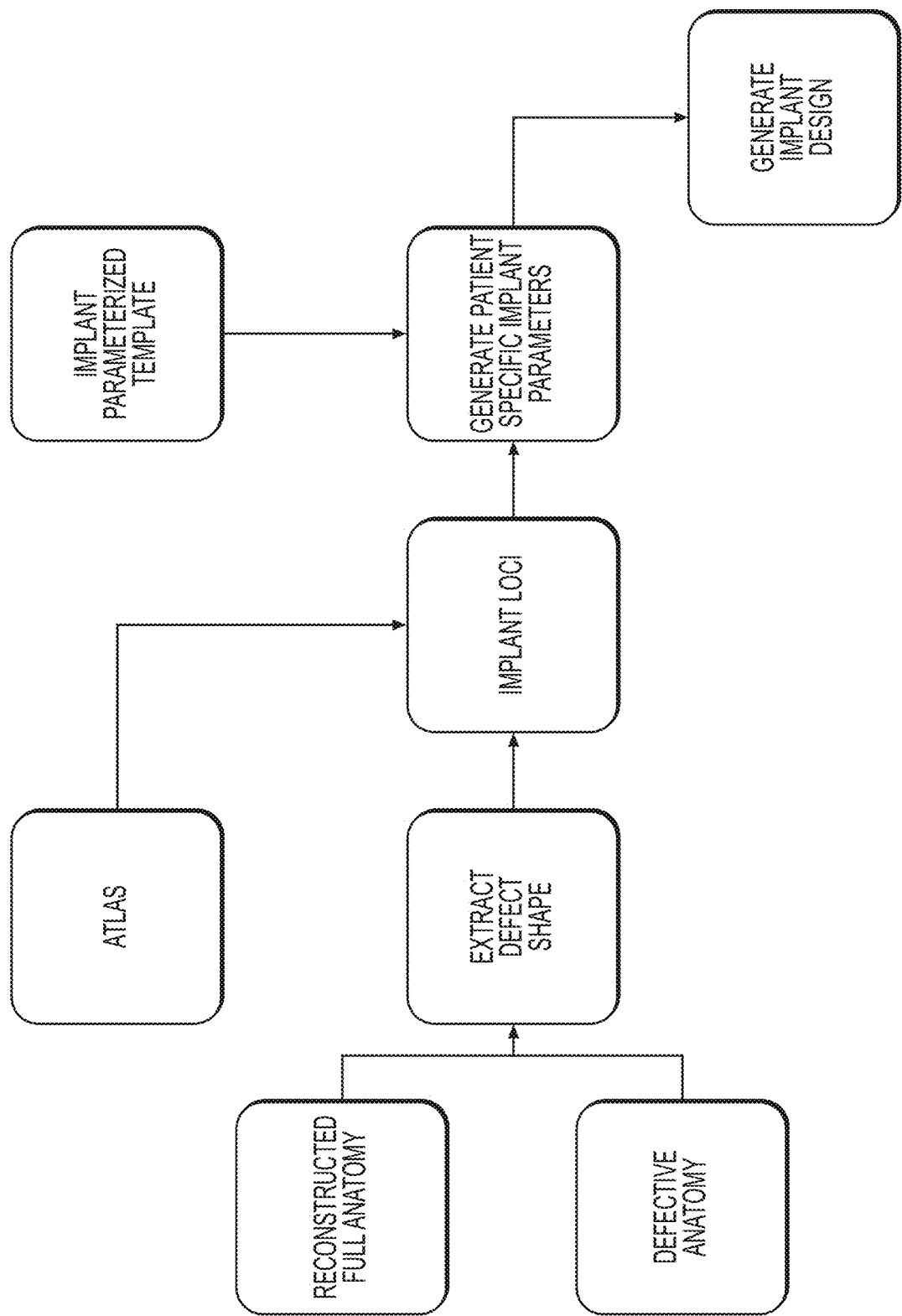
FIG. 21 is a schematic diagram of the process for implant generation depicted in FIG. 20.

Referring to FIG. 21, after generating correspondence between the reconstructed 3D model (generated from the full bone reconstruction module) and the patient-specific 3D model (generated from the input anatomical data), the missing/abnormal regions from the patient-specific 3D model are localized on the reconstructed 3D model. In other words, the reconstructed 3D model is compared to the patient-specific 3D model to identify and record bone missing from the patient-specific 3D model that is present in the reconstructed 3D model. Localization may be carried out in a multitude of fashions including, without limitation, curvature comparison, surface area comparisons, and point cloud area comparisons. Ultimately, in exemplary form, the missing/abnormal bone is localized and the output comprises two lists: (a) a first list identifying vertices corresponding to bone of the reconstructed 3D model that is absent or deformed in the patient-specific 3D model; and, (b) a second list identifying vertices corresponding to bone of the reconstructed 3D model that is also present and normal in the patient-specific 3D model.

Figure 22:
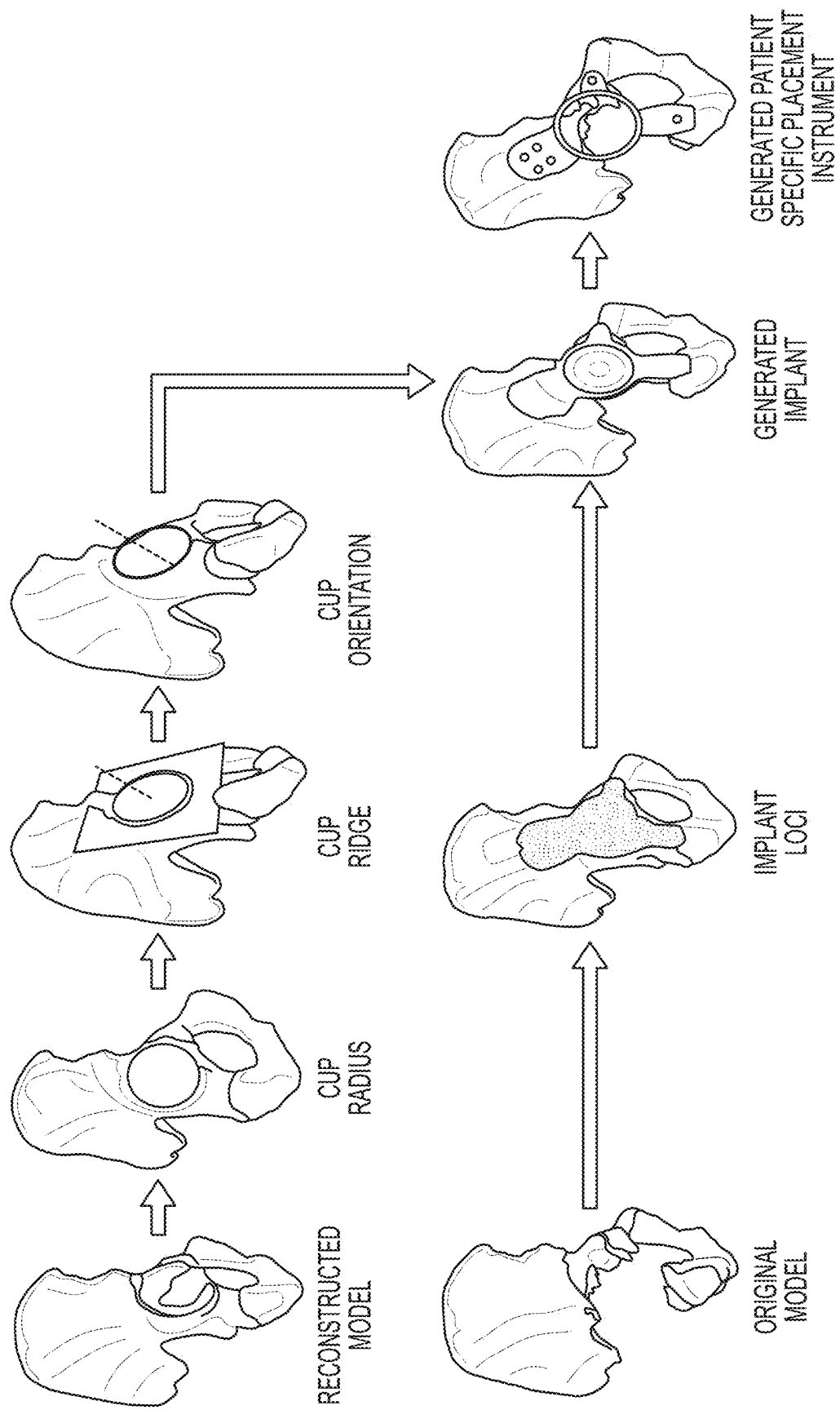
FIG. 22 is a process flow diagram showing various steps for reconstruction of patient full anatomy from partial anatomy and generation of patient specific cup implant for pelvis discontinuity.
Figure 27:
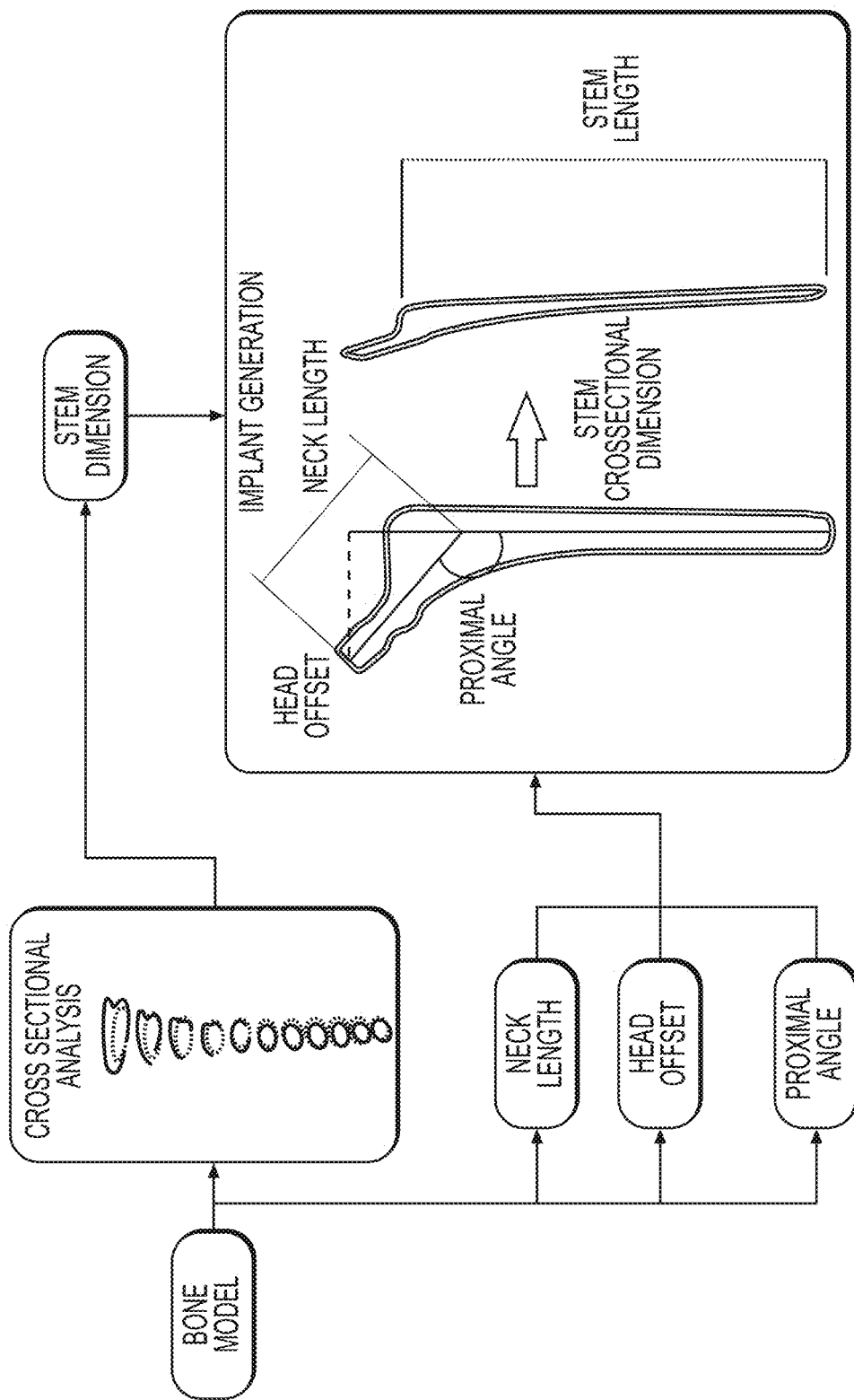
FIG. 27 is a schematic diagram of a process for generating a patient-specific hip stem for reconstructive surgeries.

Referencing FIGS. 21, 22, and 27, following the extract defect shape step, an implant loci step is performed. The two vertices lists from the extract defect shape step and a 3D model of a normal bone (e.g., pelvis, femur, etc.) from the statistical atlas (see FIGS. 1 and 2, as well as the foregoing exemplary discussion of the same) are input to discern the fixation locations for a femoral or pelvic implant. More specifically, the fixation locations (i.e., implant loci) are automatically selected so that each is positioned where a patient has residual bone. Conversely, the fixation locations are not selected in defect areas of the patient's residual bone. In this manner, the fixation locations are chosen independent of the ultimate implant design/shape. The selection of fixation locations may be automated using shape information and statistical atlas locations.

As show in FIG. 21, after the implant loci step, the next step is to generate patient-specific implant parameters. In order to complete this step, an implant parameterized template is input that defines the implant by a set number of parameters that are sufficient to define the underlying shape of the implant. By way of example, in the case of a pelvis reconstruction to replace/augment an absent or degenerative acetabulum, the implant parameterized template includes angle parameters for the orientation of the replacement acetabular cup and depth parameters to accommodate for dimensions of the femoral head. Other parameters for an acetabular implant may include, without limitation, the acetabular cup diameter, face orientation, flange locations and shapes, location and orientation of fixation screws. In the case of porous implants, the location and structural characteristics of the porosity should be included. By way of example, in the case of a femoral reconstruction to replace/augment an absent or degenerative femur, the implant parameterized template includes angle parameters for the orientation of the replacement femoral head, neck length, head offset, proximal angle, and cross-sectional analysis of the exterior femur and intercondylar channel. Those skilled in the art will understand that the parameters chosen to define the underlying shape of the implant will vary depending upon the anatomy being replaced or supplemented. Consequently, an exhaustive listing of parameters that are sufficient to define the underlying shape of an implant is impractical. Nevertheless, as depicted in FIG. 22 for example, the reconstructed 3D pelvis model may be utilized to obtain the radius of the acetabular cup, identification of pelvic bone comprising the acetabular cup circumferential upper ridge, and identification of the orientation of the acetabular cup with respect to the residual pelvis. Moreover, the parameters may be refined taking into account the implant loci so that the implant best/better fits the patient-specific anatomy.

Subsequent to finalizing the set number of parameters that are sufficient to define the underlying shape of the implant, the design of the implant is undertaken. More specifically, an initial iteration of the overall implant surface model is constructed. This initial iteration of the overall implant surface model is defined by a combination of patient-specific contours and estimated contours for the implanted region. The estimated contours are determined from the reconstructed 3D bone model, missing anatomical bone, and features extracted from the reconstructed 3D bone model. These features and the location of the implant site, which can be automatically determined, are used to determine the overall implant shape, as depicted for example in FIG. 22 for an acetabular cup implant.

Referring back to FIG. 20, the initial iteration of the overall implant surface model is processed pursuant to a custom (i.e., patient-specific) planning sequence. This custom planning sequence may involve inputs from a surgeon and an engineer as part of an iterative review and design process. In particular, the surgeon and/or engineer may view the overall implant surface model and the reconstructed 3D bone model to determine if changes are needed to the overall implant surface model. This review may result in iterations of the overall implant surface model until agreement is reached between the engineer and surgeon. The output from this step is the surface model for the final implant, which may be in the form of CAD files, CNC machine encoding, or rapid manufacturing instructions to create the final implant or a tangible model.

Figure 23:
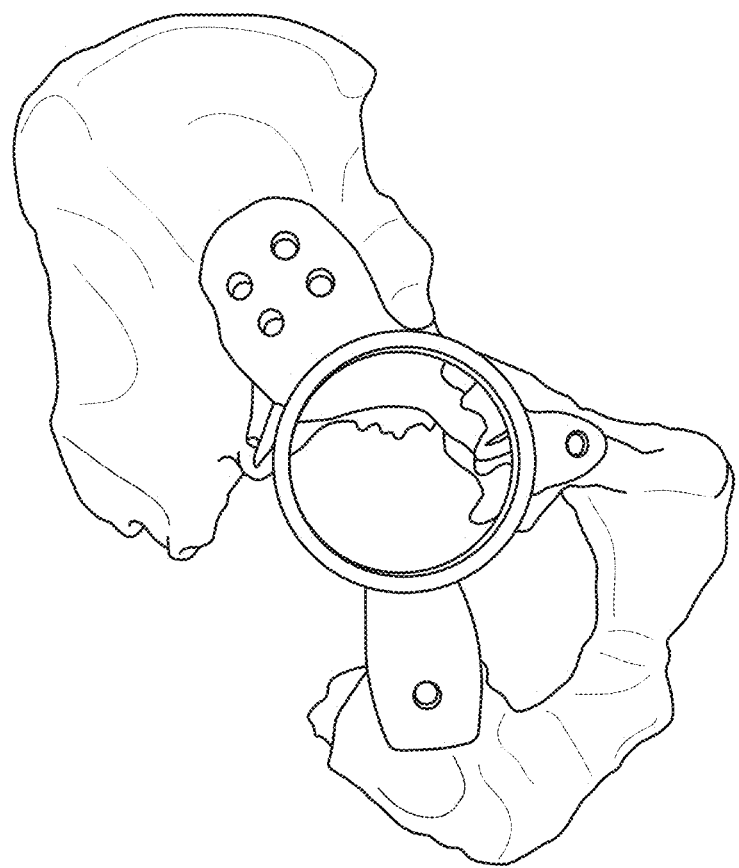
FIG. 23 is a graphical representation of a patient-specific placement guide for a patient-specific acetabular implant.
Figure 25:
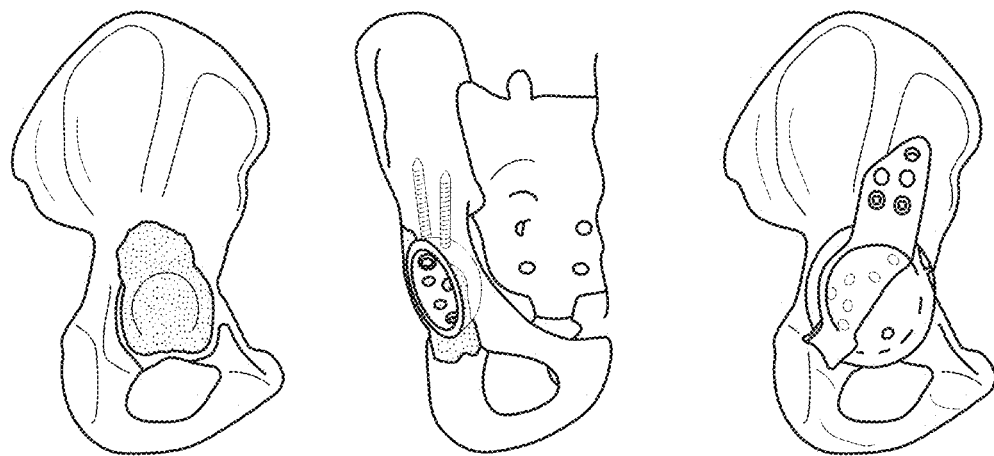
FIG. 25 comprises images showing the sequence for mass customization of acetabular cages in accordance with the instant disclosure.
Figure 24:
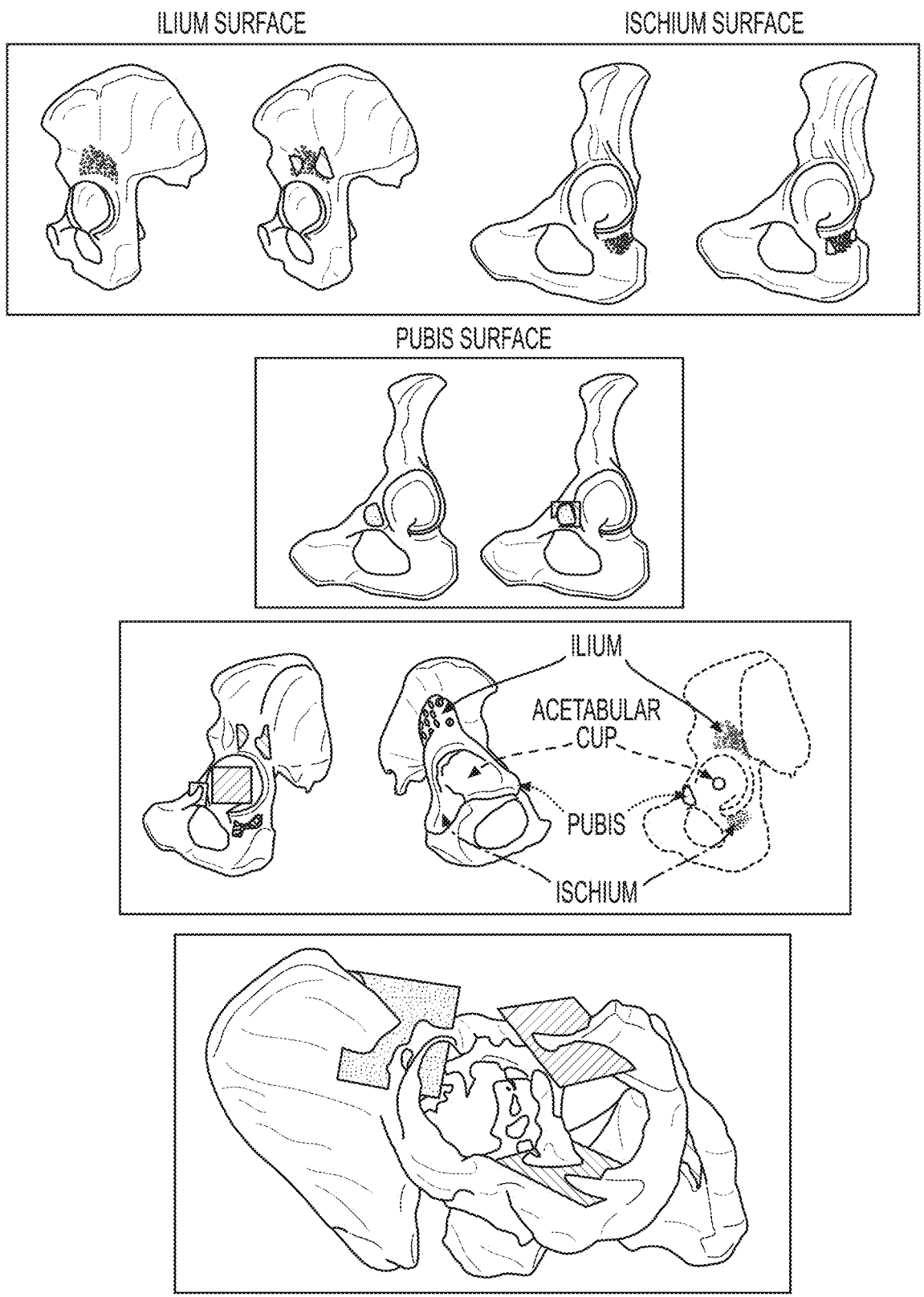
FIG. 24 comprises images studying the relationship between the three attachment sites of an implant and the cup orientation for mass customization.

Referring to FIGS. 20, 22, and 23, contemporaneous with or after the design of the patient-specific orthopedic implant is the design of a patient specific placement guide. In the context of an acetabular cup implant, as discussed in exemplary form above, one or more surgical instruments can be designed and fabricated to assist in placing the patient-specific acetabular cup. Having designed the patient-specific implant to have a size and shape to match that of the residual bone, the contours and shape of the patient-specific implant may be utilized and incorporated as part of the placement guide.

In exemplary form, the acetabular placement guide comprises three flanges that are configured to contact the ilium, ischium, and pubis surfaces, where the three flanges are interconnected via a ring. Moreover, the flanges of the placement guide may take on the identical shape, size, and contour of the acetabular cup implant so that the placement guide will take on the identical position as planned for the acetabular cup implant. In other words, the acetabular placement guide is shaped as the negative imprint of the patient anatomy (ilium, ischium, and pubis partial surfaces), just as the acetabular cup implant is, so that the placement guide fits on the patient anatomy exactly. But the implant guide differs from the implant significantly in that it includes one or more fixation holes configured to guide drilling for holes and/or placement of fasteners. In exemplary form, the placement guide includes holes sized and oriented, based on image analysis (e.g., microCT), to ensure proper orientation of any drill bit or other guide (e.g., a dowel) that will be utilized when securing the acetabular cup implant to the residual pelvis. The number of holes and orientation varies depending upon the residual bone, which impacts the shaped of the acetabular cup implant too. FIG. 23 depicts an example of a patient-specific placement guide for use in a total hip arthroplasty procedure. In another instance, the guide can be made so that it fits into the implant and guides only the direction of the fixation screws. In this form, the guide is shaped as the negative of the implant, so that it can be placed directly over the implant. Nevertheless, the incorporation of at least part of the patient-specific reconstructed implant size, shape, and contour is a theme that carries over regardless of the intended bone to which the patient-specific implant will be coupled.

Utilizing the exemplary system and method described herein can provide a wealth of information that can result in higher orthopedic placement accuracy, better anatomical integration, and the ability to pre-operatively measure true angles and plane orientation via the reconstructed three dimensional model.

Creation of Customized Implants Using Massively Customizable Components

Figure 26:
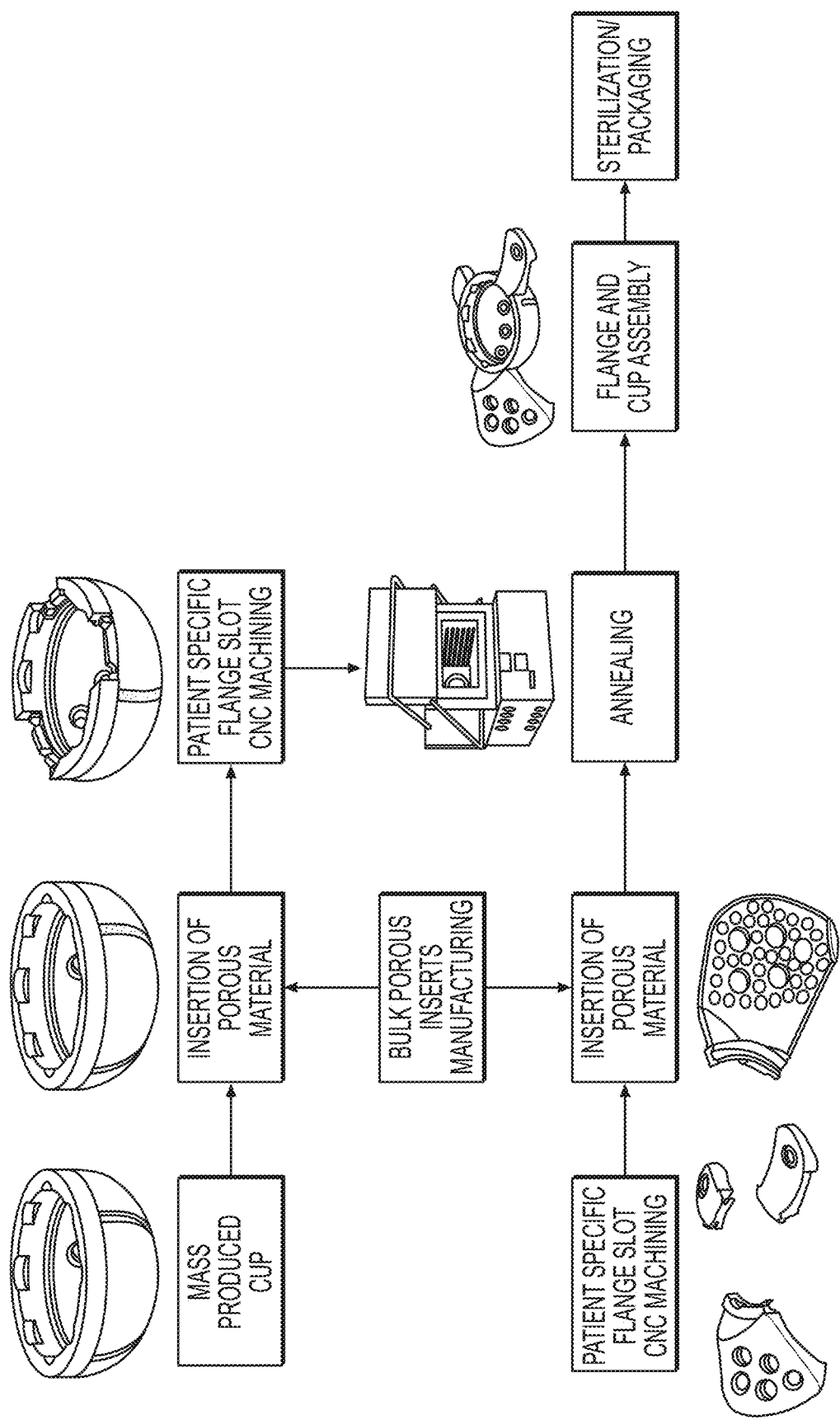
FIG. 26 is a schematic diagram for a method for manufacturing a mass produced custom acetabular component using a modular design.

Referring to FIG. 26, an exemplary process and system are described for generating customized orthopedic implants using massively customizable components. For purposes of the exemplary discussion, a total hip arthroplasty procedure will be described for a patient with severe acetabular defects. It should be understood, however, that the exemplary process and system are applicable to any orthopedic implant amenable to mass customization in instances where incomplete anatomy is present.

Severe acetabular defects require specialized procedures and implant components to repair. One approach is the custom triflange, which a fully custom implant consisting of an acetabular cup and three flanges that are attached to the ilium, ischium, and pubis. In contrast to the exemplary process and system, prior art triflange implants comprise a single complex component, which is cumbersome to manufacture and requires that the entire implant be redesigned for every case (i.e., completely patient-specific). The exemplary process and system generates a custom triflange implant that makes use of massively customizable components in addition to fully custom components in a modular way to allow custom fitting and porosity.

A preplanning step in accordance with the exemplary process is performed to determine the orientation of the three flanges relative to the cup, the flange contact locations, and the acetabular cup orientation and size. This preplanning step is conducted in accordance with the "Patient-specific Implants" discussion immediately preceding this section. By way of example, specific locations of implant fixation are determined pursuant to an implant loci step and using its prefatory data inputs as discussed in the immediately preceding section. By way of recall, as part of this implant loci step, the two vertices lists from the extract defect shape step and a 3D model of a normal pelvis from the statistical atlas (see FIGS. 1 and 2, as well as the foregoing exemplary discussion of the same) are input to discern the fixation locations for the custom triflange. More specifically, the fixation locations (i.e., implant loci) are selected so that each is positioned where a patient has residual bone. In other words, the fixation locations are not selected in defect areas of the patient's residual pelvis. In this manner, the fixation locations are chosen independent of the ultimate implant design/shape.

After determining the fixation locations, the triflange components (i.e., flanges) are designed using the "Patient-specific Implants" discussion immediately preceding this section. The flanges are designed to be oriented relative to the replacement acetabular cup so that the cup orientation provides acceptable joint functionality. Additionally, the contact surfaces of the flanges are contoured to match the patient's pelvis anatomy in that the contact surfaces of the triflanges are shaped as a "negative" of the pelvis's bony surface. The exemplary process of FIG. 23 utilizes the final step of the process depicted in FIG. 17 to rapid prototype the flanges (or use conventional computer numerical control (CNC) equipment). After the flanges are fabricated, further machining or steps may be performed to provide cavities within which porous material may be added to the triflanges.

One portion of the triflange system that does not need to be a custom component is the acetabular cup component. In this exemplary process, a family of acetabular cups is initially manufactured and provides the foundation on which to build the triflange system. These "blank" cups are retained in inventory for use as needed. If a particular porosity for the cup is desired, mechanical features are added to the cup that allows press fitting of porous material into the cup. Alternatively, if a particular porosity for the cup is desired, the cup may be coated using one or more porous coatings.

After the blank cup is formed and any porosity issues are addressed as discussed above, the cup is rendered patient-specific by machining the cup to accept the flanges. In particular, using the virtual model of the flanges, the system software constructs virtual locking mechanisms for the flanges, which are transformed into machine coding so that the locking mechanisms are machined into the cup. These locking mechanisms allow the cup to be fastened to the flanges so that when the flanges are mounted to the patient's residual bone, the cup is properly oriented with respect to the residual pelvis. This machining may use conventional CNC equipment to form the locking mechanisms into the blank cups.

Subsequent to fabrication of the locking mechanisms as part of the blank cup, the flanges are mounted to the cup using the interface between the locking mechanisms. The triflange assembly (i.e., final implant) is subjected to an annealing process to promote strong bonding between the components. Post annealing of the triflange implant, a sterilization process occurs followed by appropriate packaging to ensure a sterile environment for the triflange implant.

Creation of Mass Customized Implants

Figure 28:
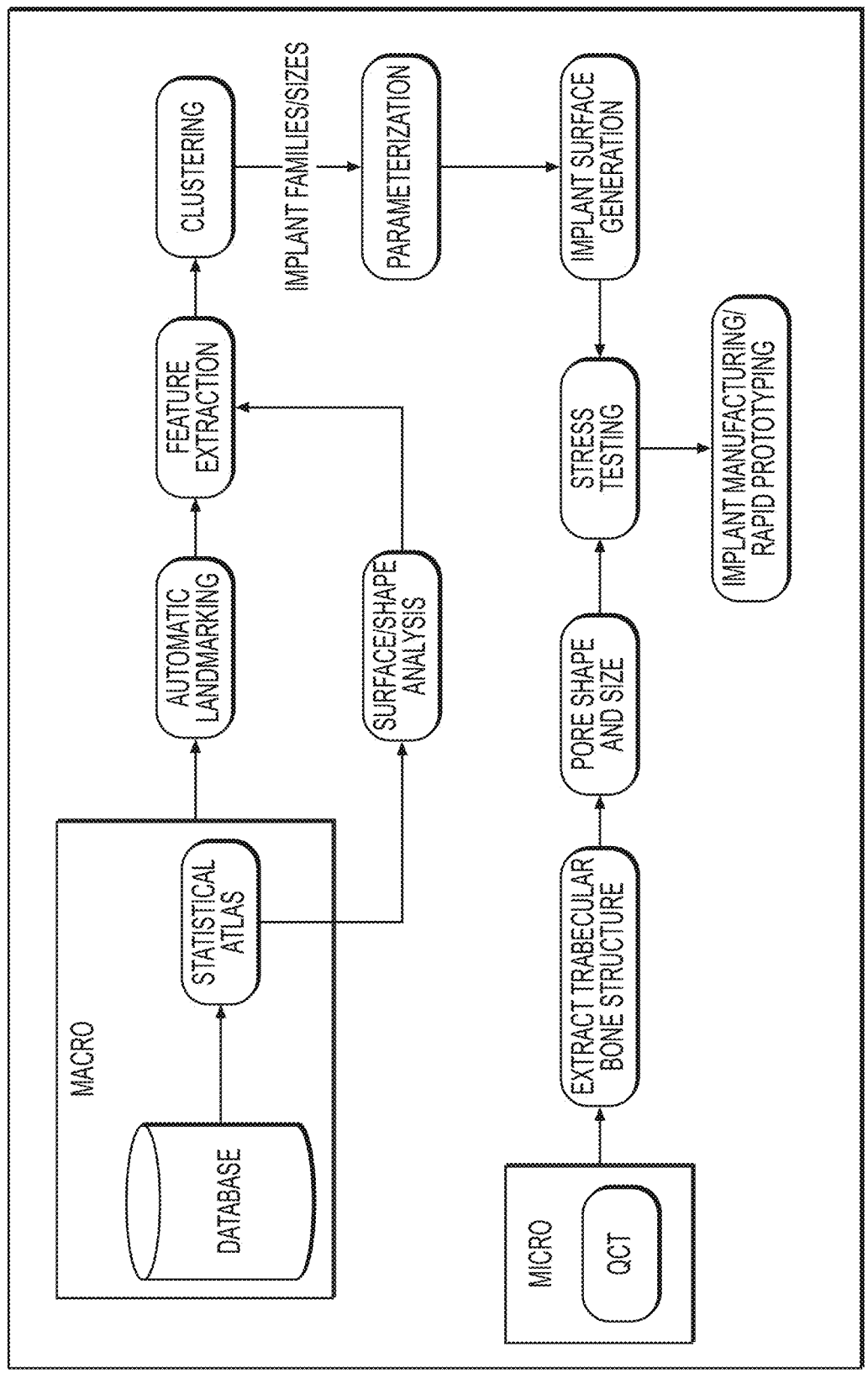
FIG. 28 is a schematic diagram of a process for mass customized implant generation.

Referring to FIG. 28, an exemplary process and system are described for generating mass customized orthopedic implant guides and associated mass customized orthopedic implants for patients afflicted with partial, deformed, and/or shattered anatomies. For purposes of the exemplary discussion, a total hip arthroplasty procedure will be described for a patient needing primary joint replacement. It should be understood, however, that the exemplary process and system are applicable to any orthopedic implant and guides amenable to mass customization in instances where incomplete anatomy is present. For example, the exemplary process and system are applicable to shoulder replacements and knee replacements where bone degeneration (partial anatomy), bone deformation, or shattered bones are present. Consequently, though a hip implant is discussed hereafter, those skilled in the art will understand the applicability of the system and process to other orthopedic implants, guides, tools, etc. for use with primary orthopedic or orthopedic revision surgeries.

The exemplary process utilizes input data from a macro perspective and a micro perspective. In particular, the macro perspective involves determination of the overall geometric shape of the orthopedic implant and corresponding anatomy. Conversely, the micro perspective involves accounting for the shape and structure of cancellous bone and its porosity.

The macro perspective includes a database communicating with a statistical atlas module that logs virtual, 3D models of one or more anatomies (e.g., bones) to capture the inherent anatomical variability in a given population. In exemplary form, the atlas logs mathematical representations of anatomical features of the one or more anatomies represented as a mean representation and variations about the mean representation for a given anatomical population. Reference is had to FIG. 2 and the foregoing discussion of the statistical atlas and how one adds anatomy to the statistical atlas of a given population. Outputs from the statistical atlas are directed to an automatic landmarking module and to a surface/shape analysis module.

The automatic landmarking module utilizes inputs from the statistical atlas (e.g., regions likely to contain a specific landmark) and local geometrical analyses to calculate anatomical landmarks for each instance of anatomy within the statistical atlas. This calculation is specific to each landmark. The approximate shape of the region is known, for example, and the location of the landmark being searched for is known relative to the local shape characteristics. For example, locating the medial epicondylar point of the distal femur is accomplished by refining the search based on the approximate location of medial epicondylar points within the statistical atlas. Accordingly, it is known that the medial epicondylar point is the most medial point within this search window, so a search for the most medial point is performed as to each bone model within the medial epicondylar region defined in the statistical atlas, with the output of the search being identified as the medial epicondylar point landmark. After the anatomical landmarks are automatically calculated for each virtual, 3D model within the statistical atlas population, the virtual, 3D models of the statistical atlas are directed to a feature extraction module, along with shape/surface analysis outputs.

The shape/surface outputs come from a shape/surface module also receiving inputs from the statistical atlas. In the context of the shape/surface module, the virtual, 3D models within the statistical atlas population are analyzed for shape/surface features that are not encompassed by the automatic landmarking. In other words, features corresponding to the overall 3D shape of the anatomy, but not belonging to features defined in the previous automatic landmarking step are calculated as well. For example, curvature data is calculated for the virtual 3D models.

Outputs from the surface/shape analysis module and the automatic landmarking module are directed to a feature extraction module. Using a combination of landmarks and shape features, mathematical descriptors (i.e. curvature, dimensions) relevant to implant design are calculated for each instance in the atlas. These descriptors are used as input to a clustering process.

The mathematical descriptor is clustered or grouped based upon a statistical analysis. In particular, the descriptor is statistically analyzed and compared to other descriptors from the remaining anatomy population to identify groups (of anatomies) having similar features within the population. Obviously, this clustering is premised upon multiple descriptors from multiple anatomies across the population. As new instances are presented to the clustering, which were not present in the initial clustering, the output clusters are refined to better represent the new population. The output from this statistical analysis is a finite number of implants (including implant families and sizes) covering all or the vast majority of the anatomical population.

For each cluster, a parameterization module extracts the mathematical descriptors within the cluster. The mathematical descriptors form the parameters (e.g., CAD design parameters) for the eventual implant model. The extracted mathematical descriptors are fed into an implant surface generation module. This module is responsible for converting the mathematical descriptors into surface descriptors to generate a 3D, virtual model of the anatomy for each cluster. The 3D, virtual model complements the micro perspective prior to stress testing and implant manufacturing.

On the micro perspective, for each anatomy of a given population, data is obtained indicative of structural integrity. In exemplary form, this data for a bone may comprise microCT data providing structural information as to the cancellous bone. More specifically, the microCT data may comprise images of the bone in question (multiple microCT images for multiple bones across a population). These images are thereafter segmented via the extract trabecular bone structure module in order to extract the three dimensional geometry of the cancellous bones and create virtual, 3D models for each bone within the population. The resulting 3D virtual models are input to a pore size and shape module. As depicted graphically in FIG. 84, the 3D virtual models include porous size and shape information, which is evaluated by the pore size and shape module to determine pore size and size for the cancellous bone. This evaluation is useful to analyze the porous size and shape of the bone within the intramedullary canal so that the stem of the femoral implant can be treated with a coating or otherwise processed to exhibit a porous exterior to promote integration between the residual bone of the femur and the femoral implant. The output from this module, in combination with the 3D virtual model output from the implant surface generation module, is directed to a virtual stress testing module.

The stress testing module combines implant porosity data from the pore size and shape module and implant shape data from the implant surface generation module to define the final implant shape model and properties. For example, the shape and properties include providing a porous coating for the final implant model that roughly matches the cancellous bone porosity for the bone in question. Once the shape and properties are incorporated, the final implant model undergoes virtual stress testing (finite-element and mechanical analysis) to verify the functional quality of the model. To the extent the functional quality is unacceptable, the parameters defining the implant shape and porosity are modified until acceptable performance is achieved. Presuming the final implant model satisfies the stress testing criteria, the final implant model is utilized to generate machine instructions necessary to convert the virtual model into a tangible implant (that may be further refined by manufacturing processes known to those skilled in the art). In exemplary form, the machine instructions may include rapid manufacturing machine instructions to fabricate the final implant through a rapid prototyping process (to properly capture porous structure) or a combination of traditional manufacturing and rapid prototyping.

Creation of Gender/Ethnic Specific Hip Implants

Figure 29:
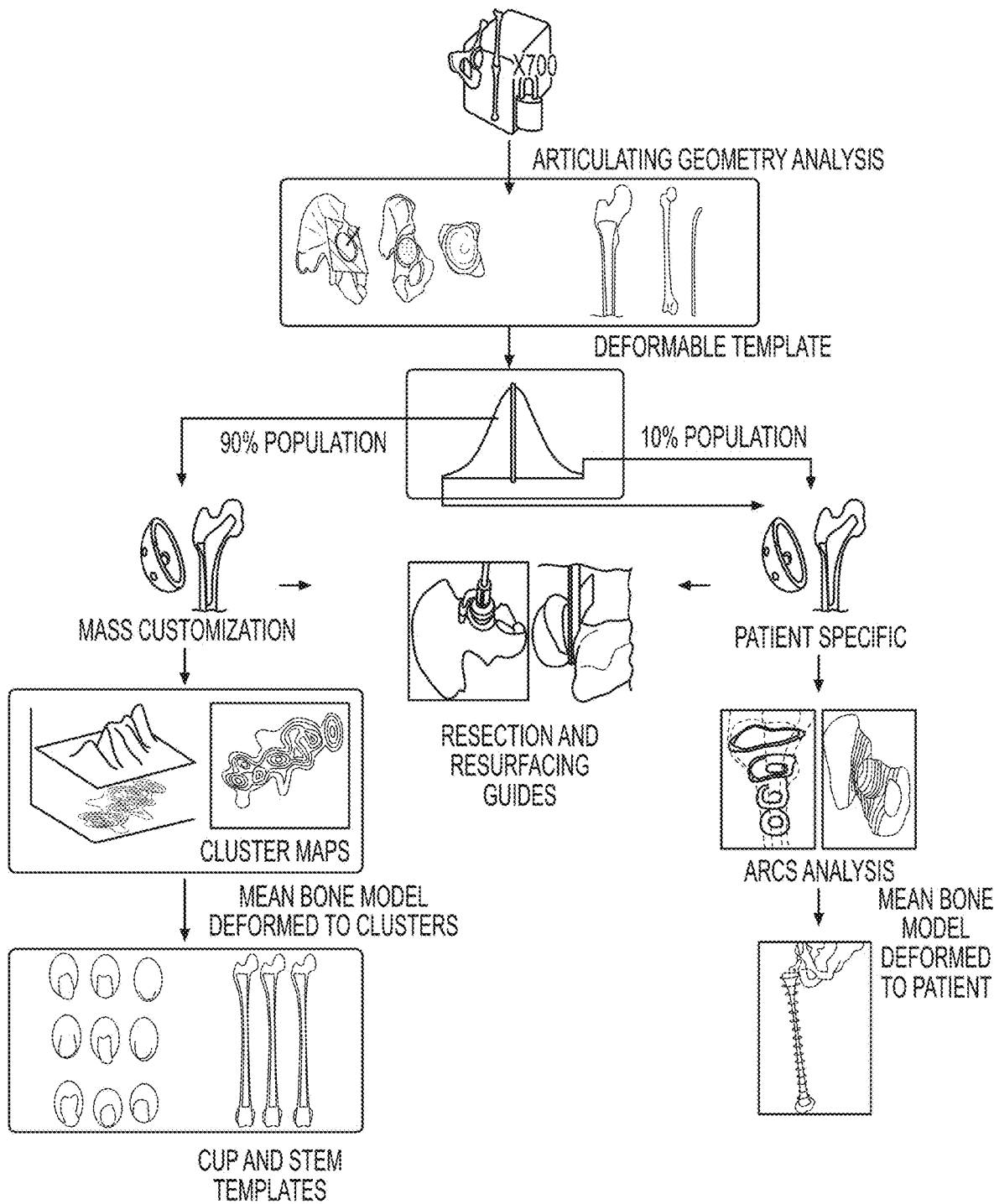
FIG. 29 is a schematic diagram depicting a process for using a statistical atlas for generation of both mass customized and patient-specific hip implants.
Figure 84:
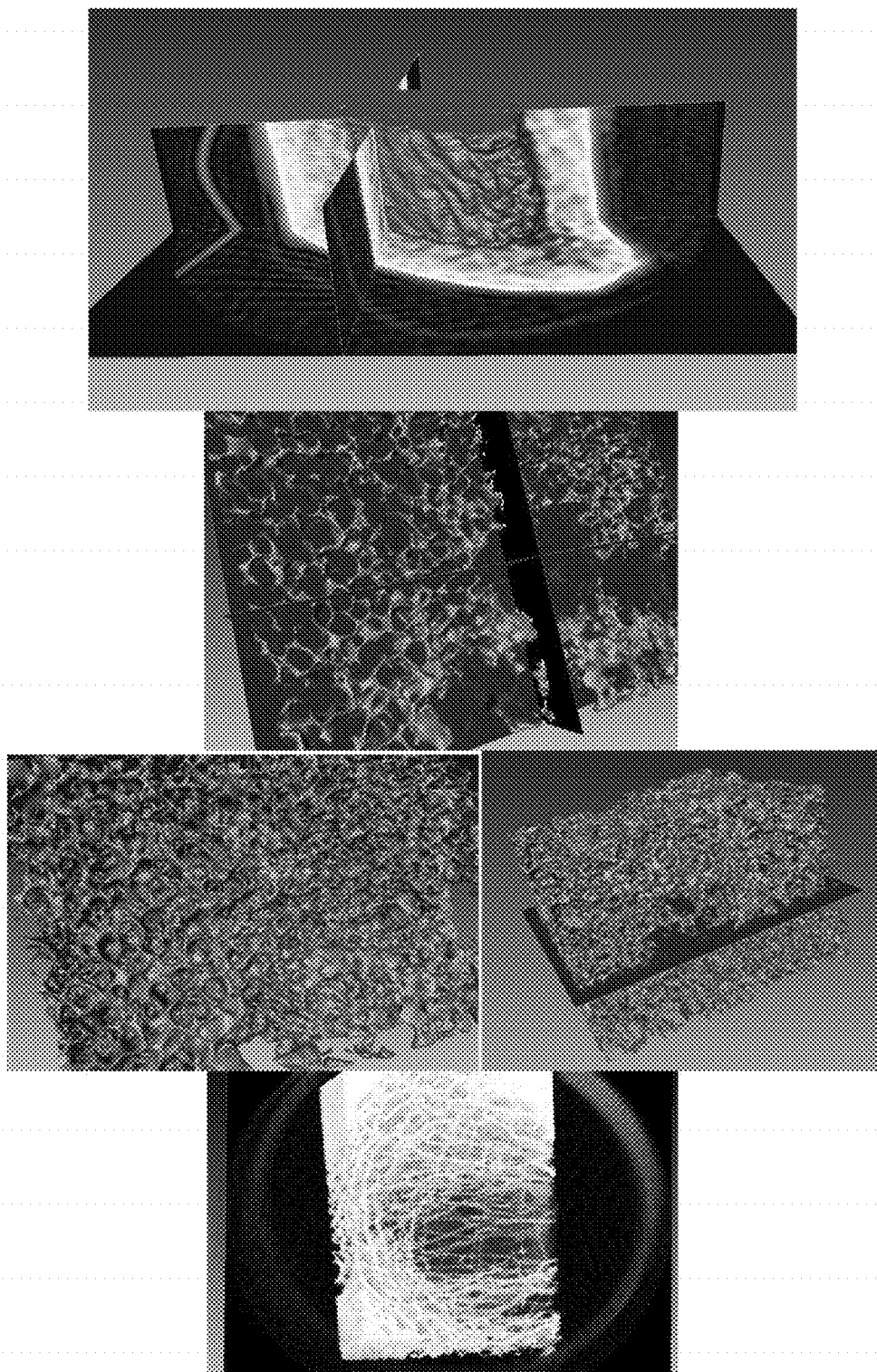
FIG. 84 is a graphical depiction of the sequence for extracting porous shapes and sizes to match a patient's bone anatomy from micro computerized tomography scans of the patient.

Referring to FIGS. 29-84, an exemplary process and system are described for generating gender and/or ethnic specific implants. For purposes of the exemplary discussion, a total hip arthroplasty procedure will be described for a patient with requiring primary joint replacement. It should be understood, however, that the exemplary process and system are applicable to any orthopedic implant amenable to customization. For example, the exemplary process and system are applicable to shoulder replacements and knee replacements and other primary joint replacement procedures. Consequently, though a hip implant is discussed hereafter, those skilled in the art will understand the applicability of the system and process to other orthopedic implants, guides, tools, etc. for use with original orthopedic or orthopedic revision surgeries.

The hip joint is composed of the head of the femur and the acetabulum of the pelvis. The hip joint anatomy makes it one of the most stable joints in the body. The stability is provided by a rigid ball and socket configuration. The femoral head is almost spherical in its articular portion that forms two-thirds of a sphere. Data has shown that the diameter of the femoral head is smaller for females than males. In the normal hip, the center of the femoral head is assumed to coincide exactly with the center of the acetabulum and this assumption is used as the basis for the design of most hip systems. However, the native acetabulum is not deep enough to cover all of the native femoral head. The almost rounded part of the femoral head is spheroidal rather than spherical because the uppermost part is flattened slightly. This spheroidal shape causes the load to be distributed in a ring-like pattern around the superior pole.

The geometrical center of the femoral head is traversed by three axes of the joint: the horizontal axis; the vertical axis; and, the anterior/posterior axis. The femoral head is supported by the neck of the femur, which joints the shaft. The axis of the femoral neck is obliquely set and runs superiorly medially and anteriorly. The angle of the inclination of the femoral neck to the shaft in the frontal plane is the neck shaft angle. In most adults, this angle varies between 90 to 135 degrees and is important because it determines the effectiveness of the hip abductors, the length of the limb, and the forces imposed on the hip joint.

An angle of inclination greater than 125 degrees is called coxa valga, whereas an angle of inclination less than 125 degrees is called coxa vara. Angles of inclination greater than 125 degrees coincide with lengthened limbs, reduced effectiveness of the hip abductors, increased load on the femoral head, and increased stress on the femoral neck. In a case of coxa vara, angles of inclination less than 125 degrees coincide with shortened the limbs, increased effectiveness of the hip abductors, decreased load on the femoral head, and decreased stress on the femoral neck. The femoral neck forms an acute angle with the transverse axis of the femoral condyles. This angle faces medially and anteriorly and is called angle of anteversion. In adult humans, this angle averages approximately 7.5 degrees.

The acetabulum lies on the lateral aspect of the hip where the ilium, ischium, and pubis meet. These three separate bones join in the formation of the acetabulum, with the ilium and ischium contributing approximately two-fifths each and the pubis one-fifth of the acetabulum. The acetabulum is not a deep enough socket to cover all of the femoral head and has both articulating and non-articulating portions. However, the acetabular labrum deepens the socket to increase stability. Together with labrum, the acetabulum covers slightly more than 50% of the femoral head. Only the sides of the acetabulum are lined with articular cartilage, which is interrupted inferiorly by the deep acetabular notch. The center part of the acetabular cavity is deeper than the articular cartilage and is nonarticular. This center part is called the acetabular fossae and is separated from the interface of the pelvic bone by a thin plate. The acetabular fossae is a region unique for every patient and is used in creating patient-specific guide for reaming and placement of the acetabular cup component. Additionally, variation of anatomical features further warrant the need for population specific implant designs.

Some of the problems associated with prior art use of cementless components can be attributed to the wide variation in size, shape, and orientation of the femoral canal. One of the challenges to orthopedic implant design of the femoral stem is large variation in the mediolateral and anteroposterior dimensions. There is also significant variation in the ratio of the proximal to distal canal size. The different combination of various arcs, taper angles, curves, and offsets in the normal population is staggering. However, that is not the only problem.

Ancestral differences in femora morphology and a lack of definite standards for modern populations makes designing the proper hip implant system problematic. For example, significant differences in anterior curvature, torsion, and cross-sectional shape exist between American Indians, American blacks, and American whites. Differences between Asian and Western populations in the femora are found in the anterior bow of the femora, where Chinese are more anteriorly bowed and externally rotated with smaller intramedullary canals and smaller distal condyles than Caucasian femora. Likewise, Caucasian femora are larger than Japanese femora in terms of length distal condyle dimensions. Ethnic differences also exist in the proximal femur mineral bone density (BMD) and hip axis length between American blacks and whites. The combined effects of higher BMD, shorter hip axis length, and shorter intertrochanteric width may explain the lower prevalence of osteoporotic fractures in American black women compared to their white counterparts. Similarly, elderly Asian and American black men were found to have thicker cortices and higher BMD than white and Hispanic men, which may contribute to greater bone strength in these ethnic groups. In general, American blacks have thicker bone cortices, narrower endosteal diameters, and greater BMD than American whites.

Combining the femur and the pelvic ancestral (and ethnic) differences becomes even more challenging to primary hip systems. Revision surgery creates more complexity. Added to these normal anatomic and ethnic variations, the difficulties faced by the surgeon who performs revision operation are compounded by: (a) distortion of the femoral canal caused by bone loss around the originally placed prostheses; and, (b) iatrogenic defects produced by the removal of the components and cement.

All of the foregoing factors have led a number of hip surgeons to look for ways to improve design of uncemented femoral prostheses. In total hip replacement (primary or revision), the ideal is to establish an optimal fit between the femoral ball and acetabular cup. The femoral stem neck should have a cruciform cross section to reduce stiffness. The stem length should be such that the stem has parallel contact with the walls of the femur over two to three internal canal diameters. The proximal one third of the stem is porous coated or hydroxylapatite (HA) coated. The stem is cylindrical (i.e. not tapered) to control bending loads and to allow transmission of all rotational and axial loads proximally. The femoral head position should reproduce the patient's own head center, unless it is abnormal.

One way to attempt to satisfy these goals is to manufacture femoral prostheses individually for each patient. In other words, make a prosthesis that is specific to a particular patient rather than trying to reshape the patient's bone to fit a readymade prosthesis.

There are some common design rules for patient-specific (or mass customization) primary and revision hip replacements. Among these design rules are: (1) the hip stem should be collarless (except in revision) to allow uniform distribution of load to the femur; (2) the hip stem should have a modified rhomboidal cross section to maximize fit/fill, but should maintain rotational stability; (3) the hip stem should be bowed when necessary to conform to patient's bone; (4) the hip stem should be inserted along a curved path, with no gaps between the prosthesis and the bone; (5) the hip stem neck should have cruciform cross section to reduce stiffness; (6) the hip stem length should be such that the stem has parallel contact with the walls of the femur over two to three internal canal diameters; (7) the proximal one third of the hip stem is porous coated or hydroxylapatite (HA) coated; (8) the hip stem is cylindrical (i.e. not tapered) to control bending loads and to allow transmission of all rotational and axial loads proximally; (9) the femoral head position of the hip stem should reproduce the patient's own head center, unless it is abnormal.

The following is an exemplary process and system for generating mass customized orthopedic implant for patients needing primary joint replacement taking into account the gender and/or ethnicity of the patient population. For purposes of the exemplary discussion, a total hip arthroplasty procedure will be described for a patient with a partial anatomy. It should be understood, however, that the exemplary process and system are applicable to any orthopedic implant amenable to mass customization in instances where incomplete anatomy is present. For example, the exemplary process and system are applicable to shoulder replacements and knee replacements where bone degeneration (partial anatomy), bone deformation, or shattered bones are present. Consequently, though a femoral component of a hip implant is discussed hereafter, those skilled in the art will understand the applicability of the system and process to other orthopedic implants, guides, tools, etc. for use with original orthopedic or orthopedic revision surgeries.

Referring to FIG. 29, an overall process flow is depicted for using a statistical atlas for generation of both mass customized and patient-specific hip implants. Initially, the process includes the statistical atlas including several instances of one or more bones being analyzed. In the exemplary context of a hip implant, the statistical atlas includes several instances of bone models for the pelvis bone and the femur bone. An articulating surface geometry analysis is conducted at least for the acetabular component (i.e., acetabulum) and the proximal femoral component (i.e., femoral head). In particular, the articulating surface geometry analysis involves calculation of landmarks, measurements, and shape features on each bone from a given population of the statistical atlas. In addition, the articulating surface geometry analysis includes generating quantitative values, such as statistics, representative of the calculations. From these calculations, a distribution of the calculations is plotted and parsed based the distribution. For a bell-shaped distribution, for example, it may be observed that approximately ninety percent (90%) of the population is grouped so that a non-patient-specific implant (e.g., a mass customized implant) may be designed and adequately fit this grouping, thereby reducing the costs for patients compared with patient-specific implants. For the remaining ten percent (10%) of the population, a patient-specific implant may be a better approach.

In the context of a mass customized implant, the statistical atlas may be utilized to quantitatively assess how many different groups (i.e., different implants) are able to encompass the overwhelming majority of a given population. These quantitative assessments may result in clusters of data indicating the general parameters for a basic implant design that, while not patient-specific, would be more specific than an off-the-shelf alternative.

In the context of a patient-specific implant, the statistical atlas may be utilized to quantitatively assess what a normal bone embodies and differences between the patient's bone and a normal bone. More specifically, the statistical atlas may include curvature data that is associated with a mean or template bone model. This template bone model can then be used to extrapolate what the form of the patient's correct bone would be and craft the implant and surgical instruments used to carry out the implant procedure.

Figure 30:
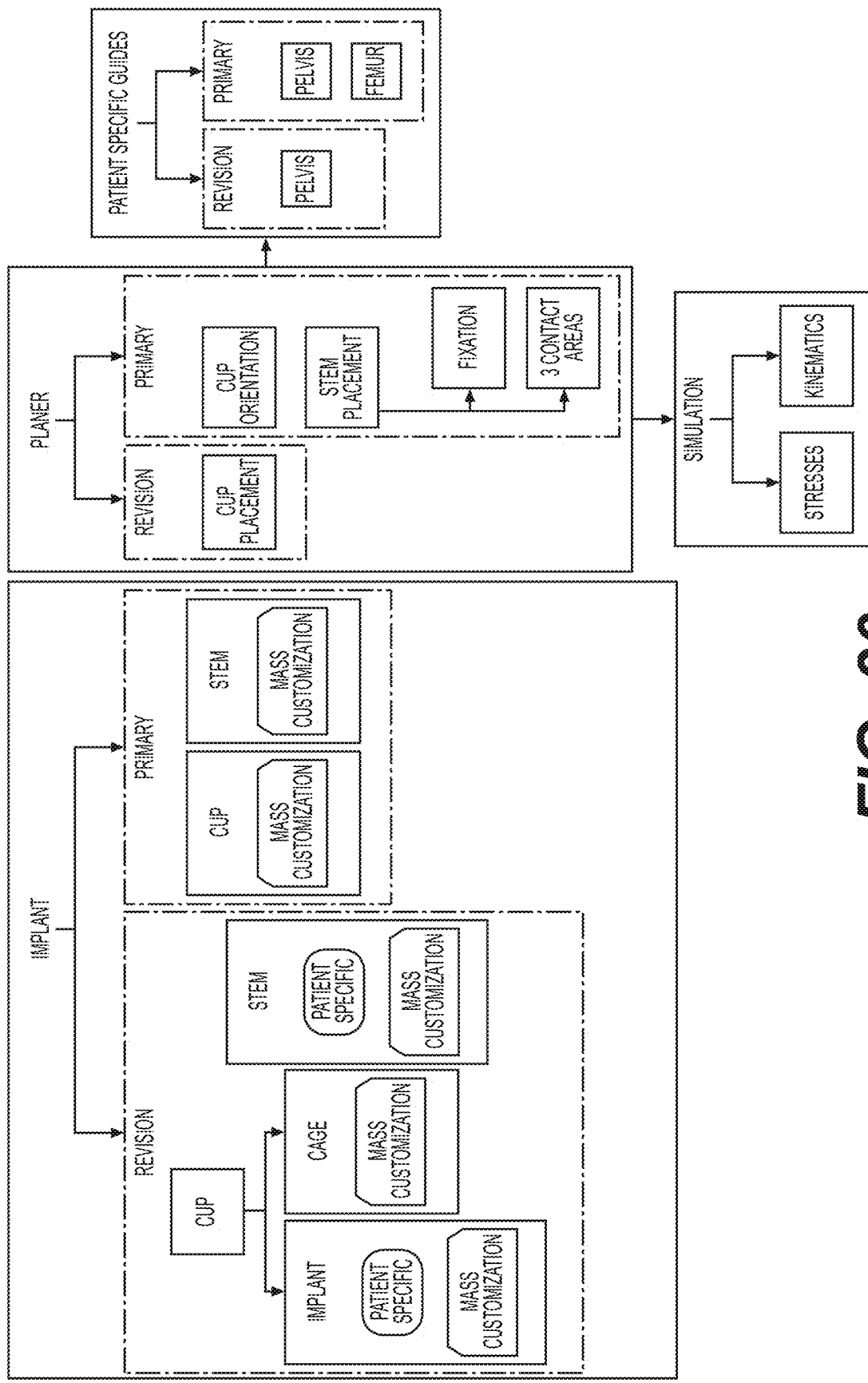
FIG. 30 is a schematic diagram depicting a process for using a statistical atlas for generation of both mass customized and patient-specific hip implant.

FIG. 30 graphically summarizes the utilization of a statistical atlas in designing mass customized and patient-specific hip implants. In the context of the implant box, reference is had back to FIGS. 20 and 21 and the associated discussion for these figures. Similarly, in the context of the planner box, reference is had back to FIG. 20 and the associated discussion of the custom planning interface. Finally, in the context of the patient-specific guides box, reference is had back to FIG. 22 and the associated discussion for this figure.

Figure 31:
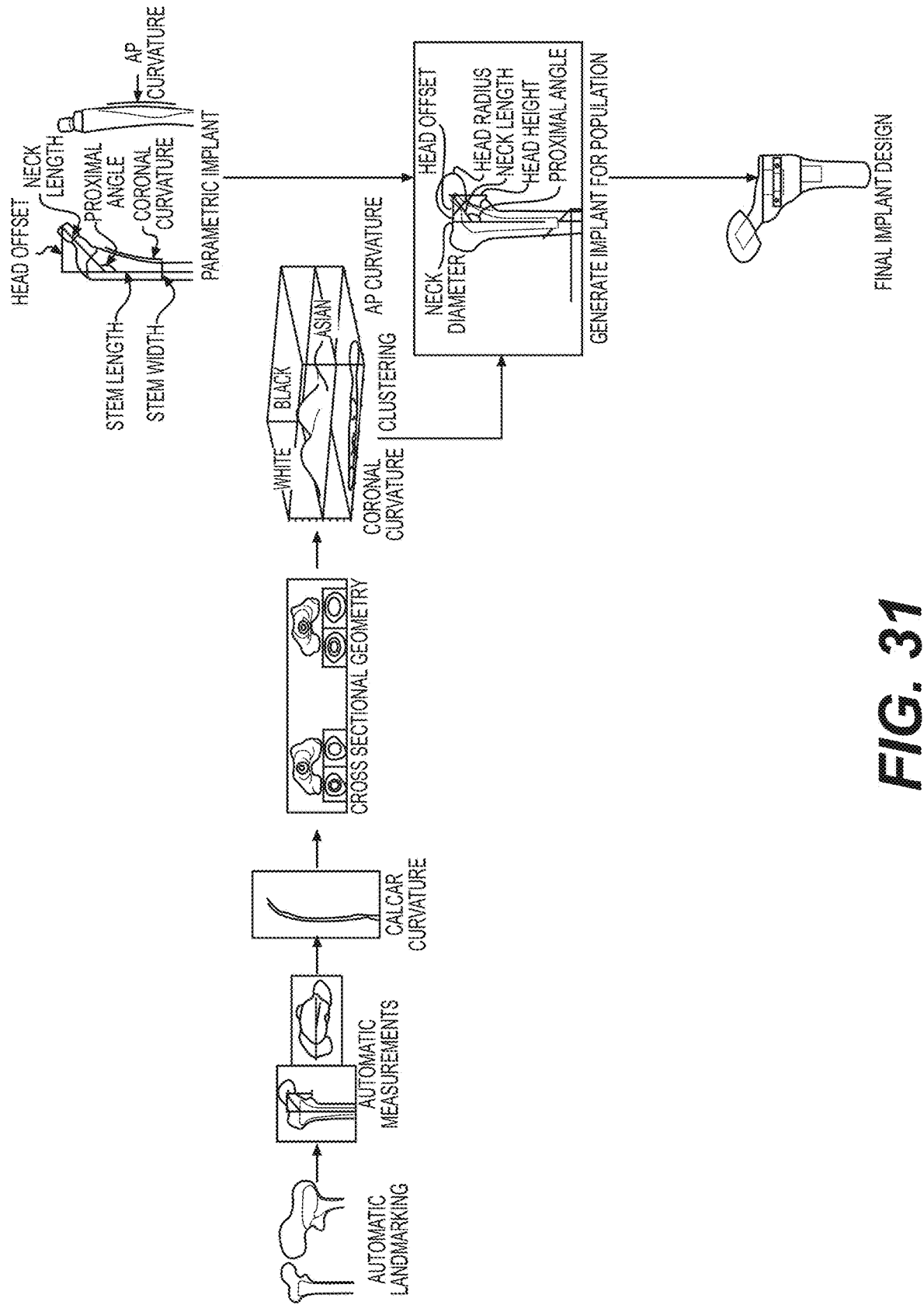
FIG. 31 is a schematic diagram depicting an outline of a process for designing population specific hip stem components.
Figure 32:
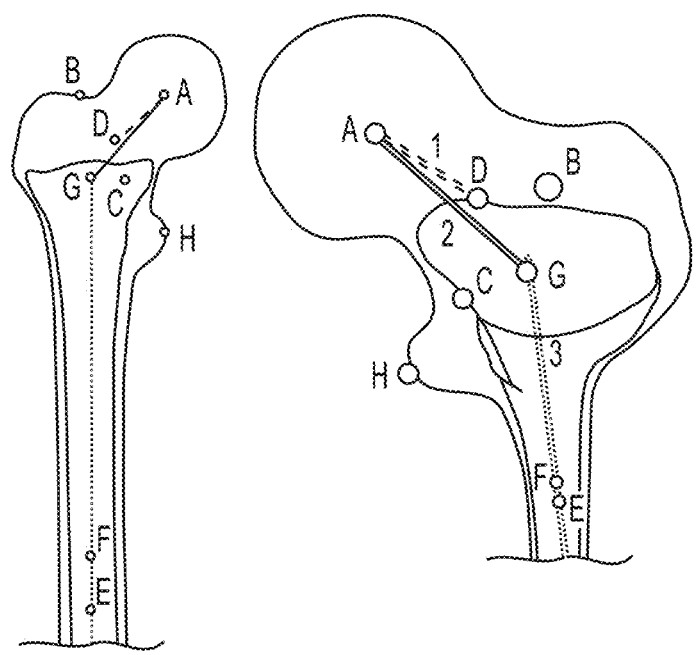
FIG. 32 is a graphical representation showing where the proximal femur landmarks are located.
Figure 33:
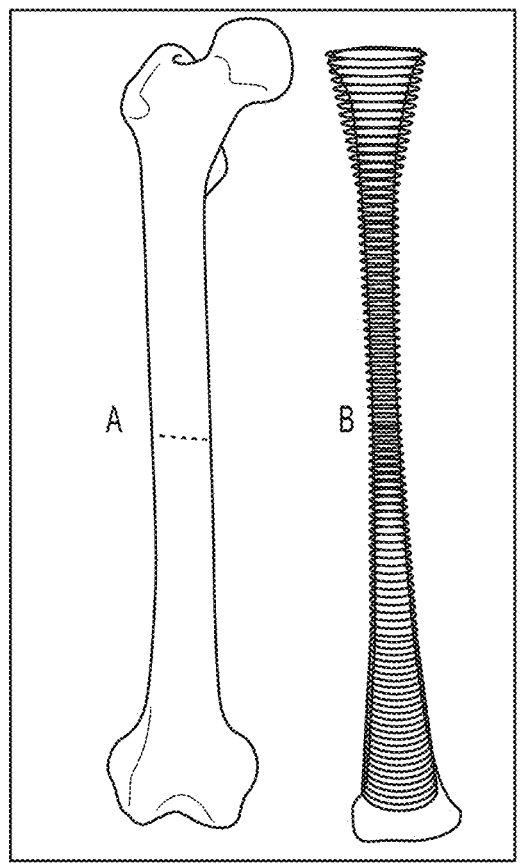
FIG. 33 is a 3D model of a femur showing canal waist in the middle of the femur and femur waist along the length of the femur.
Figure 34:
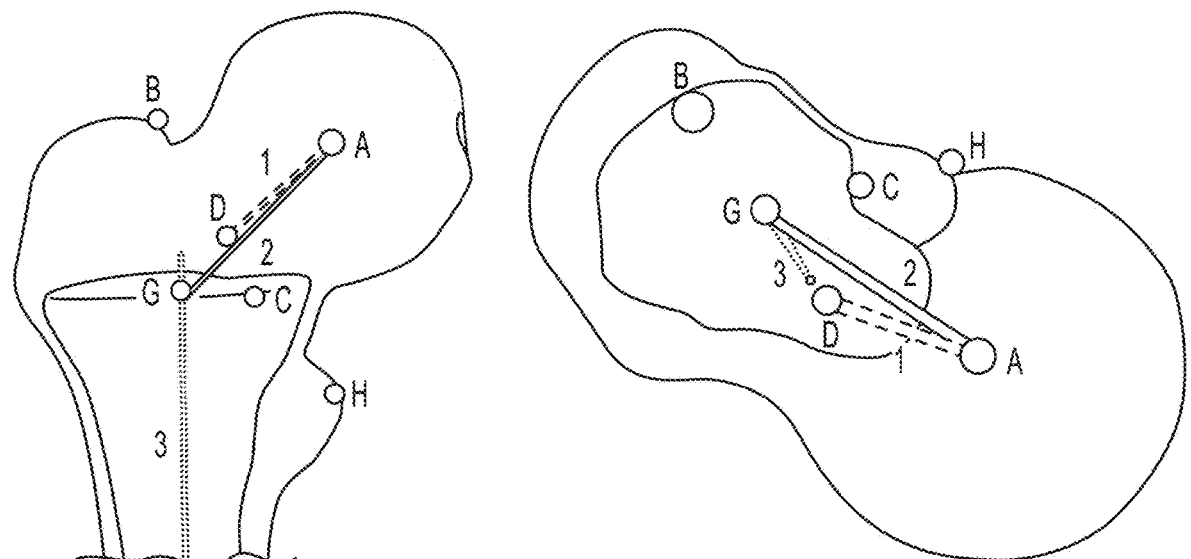
FIG. 34 is a graphical representation showing where the proximal femur axes are located.
Figure 35:
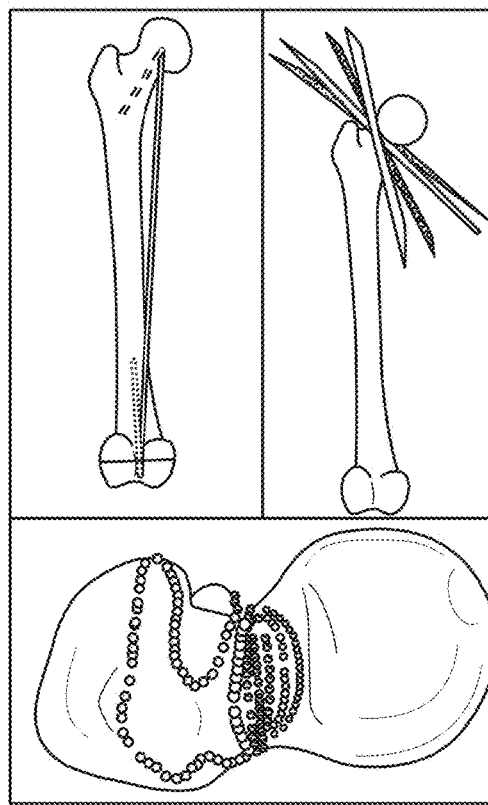
FIG. 35 is a graphical representation showing where the neck center calculation is located.
Figure 36:
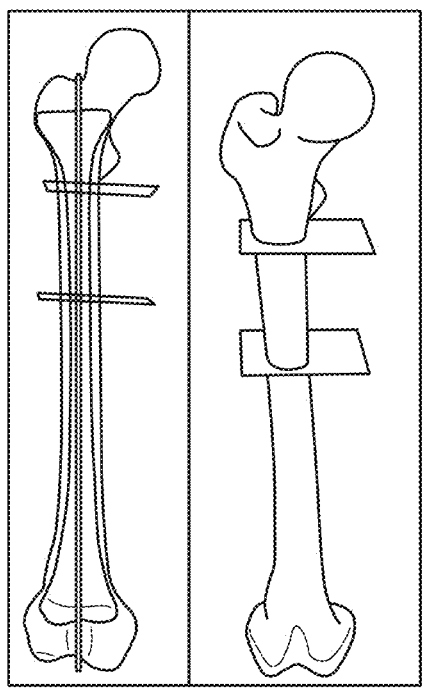
FIG. 36 is a graphical representation of two points used to define a femur proximal anatomical axis.
Figure 37:
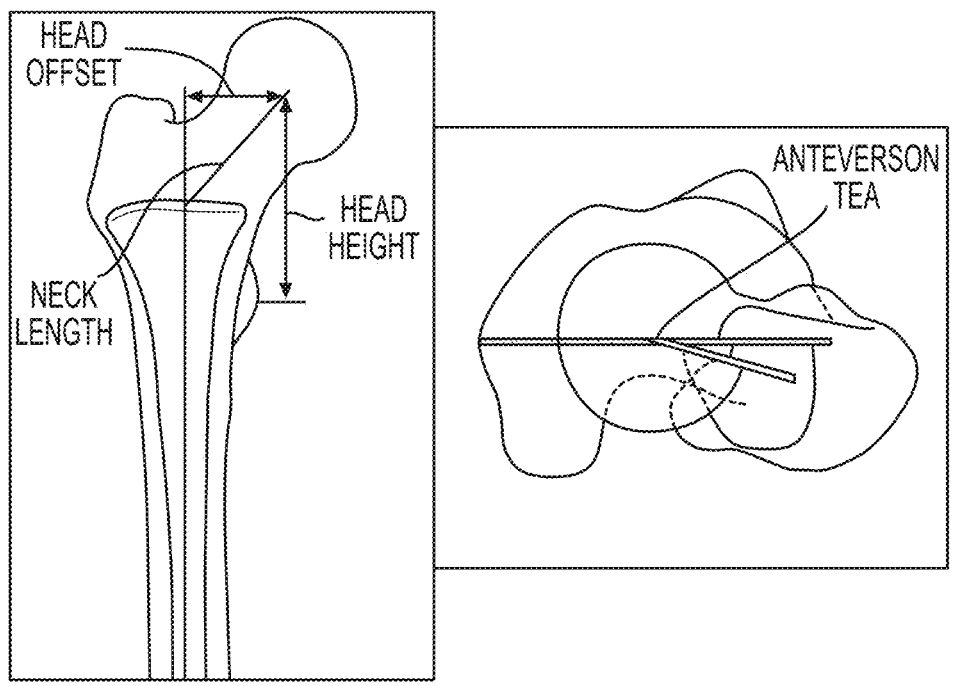
FIG. 37 is a graphical representation of 3D proximal femur measurements.
Figure 38:
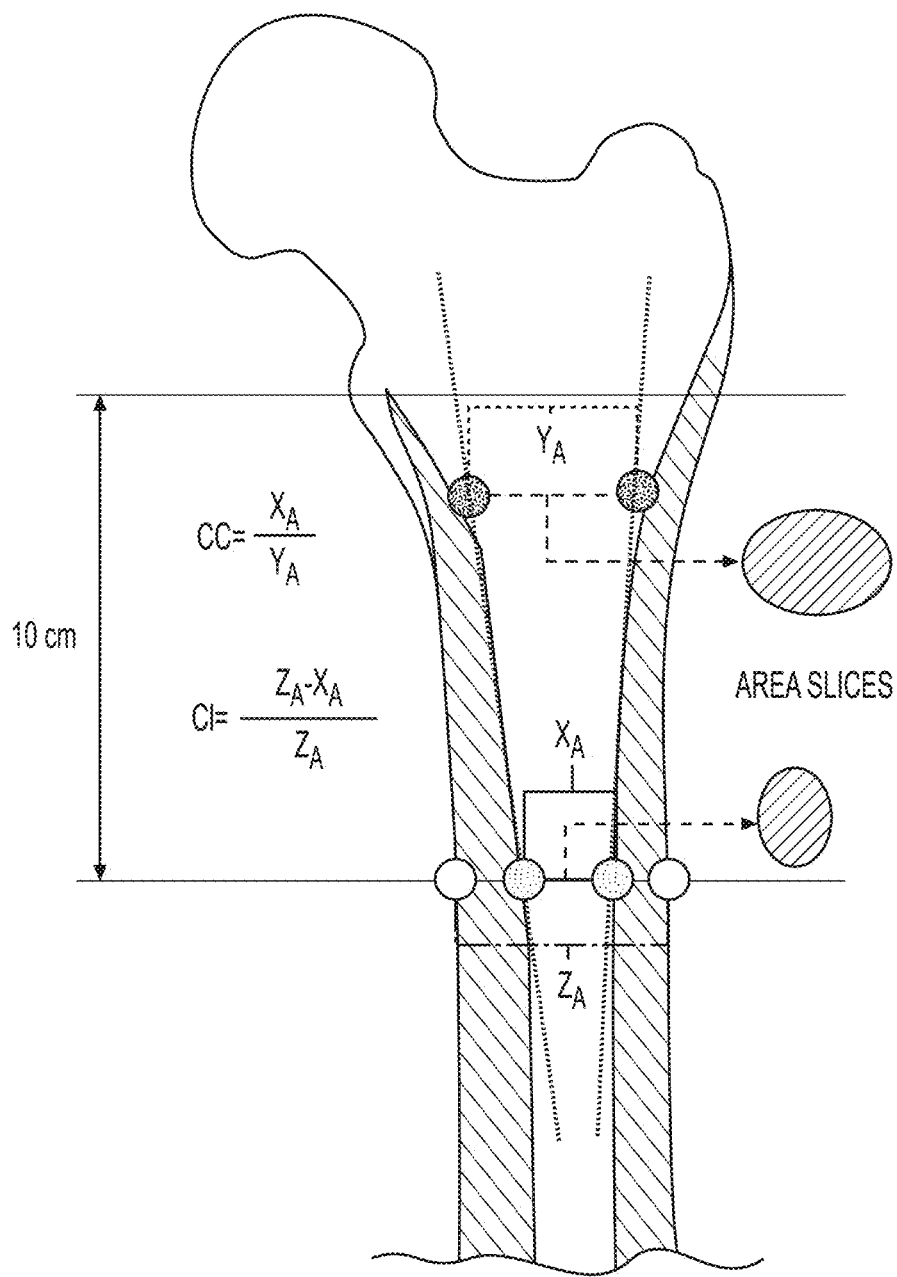
FIG. 38 is shows an exemplary Don ratio, which is generally in 2D (from XR).
Figure 39:
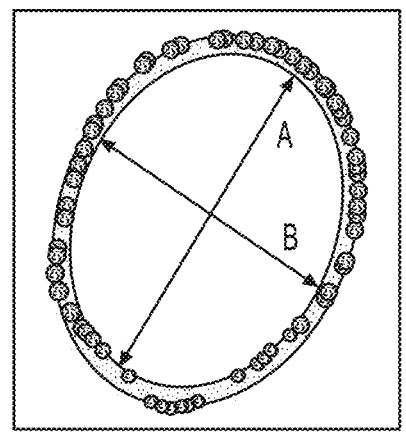
FIG. 39 is a graphical representation of the B/A ratio at the IM Isthmus.
Figure 40:
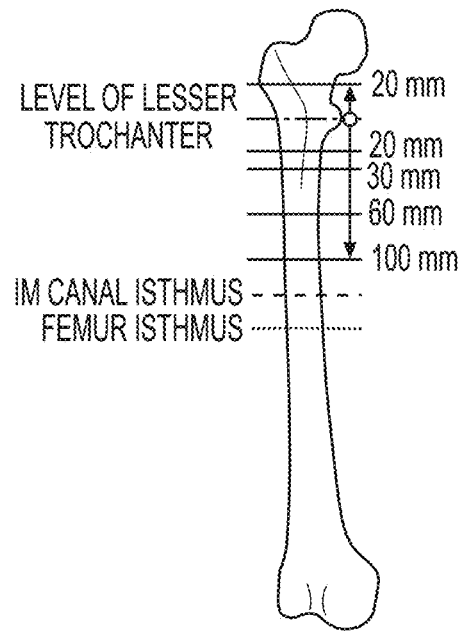
FIG. 40 is a graphical representation of IM canal measurements.
Figure 41:
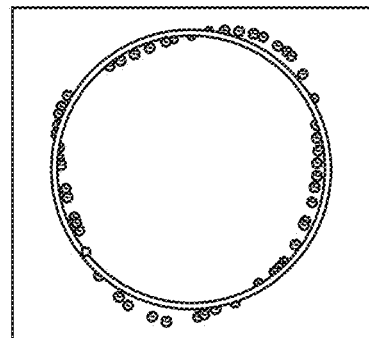
FIG. 41 is a contour and a fitted circle.
Figure 42:
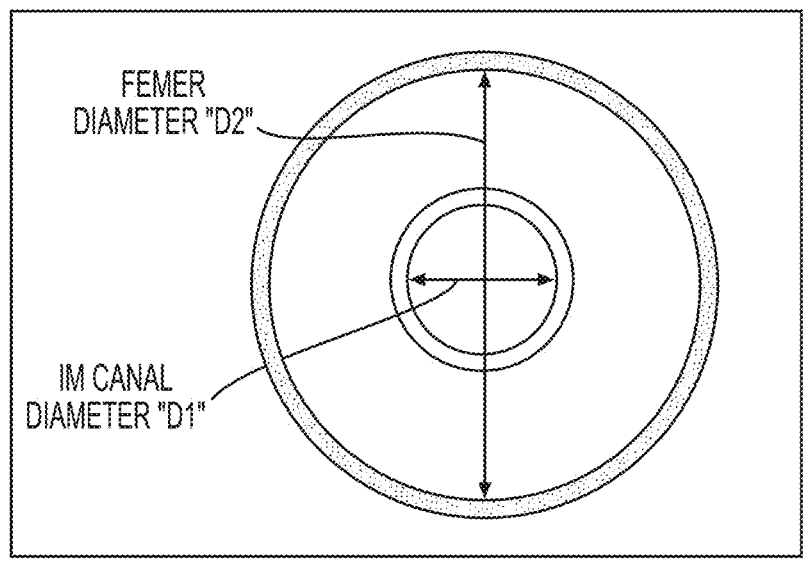
FIG. 42 is a graphical representation of the measurements taken to obtain the IM canal femur radii ratio.
Figure 43:
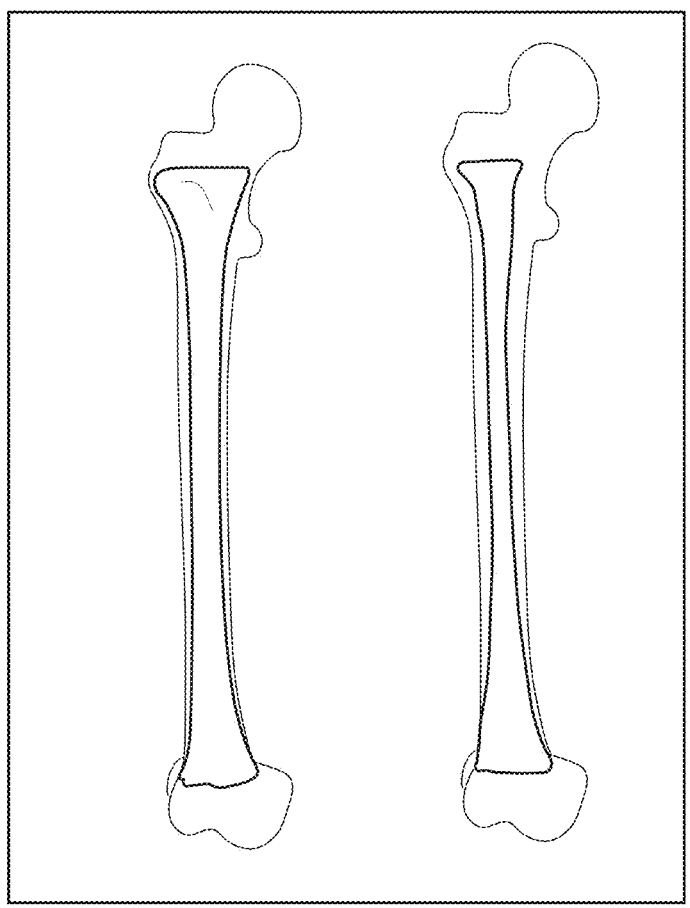
FIG. 43 depicts two femur models showing the effect of the change in the radii ratio, with the one on the left having a radii ratio of 0.69, and the one on the right having a radii ratio of 0.38.
Figure 44:
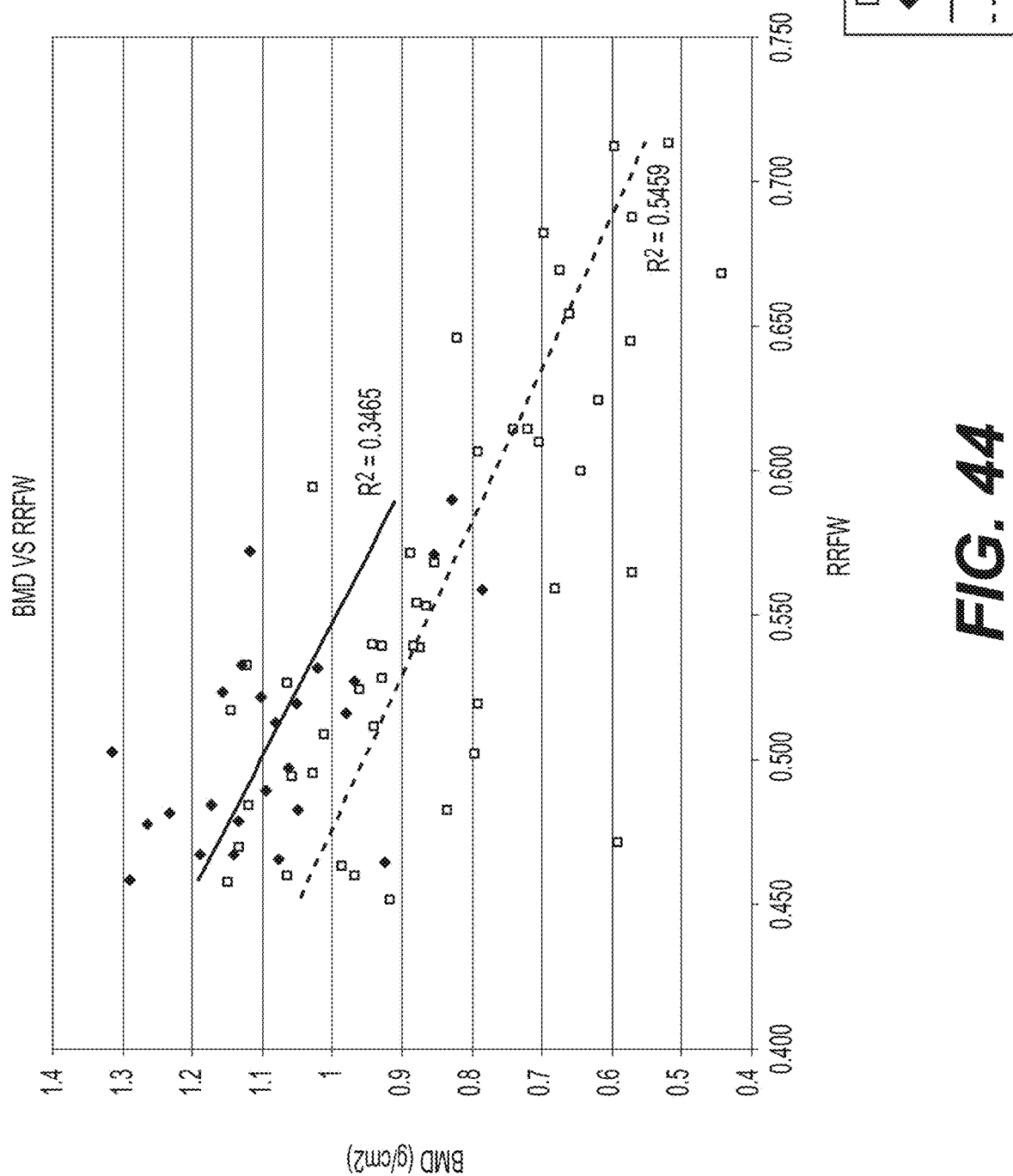
FIG. 44 is a plot of BMD versus RRFW for males and females, as well as the best line fit for each data set (male, female).
Figure 45:
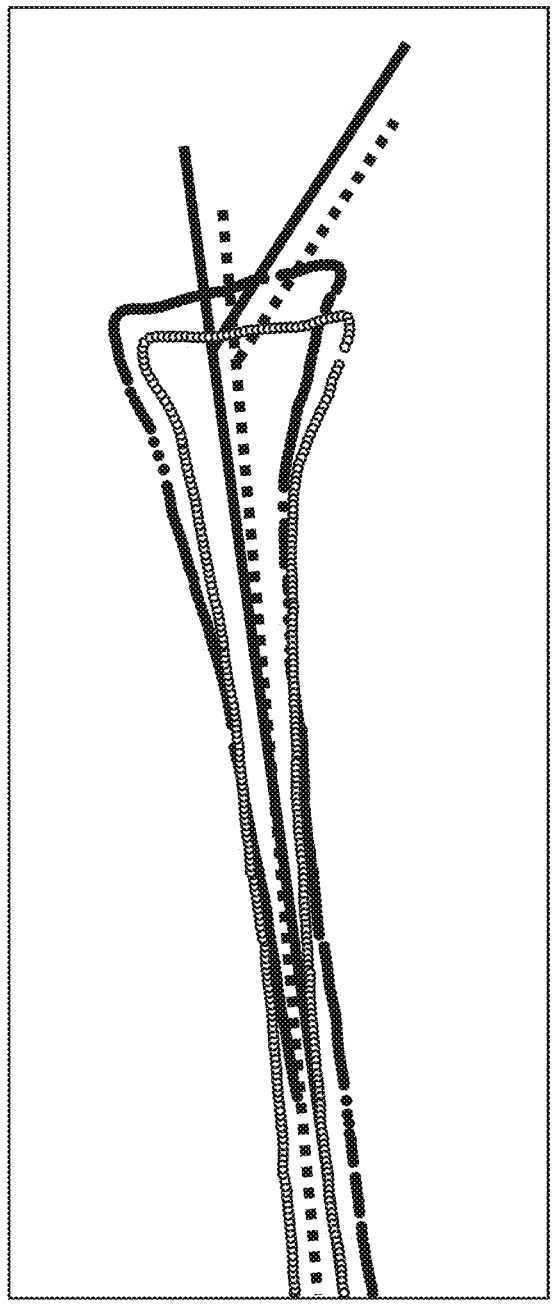
FIG. 45 is a graphical representation of medial contours, neck axis and head point of a proximal femur before alignment.
Figure 46:
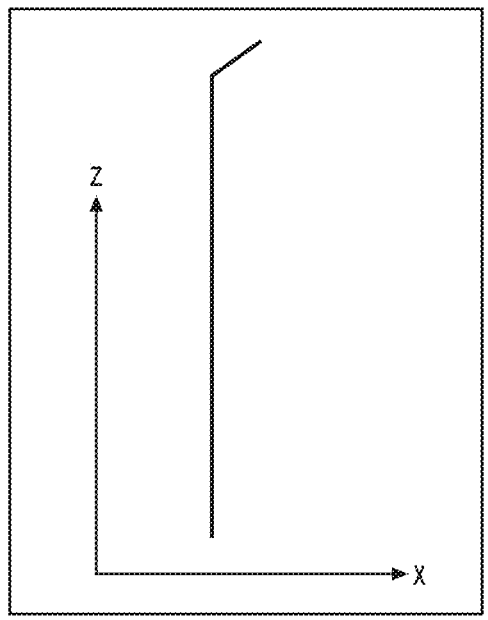
FIG. 46 is a graphical representation of an anatomical axis alignment with the Z-direction.
Figure 47:
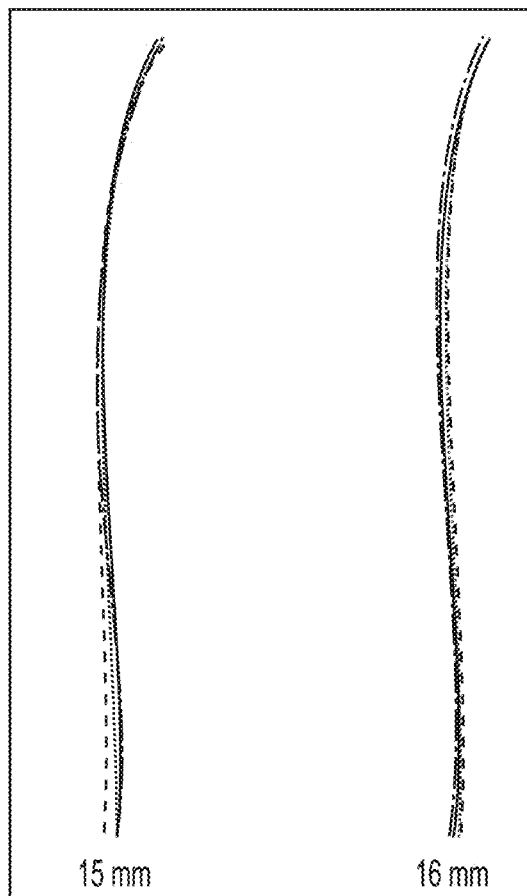
FIG. 47 is a graphical representation of medial contours aligned using the femoral neck pivot point.

As depicted in FIG. 31, a flow chart is depicted for an exemplary process that may be utilized to design and fabricate gender and/or ethnic specific hip implants. In particular, the process includes utilization of a statistical atlas containing various specimens of a proximal femur (i.e., femur including femoral head) that have been identified by associated data as being from either a male or a female and the ethnicity of the person from which the bone pertains. Moreover, the statistical atlas module logs virtual, 3D models of one or more anatomies (e.g., bones) to capture the inherent anatomical variability in a given gender and/or ethnic population. In exemplary form, the atlas logs mathematical representations of anatomical features of the one or more anatomies represented as a mean representation and variations about the mean representation for a given anatomical population that may have a common gender and/or ethnicity (or grouped to have one of a plurality of ethnicities for which anatomical commonalities exist). Reference is had to FIG. 2 and the foregoing discussion of the statistical atlas and how one adds anatomy to the statistical atlas for a given population. Outputs from the statistical atlas are directed to an automatic landmarking module and to a surface/shape analysis module.

Referring to FIGS. 31-43, the automatic landmarking module utilizes inputs from the statistical atlas (e.g., regions likely to contain a specific landmark) and local geometrical analyses to calculate anatomical landmarks for each instance of anatomy within the statistical atlas. By way of example, various proximal femur landmarks are calculated for each 3D virtual model of a femur that include, without limitation: (1) femoral head center, which is the center point of a femoral head approximated by a sphere; (2) greater trochanter point, which is the point on the greater trochanter having the minimum distance to the plane passing through the neck shaft point perpendicular to the anatomical neck center line; (3) osteotomy point, which is the point fifteen millimeters from the end of the lesser trochanter (approximately thirty millimeters from the lesser trochanter point); (4) neck shaft point, which is the point on the head sphere whose tangential plane encloses the minimum femoral neck cross-sectional area; (5) femur waist, which is the cross-section with the smallest diameter along the femur shaft; (6) intramedullary canal waist, which is the cross-section with the smallest diameter along the intramedullary canal; (7) femoral neck pivot point, which is the point on the femoral anatomical axis that forms with the femoral head center and the distal end of the femoral anatomical axis an angle equal to the femoral neck angle; and, (8) lesser trochanter point, which is the point on the lesser trochanter region that most protrudes outward. By way of further example, various proximal femur axes are calculated for each 3D virtual model of a femur using the identified anatomical landmarks that include, without limitation: (a) femoral neck anatomical axis, which is coaxial with a line connecting the femur head center with the femur neck center; (b) femoral neck axis, which is coaxial with a line joining the femur head center point and the femoral neck pivot point; and, (c) femoral anatomical axis, which is coaxial with a line connecting two points lying at a distance twenty-three percent and forty percent of the total femur length starting from the proximal end of the femur. By way of yet further example, various proximal femur measurements are calculated for each 3D virtual model of a femur using the identified anatomical landmarks and axes that include, without limitation: (i) proximal angle, which is the 3D angle between femoral anatomical axis and femoral neck anatomical axis; (ii) head offset, which is the horizontal distance between the femoral anatomical axis and the femoral head center; (iii) head height, which is the vertical distance between the lesser trochanter point (referenced previously) and femoral head center; (iv) greater trochantor to head center distance, which is the distance between the head center and the greater trochanter point (referenced previously); (v) neck length, which is the distance between the head center and the neck-pivot point (referenced previously); (vi) the head radius, which is the radius of the sphere fitted to femoral head; (vii) neck diameter, which is the diameter of the circle fitted to the neck cross section at plane normal to femoral neck anatomical axis and passing through neck center point (referenced previously); (viii) femoral neck anteversion transepicondylar angle, which is the angle between the transepicondylar axis and femoral neck axis; (ix) femoral neck anteversion posteriorcondylar angle, which is the angle between the posteriorcondylar axis and femoral neck axis; (x) LPFA, which is the angle between mechanical axis and vector pointing to the greater trochanter; (xi) calcar index area, which is defined by the equation: $(Z-X)/Z$, where Z is the femur area at 10 centimeters below the mid lesser trochanter point and X is the intramedullary canal area at 10 centimeters below the mid lesser trochanter point; (xii) canal calcar ratio area, which is the ratio between the intramedullary canal area at 3 centimeters below the mid-lesser trochanter level to the intramedullary canal area at 10 centimeters below the mid-lesser trochanter; (xiii) XYR area, which is the ratio between the intramedullary canal area at 3 centimeters below the mid-lesser trochanter to the intramedullary canal area at 10 centimeters below the mid-lesser trochanter; (xiv) minor/major axes ratio, which is the ratio between the minor axis and major axis of a fitted ellipse to the intramedullary canal cross-section at the narrowest point on intramedullary canal; and, (xv) femur radii to intramedullary canal radii ratio, which is the ratio of circle radii, using circles best fit to the circumference of the outer circumference of the femur and intramedullary canal within a plane normal to the femoral anatomical axis (this ratio reflects the thickness of the cortical bone and, accordingly, cortical bone loss in cases of osteoporosis).

Referencing FIGS. 31 and 45-47, using the output from the automatic landmarking module, parameters for the femoral stem are assessed for a given population. In particular, regardless of whether the population is grouped based upon ethnicity, gender, or a combination of the two, the medial contour, neck angle, and head offset are assessed.

In the case of the medial contour, this contour with respect to the intramedullary canal for each femur within the population is generated by intersecting the intramedullary canal with a plane extending through the femoral pivot point and having a normal axis perpendicular to both the femoral anatomical axis and the neck axis (vectors cross product).

After the contours are generated for each femur within the population, the population is subdivided into groups using intramedullary canal size. When subdivided, the contours may be out of plane, so an alignment process is carried out to align all the contours with respect to a common plane (e.g., an X-Z plane). The alignment process includes aligning the axis which is normal to both the femoral neck axis and anatomical axis to the Y axis then aligning the anatomical axis to the Z axis. In this fashion, all contours are translated relative to a specific point in order for the contours to have a common coordinate frame.

After the contours have a common coordinate frame, the femoral neck point is utilized to verify that the points of the contours are in plane. In particular, the femoral neck point is a consistent point that reflects real anatomy and guarantees the points on the contours are in plane. By verifying the points of the contour are in plane, alignment variability between population femurs can be significantly reduced, which facilitates utilization of the contours for head offset and implant angle design.

Figure 48:
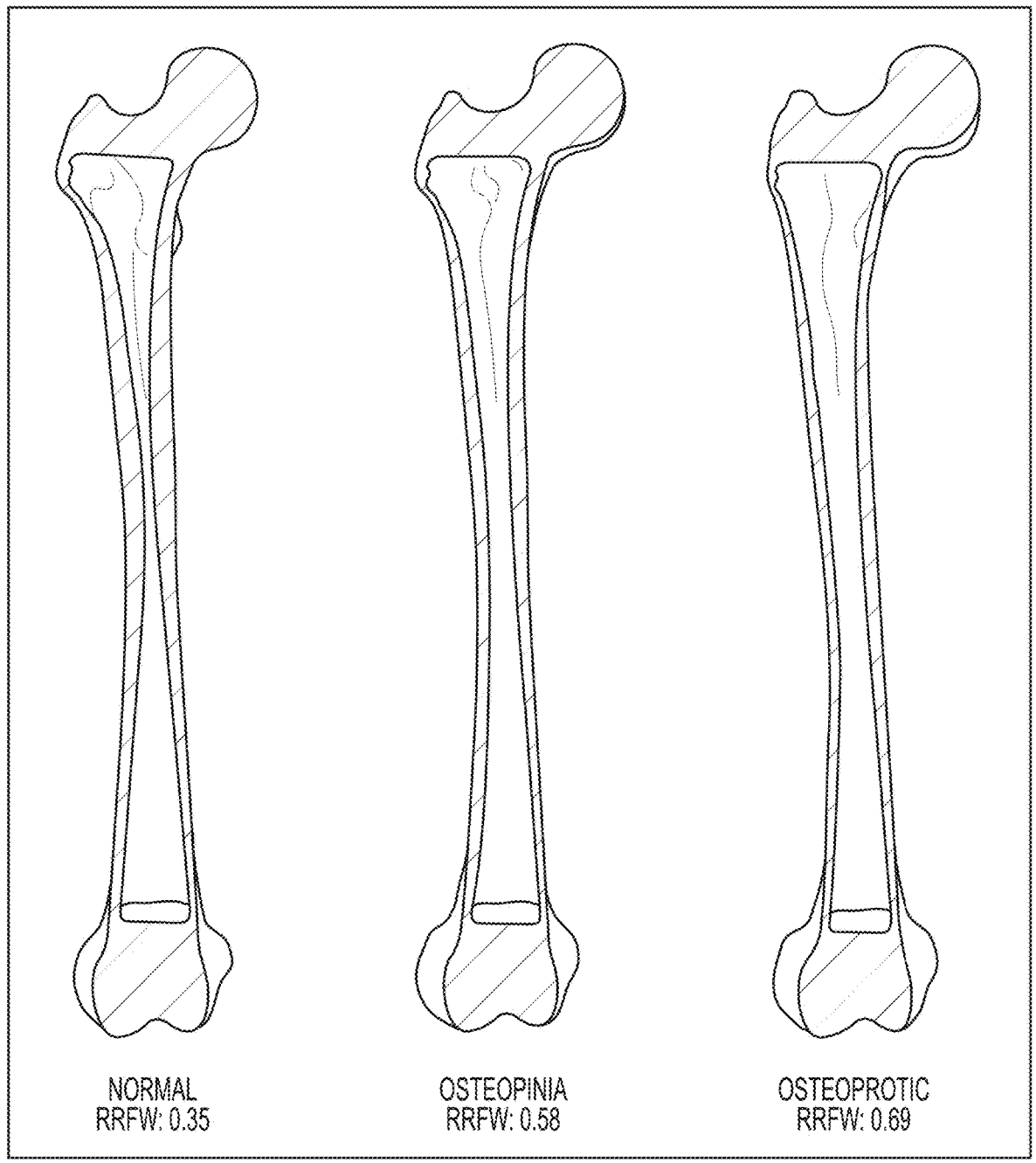
FIG. 48 is a graphical representation of different models generated using interpolation between models to show the smoothness of interpolation.
Figure 49:
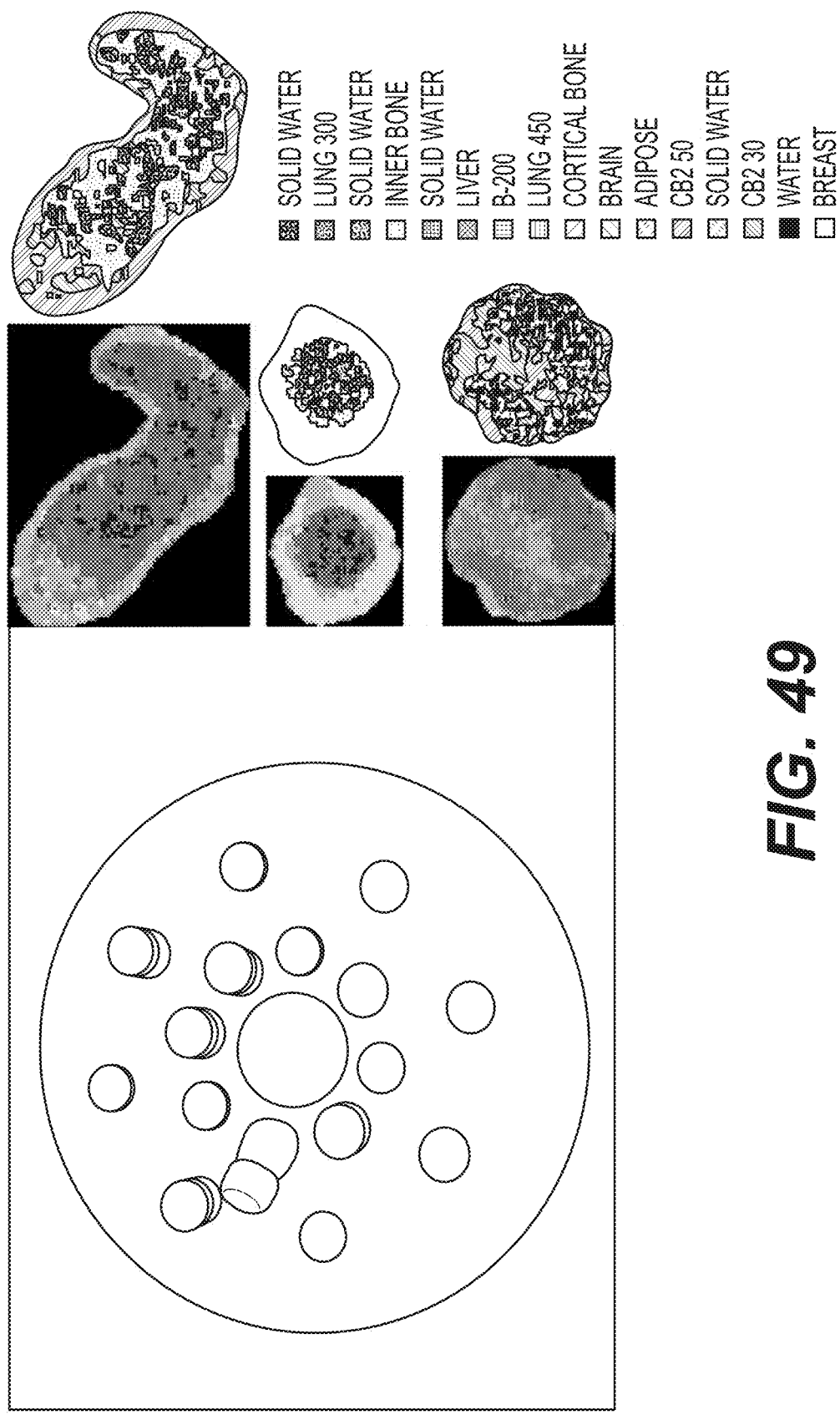
FIG. 49 is a graphical and pictorial representation of three dimensional mapping of bone density.

Referring to FIG. 48, the statistical atlas may also be useful to interpolate between normal and osteoporotic bones. When designing and sizing a femoral stem, one of the key considerations is intramedullary canal dimensions. In instances of normal bone, with respect to the femur, the intramedullary canal is significantly narrower than compared to a femur exhibiting osteoporosis. This narrower intramedullary canal dimension is the result, at least in part, of bone thicknesses (measured transverse to the dominant axis of the femur) decreasing, which correspondingly results in receding of the interior surface of the femur delineating the intramedullary channel. In this method, a synthetic population is created by interpolating between healthy and severely osteoporotic bone thicknesses and generating virtual 3D models having said thicknesses. This dataset thusly contains bones corresponding to different stages of osteoporosis. This dataset can now be used as an input to implant stem design.

In exemplary form, the statistical atlas includes a population of normal, non-osteoporotic bones and osteoporotic bones, in this case the bone is a femur. Each of these normal femurs of the atlas is quantified and represented as a 3D virtual model, in accordance with the process described herein for adding bones to a statistical atlas. Likewise, each of the osteoporotic bones of the atlas is quantified and represented as a 3D virtual model, in accordance with the process described herein for adding bones to a statistical atlas. As part of the 3D models for normal and osteoporotic bones, intramedullary canal dimensions are recorded along the longitudinal length of the femur. Using atlas point correspondence, the intramedullary canal is identified on the atlas bones as spanning a fixed percentage of the overall bone length (say 5%) proximal to the lesser trochanter and a second fixed percentage (say 2%) proximal to the distal cortex point. Additionally, points on the external bone surface falling within these proximal and distal bounds are used for determining bone thickness, defined as the distance from the external point to the nearest point on the IM canal.

Figure 59:
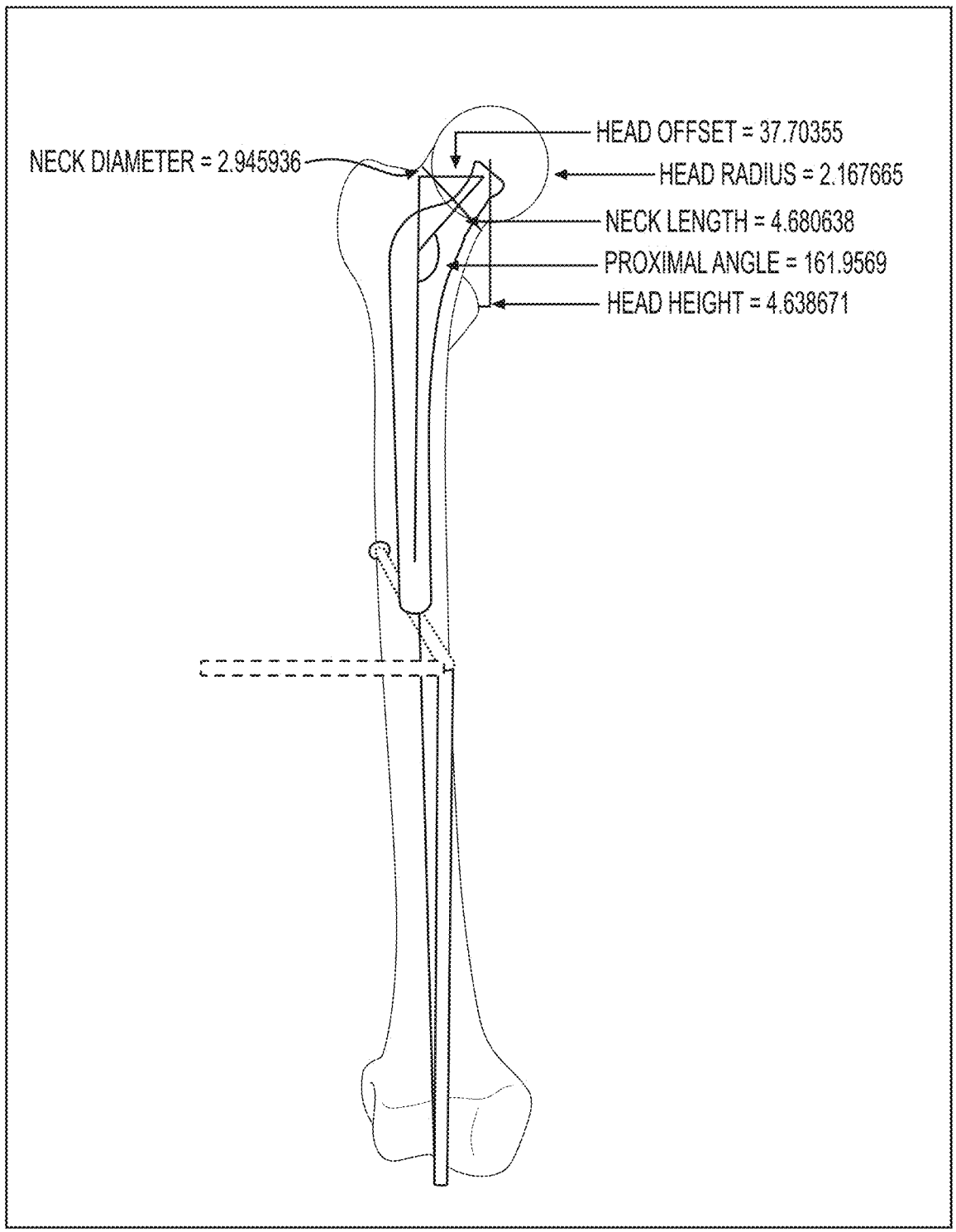
FIG. 59 is a graphical representation of female measurements with respect to a proximal femur.
Figure 60:
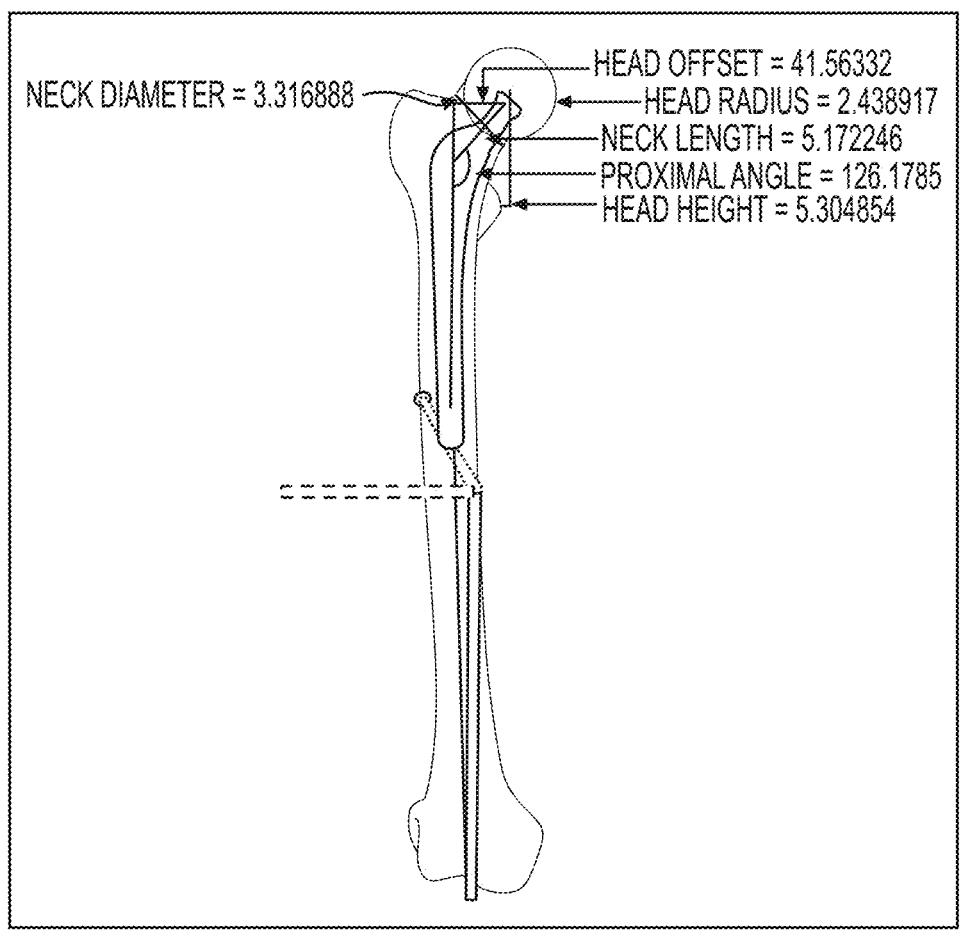
FIG. 60 is a graphical representation of male measurements with respect to a proximal femur.
Figure 61:
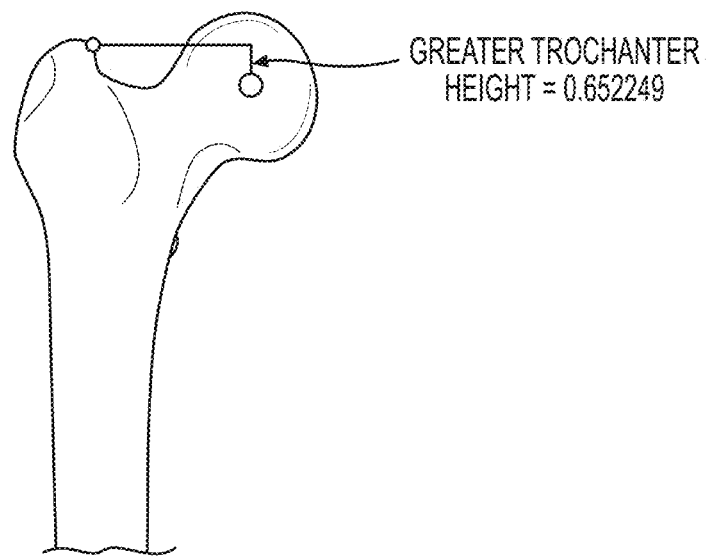
FIG. 61 is a graphical representation of female measurements with respect to the greater trochanter height.
Figure 62:
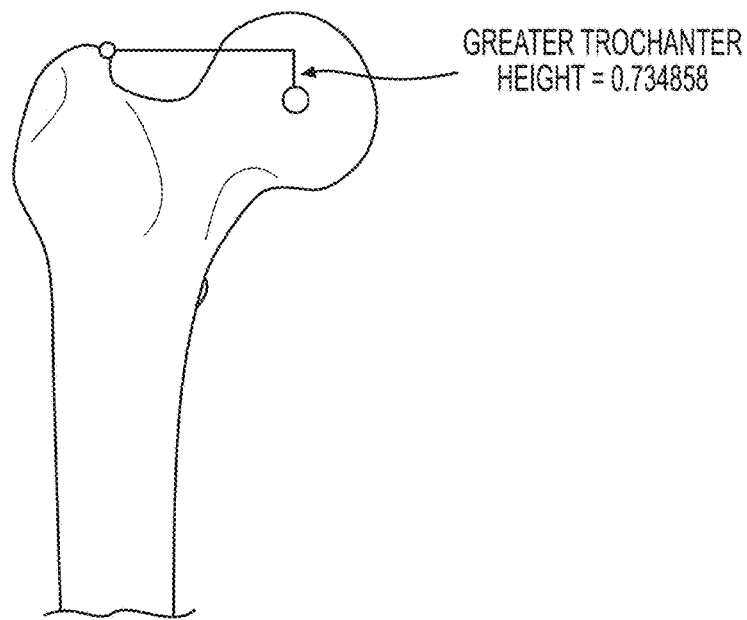
FIG. 62 is a graphical representation of male measurements with respect to the greater trochanter height.
Figure 63:
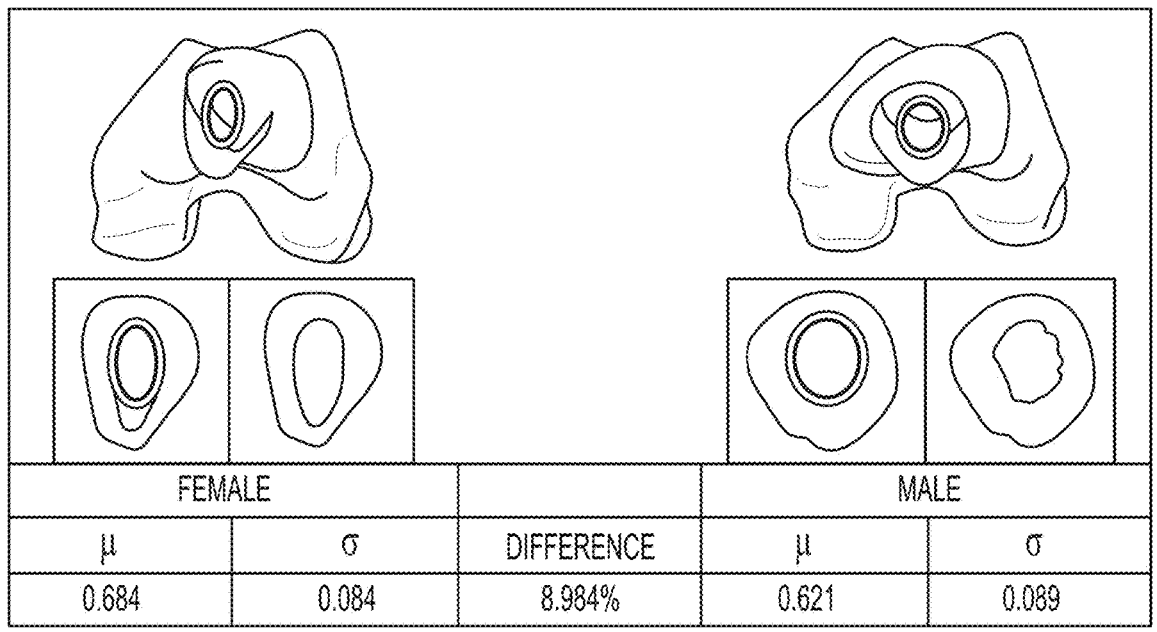
FIG. 63 is a graphical representation and table showing intramedullary canal shape differences between males and females.
Figure 64:
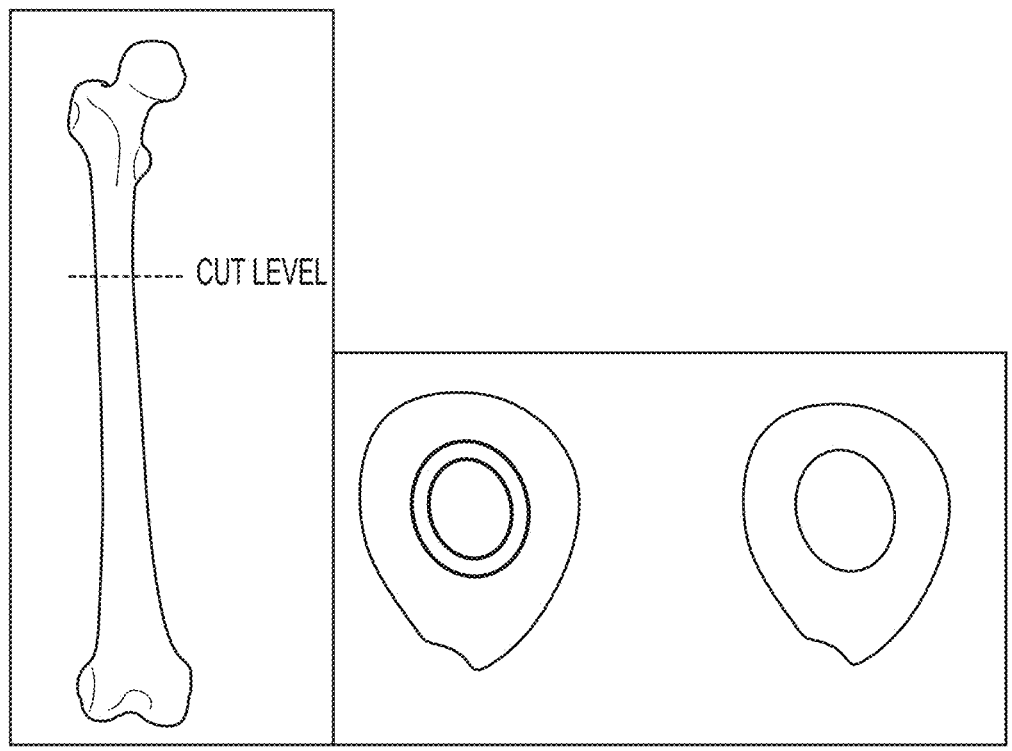
FIG. 64 depicts a female femur and intramedullary canal representative of normal bone density and quality.
Figure 65:
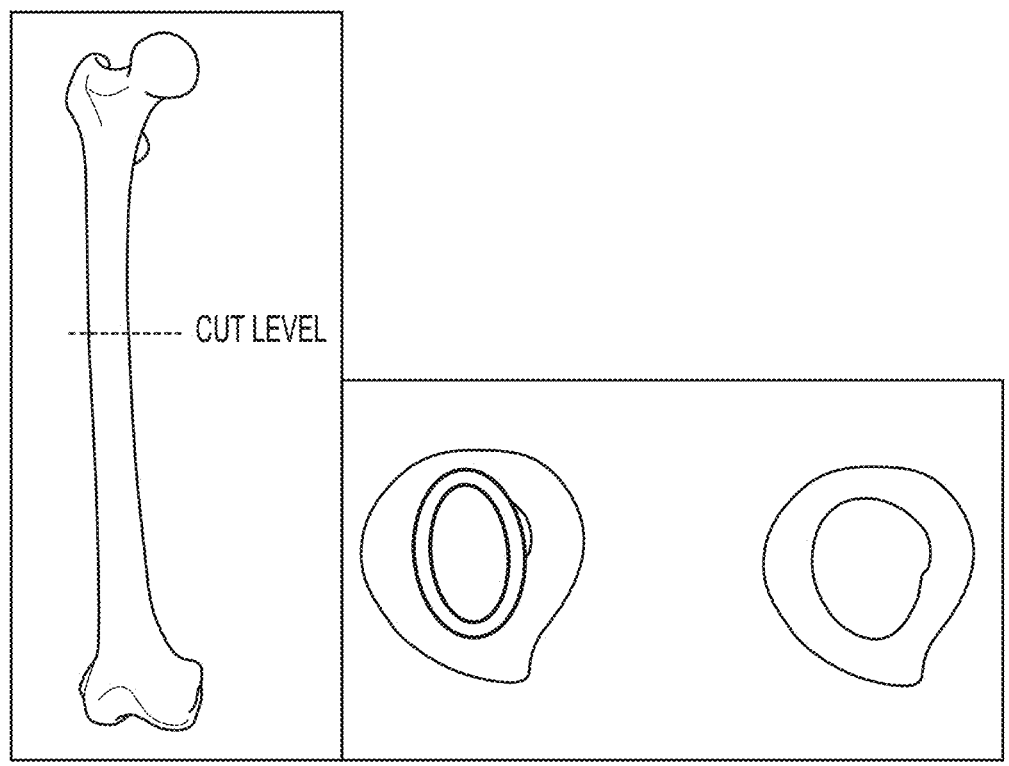
FIG. 65 depicts a female femur and intramedullary canal representative of less than normal bone density and quality.
Figure 66:
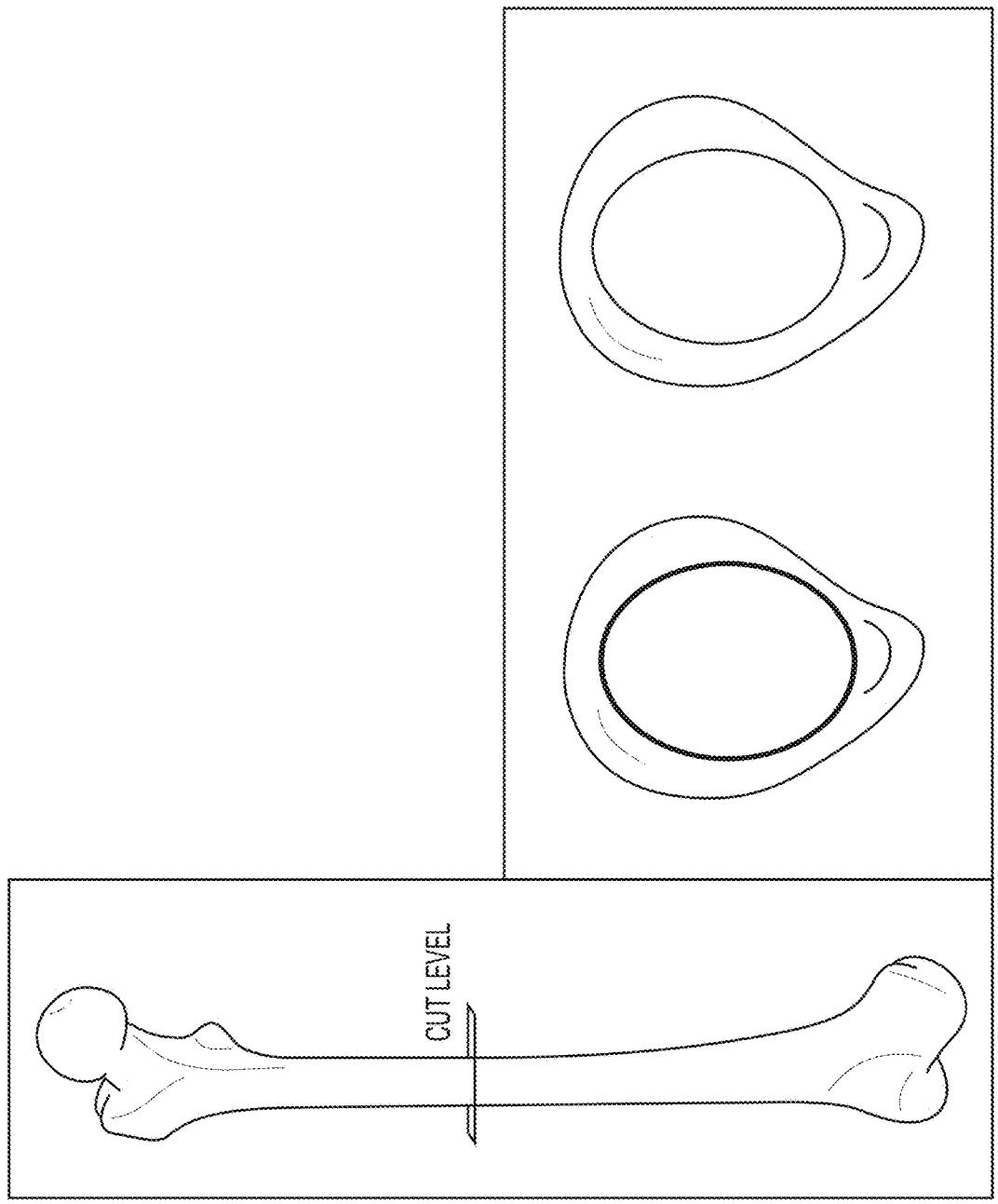
FIG. 66 depicts a female femur and intramedullary canal representative of osteoporosis.
Figure 67:
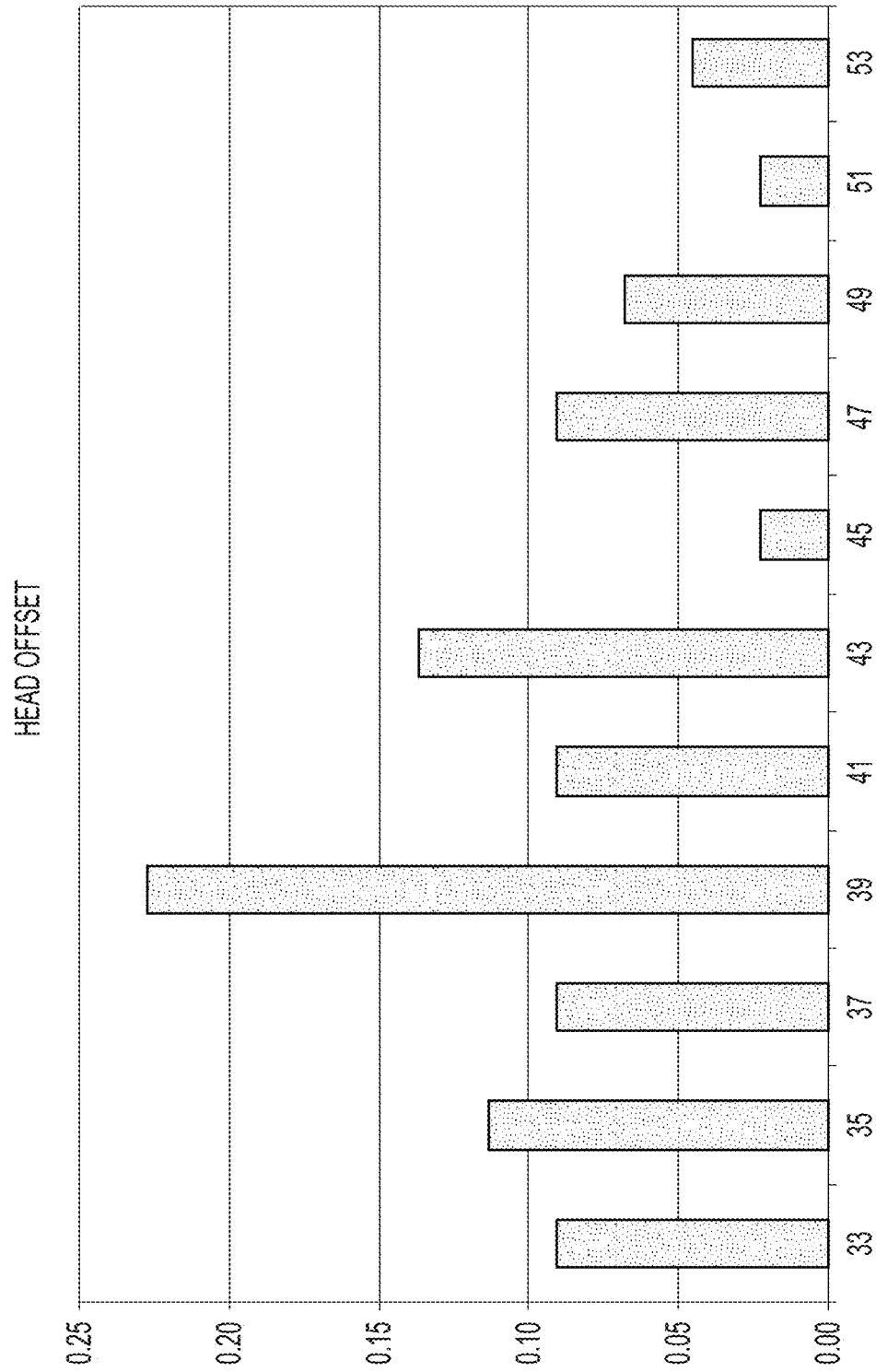
FIG. 67 is a chart comprising an interpolated dataset headoffsets histogram.
Figure 68:
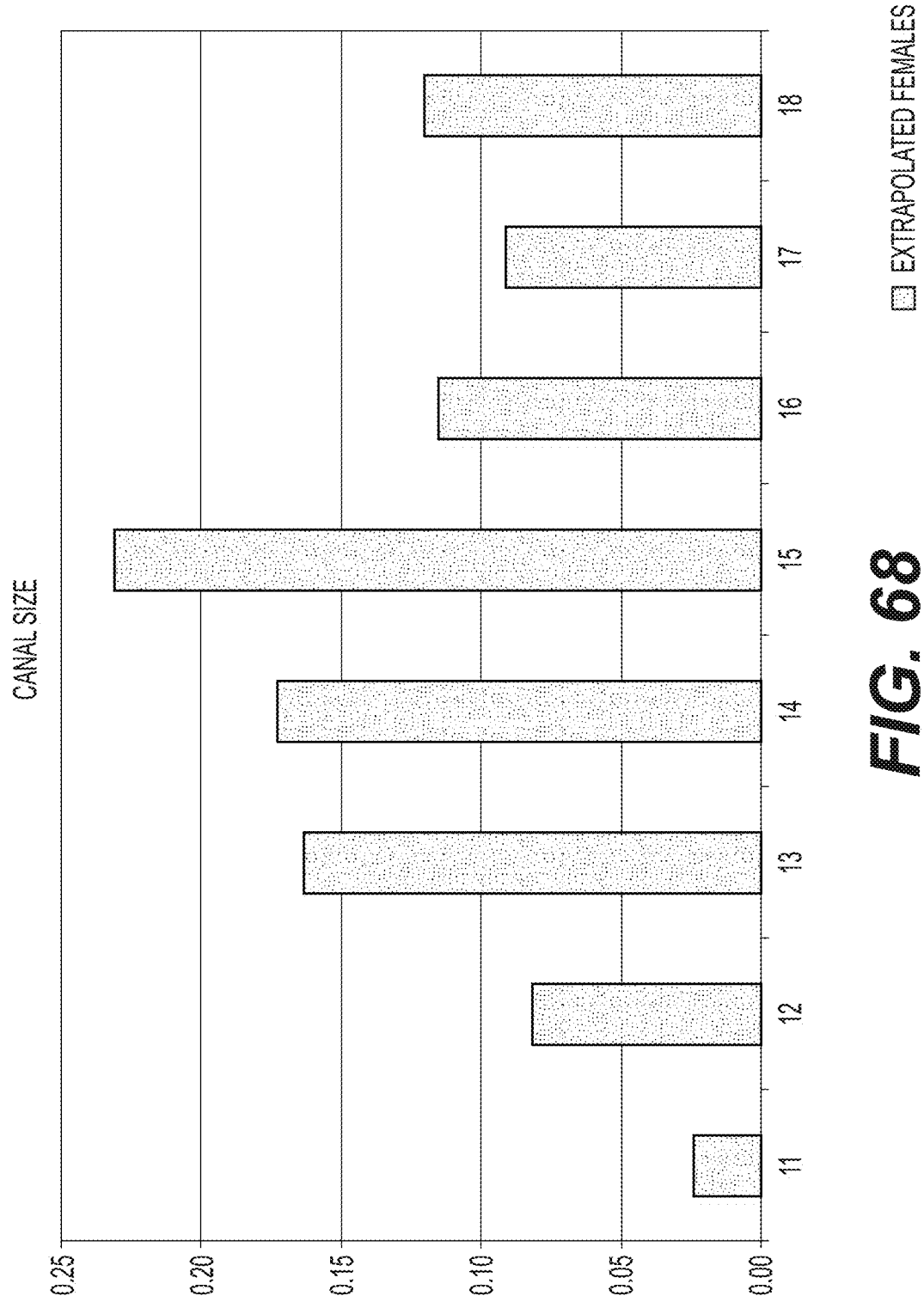
FIG. 68 is a chart comprising a canal size dataset histogram.
Figure 69:
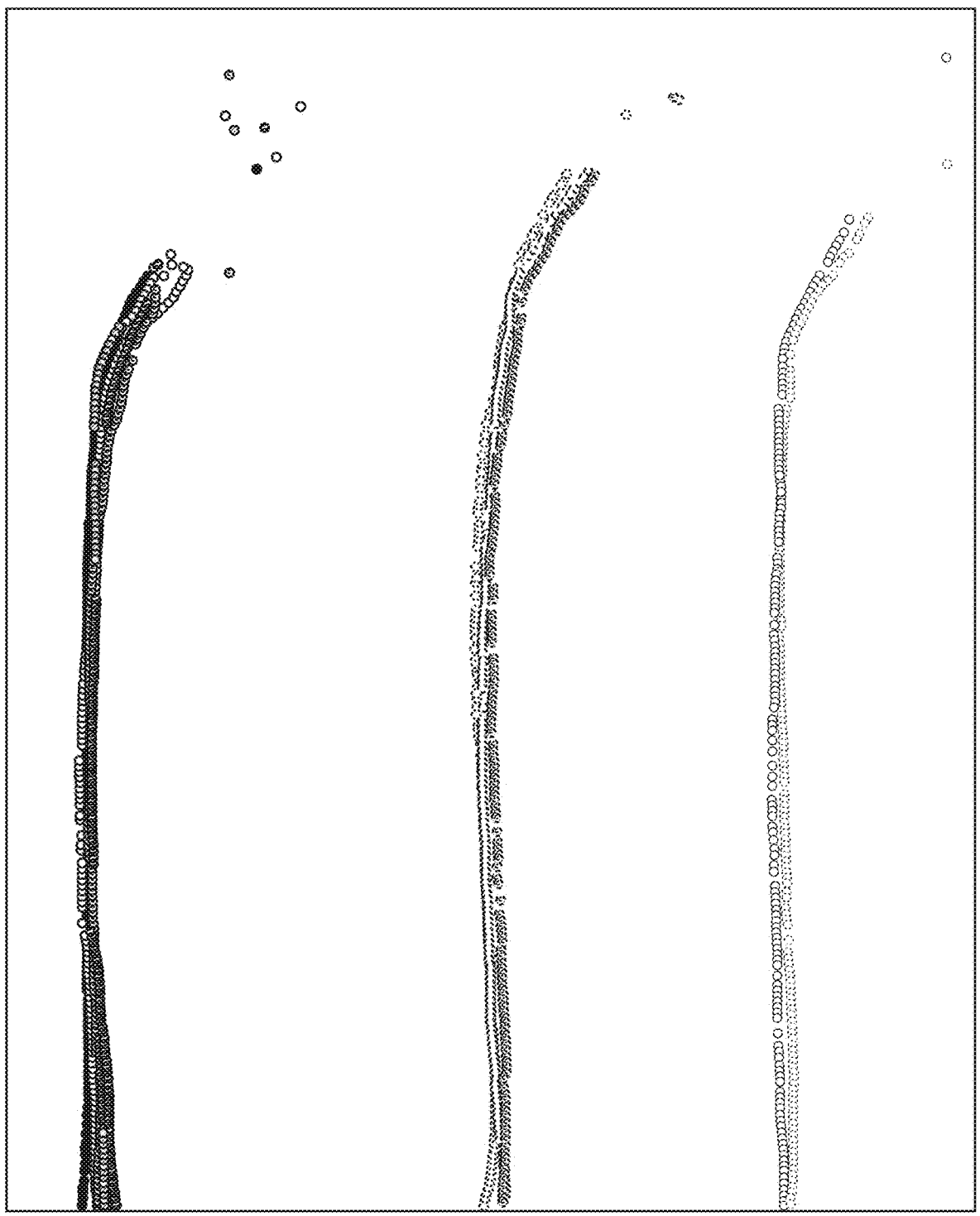
FIG. 69 depicts medial contours and head centers distribution for various femur groups.
Figure 70:
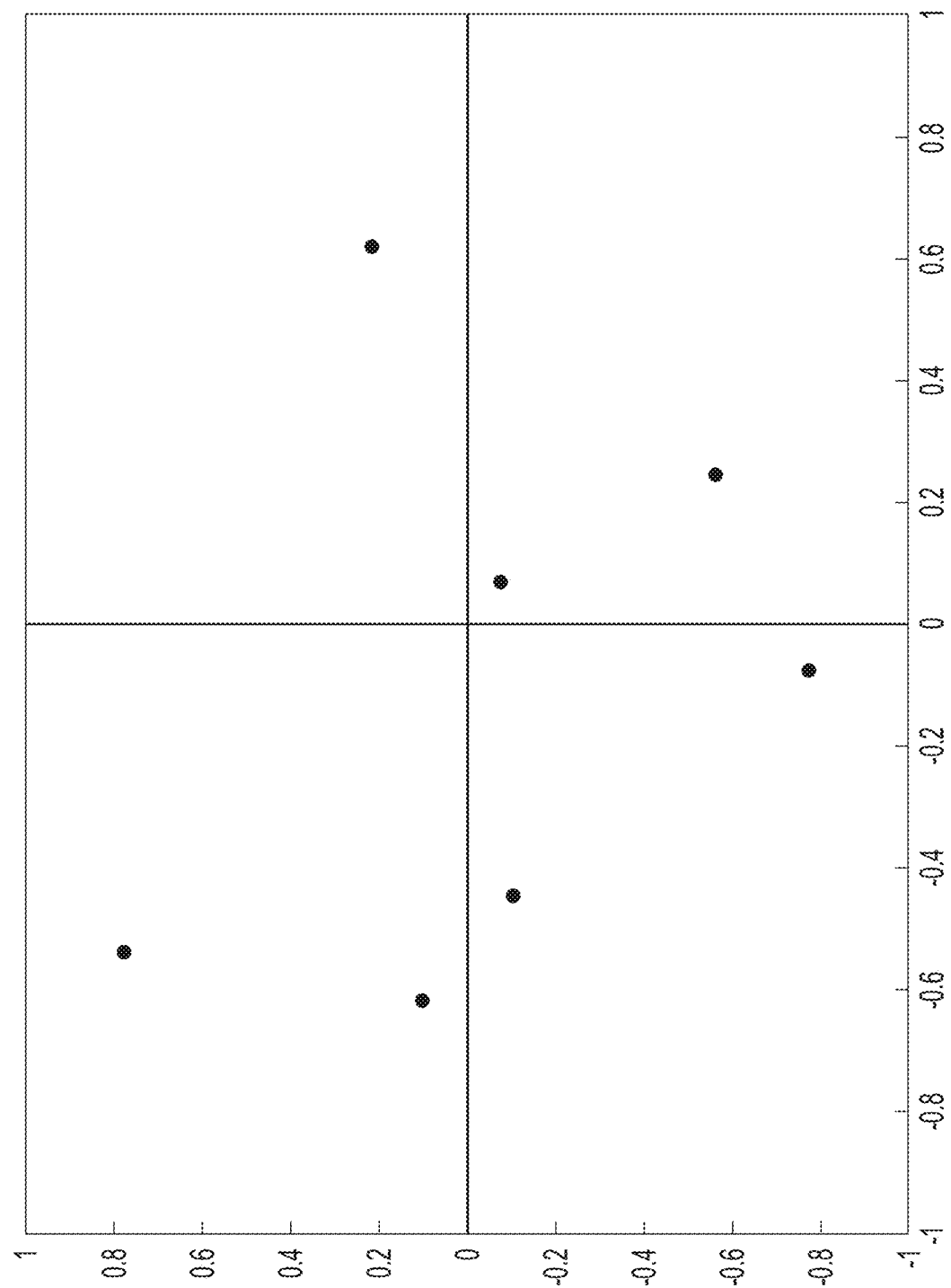
FIG. 70 is a plot showing headoffset distribution for a particular size femur group.

In the context of a proximal femur, FIGS. 51-62 confirm that gender differences exist across any ethnic population. As depicted in FIGS. 59 and 60, the template 3D model of the statistical atlas for a proximal femur of a woman exhibits statistical significant measurements when compared to the template 3D model of a proximal femur for a male. In particular, the head offset is approximately 9.3% less for females than for males. In current implants head offset increases with stem size, which is acceptable in normal female cases. But a problem arises when accounting for head offset in cases of osteoporosis and osteopinia where the bone loss leads to increase of intramedullary canal size, which means larger stem size and larger offset. Similarly, the neck diameter and head radius are approximately 11.2% less for females than for males. And the neck length is approximately 9.5% less for females than for males. In addition, the proximal angle is approximately 0.2% less for females than for males. Finally, the femoral head height is approximately 13.3% less for females than for males. Consequently, the gender bone data confirms that simply scaling a generic, femoral implant (i.e., gender neutral) will not account for differences in bone geometries and, hence, a gender based femoral implant is needed.

Referring to FIGS. 63-68, not only do the dimensions of the proximal femur widely vary across gender lines, but so too does the cross-sectional shape of the femur along the length of the intramedullary canal. In particular, across a given population within a statistical atlas of male and female femurs, males have intramedullary canal cross-sections that are closer to circular than females. More specifically, females have intramedullary canal cross-sections that are 8.98% more eccentric than for males. As will be discussed in more detail hereafter, this gender specific data comprises part of the feature extraction data that is plotted to arrive at clusters from which the number and general shape parameters are extracted to arrive at the gender specific femoral implants.

Figure 72:
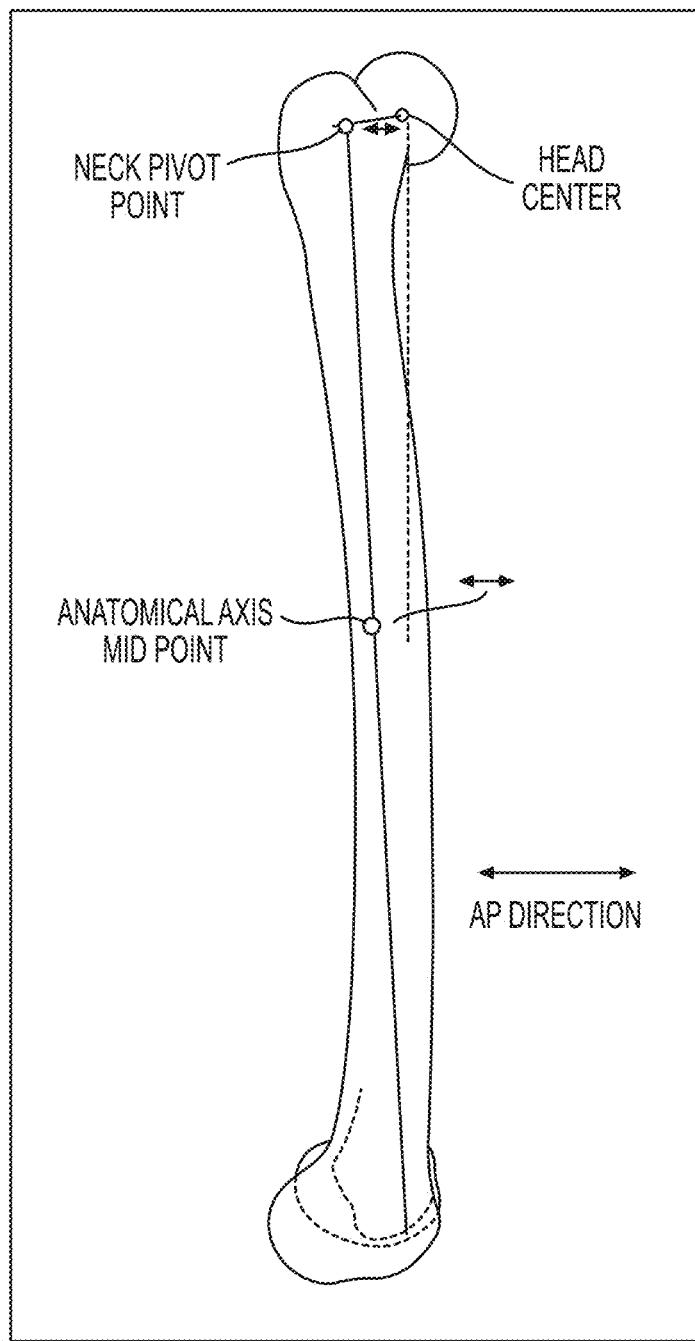
FIG. 72 is a picture depicting how anterior-posterior height is measured.
Figure 73:
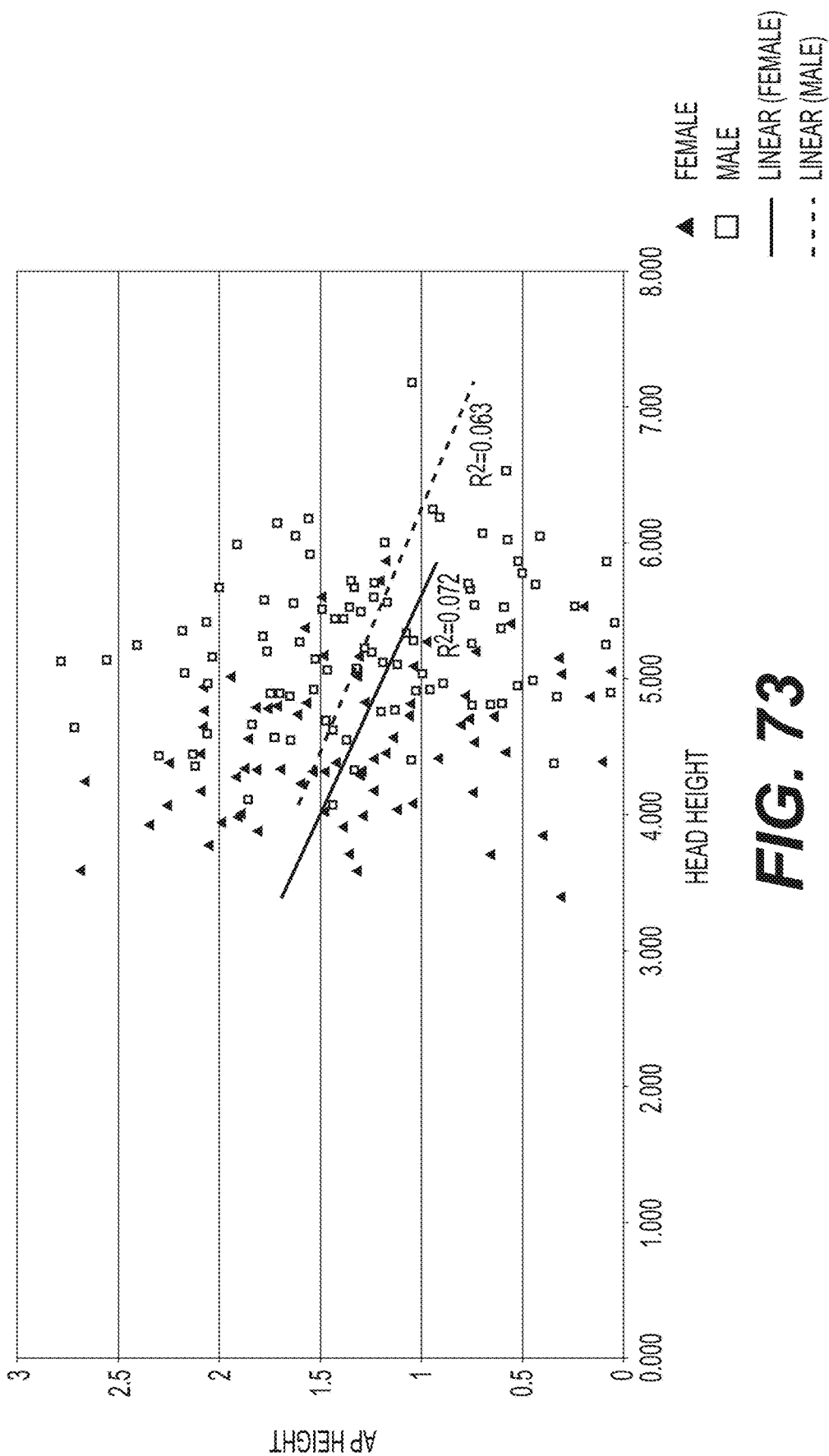
FIG. 73 is a plot of heat height versus anterior-posterior head height for a femur relative to its pivot point for males and females, which includes a linear best fit through each data set (male, female).
Figure 74:
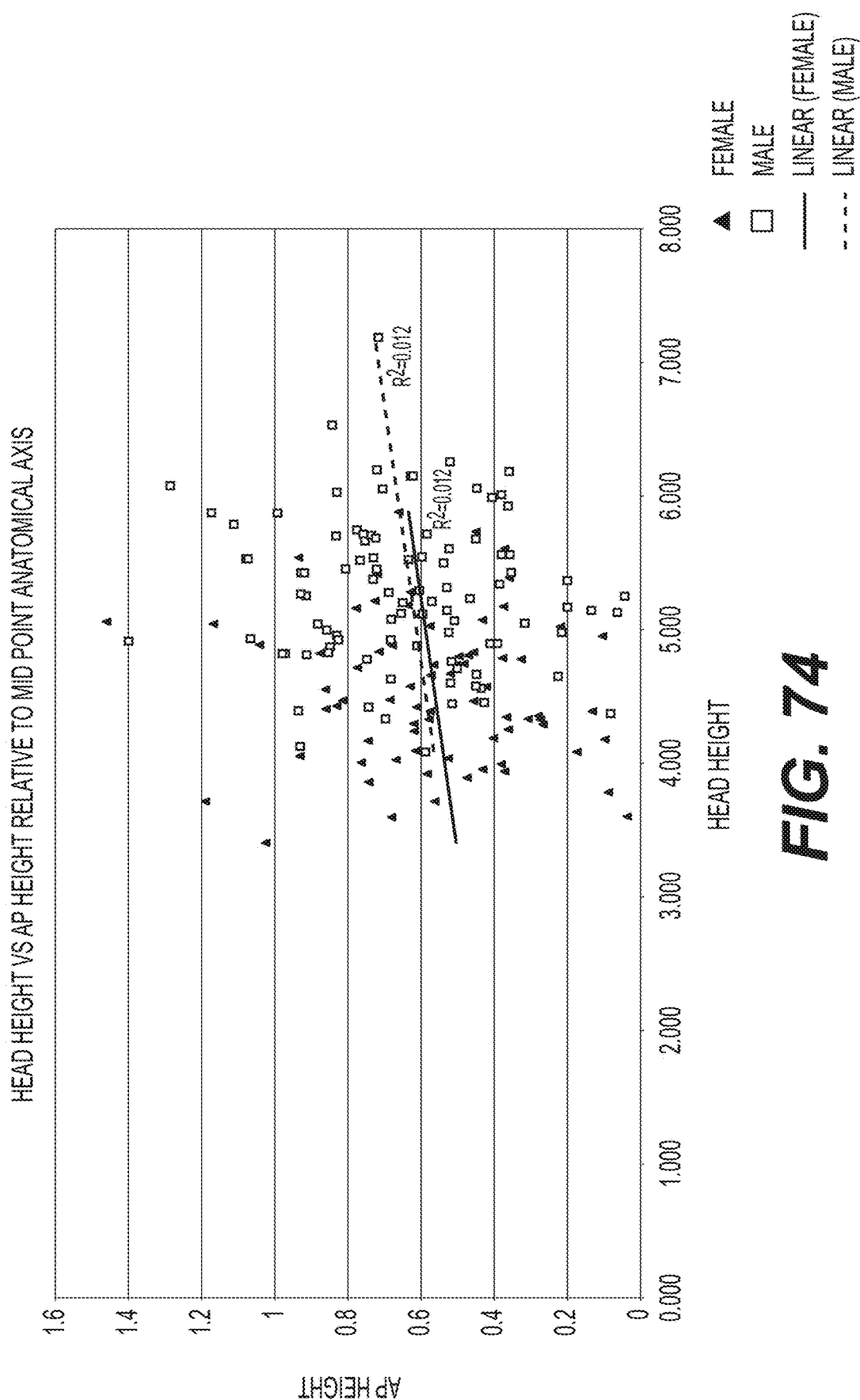
FIG. 74 is a plot of heat height versus anterior-posterior head height for a femur relative to its anatomical axis mid-point for males and females, which includes a linear best fit through each data set (male, female).
Figure 75:
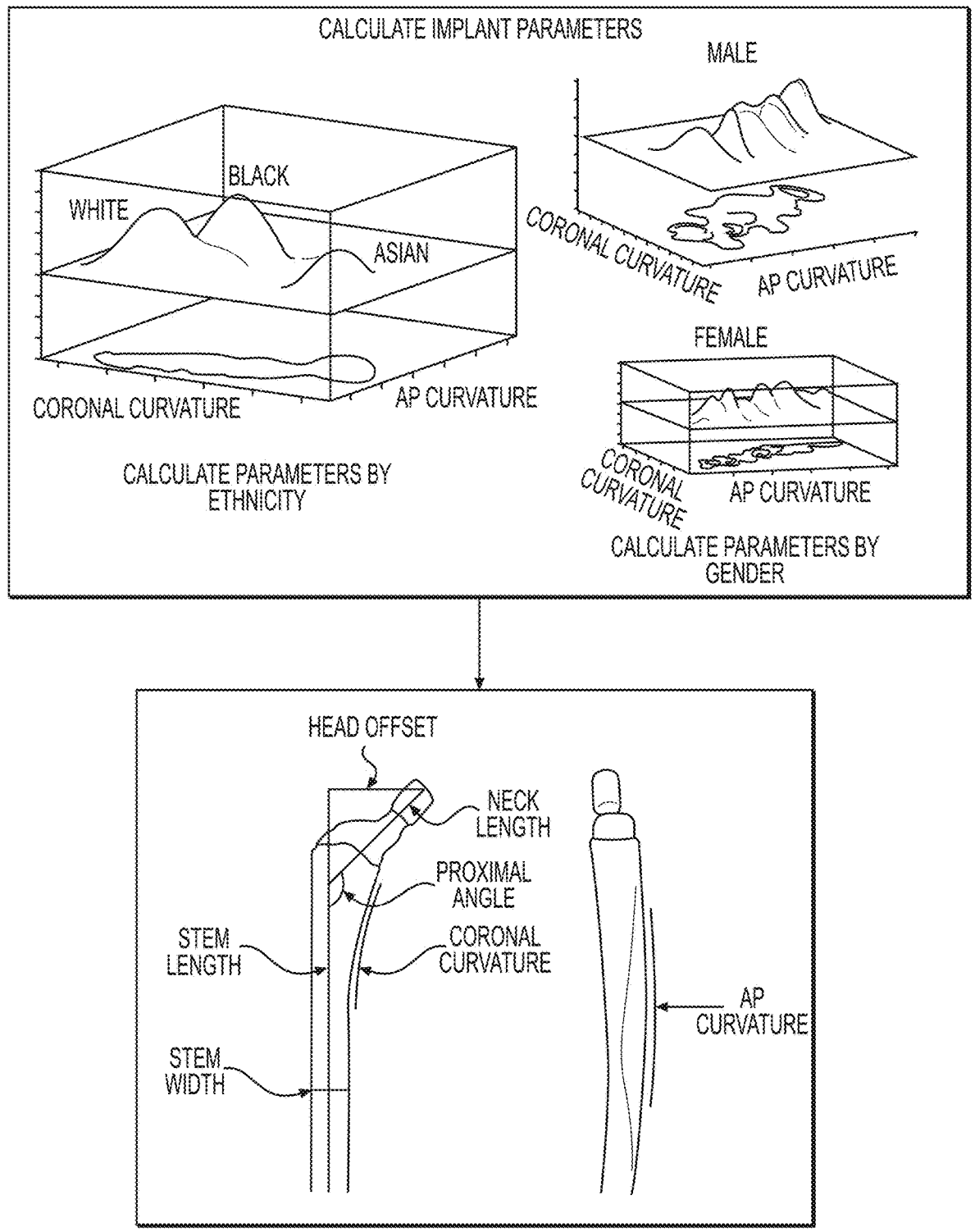
FIG. 75 is a graphical depiction of parameters utilized for creation of hip stem implant families on a gender and/or ethnicity basis in accordance with the instant disclosure.

As depicted in FIGS. 72-74, the statistical atlas includes calculations that correspond to measurements across a given population of femurs (divided by gender) as to the head center offset in the anterior-posterior (AP) direction. In exemplary form, AP direction was determined by a vector that points anteriorly perpendicular to both the mechanical axis and the posterior condylar axis. Offset was measured between the femoral head center and two reference points, with the first reference point being the midpoint of the anatomical axis, and the second reference point being the femur neck pivot point. In summary, AP head height relative to the neck pivot point and anatomical axis midpoint did not exhibit significant differences between male and female femurs. Again, this gender specific data comprises part of the feature extraction data that is plotted to arrive at clusters from which the number and general shape parameters are extracted to arrive at the gender specific femoral implants.

Referring back to FIGS. 28 and 31, the head center offset, cross-sectional shape data of the intramedullary canal, and medial contour data for the femurs within the statistical atlas population comprise part of the extracted feature data that is plotted to discern the number of clusters present across a given population (one that is gender specific, a second that is ethnic specific presuming the statistical atlas includes data as to the ethnicity associated with each bone) in order to design a gender and/or ethnic specific, mass customized implant consistent with the flow chart and associated discussion for FIG. 28. The identified clusters that are gender and/or ethnic specific are utilized to extract the parameters necessary to design a mass customized femoral implant.

Figure 76:
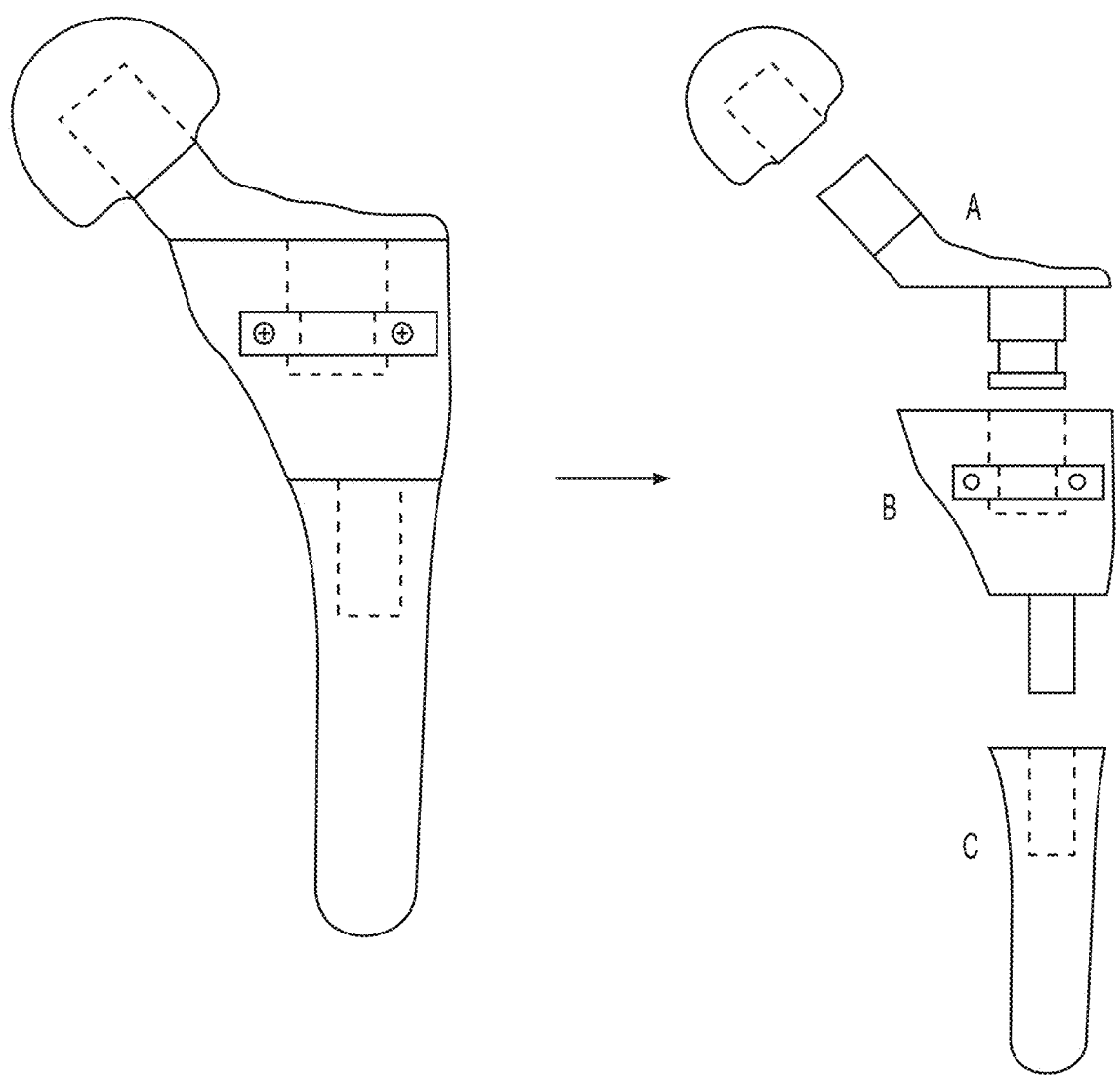
FIG. 76 depicts a primary hip stem in both assembled and exploded views.

Referring to FIG. 76, an exemplary mass-customized femoral component in accordance with the instant disclosure is depicted. In particular, the mass-customized femoral component comprises four primary elements that include a ball, neck, proximal stem, and distal stem. Each of the primary elements includes an interchangeable interface to allow interchangeable balls, necks, and stems with the other interchangeable elements. In this fashion, if a larger femoral ball is needed, only the femoral ball would be exchanged.

Likewise, if a greater neck offset was desired, the neck element would be exchanged for a different neck element providing the requisite offset, while retaining the other three elements if appropriate. In this manner, the femoral component can, within certain limits, be customized to fit the patient without necessarily sacrificing the fit or kinematics that would otherwise be surrendered by using a one-size-fits-all implant. Accordingly, all of the femoral elements can be exchanged for other mass customized elements to better suit the patient anatomy.

In this exemplary embodiment, the neck is configured to rotate about the axis of the proximal stem so that the rotational orientation of the neck with respect to the proximal stem may be adjusted intraoperatively. In particular, preoperative measurements may establish the planned rotational position of the neck with respect to the proximal stem. Nevertheless, intraoperative considerations such as in-vivo kinematic testing may result in the surgeon changing the pre-operative rotational orientation to provide improved kinematics or avoidance of a particular impingement. By way of example, the neck includes a cylindrical stud having an inset circumferential groove having a textured surface. This cylindrical stud is received within an axial cylindrical channel of the proximal stem. In addition to this cylindrical channel, a second channel intersects the cylindrical channel and is shaped to receive a plate having a semi-circular groove that is also textured and configured to engage the textured surface of the inset circumferential groove. A pair of screws fastened to the proximal stem pushes the plate into engagement with the cylindrical stud so that eventually, rotational motion of the cylindrical stud with respect to the proximal stem is no longer possible. Accordingly, when this fixed engagement is reached, the screws may be loosened to allow rotational motion between the cylindrical stud and the proximal stem, such as would be necessary to make rotational adjustments intraoperatively.

Engagement between the neck and ball may be conventional, whereas engagement between the proximal stem and the distal stem is unconventional. In particular, the proximal stem includes a distal shank that is threaded and engaged to be threadably received within a threaded opening extending into the distal stem. Accordingly, the proximal stem is mounted to the distal stem by rotation of the proximal stem with respect to the distal stem so that the threads of the shank engage the threads of the distal stem opening. Rotation of the proximal stem with respect to the distal stem is concluded when the proximal stem abuts the distal stem. However, if rotational adjustment is necessary between the proximal stem and the distal stem, washers may be utilized to provide a spacer corresponding to the correct rotational adjustment. By way of further example, if greater rotational adjustment is required, the washer will be greater in thickness, whereas a thinner washer will provide correspondingly less rotational adjustment.

Each of the primary elements may be fabricated in predetermined alternatives that account for size and contour variations within a given gender and/or ethnicity. In this fashion, the alternatives of the primary elements may be mixed and matched to approximate a patient-specific implant that more closely configures to the anatomy of the patient than conventional mass customized femoral components, but at a fraction of the cost and process utilized to generate a patient-specific femoral implant.

Figure 77:
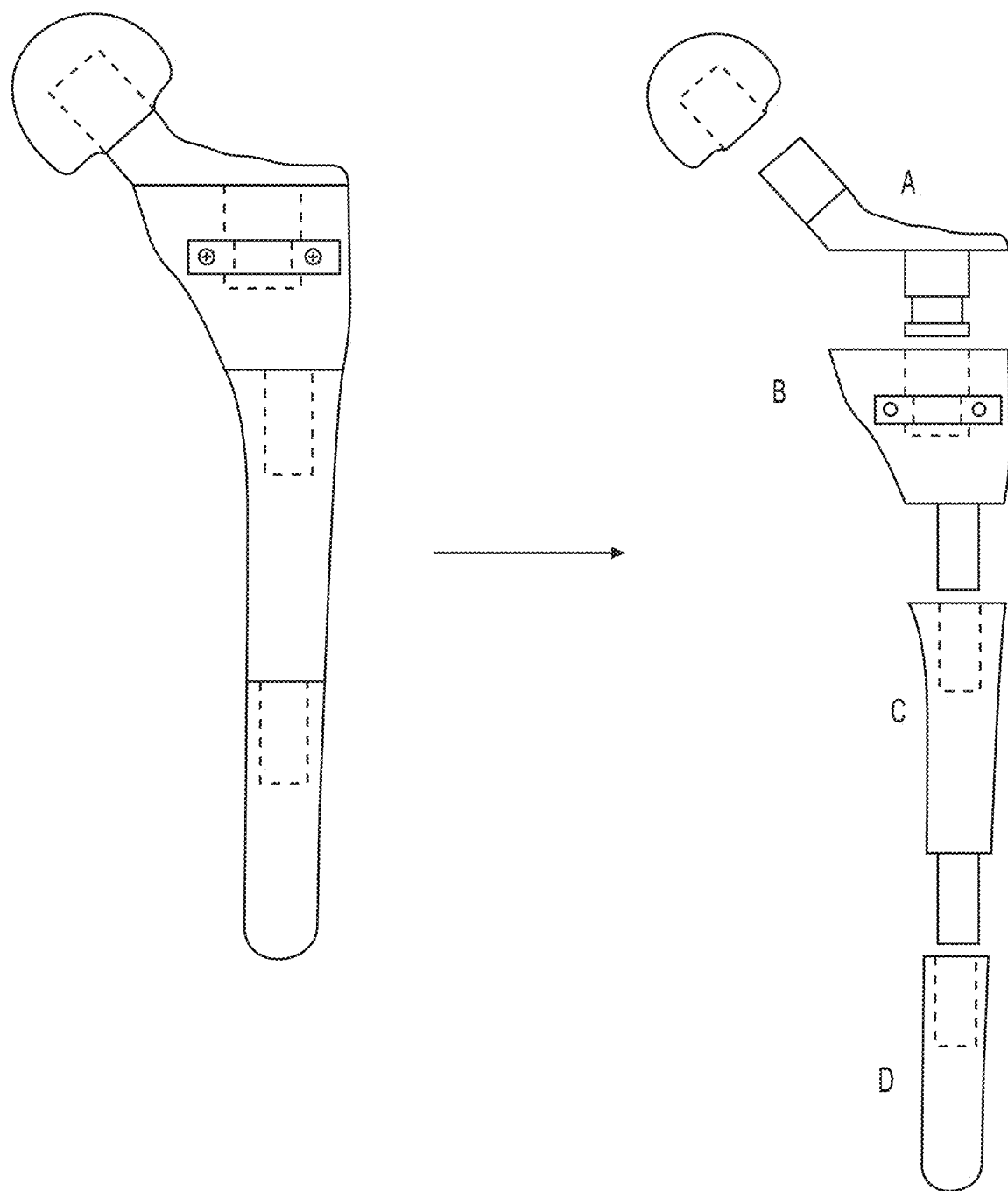
FIG. 77 depicts a revision hip stem in both assembled and exploded views.

FIG. 77 depicts a further alternate exemplary mass-customized femoral component in accordance with the instant disclosure is depicted. In particular, the mass-customized femoral component comprises five primary elements that include a ball, neck, proximal stem, intermediate stem, and distal stem. Each of the primary elements includes an interchangeable interface to allow interchangeable balls, necks, and stems with the other interchangeable elements. Those skilled in the art will understand that by increasing the number of elements of the mass-customized femoral component, akin to stacking slices of the patient's natural femur to reproduce this bone, one can increasingly approach the fit of a patient-specific implant by using mass-customized elements.

Figure 80:
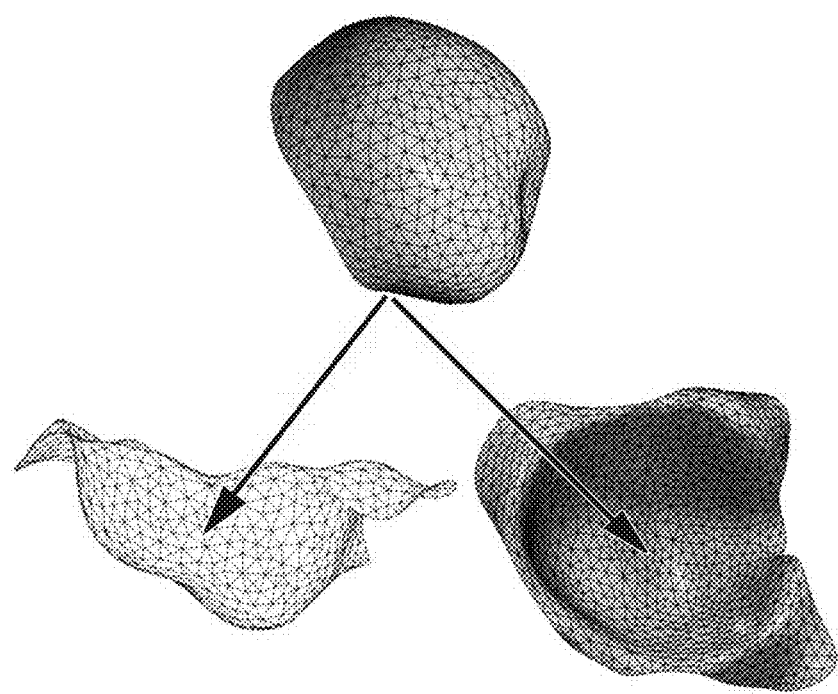
FIG. 80 graphically depicts an anatomical acetabular cup and femoral stem ball shape exhibiting multiple cup radii.
Figure 81:
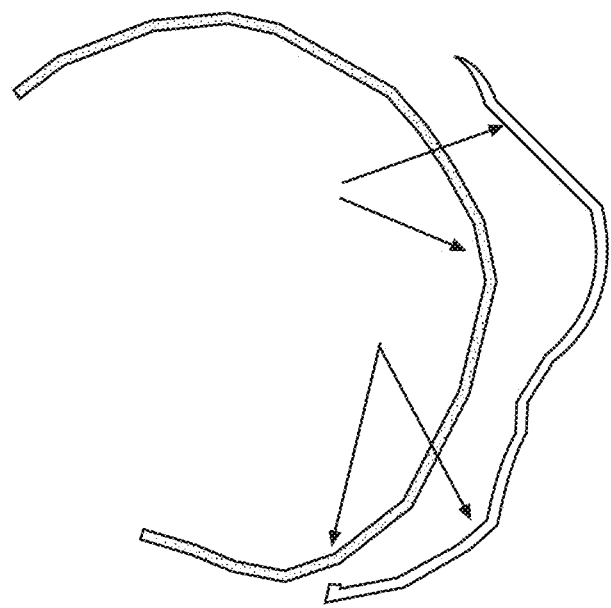
FIG. 81 is a two dimensional depiction of curvature matching between the acetabular cup and femoral head.
Figure 82:
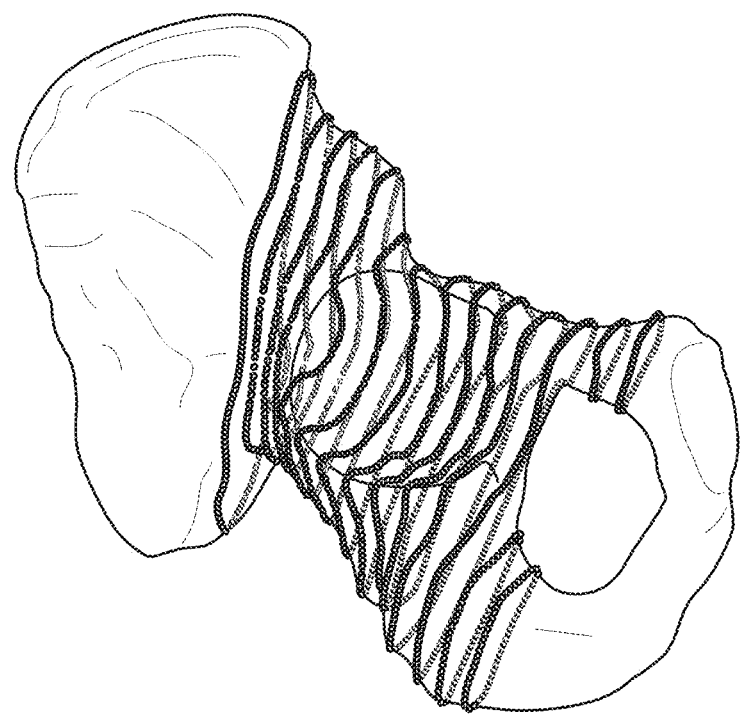
FIG. 82 is a graphical depiction of mapped contours of a pelvis used to cross-sectionally analyze the acetabular cup.
Figure 83:
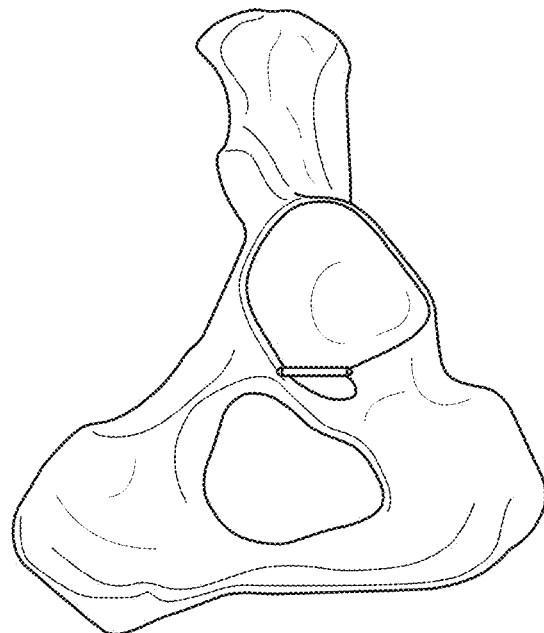
FIG. 83 is a graphical depiction of automatic detection of the transverse acetabular ligament pursuant to the instant disclosure a as method for determining acetabular implant cup orientation.

Similar to the anatomical differences between genders and ethnicities for the proximal femur, FIGS. 78-83 confirm that gender and ethnic differences exist across a general pelvis population within a statistical atlas. Referring back to FIG. 28, a series of mass customized acetabular cup implants are designed and fabricated by using statistical atlas data (i.e., pelvis population) grouped based upon at least one of gender and ethnicity. The grouped atlas data is subjected to an automatic landmarking process and a surface/shape analysis process to isolate the geometry of the acetabular cup within the population, as depicted graphically in FIG. 78. In addition, as depicted graphically in FIGS. 82 and 83, the landmarking (for location of acetabular ligament) and contour analysis (for evaluating the contours of the acetabular cup) processes lead to feature extraction, from which the anatomical cup implant surfaces are ultimately generated, as shown in FIG. 79. This analysis shows that the acetabular cup and femoral head are not composed of a single radius of curvature, but several radii, as shown in FIGS. 80 and 81.

Creation of Animal-Specific Implants

Figure 85:
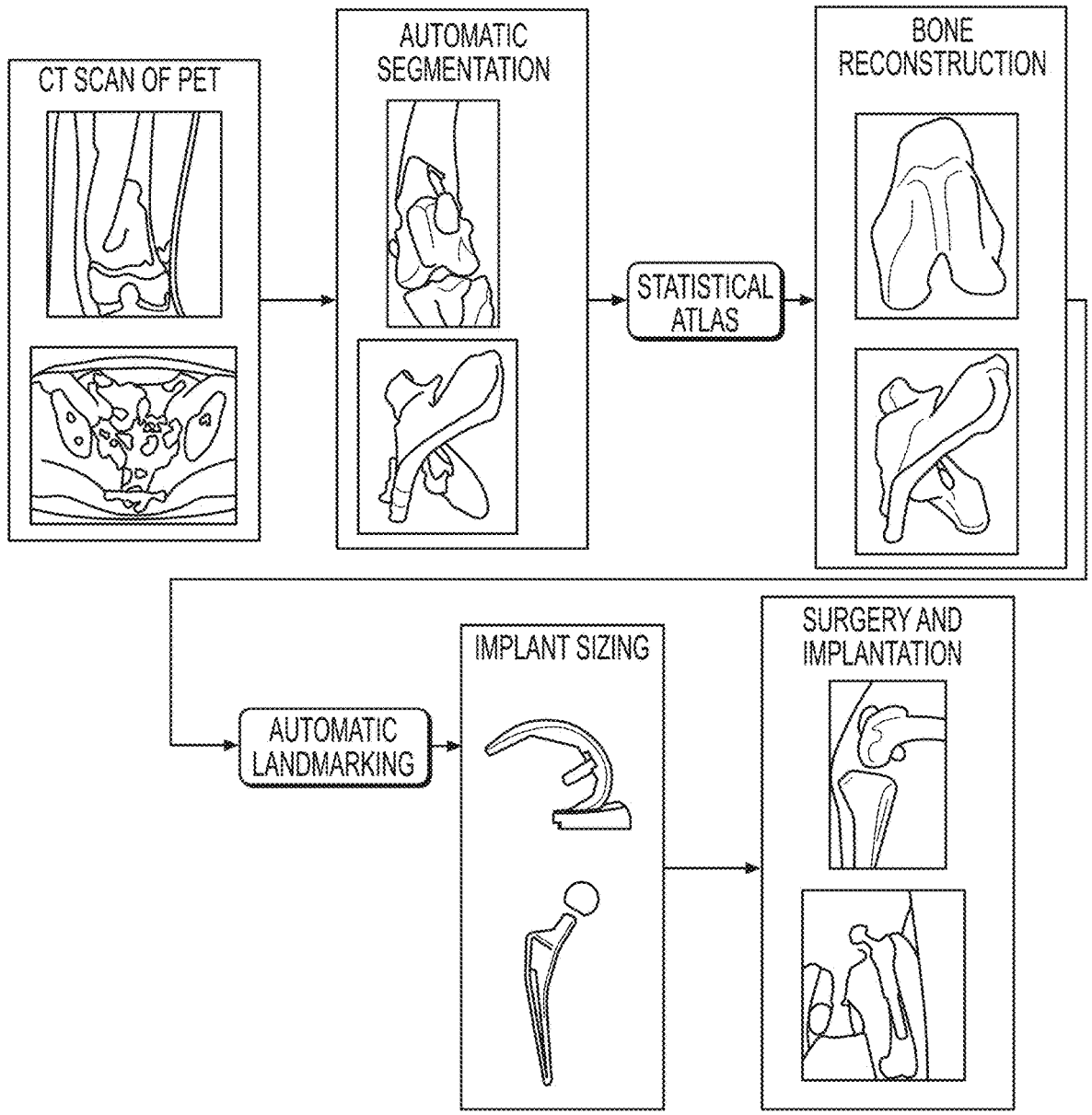
FIG. 85 is an exemplary process diagram for creating pet specific implants and cutting guides in accordance with the instant disclosure.

Referring to FIG. 85, an exemplary system and methods for designing and fabricating an animal-specific (i.e., patient-specific for an animal) implant and associated instrumentation is similar to the process depicted and explained previously with respect to FIG. 20, which is incorporated herein. As a prefatory matter, images of the animal anatomy are taken and automatically segmented to yield a virtual 3D bone model. Though graphically depicted as CT scan images, it should be understood that other imaging modalities besides CT may be utilized such as, without limitation, Mill, ultrasound, and X-ray. The virtual 3D bone model of the affected anatomy is loaded into the statistical atlas, in accordance with the previous exemplary disclosure. Thereafter, inputs from the statistical atlas are utilized to reconstruct the bone(s) and create a reconstructed virtual 3D bone model. Bone landmarks are calculated on the surface of the reconstructed virtual 3D bone model to allow determination of the correct implant size. Geometry of affected bone is then mapped and converted to parametric form, which is then used to create an animal-specific implant that mimics the residual anatomical geometry. In addition to the animal-specific implant, animal-specific instrumentation is fabricated and utilized for preparation of the animal's residual bone and placement of the animal-specific implant.

Figure 86:
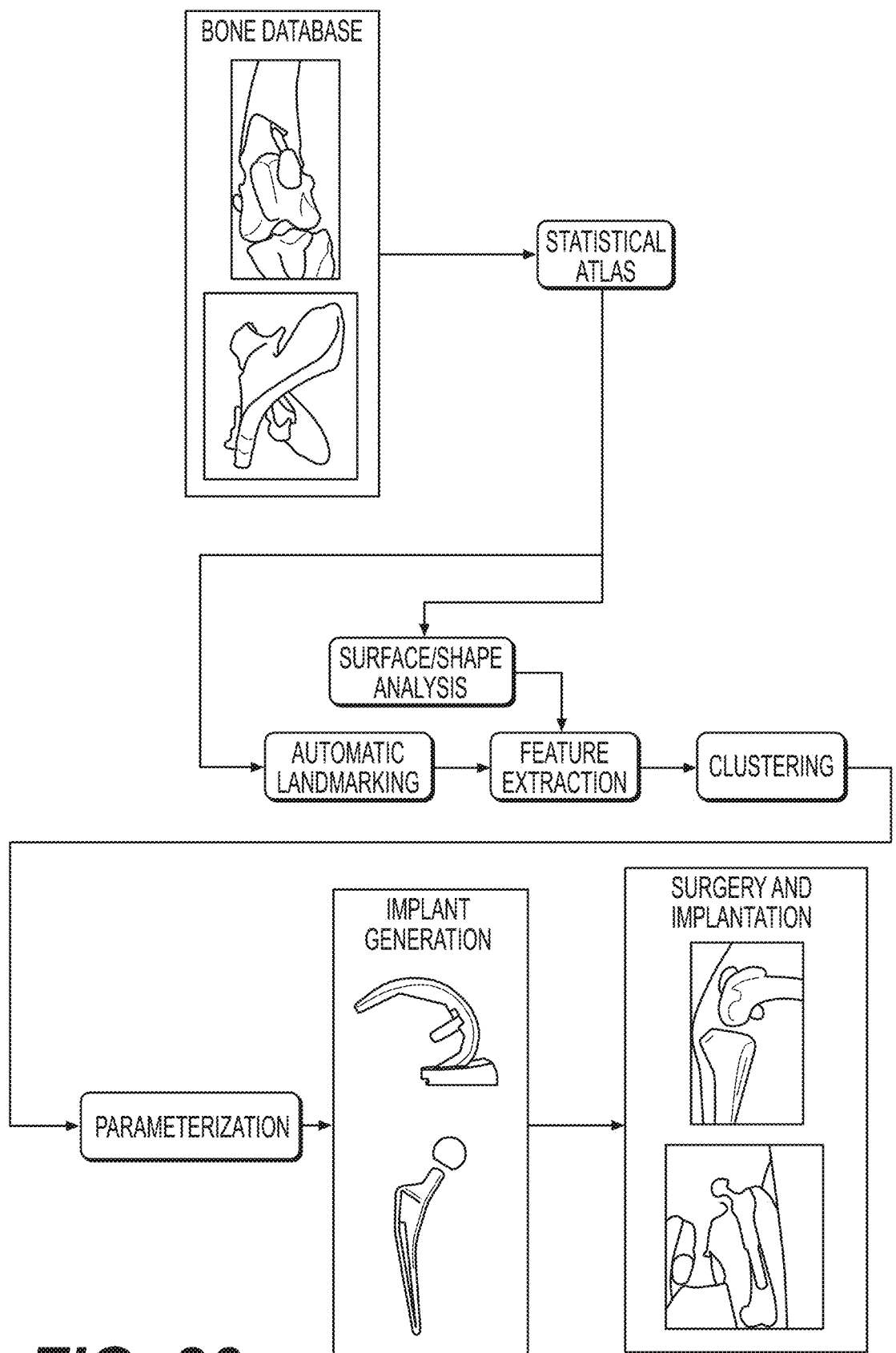
FIG. 86 is an exemplary process diagram for creating mass customized orthopedic implants for pets using statistical atlases in accordance with the instant disclosure.

Referring to FIG. 86, an exemplary system and methods for designing and fabricating a mass customized animal implant is similar to the process depicted and explained previously with respect to FIG. 28, which is incorporated herein. As a prefatory matter, 3D animal bone models from the statistical atlas pertinent to the bone(s) in question are subjected to an automatic landmarking and surface/shape analysis. The automatic landmarking process uses information stored in the atlas (e.g., regions likely to contain a specific landmark) and local geometrical analyses to automatically calculate anatomical landmarks for each 3D animal bone model. For each animal bone in question within the statistical atlas, the shape/surface analysis directly extracts features the surface geometry of the 3D virtual animal bone models. Thereafter, each of the 3D animal bone models have a feature extraction process carried out thereon that uses a combination of landmarks and shape features to calculate features relevant to implant design. These features are used as inputs to a clustering process, where the animal bone population is divided into groups having similar features using a predetermined clustering methodology. Each resulting cluster represents those instances used to define the shape and size of a single animal implant. A parameterization process follows for each cluster center (implant size) in order to extract the parameters for an overall implant model (e.g., computer aided design (CAD) parameters). Thereafter, using the extracted parameters, the overall implant surface and size are generated for each cluster. Depending upon the cluster the animal patient falls into, the mass-customized implant is selected from the requisite group and implanted.

Creation of Patient-Specific Cutting Guides

Referring to FIGS. 87-102, an exemplary process and system are described for integration of multidimensional medical imaging, computer aided design (CAD), and computer graphics features for designing patient-specific cutting guides. For purposes of exemplary explanation only, the patient-specific cutting guides are described in the context of a total hip arthroplasty procedure. Nevertheless, those skilled in the art will realize that the exemplary process and system are applicable to any surgical procedure for which cutting guides may be utilized.

Figure 87:
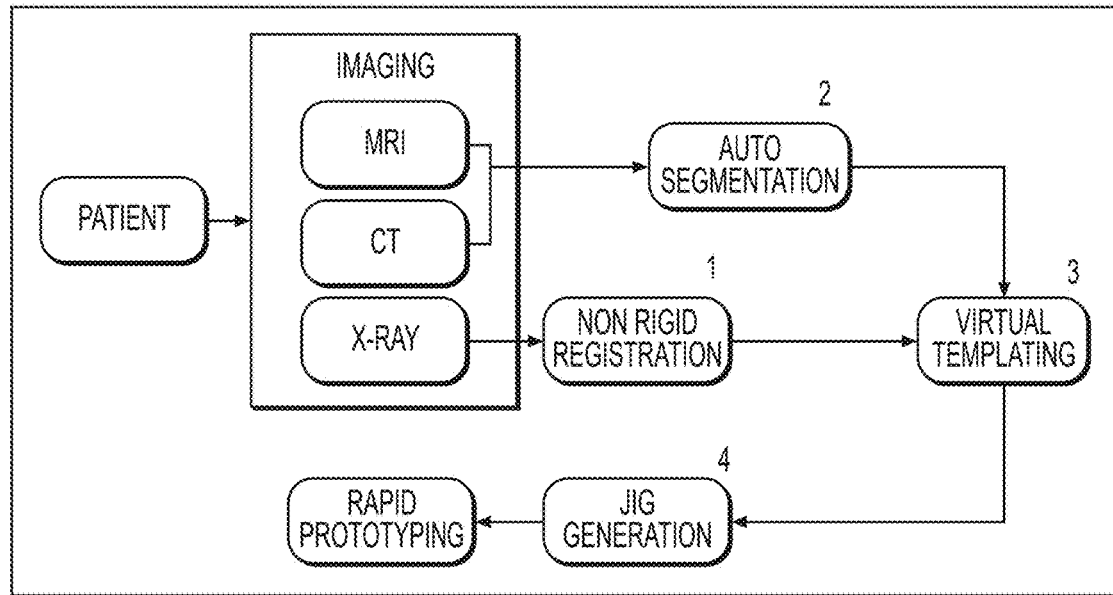
FIG. 87 is an exemplary process diagram for generating patient specific cutting and placement devices for implant systems in accordance with the instant disclosure.

As represented in FIG. 87, an overview of the exemplary system flow begins with receiving input data representative of an anatomy. Input anatomical data comprises two dimensional (2D) images or three dimensional (3D) surface representations of the anatomy in question that may, for example, be in the form of a surface model or point cloud. In circumstances where 2D images are utilized, these 2D images are utilized to construct a 3D surface representation of the anatomy in question. Those skilled in the art are familiar with utilizing 2D images of anatomy to construct a 3D surface representation. Accordingly, a detailed explanation of this process has been omitted in furtherance of brevity. By way of example, input anatomical data may comprise one or more of X-rays (taken from at least two views), computed tomography (CT) scans, magnetic resonance images (Mills), or any other imaging data from which a 3D surface representation may be generated. In exemplary form, the anatomy comprises a pelvis and a femur.

It should be understood, however, that the following is an exemplary description of anatomies that may be used with the exemplary system and in no way is intended to limit other anatomies from being used with the present system. As used herein, tissue includes bone, muscle, ligaments, tendons, and any other definite kind of structural material with a specific function in a multicellular organism. Consequently, when the exemplary system and methods are discussed in the context of bones involved with the hip joint, those skilled in the art will realize the applicability of the system and methods to other tissue.

The femur and pelvis input anatomy data of the system is directed to one of two modules depending upon the type of input data. In the case of X-ray data, the 2D X-ray images are input to a non-rigid module in order to extract 3d bone contours. If the input data is in the form of CT scans or MRI images, these scans/images are directed to an auto segmentation module where the scans/images are automatically segmented to extract the 3D bone contours (and 3D cartilage contours).

Figure 88:
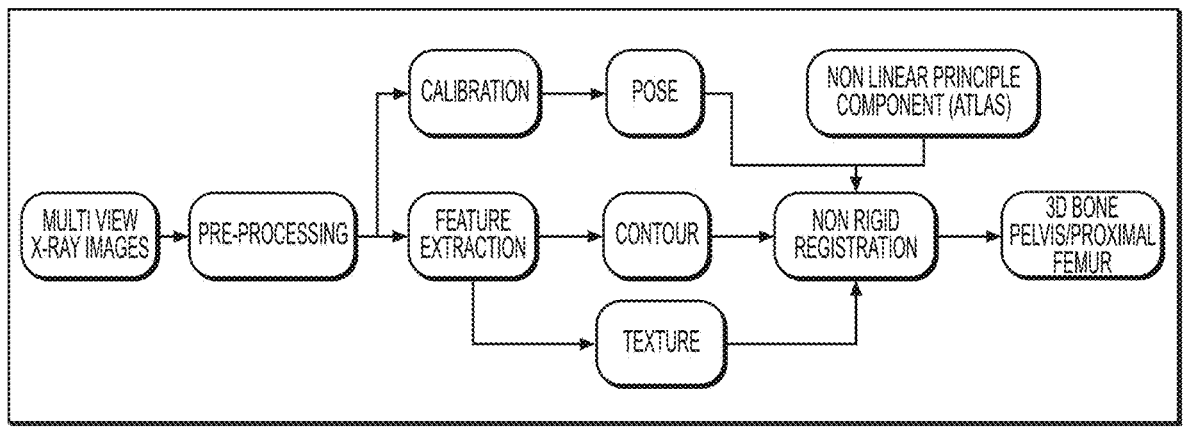
FIG. 88 is an exemplary process diagram for non-rigid registration from FIG. 87 and creation of patient specific three dimensional pelvis and proximal femur models from X-rays in accordance with the instant disclosure.
Figure 90:
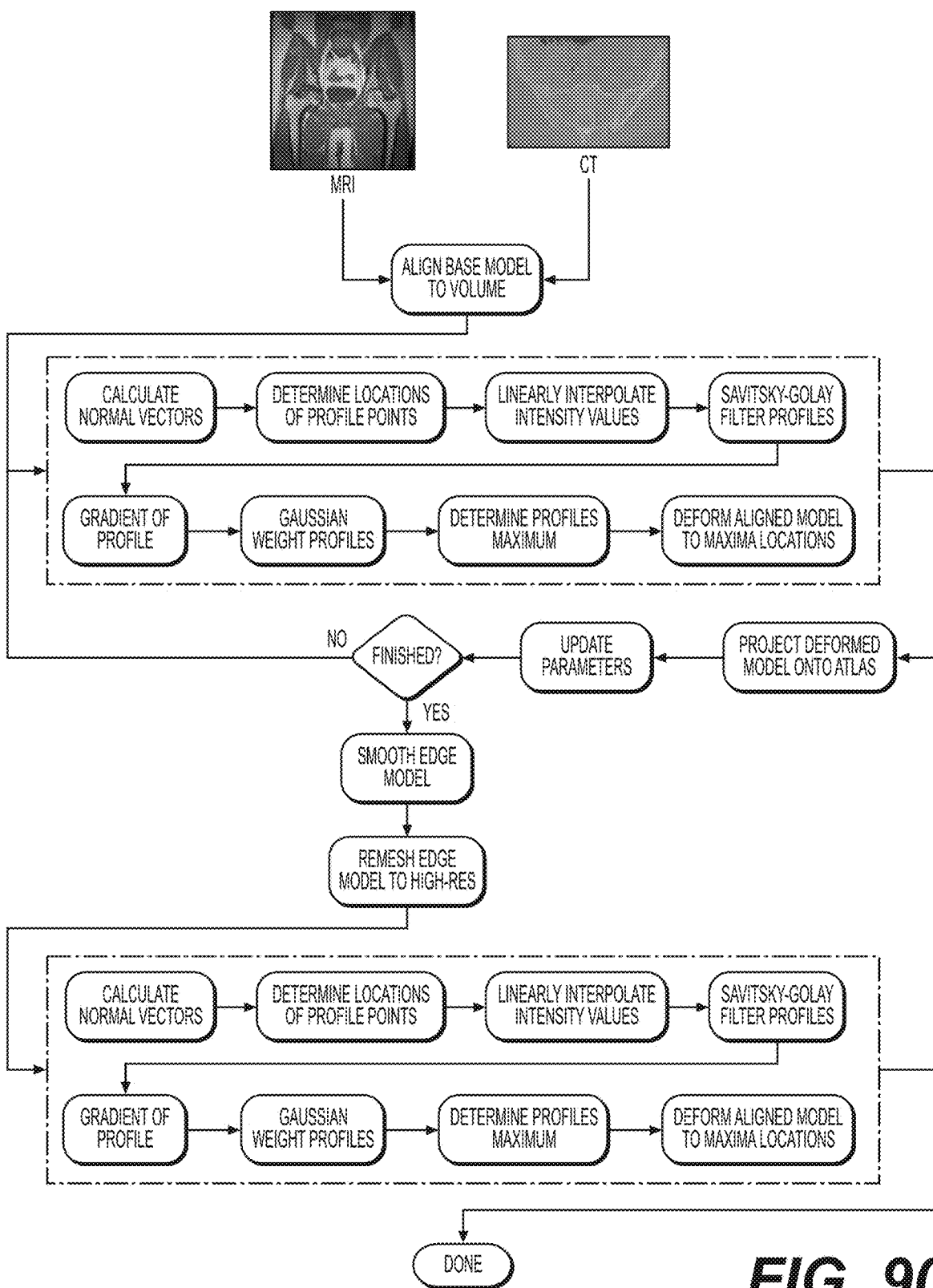
FIG. 90 is an exemplary process diagram for automatic segmentation of pelvis and proximal femur from MRI and CT scans, as described in FIG. 87.

Referring to FIG. 88, the non-rigid module uses the multiple X-ray images taken from at least two different views are subjected to one or more pre-processing steps. These steps may include one or more of the following: noise reduction and image enhancement. The resultant pre-processed X-ray images are subjected to a calibration step in order to register the X-ray images. Preferably, the X-ray images have been taken in the presence of a fixed position calibration device so that the X-ray images are registered with respect to this fixed position calibration device. But when no fixed position calibration device is present in the X-ray images, the images may nonetheless be calibrated using common detected features across multiple images. From this calibration process, the output is the position of the anatomy relative to the imager, which is identified by the "Pose" reference in FIG. 88.

The resultant pre-processed X-ray images are subjected to a feature extraction step. This feature extraction step comprises one or more computations of image features utilizing the pre-processed X-ray images. By way of example, these computations may include gradient features, contours, textural components, or any other image derived feature. In this exemplary process, the feature extraction step outputs the outline of the anatomy (e.g., bone shape) as represented by the "Contour" reference in FIG. 88, as well as image features as represented by the "Texture" reference, derived from the X-ray images. Both the outlined anatomy and image feature data is directed to a non-rigid registration step.

The non-rigid registration step registers the outputs from the feature extraction step and the calibration step to a 3D template model of the anatomy in question from a statistical atlas. By way of example, the 3D template model is generated responsive to non-linear principal components from an anatomical database comprising part of the statistical atlas. During the non-rigid registration step, the 3D template model has its shape parameters (non-linear principal components) optimized to match the shape parameters of the X-ray images resulting from the pose, contour, and texture data. The output from the non-rigid registration step is a 3D patient-specific bone model, which is directed to a virtual templating module, similar to the 3D patient-specific bone model output from the auto segmentation module for CT scans or MRI images.

Figure 91:
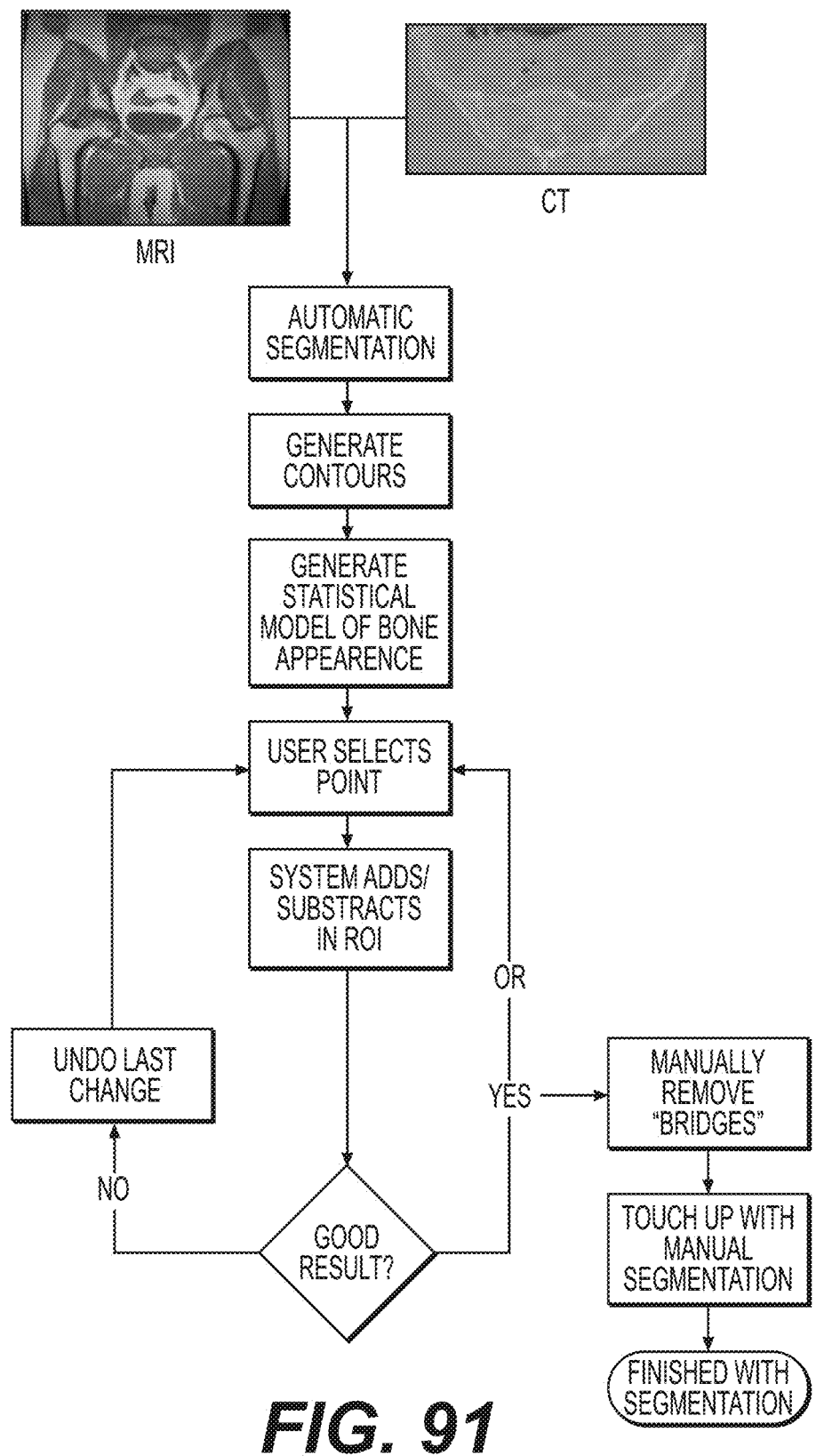
FIG. 91 is an exemplary process diagram for automatic segmentation of complex and shattered anatomy from MRI or CT scans, as outlined in FIG. 87.

Referencing FIG. 91, the auto segmentation process is initialized by taking the CT scans or MRI images, for example, and carrying out an automatic segmentation sequence. With specific reference to FIG. 90, the automatic segmentation sequence includes aligning the scans/images with respect to a base or starting 3D model of the anatomy in question. After alignment of the scans/images to the base 3D model, the scans/images are processed via an initial deformation process to calculate the normal vectors, determine locations of the profile points, linearly interpolate the intensity values, filter the resulting profiles using a Savitsky-Golay filter, generate a gradient of the profiles, weigh the profiles using a Gaussian weight profile equation, determine the maximum profiles, and use these maximum profiles to deform the base 3D model. The resulting deformed 3D model is projected onto the template 3D model from a statistical atlas for the anatomy in question. Using the parameters of the template 3D model, the deformed 3D model is further deformed in a secondary deformation process to resemble features unique to the template 3D model. After this latter deformation process, the deformed 3D model is compared to the scans/images to discern whether significant differences exist.

In circumstances where significant differences exist between the deformed 3D model and the scans/images, the deformed 3D model and the scans/images are again subjected to the initial deformation process followed by the secondary deformation process. This looping process is continued until the deformed 3D model is within a predetermined tolerance(s) for differences between the deformed 3D model and the scans/images.

After the deformed 3D model has been determined to exhibit less than significant differences with respect to the previous iteration or a maximum number of iterations is achieved, the surface edges of the deformed 3D model as smoothed, followed by a higher resolution remeshing step to further smooth the surfaces to create a smoothed 3D model. This smoothed 3D model is subjected to an initial deformation sequence (identical to the foregoing initial deformation process prior to surface smoothing) to generate a 3D segmented bone model.

Referring back to FIG. 91, the 3D segmented bone model is processed to generate contours. In particular, the intersection of the 3D segmented bone model and the scans/images are calculated, which result in binary contours at each image/scan plane.

The 3D segmented bone model is also processed to generate a statistical 3D model of the bone appearance that is patient-specific. In particular, the appearance of the bone and any anatomical abnormality is modeled based on image information present in within the contours and external to the contours.

The bone contours are thereafter reviewed by a user of the segmentation system. This user may be a segmentation expert or infrequent user of the segmentation system that notices one or more areas of the 3D model that do not correlate with the segmented regions. This lack of correlation may exist in the context of a missing region or a region that is clearly inaccurate. Upon identification of one or more erroneous regions, the user may select a "seed point" on the model indicating the center of the area where the erroneous region exists, or manually outlines the missing regions. The software of the system uses the seed point to add or subtract from the contour local to the seed point using the initial scans/images of the anatomy from CT or MRI. For example, a user could select a region where an osteophyte should be present and the software will compare the scans/images to the region on the 3D model in order to add the osteophyte to the segmentation sequence. Any changes made to the 3D model are ultimately reviewed by the user and verified or undone. This review and revision sequence may be repeated as many times as necessary to account for anatomical differences between the scans/images and the 3D model. When the user is satisfied with the 3D model, the resulting model may be manually manipulated to remove bridges and touch up areas of the model as necessary prior to being output to the virtual templating module.

Figure 92:
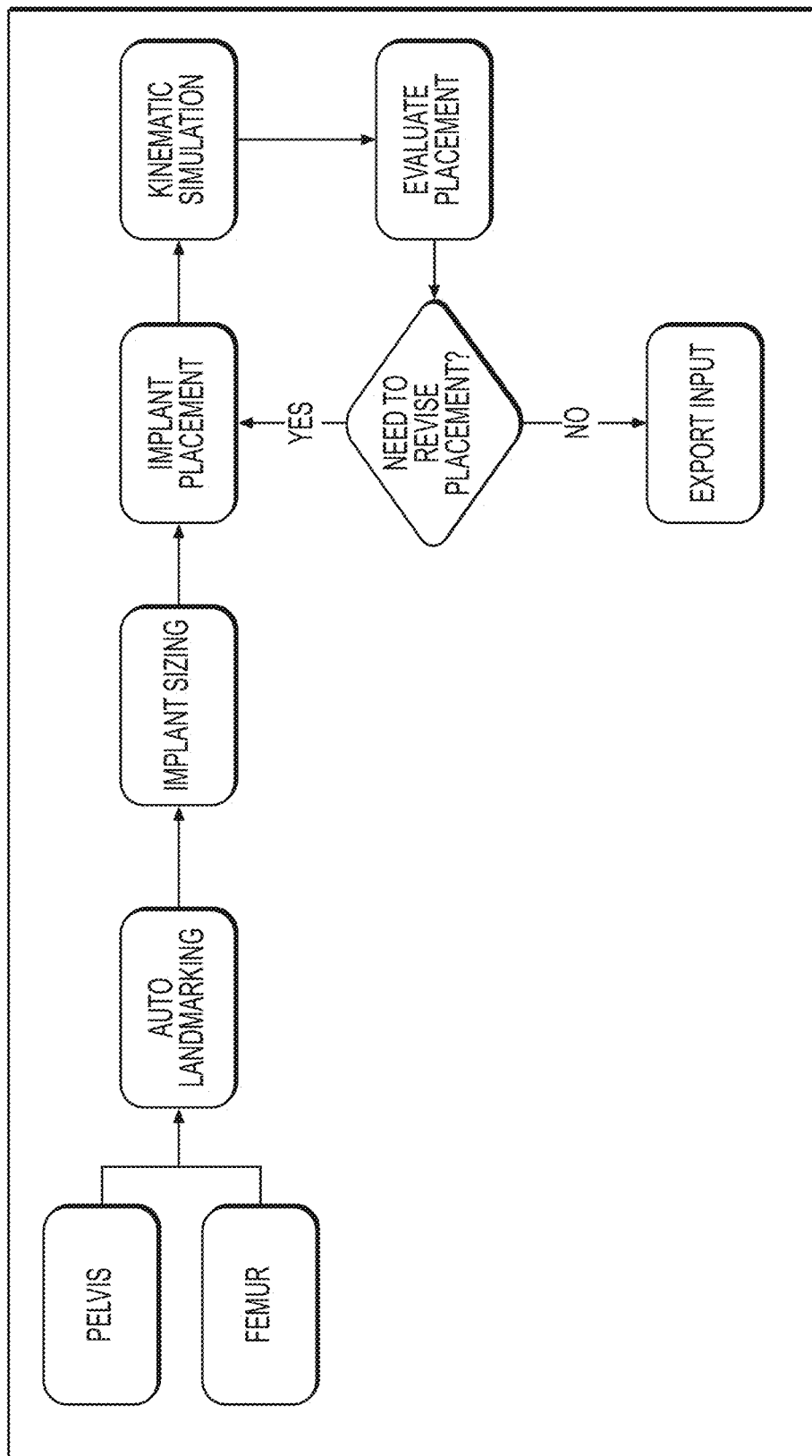
FIG. 92 is an exemplary process diagram for virtual templating both an acetabular cup and a femoral stem used with a hip replacement procedure.

As shown in FIGS. 87 and 92, the virtual templating module receives 3D patient-specific models from either or both the auto segmentation module and the non-rigid registration module. In the context of a hip joint, the 3D patient-specific models include the pelvis and the femur, which are both input to an automatic landmarking process. This automatic landmarking step calculates anatomical landmarks relevant to implant placement on the femur and pelvis 3D models using regions from similar anatomy present in a statistical atlas and local geometrical searches.

Figure 93:
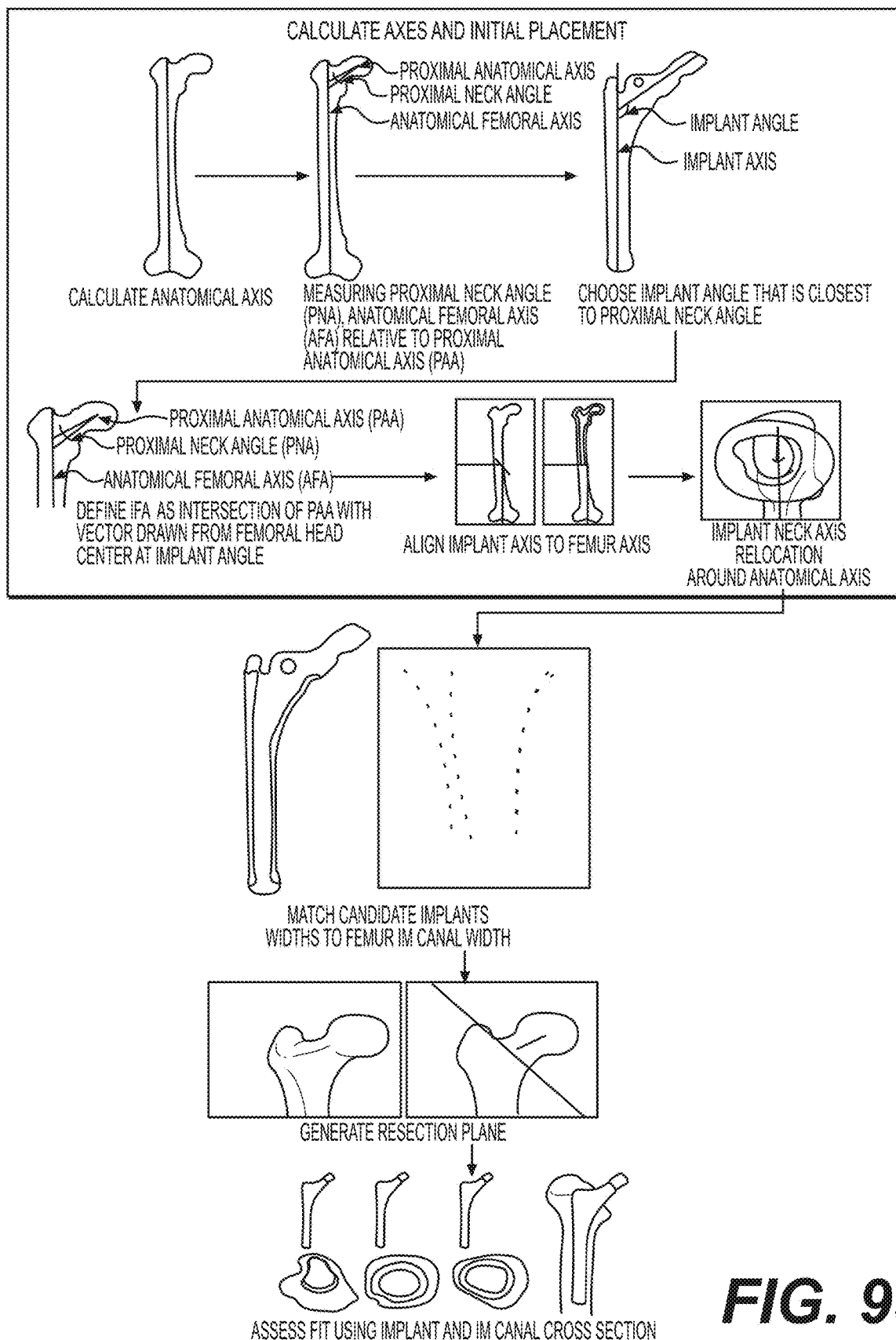
FIG. 93 is an exemplary process diagram for automatic femoral stem placement using distal fixation, which is a specific example of the general process outlined in FIG. 92.

In the context of automatic placement of the femoral stem using distal fixation, as shown in FIG. 93, the automatic landmarking includes definition of axes on the femur and the implant. With respect to the femur, the anatomical femoral axis (AFA) is calculated, followed by the proximal anatomical axis (PAA). The proximal neck angle (PNA) is then calculated, which is defined as the angle between the AFA and PNA. With respect to the femoral implant, the implant axis is along the length of the implant stem and the implant neck axis is along the length of the implant neck. Similar to the PNA of the femur, the implant angle is defined as the angle between the implant axis and the implant neck axis. The implant is then chosen which has an implant angle that is closest to the PNA. The implant fitting angle (IFA) is then defined as the intersection of the proximal anatomical axis with a vector drawn from the femoral head center at the chosen implant angle.

When using automatic placement of the femoral stem using distal fixation and the calculated anatomical landmarks, as shown in FIG. 93, an implant sizing step determines/estimates for the appropriate implant sizes for femoral components. The implant size is chosen by comparing the width of the implant to the width of the intramedullary canal and selecting the implant with the most similar width to the intramedullary canal. Thereafter, the system moves forward to an implant placement step.

In the implant placement step for a distal fixation femoral stem, based on surgeon preferred surgical technique and previously calculated anatomical landmarks, the initial implant position is determined/chosen for all relevant implanted components. A resection plane is created to simulate the proximal femur osteotomy and the implant fit is assessed. Fit assessment is conducted by analyzing the cross sections of the aligned implant and femur intramedullary canal at varying levels along the implant axis. The implant is aligned to the femur by aligning the implant axis to the anatomic femur axis then translating the implant so that the neck of the implant is in the general location of the proximal femur neck. The implant is then rotated about the anatomic femur axis to achieve desired anteversion.

As part of this implant placement step, an iterative scheme is utilized that includes using an initial "educated guess" as to implant placement as part of a kinematic simulation to evaluate the placement of the "educated guess." In exemplary form, the kinematic simulation takes the implant (based upon the placement of the implant chosen) through a range of motion using estimated or measured joint kinematics. Consequently, the kinematic simulation may be used to determine impingement locations and estimate the resulting range of motion of the implant post implantation. In cases where the kinematic simulation results in unsatisfactory data (e.g., unsatisfactory range of motion, unsatisfactory mimicking of natural kinematics, etc.), another location for implant placement may be utilized, followed by a kinematic analysis, to further refine the implant placement until reaching a satisfactory result. After the implant position is determined/chosen for all relevant implanted components, the template data is forwarded to a jig generation module.

Figure 94:
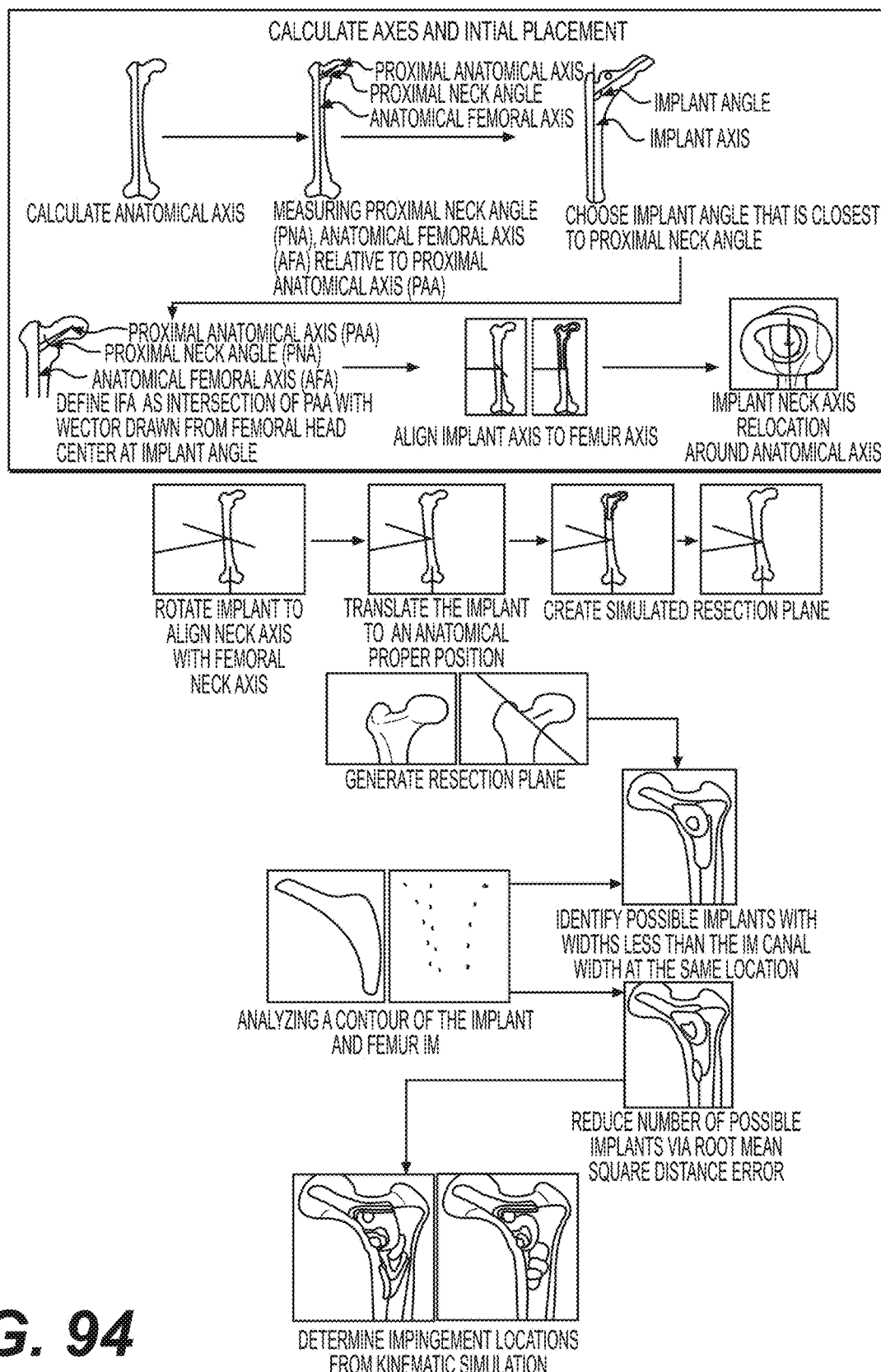
FIG. 94 is an exemplary process diagram for automatic femoral stem placement using press fit and three contacts, which is a specific example of the general process outlined in FIG. 92.
Figure 95:
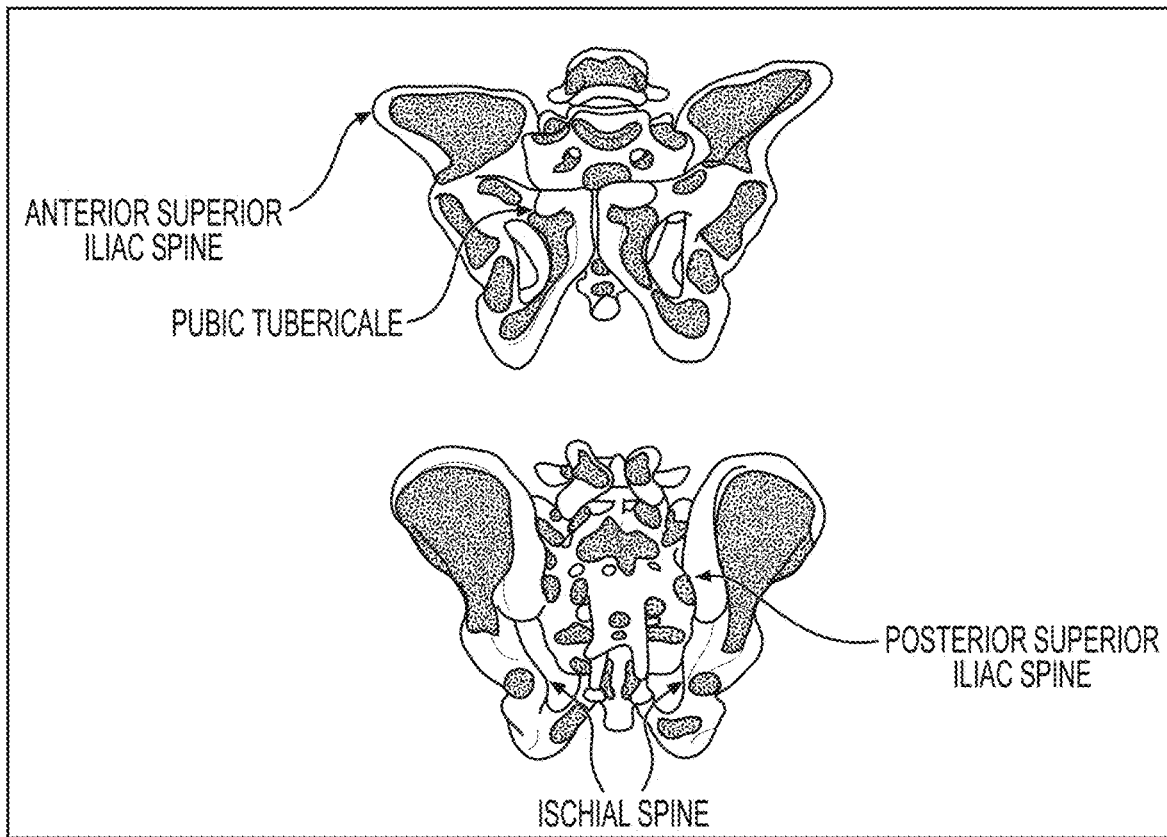
FIG. 95 is a graphical depiction of automatic pelvis landmarking in accordance with the instant disclosure.
Figure 96:
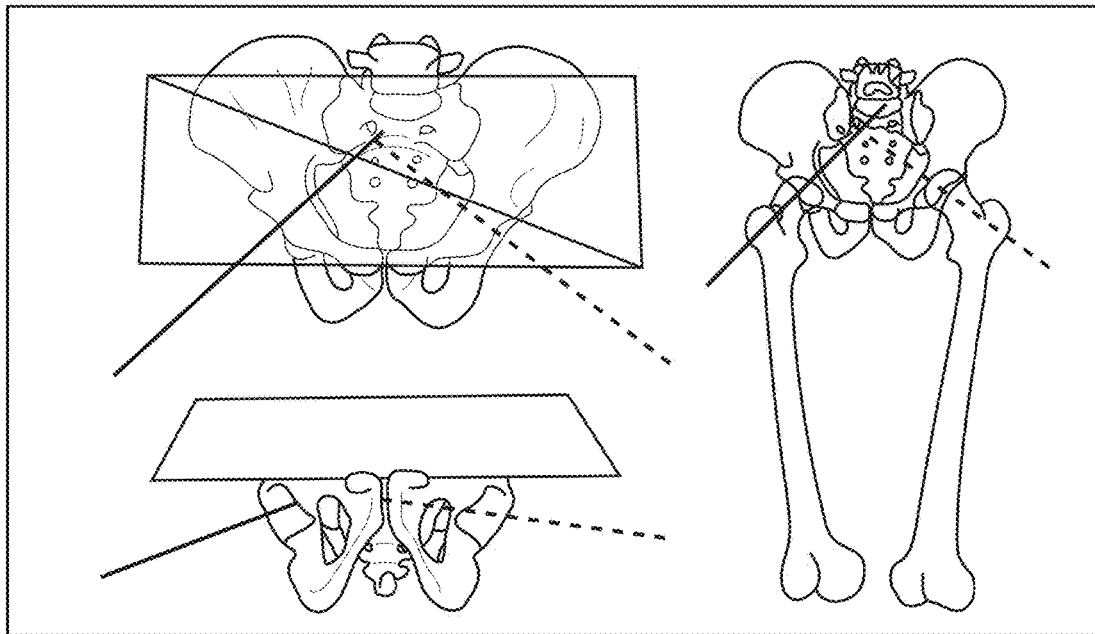
FIG. 96 is a graphical depiction of automatic cup orientation and placement in accordance with the instant disclosure.
Figure 97:
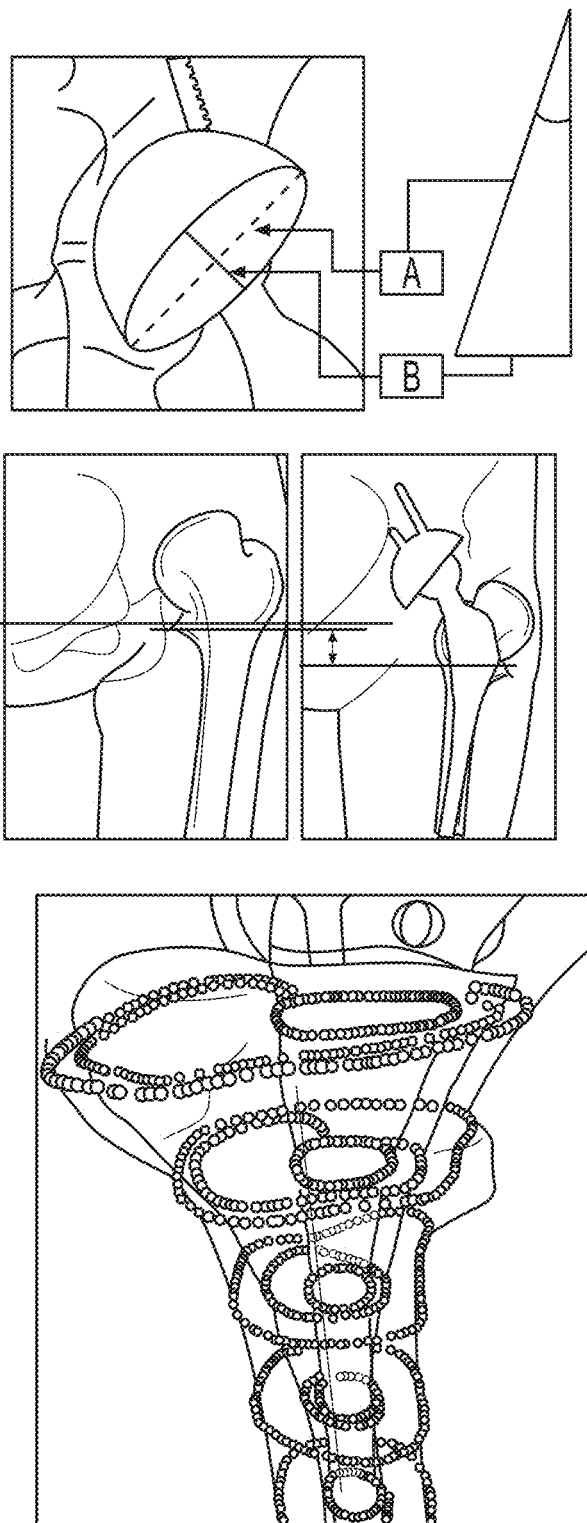
FIG. 97 comprises a series of X-rays overlaid with measurement and calculation data for acetabular cup and femoral stem placement evaluation in accordance with the instant disclosure.
Figure 98:
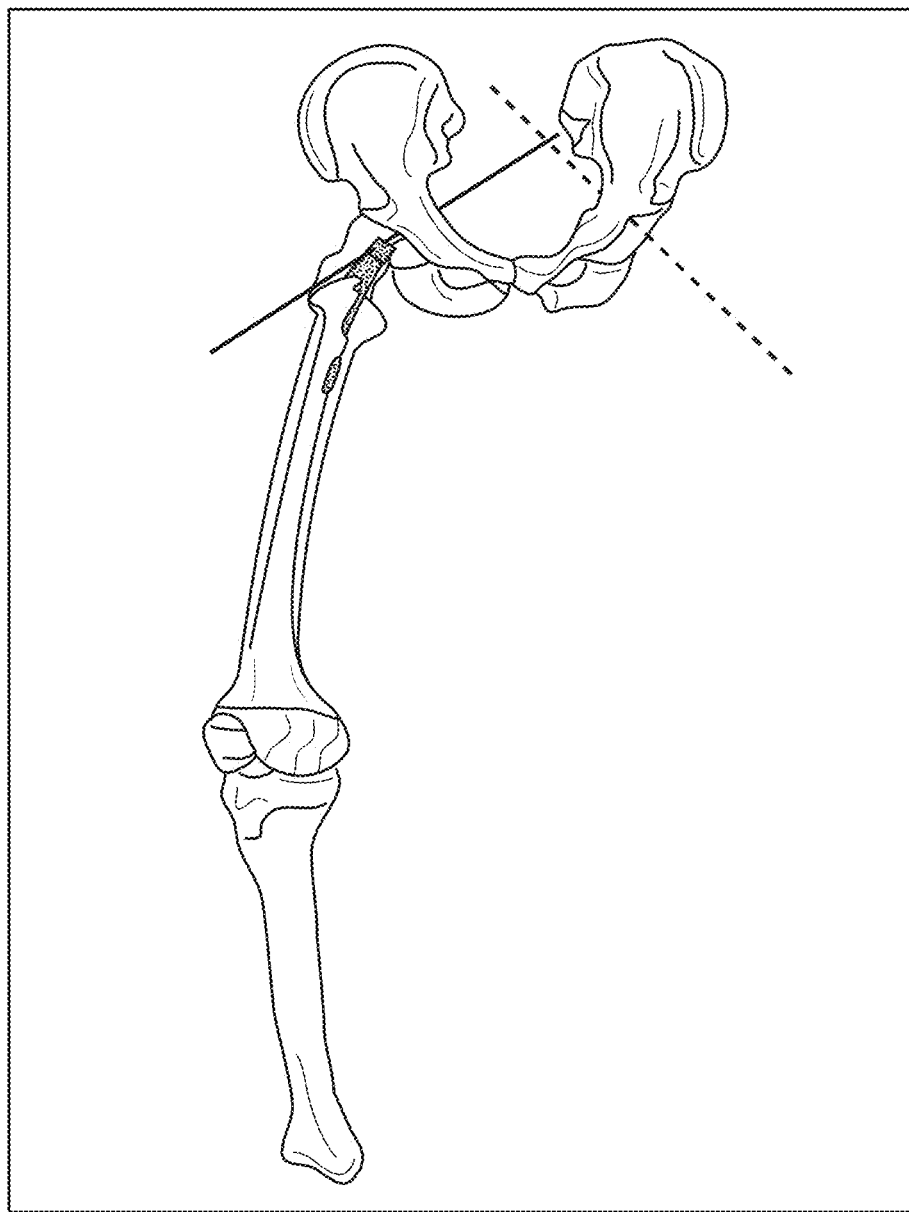
FIG. 98 is a graphical depiction of an assessment of acetabular cup and femoral stem placement to ensure overall limb length restoration and orientation in accordance with the instant disclosure.
Figure 99:
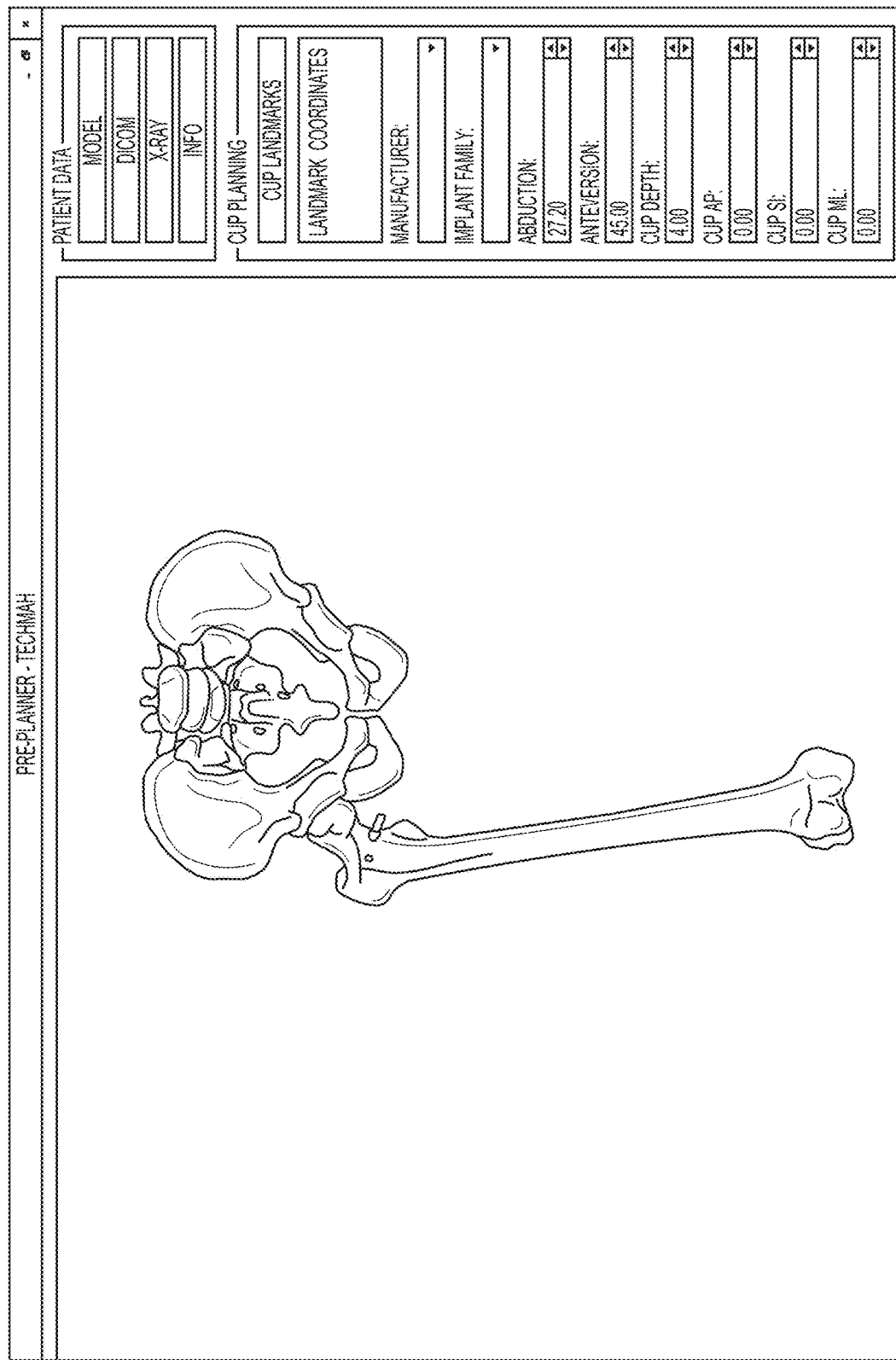
FIG. 99 is a screenshot of a preplanning interface for evaluating and modifying implant placement and sizing in accordance with the instant disclosure.

In the context of automatic placement of the femoral stem using press fit and three contacts, as shown in FIG. 94, the automatic landmarking includes definition of axes on the femur and the implant. With respect to the femur, the anatomical femoral axis (AFA) is calculated, followed by the proximal anatomical axis (PAA). The proximal neck angle (PNA) is then calculated, which is defined as the angle between the AFA and PNA. With respect to the femoral implant, the implant axis is along the length of the implant stem and the implant neck axis is along the length of the implant neck. Similar to the PNA of the femur, the implant angle is defined as the angle between the implant axis and the implant neck axis. The implant is then chosen which has an implant angle that is closest to the PNA. The implant fitting angle (IFA) is then defined as the intersection of the proximal anatomical axis with a vector drawn from the femoral head center at the chosen implant angle.

When using automatic placement of the femoral stem using press fit, three contacts, and the calculated anatomical landmarks, as shown in FIG. 94, an implant sizing step determines/estimates for the appropriate implant sizes for pelvis and femoral components. The implant size is chosen by aligning the implant to the femur by aligning the implant axis to the anatomic femur axis. The implant is then rotated to align its neck axis with the femoral neck axis. The implant is then translated to be in an anatomically proper position within the proximal femur. Thereafter, the system moves forward to an implant placement step.

In the implant placement step for a press fit femoral stem, based on surgeon preferred surgical technique and previously calculated anatomical landmarks, the initial implant position is determined/chosen for all relevant implanted components. A resection plane is created to simulate the proximal femur osteotomy and the implant fit is assessed. Fit assessment is conducted by analyzing a contour of the implant and femur intramedullary canal. The contour is created by intersecting the intramedullary canal with a plane normal to both anatomical axis and femoral neck axis, passing through the point of intersection of the anatomical axis and femur neck axis, producing a contour. When the implant and intramedullary canal contours are generated, only the implants with widths less than the intramedullary canal width at the same location are kept, resulting in many possible correct implant sizes. The group of possible sizes is reduced through two strategies reducing mean square distance error between the implant and the intramedullary canal. The first strategy minimizes the mean square error (MSE) or other mathematical error metric of the distance between both medial and lateral sides of the implant and the intramedullary canal. The second strategy minimizes the MSE of the distance between the lateral side of the implant and the intramedullary canal.

As part of this implant placement step, an iterative scheme is utilized that includes using an initial "educated guess" as to implant placement as part of a kinematic simulation to evaluate the placement of the "educated guess." In exemplary form, the kinematic simulation takes the implant (based upon the placement of the implant chosen) through a range of motion using estimated or measured joint kinematics. Consequently, the kinematic simulation may be used to determine impingement locations and estimate the resulting range of motion of the implant post implantation. In cases where the kinematic simulation results in unsatisfactory data (e.g., unsatisfactory range of motion, unsatisfactory mimicking of natural kinematics, etc.), another location for implant placement may be utilized, followed by a kinematic analysis, to further refine the implant placement until reaching a satisfactory result. After the implant position is determined/chosen for all relevant implanted components, the template data is forwarded to a jig generation module.

Referring back to FIG. 87, the jig generation module generates a patient-specific guide model. More specifically, from the template data and associated planning parameters, the shape and placement of a patient-specific implant is known with respect to the patient's residual bone. Consequently, the virtual templating module, using the patient-specific 3D bone model, calculates the position of the implant with respect to the patient's residual bone and, thus, provides the jig generation module with information as to how much of the patient's residual bone is intended to be retained. Consistent with this bone retention data, the jig generation module utilizes the bone retention data to assign one or more bone cuts to reduce the patient's current bone to the residual bone necessary to accept the implant as planned. Using the intended bone cut(s), the jig generation module generates a virtual 3D model of a cutting guide/jig having a shape configured to mate with the patient's bone in a single location and orientation. In other words, the 3D model of the cutting jig is created as a "negative" of the anatomical surface of the patient's residual bone so that the tangible cutting guide precisely matches the patient anatomy. In this fashion, any guesswork associated with positioning of the cutting jig is eliminated. After the jig generation module generates the virtual 3D model of the cutting jig, the module outputs machine code necessary for a rapid prototyping machine, CNC machine, or similar device to fabricate a tangible cutting guide. By way of example, the exemplary cutting jig for resection of the femoral head and neck comprises a hollow slot that forms an associated guide to constrain a cutting blade within a certain range of motion and maintains the cutting blade at a predetermined orientation that replicates the virtual cuts from the surgical planning and templating modules. The jig generation module is also utilized to create a placement jig for the femoral stem.

Figure 100:
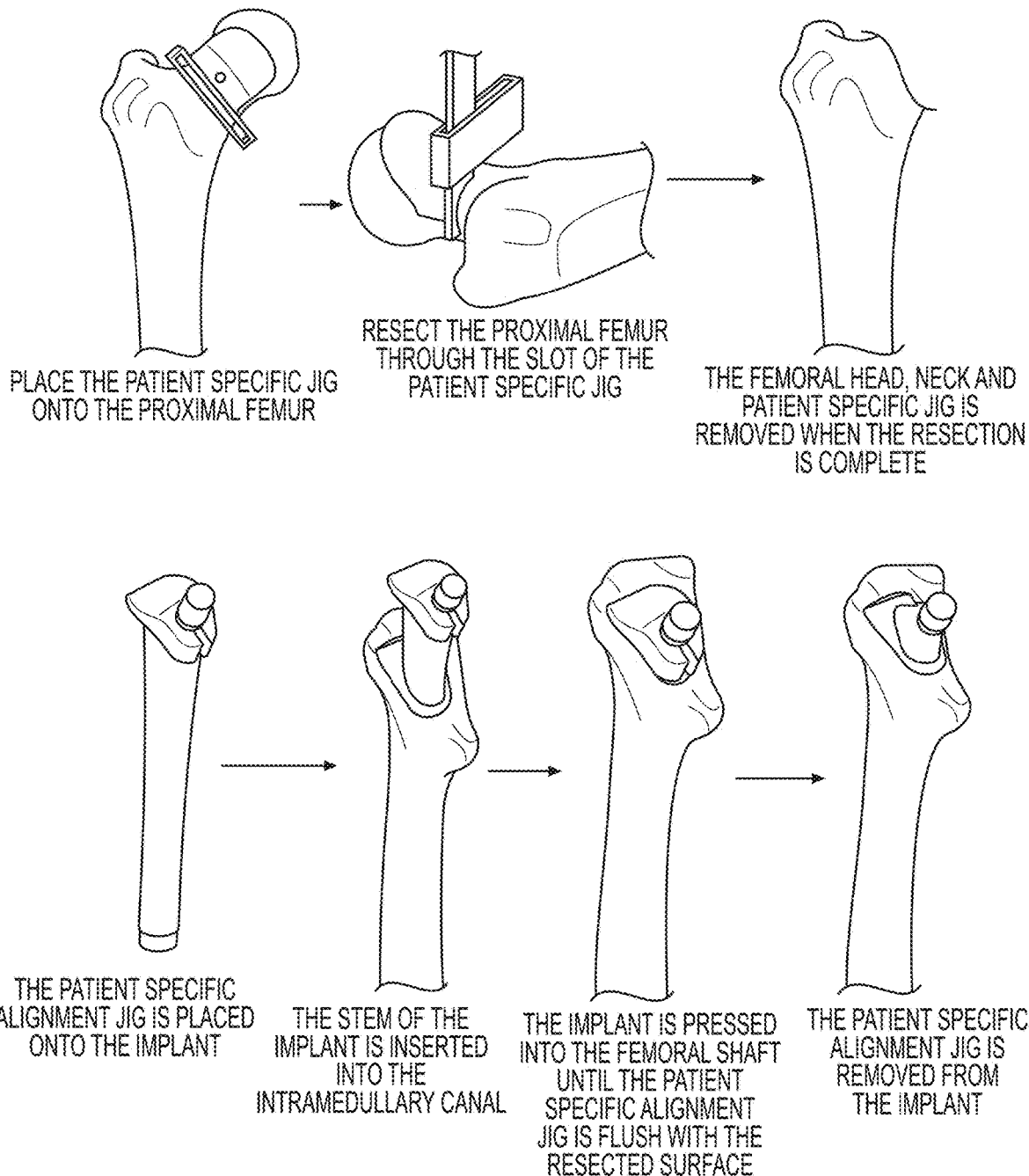
FIG. 100 comprises a series of sequential images depicting an exemplary process for using patient specific tools for resection and placement of a femoral stem.

Referring to FIG. 100, subsequent to resecting the femoral head and neck, intramedullary reaming followed by femoral stem insertion takes place. In order to prepare the femur for insertion of the femoral implant, reaming of the intramedullary canal needs to take place along an orientation consistent with the orientation of the femoral implant. If the reaming is offset, the orientation of the femoral implant may be compromised. To address this concern, the jig generation module generates a virtual guide that is a "negative" of the anatomical surface of the patient's residual or resected bone so that a rapid prototyping machine, CNC machine, or similar device can fabricate the cutting guide that precisely matches the patient anatomy. By way of example, the reaming jig may include an axial guide along which the reamer may longitudinally traverse. Using this reaming jig, the surgeon performing the reaming operation is ensured of reaming in the proper orientation.

The intramedullary canal may receive the femoral stem. Again, to ensure the femoral stem is properly positioned both from a rotational perspective and an angular perspective within the intramedullary canal, the jig generation module generates a femoral stem placement guide. By way of example, the femoral stem placement guide concurrently is a "negative" of the anatomical surface of the patient's residual or resected bone as well as the top of the femoral stem. In this manner, the placement guide slides over the femoral shaft (portion of femoral stem that the femoral ball is connected to) and concurrently includes a unique shape to interface with the patient's residual or resected bone so that only a single orientation of the femoral stem is possible with respect to the patient's femur, thereby ensuring proper implantation of the femoral stem consistent with pre-operative planning. It should be noted, however, that while the exemplary jigs have been described in the context of a primary hip implant, those skilled in the art should understand that the foregoing exemplary process and system are not limited to primary hip implants or limited to hip implant or revision surgical procedures. Instead, the process and system are applicable to any hip implants in addition to surgical procedures involving other areas of the body including, without limitation, knee, ankle, shoulder, spine, head, and elbow.

Figure 101:
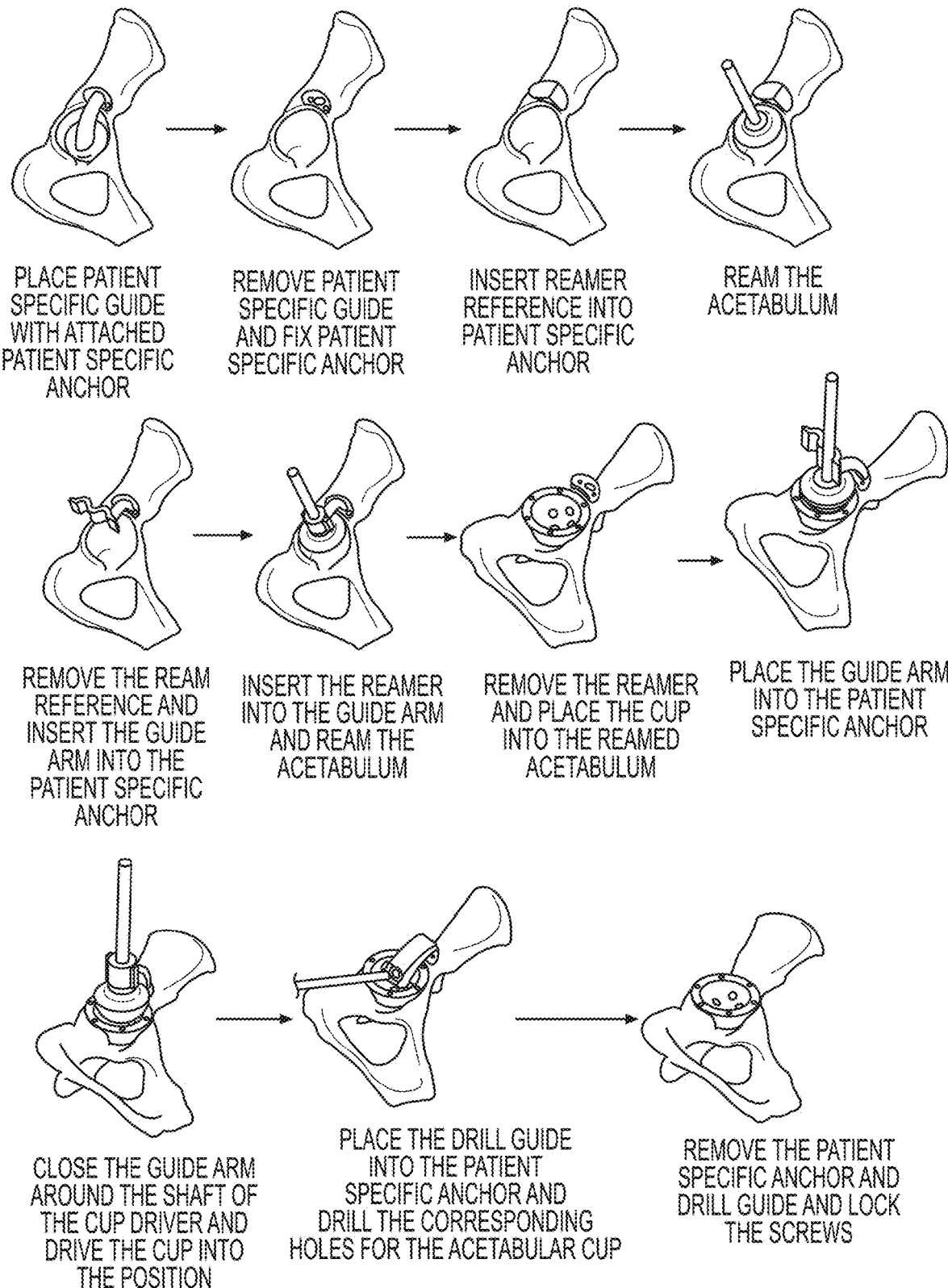
FIG. 101 comprises a series of sequential images depicting an exemplary process for using patient specific guide for reaming and placement of an acetabular cup.
Figure 102:
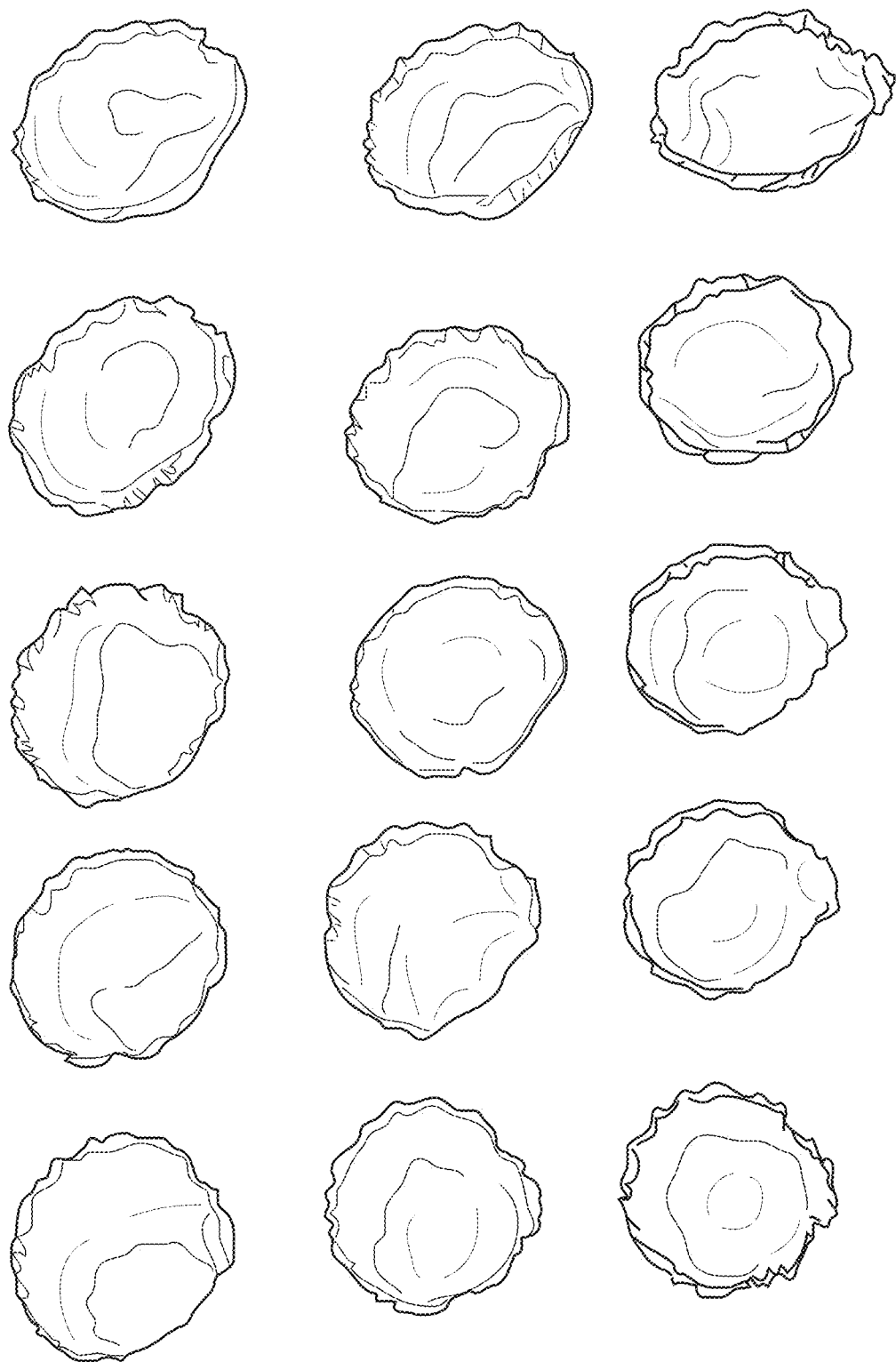
FIG. 102 depicts a series of 3D virtual maps of acetabulums that may be used for generating patient specific tools and locking mechanism in accordance with the instant disclosure.
Figure 103:
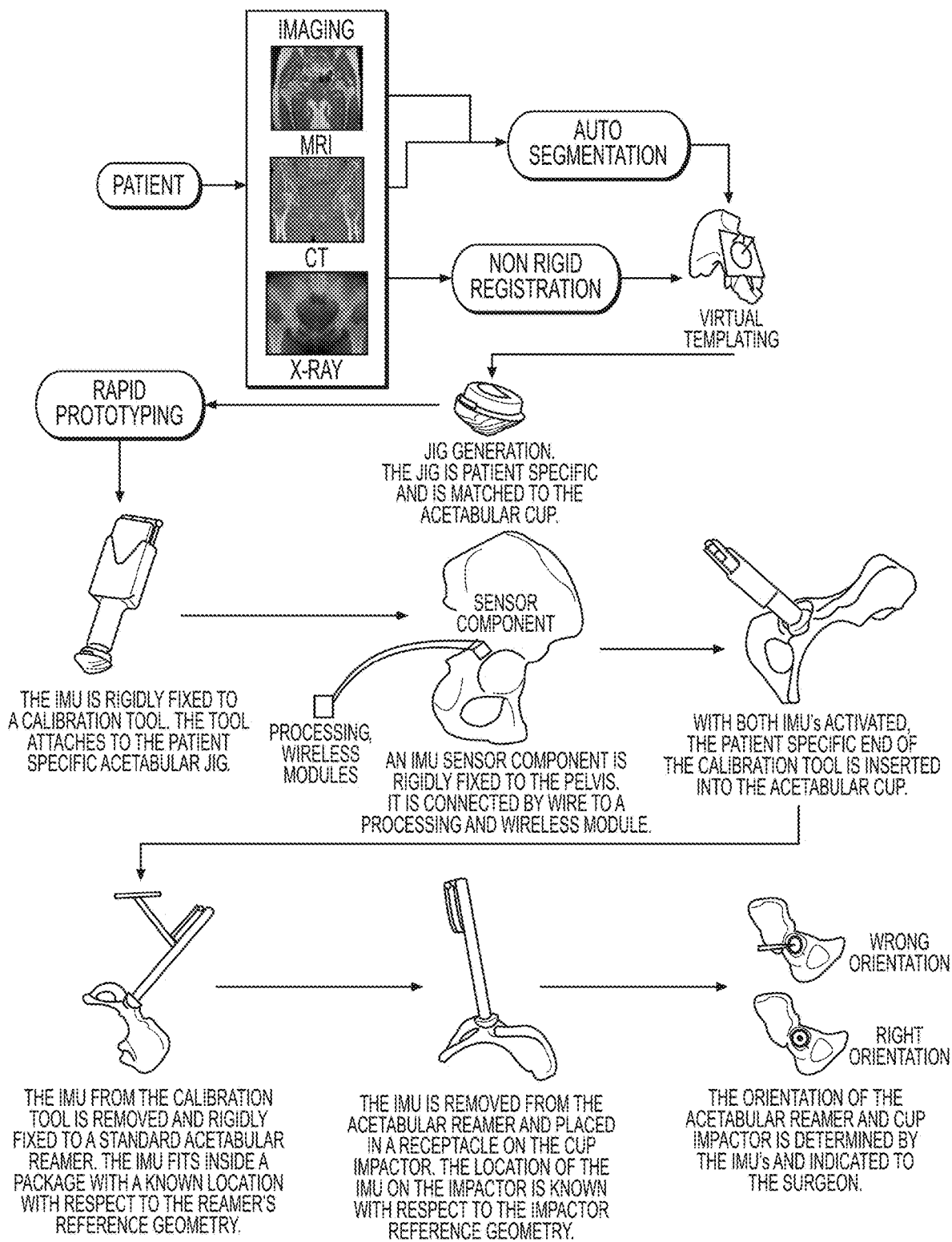
FIG. 103 is an exemplary process diagram for using inertial measurement units as part of surgical navigation during a hip replacement procedure.
Figure 104:
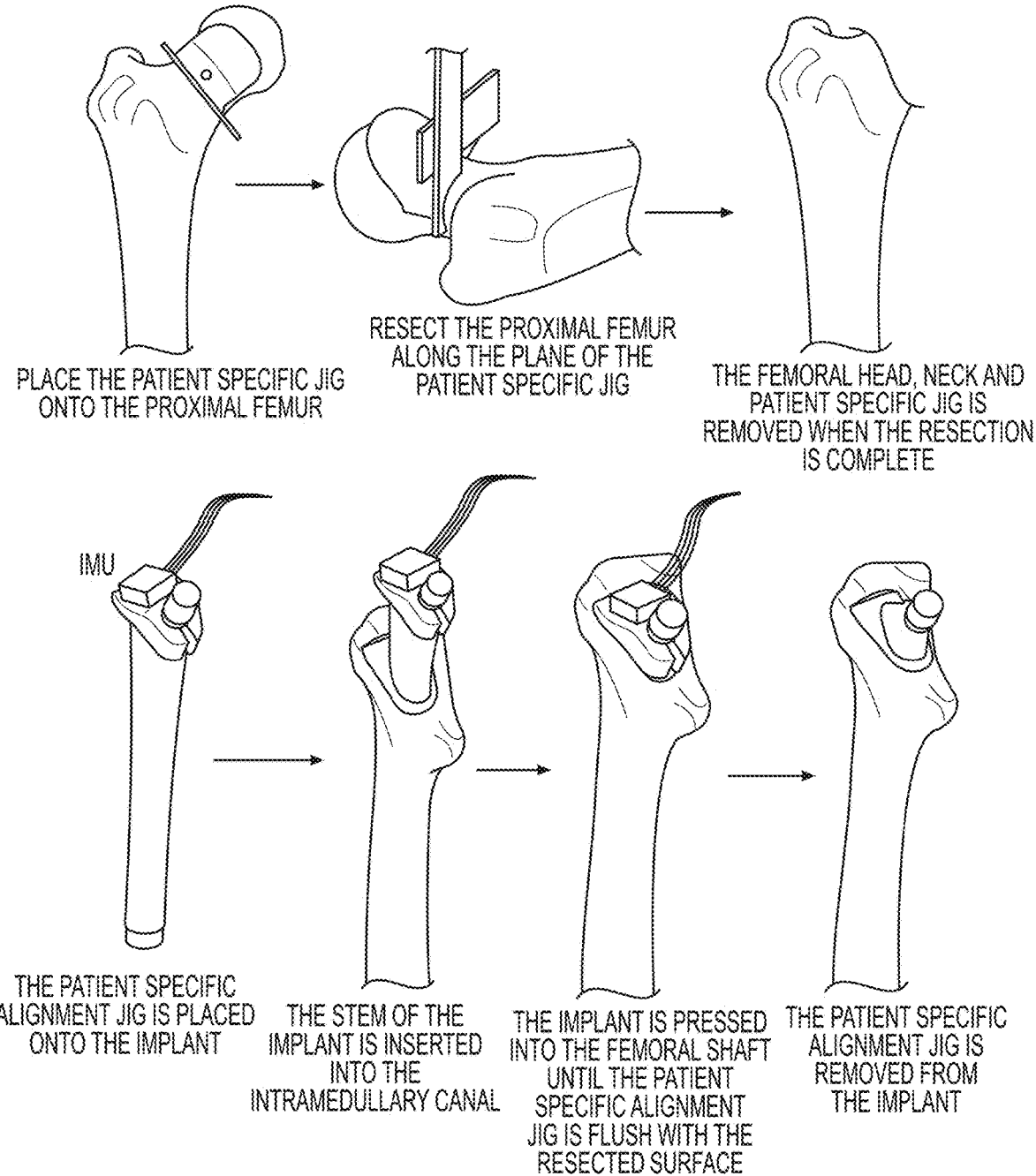
FIG. 104 is a series of sequential images depicting an exemplary process for using inertial measurement units as part of surgical navigation during a hip replacement procedure.
Figure 105:
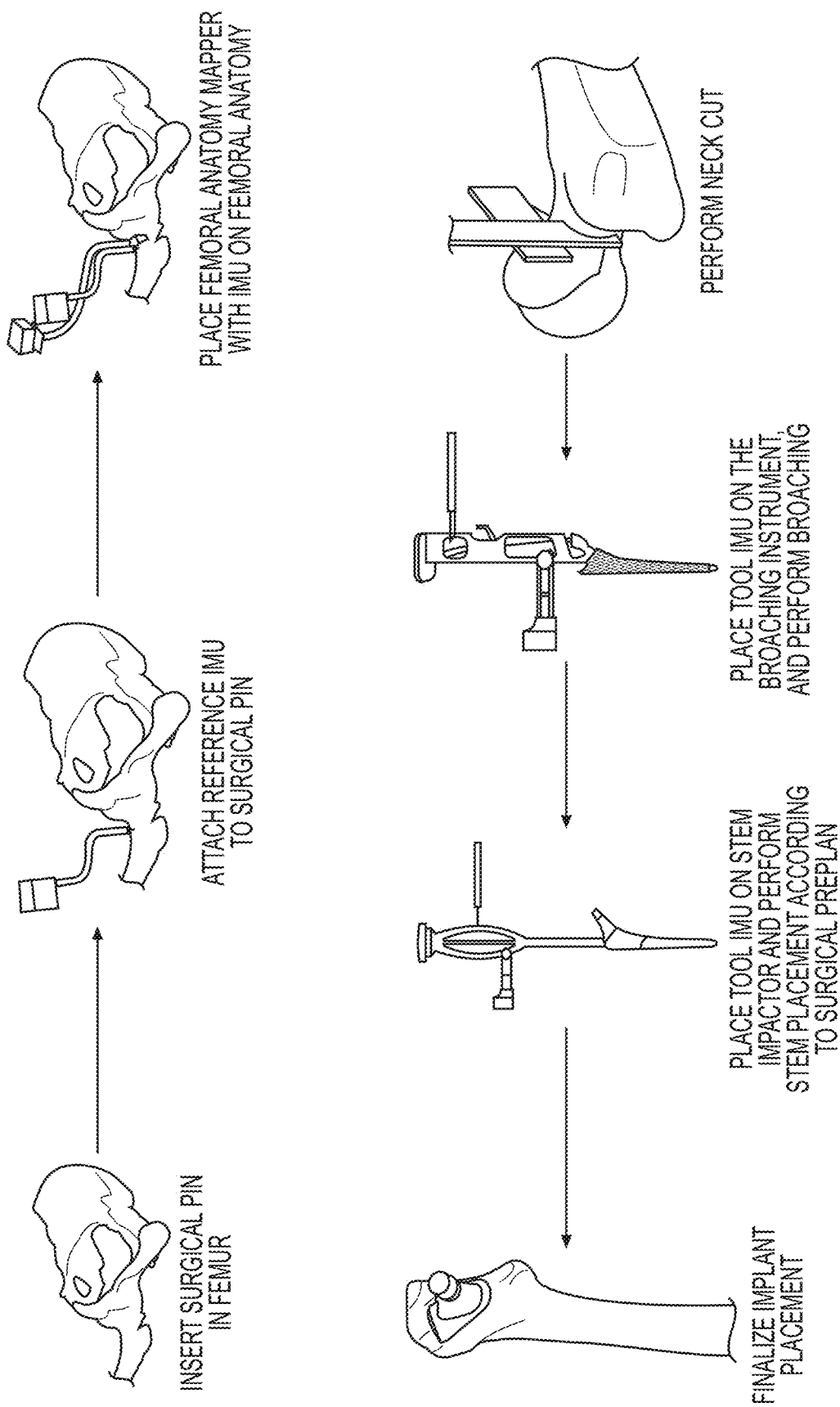
FIG. 105 is a series of sequential images depicting an exemplary process for using inertial measurement units as part of surgical navigation specific to the femur during a hip replacement procedure.
Figure 106:
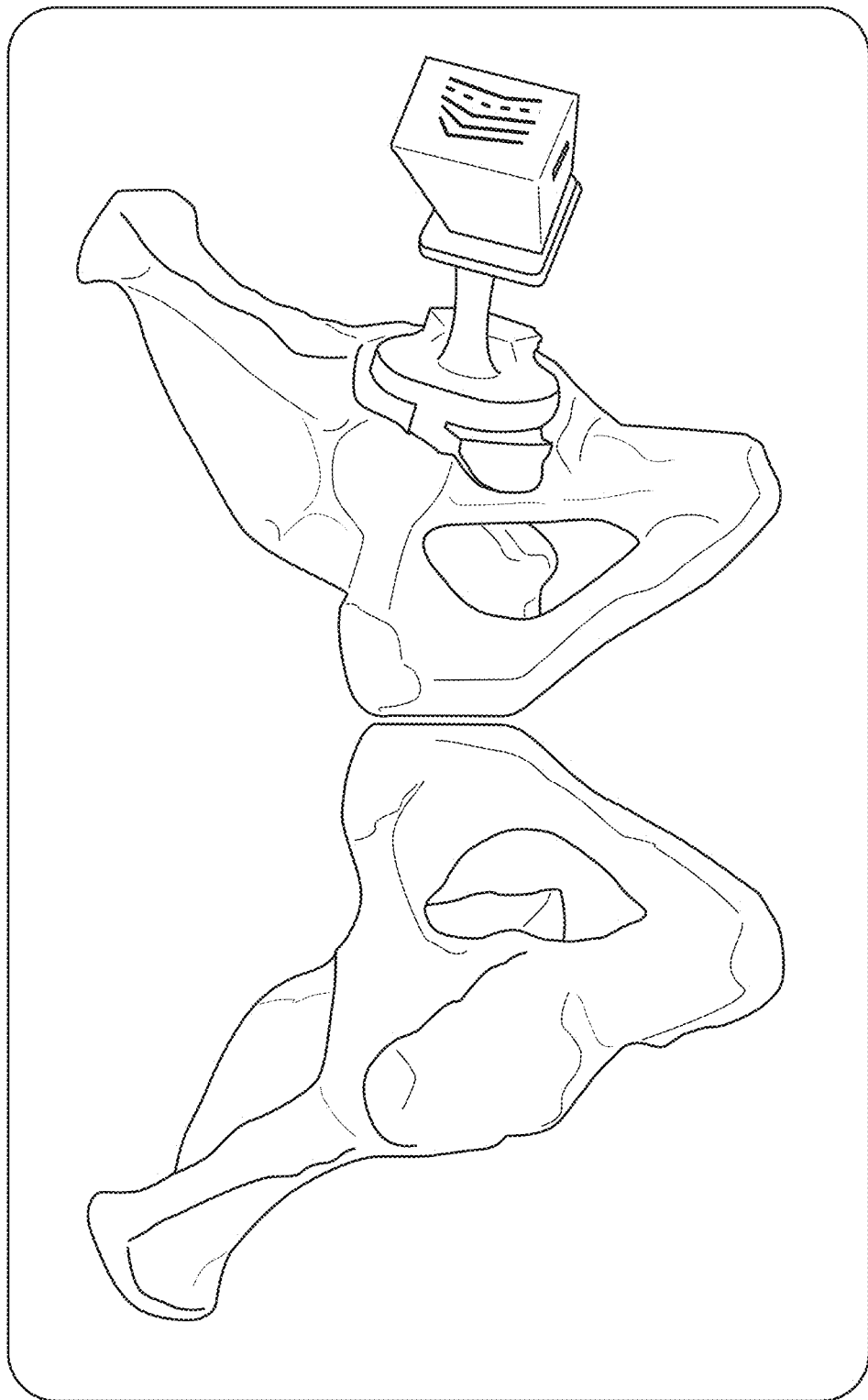
FIG. 106 graphically depicts an exemplary tool and process for calibrating the position of an inertial measurement unit for use in later surgical navigation specific to the pelvis during a hip replacement procedure.
Figure 107:
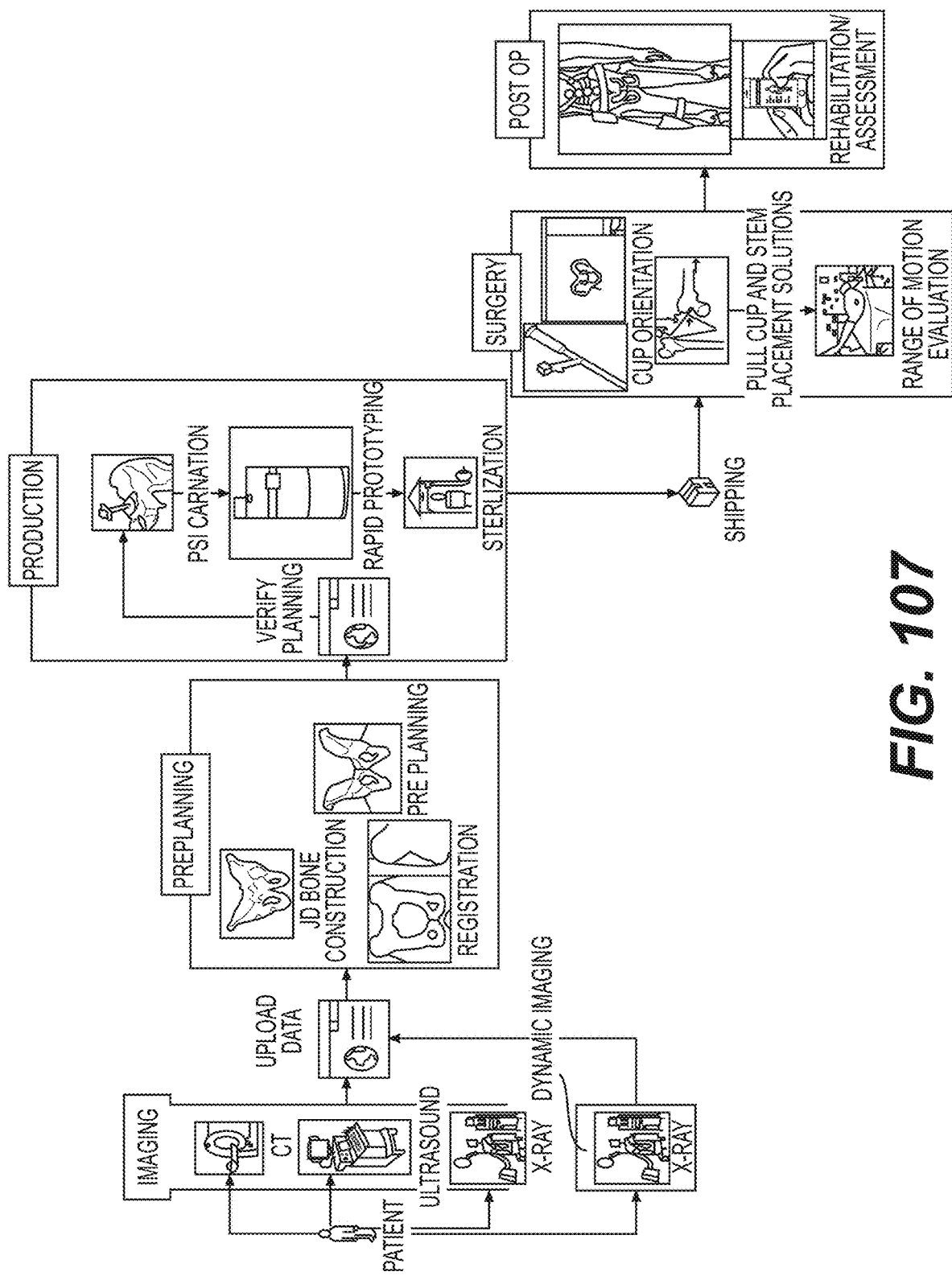
FIG. 107 is an exemplary process flow diagram for preparing to use and using inertial measurement units during a surgical procedure, as well as using inertial measurement after completion of the surgical procedure to evaluate the surgical outcome.
Figure 108:
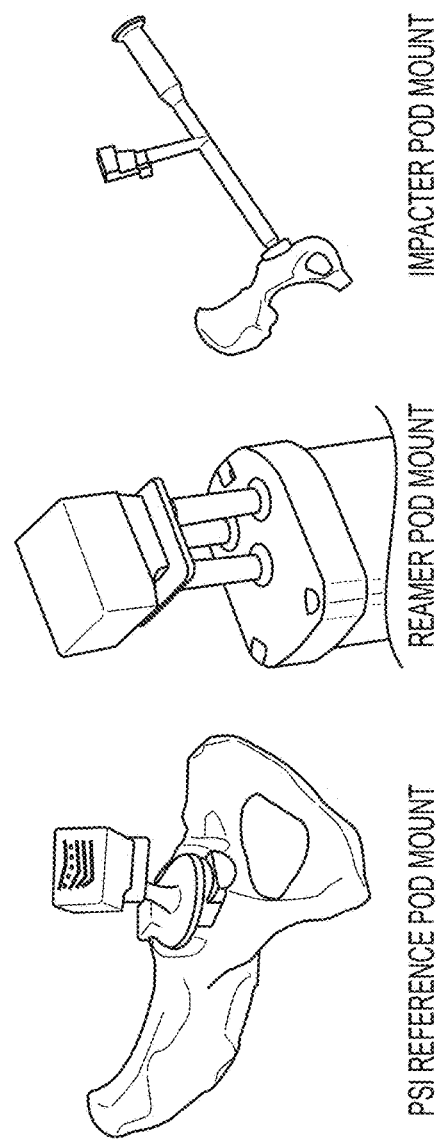
FIG. 108 depicts a series of images showing an inertial measurement unit pod/housing mounted to various tools as part of facilitating surgical navigation during a surgical procedure.
Figure 109:
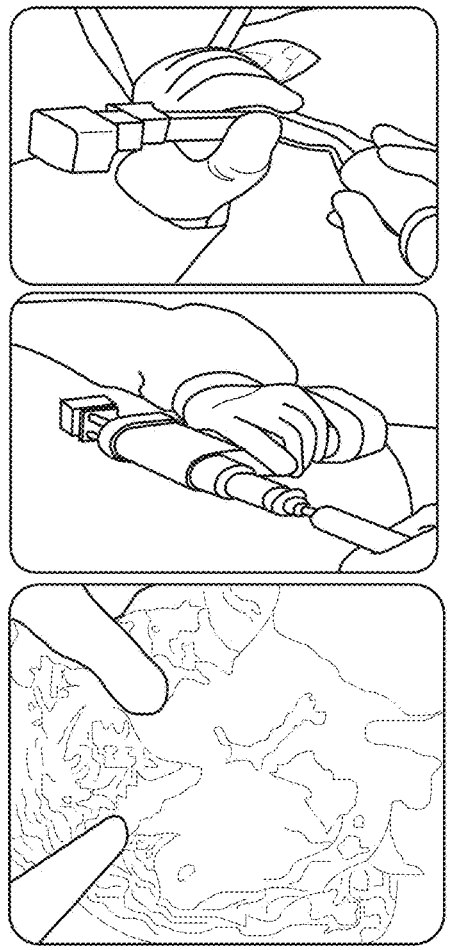
FIG. 109 depicts a series of images showing an inertial measurement unit (IMU) pod/housing, a picture of calibrating the IMU as to position with respect to the patient's anatomy; a picture showing utilization of the IMU pod to surgically navigate a reamer, and finally a picture showing utilization of the IMU pod to surgically navigate an acetabular cup impacter.
Figure 110:
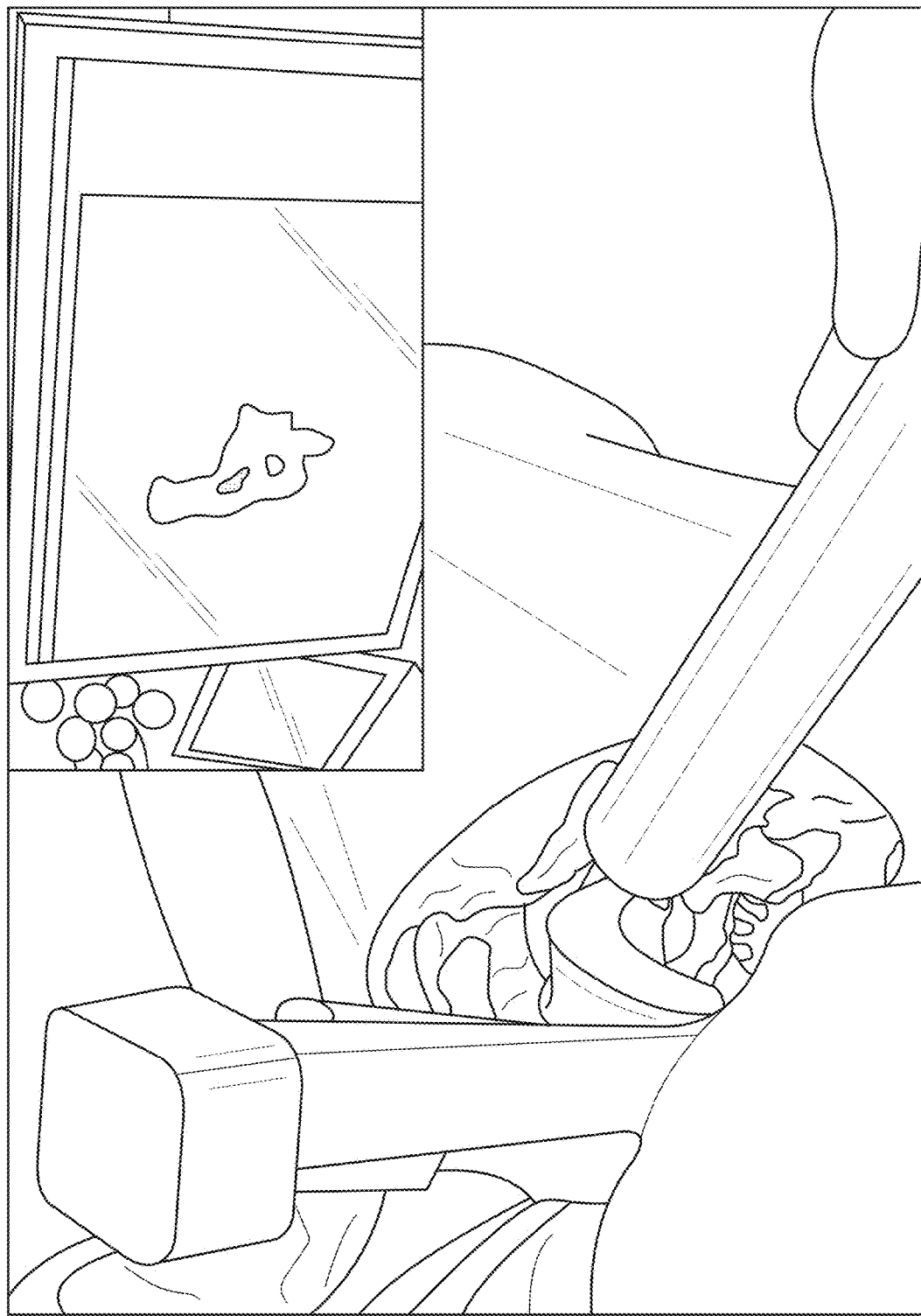
FIG. 110 depicts a picture in picture showing utilization of the IMU pod with an acetabular cup impacter as well as a graphical interface (inset picture) showing a model of the patient's anatomy (in this case, a pelvis) and the distal end of the impacter color coded to confirm that the orientation of the impacter is consistent with the surgical pre-planning orientation.

As depicted in FIG. 101, in the context of the acetabulum, the jig generation module may generate instructions for fabricating reaming and acetabular implant placement guides for the acetabular cup. In particular, from the template data and associated planning parameters, the shape and placement of a patient-specific acetabular implant is known with respect to the patient's residual pelvis. Consequently, the virtual templating module, using the patient-specific 3D acetabulum model, calculates the size and position of the acetabular cup implant with respect to the patient's residual bone and, thus, provides the jig generation module with information as to how much of the patient's residual pelvis is intended to be retained and the desired implant orientation. Consistent with this bone retention data, the jig generation module utilizes the bone retention data to assign one or more bone cuts/reaming to reduce the patient's current pelvis to the residual bone necessary to accept the acetabular implant as planned. Using the intended bone cut(s), the jig generation module generates a virtual 3D model of a cutting guide/jig having a shape configured to mate with two portions of the patient's pelvis via only one orientation. In other words, the 3D model of the cutting jig is created as a "negative" of the anatomical surface of the patient's pelvis so that the tangible reaming guide precisely matches the patient anatomy. In this fashion, any guesswork associated with positioning of the reaming jig is eliminated. After the jig generation module generates the virtual 3D model of the reaming jig, the module outputs machine code necessary for a rapid prototyping machine, CNC machine, or similar device to fabricate a tangible reaming jig. By way of example, the exemplary acetabular component jig for reaming the acetabulum comprises a four-piece structure, where a first piece is configured to be received in the native acetabulum and temporarily mount to the second piece until the second piece is secured to the pelvis using the first piece as a placement guide. After the second piece is fastened to the pelvis, the first piece may be removed. Thereafter, the third piece includes a cylindrical or partially cylindrical component that uniquely interfaces with the second piece to ensure the reamer can longitudinally traverse with respect to the third piece, but its orientation is fixed using a combination of the first and third pieces. Following reaming, the reamer is removed and the third piece is removed from the first piece. The acetabular cup implant is mounted to the reamed acetabulum using a forth piece. In particular, the fourth piece is shaped uniquely to engage the first piece in only a single orientation, while at the same time being formed to be received within the interior of the acetabular cup implant. After the implant cup is positioned, both the first and fourth pieces are removed. It should also be noted that additional jigs may be created for drilling one or more holes into the pelvis to seat the acetabular implant, where each drilling jig is mounted in succession to the first piece in order to verify the orientation of the drill bit.

Surgical Navigation

Referring to FIGS. 103-111, an alternate exemplary system and process are depicted for using one or more inertial measurement units (IMUs) to facilitate surgical navigation to accurately position orthopedic surgical tools and orthopedic implants during a surgical procedure. This first alternate exemplary embodiment is described in the context of performing a total hip arthroplasty procedure. Nevertheless, the methods, systems, and processes described hereafter are applicable to any other surgical procedure for which guidance of surgical tools and implants is useful.

As depicted schematically, the initial steps of utilizing patient images (whether X-ray, CT, MRI, etc.) and performing segmentation or registration to arrive at virtual templates of the patient's anatomy and appropriate implant size, shape, and placement parallels that previously described with reference to FIGS. 87, 88, 90-92. What differs somewhat are the modules and processes utilized downstream from the virtual templating module.

Downstream from the virtual templating module is an initialization model generation module. This module receives template data and associated planning parameters (i.e., the shape and placement of a patient-specific acetabular implant is known with respect to the patient's residual pelvis, as well as the shape and placement of a patient-specific femoral implant with respect to the patient's residual femur). Using this patient-specific information, the initialization model generation module fabricates a 3D virtual model of an initialization device for the patient's native acetabular cup and a 3D virtual model of an initialization device for the femoral implant. In other words, the 3D model of the acetabular initialization device is created as a "negative" of the anatomical surface of the patient's acetabulum so that the tangible initialization device precisely matches the patient's acetabulum. Similarly, the 3D model of the femoral stem initialization device is created as a "negative" of the anatomical surface of the patient's residual femur and femoral implant so that the tangible initialization device precisely matches the patient's residual femur and femoral implant at only a single location and single orientation. In addition to generating these initialization devices, the initialization model generation module also generates machine codes necessary for a rapid prototyping machine, CNC machine, or similar device to fabricate the tangible acetabular initialization device and femoral initialization device. The tangible acetabular initialization device and femoral initialization device are fabricated and mounted to (or formed concurrently or integrally with) or integral with surgical navigation tools configured to have at least one IMU 1002.

IMUs 1002, capable of reporting orientation and translational data, are combined with (e.g., mounted to) the surgical tools to assist in surgical navigation, which includes positioning surgical equipment and implant devices. These IMUs 1002 are communicatively coupled (wired or wireless) to a software system that receives output data from the IMUs indicating relative velocity and time that allows the software to calculate the IMU's current position and orientation, or the IMU 1002 calculates and sends the position and orientation of the surgical instrument, which will be discussed in more detail hereafter, the position and orientation of the surgical instrument associated with the IMU. In this exemplary description, each IMU 1002 includes three gyroscopes, three accelerometers, and three Hall-effect magnetometers (set of three, tri-axial gyroscopes, accelerometers, magnetometers) that may be integrated into a single circuit board or comprised of separate boards of one or more sensors (e.g., gyroscope, accelerometer, magnetometer) in order to output data concerning three directions perpendicular to one another (e.g., X, Y, Z directions). In this manner, each IMU 1002 is operative to generate 21 voltage or numerical outputs from the three gyroscopes, three accelerometers, and three Hall-effect magnetometers. In exemplary form, each IMU 1002 includes a sensor board and a processing board, with a sensor board including an integrated sensing module consisting of a three accelerometers, three gyroscopic sensors and three magnetometers (LSM9DS, ST-Microelectronics) and two integrated sensing modules consisting of three accelerometers, and three magnetometers (LSM303, ST-Microelectronics). In particular, the IMUs 1002 each include angular momentum sensors measuring rotational changes in space for at least three axes: pitch (up and down), yaw (left and right) and roll (clockwise or counter-clockwise rotation). More specifically, each integrated sensing module consisting magnetometer is positioned at a different location on the circuit board, with each magnetometer assigned to output a voltage proportional to the applied magnetic field and also sense polarity direction of a magnetic field at a point in space for each of the three directions within a three dimensional coordinate system. For example, the first magnetometer outputs voltage proportional to the applied magnetic field and polarity direction of the magnetic field in the X-direction, Y-direction, and Z-direction at a first location, while the second magnetometer outputs voltage proportional to the applied magnetic field and polarity direction of the magnetic field in the X-direction, Y-direction, and Z-direction at a second location, and the third magnetometer outputs voltage proportional to the applied magnetic field and polarity direction of the magnetic field in the X-direction, Y-direction, and Z-direction at a third location. By using these three sets of magnetometers, the heading orientation of the IMU may be determined in addition to detection of local magnetic field fluctuation. Each magnetometer uses the magnetic field as reference and determines the orientation deviation from magnetic north. But the local magnetic field can, however, be distorted by ferrous or magnetic material, commonly referred to as hard and soft iron distortion. Soft iron distortion examples are materials that have low magnetic permeability, such as carbon steel, stainless steel, etc. Hard iron distortion is caused by permanent magnets. These distortions create a non-uniform field (see FIG. 184), which affects the accuracy of the algorithm used to process the magnetometer outputs and resolve the heading orientation. Consequently, as discuss in more detail hereafter, a calibration algorithm is utilized to calibrate the magnetometers to restore uniformity in the detected magnetic field. Each IMU 1002 may be powered by a replaceable or rechargeable energy storage device such as, without limitation, a CR2032 coin cell battery and a 200 mAh rechargeable Li ion battery.

The integrated sensing modules in IMU 1002 may include a configurable signal conditioning circuit and analog to digital converter (ADC), which produces the numerical outputs for the sensors. The IMU 1002 may use sensors with voltage outputs, where an external signal conditioning circuit, which may be an offset amplifier that is configured to condition sensor outputs to an input range of a multi-channel 24 bit analog-to-digital converter (ADC) (ADS1258, Texas Instrument). The IMU 1002 further includes an integrated processing module that includes a microcontroller and a wireless transmitting module (CC2541, Texas Instrument). Alternatively, the IMU 1002 may use separate low power microcontroller (MSP430F2274, Texas Instrument) as the processor and a compact wireless transmitting module (A2500R24A, Anaren) for communication. The processor may be integrated as part of each IMU 1002 or separate from each IMU, but communicatively coupled thereto. This processor may be Bluetooth compatible and provide for wired or wireless communication with respect to the gyroscopes, accelerometers, and magnetometers, as well as provide for wired or wireless communication between the processor and a signal receiver.

Each IMU 1002 is communicatively coupled to a signal receiver, which uses a pre-determined device identification number to process the received data from multiple IMUs. The data rate is approximately 100 Hz for a single IMU and decreases as more IMUs join the shared network. The software of the signal receiver receives signals from the IMUs 1002 in real-time and continually calculates the IMU's current position based upon the received IMU data. Specifically, the acceleration measurements output from the IMU are integrated with respect to time to calculate the current velocity of the IMU in each of the three axes. The calculated velocity for each axis is integrated over time to calculate the current position. But in order to obtain useful positional data, a frame of reference must be established, which includes calibrating each IMU.

The present disclosure includes a novel system and method for calibrating one or more IMUs for use in surgical navigation. Prior patent references to utilizing IMUs as purported aids in surgical navigation have suffered from inoperability for numerous reasons. Among these reasons include IMU placement with respect to metallic surgical instruments as well as an absence of calibrating the IMUs. More specifically, in the context of IMUs incorporating magnetometers, local calibration of the magnetometers is imperative for operative tracking of surgical instruments and related orthopedic components.

Referring to FIG. 182, in accordance with the instant disclosure, a novel calibration tool 1000 is utilized to calibrate one or more IMUs 1002 that may incorporate magnetometers. In exemplary form, the calibration tool 1000 includes a stationary base 1006 within which is housed a controller 1008, a motor 1012, gearing 1016, a drive shaft 1020, and a power supply 1024. The drive shaft 1020 is mounted to a portion of the gearing 1016, as is the motor 1012, so that the motor is operative to drive the gearing and rotate the drive shaft. In particular, the motor 1012 comprises an electric motor having a single drive shaft to which is mounted a drive gear of the gearing 1016. This drive gear engages a secondary gear, which is mounted to the drive shaft 1020, so that rotational motion of the motor 1012 is converted into rotational motion of the drive shaft 1020.

In this exemplary configuration, the stationary base 1006 includes a circular exterior that partially defines a hollow interior that accommodates the motor 1012, the gearing 1016, the controller 1008, the power supply 1024, and a portion of the drive shaft 1020. By way of example, a central vertical axis extends through the stationary base 1006 that is coaxial with a central axis of the drive shaft 1020. This coaxial alignment reduces vibration occurring as a result of rotation of the drive shaft 1020 with respect to the stationary base 1006. Rotation of the drive shaft 1020 is operative to rotate an outer stage 1030 with respect to the stationary base 1006.

In exemplary form, a ring-shaped bearing plate 1034 interposes the top of the stationary base 1006 and the bottom of the outer stage 1030. Both the stationary base 1006 and the bearing plate 1034 include corresponding axial openings that allow throughput of a portion of the drive shaft 1020. An end of the drive shaft 1020 proximate the outer stage 1030 is mounted to a slip ring 1038, which is in turn mounted to the outer stage. In this fashion, rotation of the drive shaft 1020 with respect to the stationary base 1006 causes the outer stage 1030 to rotate around the central vertical axis. As will be discussed in more detail hereafter, the IMUs 1002 are calibrated in part by rotating the IMUs around the central vertical axis.

In this exemplary embodiment, the outer stage 1030 includes a block U-shaped profile with corresponding opposed fork appendages 1042. Each appendage 1042 is mounted to a roller bearing assembly 1046 that receives and is pivotally mounted to a center shaft 1050. Each center shaft 1050 is concurrently mounted to opposing lateral sides of an inner platform 1054 that sits between the fork appendages 1042. The inner platform 1054 includes a block U-shaped profile, which fits within the corresponding opposed fork appendages 1042, that includes a base having a plurality of upstanding projections 1058. As will be discussed in more detail hereafter, the upstanding projections 1058 are each configured to engage a corresponding recess associated with each IMU 1002 to fix the position of the IMU with respect to a portion of the calibration tool 1000. Each center shaft 1050 is longitudinally aligned along a central axis and is mounted to the inner platform 1054 so that rotation of the center shafts corresponds with rotation of the inner platform 1054 with respect to the outer stage 1030.

In order to rotate the inner platform 1054 with respect to the outer stage 1030, the calibration tool includes a pulley 1060 mounted to one of the center shafts 1050. In particular, one of the center shafts 1050 is longer than the other in order to accommodate mounting of the pulley 1060 and corresponding rotation of the pulley by way of a drive belt 1064 concurrently engaging an electric motor 1068. In this exemplary embodiment, an output shaft of the electric motor 1068 is mounted to its own pulley 1072, which engages the drive belt 1064 to ultimately rotate the pulley 1060 and correspondingly rotates the inner platform 1054 with respect to the outer stage 1030 (about the longitudinally aligned central axis of the center shafts 1050) when the electric motor is powered. The electric motor 1068 is mounted to a motor mount 1076 extending from an underneath side of the outer stage 1030 below one of the fork appendages 1042. As will be discussed in more detail hereafter, the IMUs 1002 are calibrated in part by rotating the inner platform 1054 with respect to the outer stage 1030, which thus rotates the IMUs with respect to the longitudinal central axis, which is perpendicular to the central vertical axis. Those skilled in the art should understand that a third rotational axis may be introduced to rotate the IMUs about an axis that is perpendicular to both the longitudinal central axis and the longitudinal vertical axis. An exemplary calibration sequence for calibrating one or more IMUs 1002 using the calibration tool 1000 will hereafter be described.

In exemplary form, the IMUs 1002 are preferably calibrated in close proximity to the location of ultimate use in surgical navigation. This may be within an operating room and, more specifically, adjacent a patient bed upon which the patient will or is lying. Calibration of the IMUs is location specific so that calibration of the IMUs farther away from the location of intended use may result in meaningful variance in the magnetic fields at the location of calibration and the area of use (i.e., the surgical area). Consequently, it is preferably to calibrate the IMUs 1002 near the area of use.

Using the novel calibration tool 1000, each IMU 1002 is mounted to one of the upstanding projections 1058 of the inner platform 1054. By way of example, each IMU 1002 is mounted to a housing having a shaped periphery delineating an open bottom. The shaped periphery of the IMU 1002 housing is configured to outline the perimeter of the upstanding projections 1058 so that the IMU housing can be snap-fit over a corresponding upstanding projection in order to maintain engagement of the IMU housing and the inner platform 1054 during a calibration sequence. By way of example, the IMU housing may have an oblong, triangular, rectangular, or other sided periphery that engages a corresponding upstanding projection 1058. By way of exemplary discussion and illustration, the IMU housing has a rectangular opening delineated by a constant vertical cross-section, which is slightly larger than the rectangular cross-section of the upstanding projection 1058. In exemplary form, the calibration tool 1000 includes four upstanding projections 1058 to allow for calibration of four IMUs 1002 simultaneously. But, it should be noted that, more or less than four upstanding projections 1058 may be included as part of the inner platform 1054 to provide for calibration of one or more IMUs at the same time.

The goal of the calibration sequence is to establish zero with respect to the accelerometers (i.e., meaning at a stationary location, the accelerometers provide data consistent with zero acceleration) and to map the local magnetic field and to normalize the output of the magnetometers to account for directional variance and the amount of distortion of the detected magnetic field. In order to calibrate the accelerometers of the IMUs 1002, the inner platform 1054 remains stationary with respect to the outer stage 1030, which also remains stationary with respect to the stationary base 1006. Multiple readings are taken from all accelerometers with the inner platform 1054 at a first fixed, stationary position with respect to the outer stage 1030. Thereafter, the inner stage is moved to a second fixed, stationary position with respect to the outer stage 1030 and a second set of multiple readings are taken from all accelerometers. The outputs from the accelerometers at the multiple, fixed positions are recorded, on an accelerometer specific basis, and utilized to establish a zero acceleration reading for the applicable accelerometer. In addition to establishing zero with respect to the accelerometers, the calibration sequence also maps the local magnetic field and normalizes the output of the magnetometers to account for directional variance and the amount of distortion of the detected magnetic field.

In order to map the local magnetic field for each magnetometer (presuming multiple magnetometers for each IMU 1002 positioned in different locations), the inner platform 1054 is rotated about the center shafts 1050 and about the central axis with respect to the outer stage 1030, in addition to the outer stage 1030 being rotated about the drive shaft 1020 and about the central vertical axis with respect to the stationary base 1006. Output data from each magnetometer is recorded while the inner platform 1054 is rotated about two axes perpendicular to one another. Repositioning of the each magnetometer about the two perpendicular axes generates a point cloud or map of the three dimensional local magnetic field sensed by each magnetometer. The views in FIG. 181 depict an exemplary local magnetic field mapped from isometric, front, and top views based upon data received from a magnetometer while being concurrently rotated in two axes. As is reflected in the local magnetic field map, the local map embodies an ellipsoid. This ellipsoid shape is the result of distortions in the local magnetic field caused by the presence of ferrous or magnetic material, commonly referred to as hard and soft iron distortion. Soft iron distortion examples are materials that have low magnetic permeability, such as carbon steel, stainless steel, etc. Hard iron distortion is caused by material such as permanent magnets.

It is presumed that but for distortions in the local magnetic field, the local magnetic field map would be spherical. Consequently, the calibration sequence is operative to collect sufficient data point to describe the local magnetic field in different orientations by either the calibration tool 1000 or manual manipulation of the IMU. A calibration algorithm calculates the correction factors to map the distorted elliptic local magnetic field into a uniform spherical field.

Referencing FIG. 184, the multiple magnetometers positioned in different locations with respect to one another as part of an IMU 1002 is used to detect local magnetic after the calibration is complete. Absent any distortion in the magnetic field, each of the magnetometers should provide data indicative of the exact same direction, such as polar north. But distortions in the local magnetic field, such as the presence of ferrous or magnetic materials (e.g. surgical instruments), causes the magnetometers to provide different data as to the direction of polar north. In other words, if the outputs from the magnetometers are not uniform to reflect polar north, a distortion has occurred and the IMU 1002 may temporary disable the tracking algorithm from using the magnetometer data. It may also alert the user that distortion has been detected.

Referring to FIGS. 185 and 186, the exemplary surgical tools that receive an IMU 1002 include an electrical switch pattern or grid that is unique for each instrument. More specifically, each surgical tool includes a projection having a top surface that is predominantly planar, but for one or more cylindrical cavities. In exemplary form, each IMU 1002 includes a housing defining a bottom opening that is configured to receive the surgical tool projection. Within this bottom opening are four switches that each includes a biased cylindrical button so that when the button is depressed, the switch is closed and sends a corresponding signal to the IMU 1002 processor. Conversely, when the button is not depressed, the switch remains open and no corresponding signal of switch closure is sent to the IMU 1002 processor. In this fashion, the processor determines which switches are open and which switches are closed and uses this information to identify which surgical tool the IMU 1002 is mounted to.

As part of identifying the surgical tool, zero to four of the switches may be depressed depending upon the top surface topography of the projection. As depicted graphically, a projection of a surgical tool is received within the IMU 1002 housing bottom opening so that the top surface of the projection is pushed adjacent the switches. It should be noted that the projection and bottom opening in the IMU 1002 housing are configures so that the projection is received within the bottom opening in only a single rotational orientation, thereby limiting the chance of misalignment between the projection and switches that might otherwise lead to a misidentification of the surgical tool.

In particular, as depicted in FIG. 185, the calibration adapter surgical tool includes a single cylindrical cavity positioned near the front right corner of the projection (opposite the shaved corner) in order to provide a unique configuration. Accordingly, when the projection of the calibration adapter surgical tool is received within the bottom opening of the IMU 1002 housing, only a single switch of the 2&2 grid of switches is activated nearest the front right corner of the IMU 1002 housing, which tells the IMU 1002 processor that the IMU 1002 is mounted to the calibration adapter surgical tool. In contrast, the patient anatomical mapping (PAM) registration tool adapter surgical tool includes two cylindrical cavities positioned near the right front and rear corners of the projection, in a second unique configuration. Accordingly, when the projection of the PAM adapter surgical tool is received within the bottom opening of the IMU 1002 housing, only two switches of the 2&2 grid of switches are activated nearest the right side of the IMU 1002 housing, which tells the IMU 1002 processor that the IMU 1002 is mounted to the PAM adapter surgical tool. Moreover, the reamer adapter surgical tool includes two cylindrical cavities positioned near the front of the projection (i.e., adjacent the front left and right corners). Accordingly, when the projection of the reamer adapter surgical tool is received within the bottom opening of the IMU 1002 housing, only two switches of the 2&2 grid of switches are activated nearest the front of the IMU 1002 housing, which tells the IMU 1002 processor that the IMU 1002 is mounted to the reamer adapter surgical tool. Finally, the impacter adapter surgical tool includes three cylindrical cavities positioned near the front and rights sides of the projection (i.e., adjacent the front left and right corners, and rear right corner). Accordingly, when the projection of the impacter adapter surgical tool is received within the bottom opening of the IMU 1002 housing, only three switches of the 2&2 grid of switches are activated nearest the front and right sides of the IMU 1002 housing, which tells the IMU 1002 processor that the IMU 1002 is mounted to the impacter adapter surgical tool. Those skilled in the art will understand the variation that may be provided by providing a plurality of switches or electrical contacts as part of the IMU 1002 that interface with a plurality of projections, cavities, or electrical contacts associated with the surgical tool in order to unambiguously identify the surgical tool to which the IMU 1002 is mounted.

Identification of the surgical tool to which the IMU 1002 is mounted is important for accurate surgical navigation. In particular, the surgical navigation system in accordance with the instant disclosure includes a software package that has been preloaded with CAD models or surface models of each surgical tool to which the IMU 1002 could possibly be mounted. In so doing, the software package knows the relative dimensions of each surgical tool such as, without limitation, length in the X-direction, width in the Y-direction, and height in the Z-direction and how these dimensions change along the length, width, and height of the surgical tool. Thus, when the IMU 1002 is mounted to the surgical tool in a known location, the location and orientation information (by way of the gyroscopes, accelerometers, and magnetometers) from the IMU 1002 can be translated into location and orientation information for the surgical tool. Therefore, by tracking the IMU 1002 in 3D space, the software package is able to track the surgical tool to which the IMU 1002 is mounted in 3D space and relay this location and orientation to a user, such as a surgeon or a surgeon's assistant.

In exemplary form, the software package includes a visual display that is operative to display each surgical tool as a 3D model. When an IMU 1002 is mounted to a surgical tool, the IMU 1002 processor sends data to the software package that allows the software package to identify which surgical tool the IMU 1002 is mounted to. After making this identification, the software package displays a 3D model of the surgical tool that is mounted to the IMU 1002 in an orientation that is consistent with the orientation information derived from the IMU. In addition to providing orientation information by manipulating the 3D virtual model of the surgical tool in real-time, the software package also provides real-time data about the location of the surgical tool by using a second, reference IMU 1002 that is mounted to a reference object (i.e., a bone of a patient). But before the software package can provide meaningful location information, the IMUs 1002 (IMU #1 mounted to a surgical tool and IMU #2 mounted to a reference object (i.e., bone)) need to be registered with respect to one another.

In exemplary form in the context of a total hip arthroplasty procedure, as depicted in FIGS. 103-110, registration tools are utilized to recreate the template surgical plan by engaging the patient anatomy in a predetermined orientation. When each utility IMU 1002 is mounted to its registration tool (one for the femur, a second for the pelvis), the registration tool is mounted to the relevant bone in a predetermined orientation (only one orientation that precisely matches the patient anatomy to "zero" the IMU). In order to carry this registration out, a second reference IMU is rigidly mounted to the bone in question (one IMU mounted to the pelvis and a second IMU mounted to the femur). In other words, one utility IMU is mounted to the acetabular registration tool while a second reference IMU is rigidly mounted to the pelvis. In the context of the femur, one utility IMU is mounted to the femoral registration tool while a second reference IMU is rigidly mounted to the femur. As part of the registration process, the software of the computer utilizes the outputs from both IMU (utility and reference) to calculate the "zero" location for the utility IMU when the registration tool is finally stationary and located in its unique location and orientation. Thereafter, the IMU 1002 may be removed from the relevant registration tool and mounted in a predetermined fashion to surgical tools (reamer, saw, implant placement guide, etc.) to ensure the proper orientation and placement of the surgical tools. The IMU 1002 may be mounted and removed from each surgical tool in succession until the surgical procedure is finished.

In this exemplary embodiment, the acetabular registration tool includes an elongated shaft having a unique projection shaped to fit within the patient's acetabular cup in only a single orientation (including rotational position and angular position). A proximal end of the registration tool includes an IMU 1002 registration holster to receive the IMU 1002 so that when the IMU 1002 is locked within the holster, the IMU 1002 is rigidly fixed relative to the registration tool and unique projection. Coincident with the registration tool, a second reference IMU 1002 is rigidly fixed to the pelvis at a known location. When the unique projection of the registration tool is correctly oriented within the patient's acetabular cup (and the IMU 1002 locked within the registration holster and the IMU 1002 mounted to the pelvis are activated), the orientation of the IMU 1002 locked to the registration holster relative to the planned implant cup orientation (which is set when the unique projection is received within the acetabular cup in only a single correct orientation) is known. An operator indicates to the software system that the IMUs are in the correct position and the software records the position of each IMU. The registration tool (with the IMU 1002 locked in the holster) is removed from the anatomy and thereafter the IMU 1002 is removed from the registration holster in preparation for mounting the IMU 1002 to surgical tools.

By way of example, the IMU 1002 previously mounted to the acetabular registration tool is removed from the tool and mounted to a surgical tool in a known location. In exemplary form, the IMU 1002 (previously mounted to the acetabular registration tool) is fixed rigidly to a cup reamer with a known orientation relative to the reaming direction so that the orientation of the cup reamer with respect to the pelvis is known and dynamically updated via both IMUs (IMU 1002 mounted to the cup reamer and IMU 1002 mounted to pelvis).

The software program provides a graphical user interface for a surgeon that displays virtual models of the patient's pelvis and a virtual model of the surgical tool in question, in this case a cup reamer (the virtual model of the patient's pelvis having already been completed pursuant to the virtual templating step, and the virtual model of the cup reamer or other surgical tool having been previously loaded into the system for the particular cup reamer and other surgical tools that may be utilized), and updates the orientation of the pelvis and surgical tool in real time via the graphical user interface providing position and orientation information to the surgeon. Rather than using a graphical user interface, the instant system may include surgical devices having indicator lights indicating to the surgeon whether the reamer is correctly oriented and, if not, what direction(s) the reamer needs to be repositioned to correctly orient the reamer consistent with the pre-operative planning. After resurfacing using the cup reamer is complete, the IMU 1002 is removed from the cup reamer and fixed rigidly to a cup inserter with a known orientation relative to the inserter direction. The cup inserter is then utilized to place the cup implant, with the IMUs continuing to provide acceleration feedback that the software utilizes to calculate position to provide real time feedback as to the position of the pelvis with respect to the cup inserter. To the extent that holes are drilled into the pelvis before or after cup positioning, the IMU 1002 previously mounted to the registration tool may be rigidly fixed to a surgical drill to ensure the correct orientation of the drill with respect to the pelvis. An analogous registration tool and set of IMUs may be used with the software system to assist with placement of the femoral stem component.

In one exemplary embodiment, the femoral registration tool includes an elongated shaft having a distal form shaped to fit partially over the patient's femoral neck in only a single orientation (including rotational position and angular position). A proximal end of the registration tool includes an IMU 1002 registration holster to receive the IMU 1002 so that when the IMU 1002 is locked within the holster, the IMU 1002 is rigidly fixed relative to the registration tool and distal form. Coincident with the registration tool, a second reference IMU 1002 is rigidly fixed to the femur at a known location. When the distal form of the registration tool is correctly oriented with respect to the femoral neck (and the IMU 1002 locked within the registration holster and the IMU 1002 mounted to the femur are activated), the orientation of the IMU 1002 locked to the registration holster relative to the femur orientation (which is set when the distal form is received over the femoral neck in only a single correct orientation) is known. An operator indicates to the software system that the IMUs are in the correct position and the software records the position of each IMU. The registration tool (with the IMU 1002 locked in the holster) is removed from the anatomy and thereafter the IMU 1002 is removed from the registration holster in preparation for mounting the IMU 1002 to surgical tools.

By way of example, the IMU 1002 previously mounted to the femoral registration tool is removed from the tool and mounted to another surgical tool in a known location. In exemplary form, the IMU 1002 (previously mounted to the femoral registration tool) is fixed rigidly to a surgical saw in a known location so that movement of the IMU 1002 correspondingly translates into known movement of the surgical saw. Given the other IMU 1002 being fixedly mounted to the femur in a known location, the IMUs work together to provide dynamically updated information to the software system about changes in the position (via acceleration data) of both the femur and surgical saw.

The software program provides a graphical user interface for a surgeon that displays virtual models of the patient's femur and a virtual model of the surgical tool in question, in this case a surgical saw (the virtual model of the patient's femur having already been completed pursuant to the virtual templating step, and the virtual model of the surgical saw or other surgical tool having been previously loaded into the system for the particular surgical saw and other surgical tools that may be utilized), and updates the orientation of the femur and surgical tool in real time via the graphical user interface providing position and orientation information to the surgeon. Rather than using a graphical user interface, the instant system may include surgical devices having indicator lights indicating to the surgeon whether the surgical saw is correctly oriented and, if not, what direction(s) the surgical saw needs to be repositioned to correctly orient the surgical saw to make the correct bone cuts consistent with the pre-operative planning. After making the requisite bone cuts, the IMU 1002 is removed from the surgical saw and fixed rigidly to a reamer (to correctly ream the intramedullary canal) and thereafter mounted to a femoral stem inserter with a known orientation relative to the inserter direction. The stem inserter is then utilized to place the femoral stem implant within the reamed intramedullary canal, with the IMUs continuing to provide acceleration feedback that the software utilizes to calculate position of the femur and stem inserter in real time and display this position data to the surgeon via the graphical user interface.

In exemplary form in the context of a total shoulder arthroplasty procedure, as depicted in FIGS. 187 and 188, registration tools are utilized to recreate the template surgical plan by engaging the patient anatomy in a predetermined orientation. When each utility IMU 1002 is mounted to its registration tool (one for the humerus, a second for the scapula), the registration tool is mounted to the relevant bone in a predetermined orientation (only one orientation that precisely matches the patient anatomy to "zero" the IMU). In order to carry this registration out, a second reference IMU is rigidly mounted to the bone in question (one IMU mounted to the humerus and a second IMU mounted to the scapula). In other words, one utility IMU is mounted to the humeral registration tool while a second reference IMU is rigidly mounted to the humerus. In the context of the scapula, one utility IMU is mounted to the scapular registration tool while a second reference IMU is rigidly mounted to the scapula. As part of the registration process, the software of the computer utilizes the outputs from both IMU (utility and reference) to calculate the "zero" location for the utility IMU when the registration tool is finally stationary and located in its unique location and orientation. Thereafter, the IMU 1002 may be removed from the relevant registration tool and mounted in a predetermined fashion to surgical tools (reamer, saw, implant placement guide, etc.) to ensure the proper orientation and placement of the surgical tools. The IMU 1002 may be mounted and removed from each surgical tool in succession until the surgical procedure is finished.

In this exemplary embodiment, as depicted in FIG. 188, the scapular registration tool includes an elongated shaft having a unique projection shaped to fit within the patient's glenoid cavity in only a single orientation (including rotational position and angular position). A proximal end of the registration tool includes an IMU 1002 registration holster to receive the IMU 1002 so that when the IMU 1002 is locked within the holster, the IMU 1002 is rigidly fixed relative to the registration tool and unique projection. Coincident with the registration tool, a second reference IMU 1002 is rigidly fixed to the scapula at a known location. When the unique projection of the registration tool is correctly oriented within the patient's glenoid cavity (and the IMU 1002 locked within the registration holster and the IMU 1002 mounted to the scapula are activated), the orientation of the IMU 1002 locked to the registration holster relative to the planned implant cup orientation (which is set when the unique projection of the registration tool is received within the glenoid cavity in only a single correct orientation) is known. An operator indicates to the software system that the IMUs are in the correct position and the software records the position of each IMU. The registration tool (with the IMU 1002 locked in the holster) is removed from the anatomy and thereafter the IMU 1002 is removed from the registration holster in preparation for mounting the utility IMU 1002 to other surgical tools.

By way of example, the IMU 1002 previously mounted to the scapular registration tool is removed from the tool and mounted to a surgical tool in a known location. In exemplary form, the IMU 1002 (previously mounted to the scapular registration tool) is fixed rigidly to a cup reamer with a known orientation relative to the reaming direction so that the orientation of the cup reamer with respect to the scapula is known and dynamically updated via both IMUs (IMU 1002 mounted to the cup reamer and IMU 1002 mounted to pelvis).

The software program provides a graphical user interface for a surgeon that displays virtual models of the patient's scapula and a virtual model of the surgical tool in question, in this case a cup reamer (the virtual model of the patient's scapula having already been completed pursuant to the virtual templating step, and the virtual model of the cup reamer or other surgical tool having been previously loaded into the system for the particular cup reamer and other surgical tools that may be utilized), and updates the orientation of the scapula and surgical tool in real time via the graphical user interface providing position and orientation information to the surgeon. Rather than using a graphical user interface, the instant system may include surgical devices having indicator lights indicating to the surgeon whether the reamer is correctly oriented and, if not, what direction(s) the reamer needs to be repositioned to correctly orient the reamer consistent with the pre-operative planning. After resurfacing using the cup reamer is complete, the utility IMU 1002 is removed from the cup reamer and fixed rigidly to a cup inserter with a known orientation relative to the inserter direction. The cup inserter is then utilized to place the cup implant, with the IMUs continuing to provide acceleration feedback that the software utilizes to calculate position to provide real time feedback as to the position of the scapula with respect to the cup inserter. To the extent that holes are drilled into the scapula before or after cup positioning, the utility IMU 1002 previously mounted to the registration tool may be rigidly fixed to a surgical drill to ensure the correct orientation of the drill with respect to the scapula. An analogous registration tool and set of IMUs may be used with the software system to assist with placement of the humeral stem component.

In one exemplary embodiment, the humeral registration tool includes an elongated shaft having a distal form shaped to fit partially over the patient's humeral neck in only a single orientation (including rotational position and angular position). A proximal end of the registration tool includes an IMU 1002 registration holster to receive the IMU 1002 so that when the IMU 1002 is locked within the holster, the IMU 1002 is rigidly fixed relative to the registration tool and distal form. Coincident with the registration tool, a second reference IMU 1002 is rigidly fixed to the humerus at a known location. When the registration tool is correctly oriented with respect to the humeral neck (and the IMU 1002 locked within the registration holster and the reference IMU 1002 mounted to the humerus are activated), the orientation of the IMU 1002 locked to the registration holster relative to the humerus orientation (which is set when the distal form is received over the humeral neck in only a single correct orientation) is known. An operator indicates to the software system that the IMUs are in the correct position, and stationary, and the software records the position of each IMU to establish the reference orientation of the pre-planned direction. The registration tool (with the IMU 1002 locked in the holster) is removed from the anatomy and thereafter the utility IMU 1002 is removed from the registration holster in preparation for mounting the IMU 1002 to other surgical tools.

By way of example, the IMU 1002 previously mounted to the humeral registration tool is removed from the tool and mounted to another surgical tool in a known location. In exemplary form, the IMU 1002 (previously mounted to the humeral registration tool) is fixed rigidly to a surgical saw in a known location so that movement of the IMU 1002 correspondingly translates into known movement of the surgical saw. Given the reference IMU 1002 being fixedly mounted to the humerus in a known location, the IMUs work together to provide dynamically updated information to the software system about changes in the position (via acceleration data) of both the humerus and surgical saw.

The software program provides a graphical user interface for a surgeon that displays virtual models of the patient's humerus and a virtual model of the surgical tool in question, in this case a surgical saw (the virtual model of the patient's humerus having already been completed pursuant to the virtual templating step, and the virtual model of the surgical saw or other surgical tool having been previously loaded into the system for the particular surgical saw and other surgical tools that may be utilized), and updates the orientation of the humerus and surgical tool in real time via the graphical user interface providing position and orientation information to the surgeon. Rather than using a graphical user interface, the instant system may include surgical devices having indicator lights indicating to the surgeon whether the surgical saw is correctly oriented and, if not, what direction(s) the surgical saw needs to be repositioned to correctly orient the surgical saw to make the correct bone cuts consistent with the pre-operative planning. After making the requisite bone cuts, the utility IMU 1002 is removed from the surgical saw and fixed rigidly to a reamer (to correctly ream the humeral canal) and thereafter mounted to a humeral stem inserter with a known orientation relative to the inserter direction. The stem inserter is then utilized to place the humeral stem implant within the reamed canal, with the IMUs continuing to provide acceleration feedback that the software utilizes to calculate position of the humerus and stem inserter in real time and display this position data to the surgeon via the graphical user interface.

In exemplary form in the context of a reverse shoulder implant procedure, as depicted in FIGS. 189 and 190, registration tools are utilized to recreate the template surgical plan by engaging the patient anatomy in a predetermined orientation. When each utility IMU 1002 is mounted to its registration tool (one for the humerus, a second for the scapula), the registration tool is mounted to the relevant bone in a predetermined orientation (only one orientation that precisely matches the patient anatomy to "zero" the IMU). In order to carry this registration out, a second reference IMU is rigidly mounted to the bone in question (one IMU mounted to the humerus and a second IMU mounted to the scapula). In other words, one utility IMU is mounted to the humeral registration tool while a second reference IMU is rigidly mounted to the humerus. In the context of the scapula, one utility IMU is mounted to the scapular registration tool while a second reference IMU is rigidly mounted to the scapula. As part of the registration process, the software of the computer utilizes the outputs from both IMU (utility and reference) to calculate the "zero" location for the utility IMU when the registration tool is finally stationary and located in its unique location and orientation. Thereafter, the IMU 1002 may be removed from the relevant registration tool and mounted in a predetermined fashion to surgical tools (reamer, saw, inserter, drill guide, drill, etc.) to ensure the proper orientation and placement of the surgical tools. The IMU 1002 may be mounted and removed from each surgical tool in succession until the surgical procedure is finished.

In this exemplary embodiment, as depicted in FIG. 190, the scapular registration tool includes an elongated shaft having a unique projection shaped to fit within the patient's glenoid cavity in only a single orientation (including rotational position and angular position). A proximal end of the registration tool includes an IMU 1002 registration holster to receive the IMU 1002 so that when the IMU 1002 is locked within the holster, the IMU 1002 is rigidly fixed relative to the registration tool and unique projection. Coincident with the registration tool, a second reference IMU 1002 is rigidly fixed to the scapula at a known location. When the unique projection of the registration tool is correctly oriented within the patient's glenoid cavity (and the IMU 1002 locked within the registration holster and the IMU 1002 mounted to the scapula are activated), the orientation of the IMU 1002 locked to the registration holster relative to the planned implant cup orientation (which is set when the unique projection is received within the glenoid cavity in only a single correct orientation) is known. An operator indicates to the software system that the IMUs are in the correct position and the software records the position of each IMU. The registration tool (with the IMU 1002 locked in the holster) is removed from the anatomy and thereafter the IMU 1002 is removed from the registration holster in preparation for mounting the utility IMU 1002 to other surgical tools.

By way of example, the IMU 1002 previously mounted to the scapular registration tool is removed from the tool and mounted to a surgical tool in a known location. In exemplary form, the IMU 1002 (previously mounted to the scapular registration tool) is fixed rigidly to a cup reamer with a known orientation relative to the reaming direction so that the orientation of the cup reamer with respect to the scapula is known and dynamically updated via both IMUs (IMU 1002 mounted to the cup reamer and IMU 1002 mounted to pelvis).

The software program provides a graphical user interface for a surgeon that displays virtual models of the patient's scapula and a virtual model of the surgical tool in question, in this case a cup reamer (the virtual model of the patient's scapula having already been completed pursuant to the virtual templating step, and the virtual model of the cup reamer or other surgical tool having been previously loaded into the system for the particular cup reamer and other surgical tools that may be utilized), and updates the orientation of the scapula and surgical tool in real time via the graphical user interface providing position and orientation information to the surgeon. Rather than using a graphical user interface, the instant system may include surgical devices having indicator lights indicating to the surgeon whether the reamer is correctly oriented and, if not, what direction(s) the reamer needs to be repositioned to correctly orient the reamer consistent with the pre-operative planning. After resurfacing using the cup reamer is complete, the utility IMU 1002 is removed from the cup reamer and fixed rigidly to a drill plate with a known orientation and location. The drill plate is then utilized to drill holes into the scapula, with the IMUs continuing to provide acceleration feedback that the software utilizes to calculate position to provide real time feedback as to the position of the scapula with respect to the drill plate, followed by positioning of the glenoid base plate and mounting of the glenoid component ball. Though not required, when drilling holes through the drill plate, the utility IMU 1002 may be rigidly fixed to a surgical drill to ensure the correct orientation of the drill with respect to the drill plate. An analogous registration tool and set of IMUs may be used with the software system to assist with placement of the humeral stem component.

In one exemplary embodiment, the humeral registration tool includes an elongated shaft having a distal form shaped to fit partially over the patient's humeral neck in only a single orientation (including rotational position and angular position). A proximal end of the registration tool includes an IMU 1002 registration holster to receive the IMU 1002 so that when the IMU 1002 is locked within the holster, the IMU 1002 is rigidly fixed relative to the registration tool and distal form. Coincident with the registration tool, a second reference IMU 1002 is rigidly fixed to the humerus at a known location. When the registration tool is correctly oriented with respect to the humeral neck (and the IMU 1002 locked within the registration holster and the reference IMU 1002 mounted to the humerus are activated), the orientation of the IMU 1002 locked to the registration holster relative to the humerus orientation (which is set when the distal form is received over the humeral neck in only a single correct orientation) is known. An operator indicates to the software system that the IMUs are in the correct position, and stationary, and the software records the position of each IMU to "zero" the utility IMU. The registration tool (with the IMU 1002 locked in the holster) is removed from the anatomy and thereafter the utility IMU 1002 is removed from the registration holster in preparation for mounting the IMU 1002 to other surgical tools.

By way of example, the IMU 1002 previously mounted to the humeral registration tool is removed from the tool and mounted to another surgical tool in a known location. In exemplary form, the IMU 1002 (previously mounted to the humeral registration tool) is fixed rigidly to a humeral resection block in a known location so that movement of the IMU 1002 correspondingly translates into known movement of the resection block. Given the reference IMU 1002 being fixedly mounted to the humerus in a known location, the IMUs work together to provide dynamically updated information to the software system about changes in the position (via acceleration data) of both the humerus and resection block.

The software program provides a graphical user interface for a surgeon that displays virtual models of the patient's humerus and a virtual model of the surgical tool in question, in this case a humeral resection block (the virtual model of the patient's humerus having already been completed pursuant to the virtual templating step, and the virtual model of the resection block or other surgical tool having been previously loaded into the system for the particular resection block and other surgical tools that may be utilized), and updates the orientation of the humerus and surgical tool in real time via the graphical user interface providing position and orientation information to the surgeon. Rather than using a graphical user interface, the instant system may include surgical devices having indicator lights indicating to the surgeon whether the resection block is correctly oriented and, if not, what direction(s) the resection block needs to be repositioned to correctly orient the resection block to make the correct bone cuts consistent with the pre-operative planning. In addition or alternatively, the utility IMU 1002 may be mounted to a drill plate used to drill one or more holes into each of which a reference pin is inserted. In such an instance, the resection block may not necessarily be accompanied by an IMU if the surgical block is located and oriented properly using one or more reference pins. In any event, after making the requisite bone cuts, the utility IMU 1002 is removed from the surgical tool and fixed rigidly to a reamer (to correctly ream the humeral canal) and thereafter mounted to a humeral stem inserter with a known orientation relative to the inserter. The stem inserter is then utilized to place the humeral stem implant within the reamed canal, with the IMUs continuing to provide acceleration feedback that the software utilizes to calculate position of the humerus and stem inserter in real time and display this position data to the surgeon via the graphical user interface.

In addition to component placement, potential impingement of the components can be tested using the IMUs mounted to the pelvis and femur to track component rotation to prevent post-operative complications and improve overall patient satisfaction.

Pursuant to the foregoing disclosure of using IMUs 1002, the following is an exemplary discussion of the mathematical model and algorithms utilize to generate three dimensional position data from the gyroscopes, accelerometers, and magnetometers of each IMU. In exemplary form, each IMU processor is programmed to utilize a sequential Monte Carlo method (SMC) with von Mises-Fisher density algorithm to calculate changes in position of the IMU 1002 based upon inputs from the IMU's gyroscopes, accelerometers, and magnetometers. The IMU data stream consists of 1 set of gyroscopic data on three X, Y, Z axes (G1), 3 sets of accelerometers data on X, Y, Z axes (A1-A3), and 3 sets of magnetometers data on three X, Y, Z axes (M1-M3). Orientation tracking of the IMU 1002 may be accomplished with one set of data from each sensors (i.e., G1, A1, M1).

Using G1, A1, and M1 as an example, and assuming all of the sensor raw data has been converted and processed:

At time and state=1:
1) The algorithm first generates a set of N particles around the neutral position with a pre-determined dispersion factor of the von Mises-Fisher density, as represented by Algorithm 1 identified below. Each particles represents the orientations around X, Y, Z axis in quaternion form. In other words, the particles comprise a set of independent and identically distributed random variables drawn from the same probability density space. In orientation tracking applications, the particles are the statistically constrained variations of the observed orientations. But it should be noted that the exact statistic (dispersion factor) does not need to be 'known' as the algorithm optimizes its properties as it gathers more samples. It is preferred to use a higher variability as the initial guess and allow the algorithm to refine it.

---

Algorithm 1 – Pseudo code to generate samples from von Mises-Fisher density
Input: µ (Mean vector),
 κ (Dispersion factor),
 N (Number of samples/particles)

1. $b = -\kappa + \sqrt{\kappa^2 + 1}$

2. $x_0 = \dfrac{1-b}{1+b}$

-continued

```
3.      c = κ(x₀) + 2log(1 − x₀x₀)
4.      for n = 1 → N
5.          while t ≤ u
6.              while s ≤ 1
7.                  uu~ Π(−1,1) , vv~ Π(0,1)
8.                  s = uu + vv
              end
```

9.  $$z = \frac{1}{2} + uu * vv * \frac{\sqrt{1-s}}{s}$$

10.     u~ Π(0,1)

11.  $$w = \frac{1 - z(1 + b)}{1 - z(1 - b)}$$

```
12.         t = κ(w) + 2 log(1 − x₀w) − c
          end
13.     θ~ Π(0,2π), u~ Π(−1,1)
14.     v = √(1−uu)
15.     rand3DVec = v * cos(θ) v * sin(θ) u]
16.     q_r = w
17.     q_{x,y,z} = √(1−w²) * rand3DVec
18.     q = [q_r q_x q_y q_z]
19.     q_vMF(n) = q ⊗ μ
        End
        Return q_vMF
```

After the first data set are received from G1, A1, and M1, an estimate of the current orientation of the IMU is calculated. This is accomplished by first knowing the tilt, which is measured from A1. The tilt information is needed to mathematically correct (de-rotate) the magnetometers readings, as depicted as steps 2 and 3 in Algorithm 2 identified below. Thereafter, the A1 and M1 data is used to estimate the initial orientation of the IMU via Algorithm 2, which is based on a Gauss Newton optimization method. The goal of Algorithm 2 is to iteratively determine the orientations ($q_{obv}$) so that the tilt and heading components of the estimation are the same as the reading from A1 and M1 with acceptable margins of error. It should be noted that while Algorithm 2 requires an input from a previous state, but since there is no previous state at time=1, any input will suffice. The reason that accelerometers and magnetometers cannot be used solely for tracking orientations is the limitation of how accelerometers measures tilts. By way of example, it is possible that in several specific orientation, because of the nature of trigonometry quadrants, the outputs of tilt may be the same despite the IMU being in different orientations. Thus, the gyroscopes are necessary to keep track of which quadrants the IMU is in.

Algorithm 2 – Pseudo code calculate observation quaternion based on Gauss Newton method
Input: $A_i$, i = x, y, z (Accelerometers data),
    $M_i$, i = x, y, z (Magnetometers data),
    N (Number of steps),
    $q_{obv}$ (Observation quaternion from previous state)

1.  for $n = 1 \to N$

2.  $h_{1,2,3,4} = q_{obv} \otimes \{[0 \quad M_x \quad M_y \quad M_z] \otimes conj(q_{obv})\}$ 3.  $b_{r,x,y,z} = [0 \quad \sqrt{h_2^2 + h_3^2} \quad 0 \quad h_4]$ 4.      Compute Jacobian matrix 5.      Compute rotational matrix R of $q_{obv}$
        Perform Gauss Newton step 6.  $$qn_{x,y,z,r} = q^T_{obv_{x,y,z,r}} - \left(\frac{1}{J^T J}\right) J^T (y_e - M(y_b))$$

where $y_e = \begin{bmatrix} 0 & 0 & 1 \\ b_x & b_y & b_z \end{bmatrix}$, $y_b = \begin{bmatrix} A_x & A_y & A_z \\ M_x & M_y & M_z \end{bmatrix}$, $M = \begin{bmatrix} R & \\ & R \end{bmatrix}$ 7.      Normalize $qn_{x,y,z,r}$
8.      $q_{obv} = qn_{r,x,y,z}$
      end
      Return $q_{obv}$ Next, the set of N particles in neutral position ($q_{vMF}$) are 'rotated' so that their mean is centered on the orientation estimation from A1 and M1, pursuant to the following equation:

$$q_{est,i}(t) = q_{vMF} \otimes q_{obs}(t), i = 1 \ldots N$$

Thereafter, all the particles are estimated forward in time based on G1, using the following equation:

$$q_{est,i}(t+1) = q_{est,i}^K(t) + 0.5(q_{est,i}^K(t) \otimes [0\omega_x, \omega_y, \omega_z])$$
$$\Delta t, i = 1 \ldots N$$

where ω are the angular rate measured at time t, and Δt is the sampling period.

In other words, if G1 is indicating an angular velocity around X axis; all the particles will be rotated around X axis based on the Newton's equations of motion.

The orientations expectation in the current state is achieved by averaging the particles estimate ($q_{est,i}(t+1)$) with Algorithm 3, identified below. Because a quaternion is a four dimensional vector, the averaging is done in a different manner. Algorithm 3 iteratively interpolates two quaternions from the particle sets until only one remains.

Algorithm 3 – Pseudo code for calculating the expectation from a set of quaternions Input: $q_{est,i}$, i = 1 → N (Estimation data),
    $w_i$, i = x, y, z (Data weights),
    N (Number of particles)
1.  for x = 1 → log(N)/log(2)
2.      for k = 1 → (size($q_{est,i}$))/2
3.          $w_n = w_{2k-1}/(w_{2k-1} + w_{2k})$
4.          $θ = acos(q_{est,2k-1} \cdot q_{est,2k})$ 5.  $$q_{V,k} = q_{est,2k-1}\left(\frac{\sin((1-w_n)\theta)}{\sin\theta}\right) + q_{est,2k}\left(\frac{\sin((w_n)\theta)}{\sin\theta}\right)$$

6.          $w_{V,k} = w_{2k-1}(w_n) + w_{2k}(1 - w_n)$
        end
7.      $q_{V,k} \to q_{est,i}$, i = 1 → k
8.      $w_{V,k} \to w_i$, i = 1 → k
    end
    Return $q_V$ At time and state=2, the second data set is received. Using the same method (Algorithm 2) as described above, the latest orientation estimation is calculated, which is then compared to all the particles estimates from previous state ($q_{est,i}(t-1)$). The errors/residuals between each particles and the current orientation estimate are used to weight the accuracy of the particles (i.e., the particles closer to the estimation will receive higher weight than particles further away.) using the following equations:

$$q_{res,i}(t) = q_{est,i}(t) \otimes conj(q_{obs}(t)), i = 1 \ldots N$$

$$\delta_{res,i} = 2\cos(q_{res,i}(t) \cdot q_0)$$

$$w_i = \frac{1/\delta_{res,i}}{\sum_i^N (1/\delta_{res,i})}$$

$\delta_{res,i}$ is the residual 3D angle difference between the particle and current observation.

$w_i$ is the weight of the particle.

Next, the quality of the particles is evaluated to eliminate and resample particles having very low weight. This can be done by using a deterministic, a residual or an auxiliary resampling scheme. As the algorithm favors particles closer to the observation, the particle set will begin to lose diversity over time. The particles will become highly concentrated and no longer carry any statistical meaning. At that time, a small portion of the particles will be replaced to increase diversity. This is done by first evaluating the current dispersion factor of the particles. If the dispersion factor indicates a high concentration, a set of new particles are generated in neutral position based on a predetermined dispersion factor to replace a portion of the current particles. The new particles are rotated from the neutral position to the current orientation expectation. This is summarized in the following equation:

$$q_{rs,i}(t) \sim vMF\left(f\left(\sqrt{\sum_i^N \delta_{res,i}^2}\right)\right) \otimes (q_{exp(t+1)})$$

$$\text{where } f\left(\sqrt{\sum_i^N \delta_{res,i}^2}\right) = ae^{-b\left(\sqrt{\sum_i^N \delta_{res,i}^2}\right)} + ce^{-d\left(\sqrt{\sum_i^N \delta_{res,i}^2}\right)},$$

$$i = 1 \ldots N$$

In addition, because this SMC method algorithm is temporal dependent, a delay in the received signal or temporarily losing connection to the IMU data stream can produce adverse effects on the estimation. If connection to the IMU data stream is not closely monitored, the particle set can diverge and destabilize the filter. This SMC method algorithm tracks the properties of the particle sets after each iteration to prevent excess divergence.

Finally, the particles are estimated forward in time based on new data from G1 and the current orientation state is calculated again. The foregoing process and algorithms are reused each time new data from G1, A1, and M1 are received.

Creation of Trauma Plates

Referring to FIGS. 112-125, an exemplary process and system are described for creating bone plates (i.e., trauma plates) across a predetermined population. Those skilled in the art are aware that bone is able to undergo regeneration to repair itself subsequent to a fracture. Depending on the severity and location of the fracture, prior art trauma plates were utilized that often required bending or other modifications in the operating room to conform to an irregular bone shape and achieve maximum contact between the bone fragments. However, excessive bending decreases the service life of the trauma plate, which may lead to bone plate failure and/or trauma plate-screw fixation loosening. The instant process and system provides a more accurate trauma plate shape to reduce or eliminate having to contour the plate interoperatively, thereby increasing plate service life and increasing the time until any bone plate-screw fixation loosening occurs.

The foregoing exemplary explanation for creating trauma plates is applicable to any and all bones for which trauma plates may be applied. For purposes of brevity, the exemplary explanation describes the system and process for creation of a trauma plate for use with the humerus bone. But it should be understood that the process and system is equally applicable to other bones of the body and fabrication of corresponding trauma plates and is in no way restricted to humerus trauma plates.

As part of the exemplary process and system for creating trauma plates, a statistical bone atlas is created and/or utilized for the bone(s) in question. By way of explanation, the bone in question comprises a humerus. Those skilled in the art are familiar with statistical atlases and how to construct a statistical atlas in the context of one or more bones. Consequently, a detailed discussion of constructing the statistical bone atlas has been omitted in furtherance of brevity. Nevertheless, what may be unique as to the statistical bone atlas of the exemplary system and process is categorizing humeri within the statistical bone atlas based upon gender, age, ethnicity, deformation, and/or partial construction. In this fashion, one or more trauma plates may be mass customized to one or more of the foregoing categories, where the one or more categories establish a particular bone population.

In exemplary form, the statistical bone atlas includes anatomical data that may be in various forms. By way of example, the statistical bone atlas may include two dimensional or three dimensional images, as well as information as to bone parameters from which measurements may be taken. Exemplary atlas input data may be in the form of X-ray images, CT scan images, MRI images, laser scanned images, ultrasound images, segmented bones, physical measurement data, and any other information from which bone models may be created. This input data is utilized by software accessing the statistical atlas data to construct three dimensional bone models (or access three dimensional bone models having already been created and saved as part of the statistical atlas), from which the software is operative to create a mean bone model or template bone model in three dimensions.

Using the template bone model, the software can automatically designate or allows manual designation of points upon the exterior surface of the template bone model. By way of explanation, in the context of the mean humerus model, a user of the software establishes a general boundary shape for the eventual trauma plate by generally outlining the shape of the trauma plate on the exterior surface of the humerus model. The general boundary shape of the trauma plate can also be accomplished by the user designating a series of points on the exterior surface of the humerus model that correspond to an outer boundary. Once the outer boundary or boundary points are established, the software may automatically designate or allows manual designation of points on the exterior surface of the humerus model within the established boundary. By way of example, the software provides a percent fill operation upon which the user can designate that percentage within the boundary of the trauma plate to be designated by a series of points, each corresponding to a distinct location on the exterior of the humerus model. In addition, the software provides a manual point designation feature upon which the user may designate one or more points upon the exterior surface of the humerus model within the boundary. It should be noted that in cases where manual point designation is utilized, the user need not establish a boundary as a prefatory matter to designating points upon the exterior of the humerus model. Rather, when the manual designation of points is completed, the boundary is established by the outermost points designated.

After the designation of points on the exterior surface of the template bone model, the localized points are propagated throughout the bone population in question. In particular, the localized points are automatically applied to each three dimensional bone model within the given population by the software via point correspondence of the statistical atlas. By way of example, the given bone population may be gender and ethnic specific to comprise humeri from Caucasian women. Using the propagated points for each bone model of the population, the software fills in the voids between points within the boundary using a three dimensional filling process to create a three dimensional rendering of the trauma plate for each bone. Thereafter, the software calculates the longitudinal midline of the three dimensional rendering of each trauma plate via a thinning process.

The midline of each three dimensional trauma plate rendering comprises a three dimensional midline having various curvatures along the length thereof. The software extracts the three dimensional midline and, using a least square fitting, determines the preferred number of radii of curvature that cooperatively best approximate the predominant curvature of the three dimensional midline. In the context of humeri, it has been determined that three radii of curvature accurately approximate the midline curvature. But this number may vary depending upon the bone population and the boundary of the trauma plate. Additional features can be included here as well, such as cross-sectional curvature at one or more locations along the length of the plate, location of muscles, nerves and other soft tissues to avoid, or any other feature relevant to defining plate size or shape. By way of example, the three radii of curvature for the midline represent the bend in the trauma plate in the proximal humerus, the transition between the humeral shaft and the humeral head, and the curvature of the humeral shaft. Each radii of curvature is recorded and a four dimensional feature vector was applied to the radii of curvature data to cluster the radii into groups that best fit the population. In exemplary form, the cluster data may indicate that multiple trauma plates are necessary to properly fit the population. Once the radii of curvature data is clustered, the trauma plate dimensions may be finalized.

Upon feature extraction related to the plate design, the software determines the best number of clusters that fits the population. It must be noted that there are some instances where there are two or more clusters that provide local minima as outlined in FIG. 120. In order to determine the optimum choice that provides acceptable error tolerance as well as reasonable number of plates in each family, the software generates three dimensional surface model for the plates in each clusters. Automatic evaluation is then performed by placing those plates on the population and computing the mismatch between the plate and the bone surface. Results of this analysis allow the software to pick the optimal number of plates to be used for this specific population. The final plate models are then parameterized and screw locations are placed on each plate in such a fashion as to avoid muscle and soft tissue locations as well as maximize fixation. The width of the screws are determined by the cross sectional analysis of the bone at each screw level across the population.

The instant process and method was validated for the humerus using a cadaver study. In particular, CT scans were taken of cadaver humerus bones from Caucasian white females. These CT scans were utilized by the software to create separate three dimensional models for each humeri. It should be noted that neither the CT scans nor the three dimensional models utilized during this validation study were part of the statistical atlas and relevant population utilized to create the humeral trauma plates. Consequently, the CT scans nor the three dimensional models comprised new data and models used to validate the humeral trauma plates designed. After the three dimensional validation models had been generated, each of the models was categorized to a particular cluster (the clusters resulting from designing the humeral trauma plate from the design population). Based upon which cluster the validation model was categorized to, the designed humeral trauma plate for that cluster was fitted to the appropriate validation three dimensional humeral bone model and measurements were calculated showing any spacing between the exterior surface of the validation three dimensional humeral bone model and the underside surface of the humeral trauma plate. FIG. 124 depicts a distance map of the trauma plate fitted upon to the validation three dimensional humeral bone model to show areas of maximum distance between the bone and trauma plate. It can be seen that a majority of the trauma plate is minimally spaced from the bone, while areas of less conformity only show spacing that ranges between 0.06 and 0.09 centimeters. Consequently, it was determined at the conclusion of this cadaver study that the trauma plates designed pursuant to the foregoing exemplary process using the foregoing system had extraordinary contour matching that, when applied intraoperatively, obviated the practice of surgeons having to bend or manually reshape bone plates.

Referencing FIGS. 131-138, in another exemplary instance of this process, trauma plates were created for the clavicle. Here, a statistical atlas was created from numerous clavicle bones, which sufficiently captured the variation within Caucasian population, for example. It should be noted that the statistical atlas may include clavicle bones from numerous ethnicities, from numerous ages of patients, and from various geographical regions. The exemplary disclosure happens to be in the context of a Caucasian population data set, though those skilled in the art will understand that the system and methods described are not limited to only a Caucasian population statistical atlas. FIG. 132 depicts a generic clavicle anatomy.

In exemplary form, the statistical atlas of clavicle bones also defines locations relating to muscle attachment sites for each clavicle, as depicted in FIG. 134. In addition, cross-sectional contours were extracted at 10% increments along the entire bone (see FIG. 138), as well as at muscle attachment sites and at the clavicle waist (see FIG. 137). Maximum and minimum dimensions of each cross-sectional contour were calculated. In addition, the entire three-dimensional surface was examined for asymmetry by analyzing the magnitude and directional differences between homologous points across all clavicle surfaces in the dataset. The results confirm the existing studies on clavicle asymmetry, namely that the left clavicle is longer than the right, but the right is thicker than the left. However, the patterns of asymmetry differ between males and females, as depicted in FIG. 139.

Additionally, as shown in FIG. 133, the clavicle midline does not follow a symmetrical "S" shape, as is the case for existing clavicle trauma plate designs. Thus, the present disclosure confirms that present day clavicle trauma plates fail to mimic the anatomical curvature of the clavicle. With respect to FIGS. 135 and 136, male clavicles are significantly asymmetric in all dimensions and at muscle and ligament attachment site contours (p<0.05), whereas female asymmetry is more variable. However, an area with no muscle attachments on the posterior midshaft was significantly asymmetric in both sexes.

From the extracted clavicle features across the statistical atlas, clustering (in accordance with previously described methods of clustering in the instant application, which are incorporated herein by reference) was performed to determine distinct groupings of similarities (i.e., a population) from which each distinct group was associated with a particular clavicle trauma plate to optimally fit the population. Additionally, screw fixation locations and length were determined for each trauma plate population to optimally avoid soft tissues (muscle attachments) and prevent additional fractures or plate loosening as a result of screws that are too long or too short. Using the process, several clavicle trauma plate families were designed corresponding to mass-customized clavicle trauma plates, as depicted in FIGS. 140-149.

Creation of Patient-Specific Trauma Plates

Referencing FIG. 126, a patient-specific trauma process is graphically depicted to include various component parts. Among these component parts are pre-operative surgical planning, generation of pre-contoured patient-specific trauma plate(s), intra-operative guidance to position and secure the patient-specific trauma plate(s), and optional post-operative evaluation of the patient-specific trauma plate(s). A more detailed discussion of these component parts and the exemplary process and structures involved for each component part is discussed in turn.

Referring to FIG. 126-130, an exemplary process flow is depicted for the pre-operative surgical planning component part. An initial input of anatomical data is obtained for the anatomy in question. For purposes of exemplary illustration only, a clavicle will be described as the fractured or deformed anatomy and a clavicle trauma plate will be described as the patient-specific trauma plate. Anatomical data is input to a software package configured to select or create patient-specific clavicle trauma plate, where the anatomical data comprises two dimensional (2D) images or three dimensional (3D) surface representations of the clavicle that may, for example, be in the form of a surface model or point cloud. In circumstances where 2D images are utilized, these 2D images are utilized to construct a 3D virtual surface representation of the fractured clavicle. Those skilled in the art are familiar with utilizing 2D images of anatomy to construct a 3D surface representation. Accordingly, a detailed explanation of this process has been omitted in furtherance of brevity. By way of example, input anatomical data may comprise one or more of X-rays, computed tomography (CT) scans, magnetic resonance images (MRIs), or any other imaging data from which a 3D surface representation of the tissue in question may be generated. The output from this anatomical data input is a 3D virtual surface representation of the fractured clavicle component parts.

The 3D virtual surface representation of the fractured clavicle component parts is then evaluated to identify the location and shape of the fracture or, in the case of a complete fracture and separation of bone component parts, the location and shape of the bone components with respect to one another.

In the circumstance of a complete fracture and separation of bone component parts, the process and associated software carries out a fracture reduction process that may allow for manual repositioning of the 3D virtual surface representation of the fractured clavicle to construct a patchwork clavicle. In such a circumstance, a user repositions and reorients the 3D virtual surface representations of the fractured clavicle to create a 3D patchwork clavicle model resembling a clavicle assembled from component parts comprising the 3D virtual surface representations. Alternatively, the process and associated software may provide for automatic repositioning and reconstruction of the 3D virtual surface representations of the fractured clavicle to construct a patchwork clavicle model, optionally using a 3D template model of a clavicle. More specifically, the software initially detects one or more fracture sites from the 3D virtual surface representation for each fractured bone component (i.e., the edge(s) of the bone fracture) comprising the 3D virtual surface representation and extracts the contours from each fracture site. The software then compares the extracted contours with the contours of a 3D template clavicle model in order to match, in a pair wise manner, these contours and locate matching bone components/pieces for each fracture site. Those matched components/pieces are then grouped together. Following grouping of the matched components/pieces, the software matches the grouped pieces to the 3D template clavicle model to identify the correct location of all the bone components/pieces in relation to the 3D template clavicle model. The matched components/pieces are thereafter reduced into a 3D patchwork clavicle model resembling the 3D template clavicle model, which as discussed hereafter is utilized by the software to construct a 3D reconstructed clavicle model.

After reduction, referring back to FIGS. 7 and 127, the 3D patchwork clavicle is used to identify the anatomical model (e.g., complete bone model) in the statistical atlas that most closely resembles the 3D patchwork clavicle model of the patient in question. This step is depicted in FIG. 3 as finding the closest bone in the atlas. In order to initially identify a bone model in the statistical atlas that most closely resembles the 3D patchwork clavicle model, the 3D patchwork clavicle model is compared to the bone models in the statistical atlas using one or more similarity metrics. The result of the initial similarity metric(s) is the selection of a bone model from the statistical atlas that is used as an "initial guess" for a subsequent registration step. The registration step registers the 3D patchwork clavicle model with the selected atlas bone model (i.e., the initial guess bone model) so that the output is a patient-specific reconstructed bone model that is aligned with the atlas bone model. Subsequent to the registration step, the shape parameters for aligned "initial guess" are optimized so that the shape matches the 3D patchwork clavicle model.

Shape parameters, in this case from the statistical atlas, are optimized so that regions of non-fractured bone are used to minimize the error between the reconstructed patient-specific bone model and 3D patchwork clavicle model. Changing shape parameter values allows for representation of different anatomical shapes. This process is repeated until convergence of the reconstructed shape is achieved (possibly measured as relative surface change between iterations or as a maximum number of allowed iterations).

A relaxation step is performed to morph the optimized bone to best match the 3D patchwork clavicle model. Consistent with the exemplary case, the missing anatomy from the 3D patchwork clavicle model that is output from the convergence step is applied to the morphed 3D clavicle model, thereby creating a patient-specific 3D model of the patient's reconstructed clavicle. More specifically, surface points on the 3D patchwork clavicle model are relaxed (i.e., morphed) directly onto the patient-specific 3D clavicle model to best match the reconstructed shape to the patient-specific shape. The output of this step is a fully reconstructed, patient-specific 3D clavicle model representing what should be the normal/complete anatomy of the patient's clavicle.

Following full anatomy reconstruction, the system software initiates a plan reduction order process. In this plan reduction order process, the software allows for manual or automatic determination of which clavicle bone component parts (i.e., fractured clavicle bone pieces) will be reassembled and mounted to one another, and in what order. In so doing, the software records in memory a 3D model of the progressive assembly of the clavicle from the bone component parts. Thus, presuming the clavicle is fractured into six component parts, the software would record a first 3D model showing assembly of the first and second bone fractured component parts being assembled, followed by a second 3D model showing assembly of the first, second, and third bone fractured component parts being assembled, and so on until arriving at a final 3D model reflecting the assembled position and orientation of all six fractured bone component parts, thereby resembling the 3D patchwork clavicle model.

Using the reduction order determination, the software allows manual or automatic selection from one of a plurality of clavicle trauma plate templates using the 3D patchwork clavicle. More specifically, the clavicle trauma plate templates comprise a series of 3D virtual surface representations of clavicle trauma plates having been generically shaped to match the size and shape parameters associated with a given population taken from a statistical bone atlas. In other words, the statistical bone atlas includes surface models of a plurality of normal, full anatomy clavicles having been categorized based upon one or more of size, ethnicity, age, sex, and any other marker indicative of bone shape. An exemplary discussion of the procedure to arrive at the template bone plates has been previously described with respect to FIGS. 112-125 and is incorporated herein by reference. In the automatic selection mode, the software compares the dimensions and contours of the plurality of clavicle trauma plate templates to the 3D patchwork clavicle to discern which of the templates most closely conforms to the 3D patchwork clavicle (i.e., contour and shape similarity with respect to the bony anatomy).

Using the clavicle trauma plate template that most closely conforms to the 3D patchwork clavicle, the software allows for manual or automatic identification of fixation site locations through the trauma plate as well as determining direction and length of fixation devices to be utilized (e.g. surgical screws). In automatic fixation site identification mode, the software accounts for muscle and attachment locations, as well as nerve locations, to avoid placing any fixation hole in the path of a nerve or muscle attachment site. In addition, the software allows for manual or automatic selection of fixation fasteners to be used with the trauma plate. In this manner, the software may automatically select fasteners taking into account the size and shape of the clavicle bone fracture components, the location and orientation of the fastener holes extending through the trauma plate, and the geometry of the fasteners (e.g., screws) so as to increase fixation strength and attempting to avoid unnecessary compromises in clavicle bone integrity.

After selection of the clavicle trauma plate template, the fixation hole location(s), and the fixation fasteners, the software carries out a virtual bone plate placement. This includes positioning the clavicle trauma plate template onto the 3D patchwork clavicle and manually or automatically deforming the clavicle trauma plate template to match the exterior surface contours of the 3D patchwork clavicle, thereby creating a virtual 3D patient-specific clavicle trauma plate with size, length, and contour dimensions. The software logs the patient-specific clavicle trauma plate dimensions and converts these virtual dimensions into machine code that allows for generation of a tangible patient-specific clavicle trauma plate that can be rapid manufactured.

Using the patient-specific clavicle trauma plate dimensions, the software also receives anatomical data as to the position and location of the patient's soft tissue, vessels, and nerves within the area of the fractured clavicle to construct an incision plan. The incision plan is pre-operative and suggests a surgical approach to make one or more incisions that increases access to the fractured clavicle bone component parts, while at the same time decreases the invasiveness of the surgical procedure, thereby potentially decreasing recovery time and ancillary post-operative trauma. FIG. 134 shows a 3D patchwork clavicle having surface coloring indicative of locations where muscle attaches to the patient's clavicle. Consequently, the patterned circles extending longitudinally along the 3D patchwork clavicle correspond to the location of fixation fasteners, which are oriented to locations predominantly free of muscle attachment.

After the incision plan is constructed, a surgeon reviews the incision plan to make any modifications prior to approval of the plan. Post approval of the incision plan, the plan may be exported to an intraoperative surgical guidance system. Likewise, the incision plan may be utilized to construct a preoperative tangible clavicle model for estimating the shape of the reconstructed clavicle bone components mounted to one another to simulate the patient's normal clavicle. This tangible clavicle model may then be used to test fit the clavicle trauma plate and make any contour modifications via bending that may be desired by the surgeon preoperatively. Alternatively, tangible clavicle model may comprise the clavicle bone components in loose form so that mounting one or more of the trauma plates thereto is necessary to hold the clavicle bone components together, thereby allowing the surgeon to test fit the trauma plate(s) ex-vivo and also make any modifications to the trauma plate(s) ex-vivo.

Referencing FIGS. 128 and 129, the exemplary patient-specific clavicle trauma plate(s) may be positioned intraoperatively using fluoroscopy. While the exemplary technique will be described with respect to attaching a patient-specific clavicle trauma plate to a patient's clavicle or clavicle bone component parts, it should be understood that the exemplary process is equally applicable to attaching non-patient-specific trauma plates to a clavicle and, more generally, to attaching any trauma plate to any bone or fractured bone component part.

FIG. 128 depicts a process flow depicts various steps involved as part of a trauma plate placement system for positioning a patient-specific trauma plate intraoperatively using fluoroscopy, which includes utilizing pre-planning data along with placement of fudicial markers to establish a patient location registration. More specifically, the pre-planning data is loaded into a software package of the trauma plate placement system and may include patient geometries bone and tissue geometries, location of each trauma plate, the type and location of fixation devices utilized to secure the trauma plate to the bone or bone component part in question, and any other relevant information bearing on operative location and techniques. Fudicial markers for use with fluoroscopy include, without limitation, optical, electromagnetic, IMUs (though optical markers are referenced in the process flow of FIG. 128, which are positioned at known locations relative to anatomical landmarks on the patient. Using the fudicial markers and known anatomical locations and dimensions of the patient, the trauma plate placement system registers the patient with respect to a pre-operative coordinate system. Thereafter, the fudicial markers are tracked in space so that feedback from the trauma plate placement system is provided to the surgeon consistent with the pre-operative plan indicating the location of one or more incisions with respect to a fixed patient frame of reference. Exemplary feedback systems that may be utilized as part of the trauma plate placement system include, without limitation, visual displays that are projected on to the surface of the patient outlining the location and length of each incision.

In the context of a fractured clavicle, where the clavicle is comprised of separate bone component parts, the trauma plate placement system is also capable of visually displaying identification indicia on multiple clavicle bone components to indicate the order of assembly of the bone components. In exemplary form, the visual display includes colored numerals that are displayed on each bone component that is visible. The colored numerals change colors depending upon the orientation and location of the bone components with respect to one another. In exemplary form, the first bone component is identified by a displayed numeral "1" that is projected onto the exterior surface. Depending upon the orientation and position of the bone, the displayed numeral "1" may be colored red, yellow, or green. A red numeral indicates the orientation and location are incorrect. Upon movement, the indicia changes to yellow if the surgeon is moving the bone component in the correct direction to achieve placement consistent with the pre-operative plan. Upon continued movement, the numeral turns green when the proper location is achieved. This repositioning process is repeated for each of the clavicle bone components.

In order to provide this visual feedback to the surgeon regarding the location and orientation of the fractured bone components, the trauma plate placement system uses fluoroscopy to track the bone components in 3D space to discern whether the bone location and orientation is consistent with the pre-operative plan. Prior to bone component tracking, the bone components are registered using pre-operative data in order to provide real-time updated information to the surgeon, via the projected display, as to the correct location and orientation of the bone components. As each bone fragment is tracked, and eventually mounted to the clavicle trauma plate, the system confirms the progress of the trauma plate placement using fluoroscopic images to confirm the plate orientation and location as well as that of the fixation devices (e.g., screws) and bone components. Finally, when the bone components are coupled to one another via one or more clavicle trauma plates, the system displays a final indicia indicating to the surgeon that the procedure has met the objectives of the pre-operative planning and can be concluded.

FIG. 130 depicts a process flow diagram for various steps involved as part of a trauma plate placement system for positioning a patient-specific trauma plate intraoperatively using ultrasound in lieu of fluoroscopy. The foregoing explanation with respect to FIG. 128 parallels that of FIG. 130, which is incorporated herein by reference, with the exception of the system tracking bone components, trauma plate(s), and fixation devices using ultrasound in lieu of fluoroscopy. Consequently, a redundant explanation has been omitted in furtherance of brevity.

Creation of Trauma Plate Placement Guides

Referring to FIG. 150, an exemplary process and system are described for creating trauma plate placement guides that are patient-specific. Those skilled in the art are aware that bone can fracture at one or more locations resulting in bone fragments that are separated from one another. As part of reconstructive surgery to repair the bone, these fragments are held in a fixed orientation using one or more trauma plates. Reconstructive surgeons attempted to piece the bone back together using innate knowledge rather than patient-specific anatomical fact. Consequently, to the extent patient bone anatomy varied from normal, the bone fragments were grossly distorted, or the number of bone fragments was large, surgeons would resort to using prior art trauma plates and having the bone fragments match the shape of the plate rather than vice versa. The instant process and system improves upon prior art trauma plate application by creation of trauma plate placement guides and customized trauma plates that match the trauma plates to the bone to replicate the original bone shape and orientation.

The exemplary system flow begins with receiving input data representative of a fractured anatomy. For purposes of explanation only, the fractured anatomy comprises a human skull. It should be noted that the foregoing process and system is equally applicable to other anatomies/bones including, without limitation, bones in the arms, legs, and torso. In exemplary form, anatomy data input may be in the form of X-rays, CT scans, MRIs, or any other imaging data from which bone size and shape may be represented.

The input anatomy data is utilized to construct a three dimensional virtual model of the fractured anatomy. By way of example, the input anatomy data comprises a computed tomography scan of a fractured skull that is processed by software to segment this scan and generate a three dimensional model. Those skilled in the art are familiar with how to utilize computed tomography scans to construct three dimensional virtual models. Consequently, a detailed description of this aspect of the process has been omitted in furtherance of brevity.

Subsequent to generation of the three dimensional virtual model of the fractured skull, the software compares the three dimensional virtual model of the skull with data from a statistical atlas to determine areas in the three dimensional virtual model where the skull is fractured. In particular, the software utilizes features extracted from the surface model of the input anatomy (ex: surface roughness, curvature, shape index, curvedness, neighbor connectivity) to extract areas of fracture sites. The outline contours of those fracture sites are then extracted and matched together to find the matching fracture sites. Fractured fragments are also matched with the atlas to indicate the best location to place the matched fracture sites in order to reconstruct the normal anatomy.

After the software generates a reconstructed three dimensional virtual model of the fractured skull, buttresses may be manually and/or automatically positioned on the exterior of the reconstructed three dimensional virtual skull model. The automatic placement of the buttresses is the result of programmed logic to maximize stability of the bone fragments while minimizing the number of buttresses. As used herein, the term buttress and plurals thereof refer to any support used to steady bone fragments with respect to one another. In certain instances, practical experience by a surgeon or other learned user may supplement or supplant to the logic when making use of the manual buttress placement feature. In any event, a series of buttresses are programmed into the software that allows the software or a user of the software to select differing buttresses for differing applications. At the same time, the length of the buttresses may be manually or automatically manipulated based upon the dimensions of the fracture and bone fragments.

Subsequent to buttress assignment and placement on the reconstructed three dimensional virtual skull model, the software dimensions and contour of each buttress is recorded by the software. This recordation includes information necessary for fabrication of each buttress or at the very least information helpful to allow a surgeon or other learned individual to take existing buttresses and conform each to a placement guide. In the context of molding an existing buttress, the software extracts the contours of the reconstructed three dimensional virtual skull model to generate computer-aided design (CAD) instructions for creation of one or more tangible models indicative of the reconstructed three dimensional skull model. These CAD instructions are sent to a rapid prototyping machine, which creates the one or more tangible models indicative of the reconstructed three dimensional skull model. By recreating the proper anatomical surface as a tangible model, each buttress may be applied to the tangible model at the target location and manually conformed prior to implantation and fastening to the patient's skull.

Based upon the location and length of any buttress, the software also extracts the contours of the reconstructed three dimensional virtual skull model to generate contour data for one or more patient-specific buttress placement guides. In particular, a placement guide may be generated for each buttress. In this manner, the placement guide includes a surface contour that matches the contour of the patient's skull in a single orientation. Given that the location of the buttress is known on the virtual model of the reconstructed skull, as is the contour of the adjacent exterior skull surface, the software combines the two to create a virtual patient-specific placement guide. This virtual guide is output in the form of CAD instructions to a rapid prototyping machine for fabrication.

In this exemplary embodiment, the fabricated patient-specific placement guide comprises an elongated handle configured to be gripped by a surgeon. Extending from the end of the elongated handle is a block C-shaped contour plate. The underside of the contour plate is concave to match the convex topography of the skull at the location where the buttress should be positioned. Though not required, the ends (or another portion) of the contour plate may be fastened to the buttress, or the contour plate may simple provide a working window within which the buttress is aligned and ultimately fastened to the skull. Post attachment of the buttress to the skull, the contour plate may be removed.

Customized Cutting & Placement Guides, Plates

Referring to FIG. 151, reconstruction of a deformed, fractured, or partial anatomy is one of the complex problems facing healthcare providers. Abnormal anatomy may be the result of birth conditions, tumors, diseases, or personal injuries. As part of providing treatment for various ailments, healthcare providers may find it advantageous to reconstruct an anatomy or construct an anatomy to facilitate treatment for various conditions that may include, without limitation, broken/shattered bones, bone degeneration, orthopedic implant revision, orthopedic initial implantation, and disease.

The present disclosure provides a system and methods for bone and tissue reconstruction using bone grafts. In order to carry out this reconstruction, the system and associated methods utilizes current anatomy images of a patient to construct two virtual 3D models: (a) a first 3D model representative of the current abnormal anatomy; and, (2) a second 3D model representative of the reconstructed anatomy of the patient. Reference is had to the prior "Full Anatomy Reconstruction" section for a detailed explanation of using patient images (X-rays, CT scans, MRI images, etc.) to arrive at virtual models of the patient's abnormal anatomy and reconstructed anatomy. The present system and methods builds upon the system described in the "Full Anatomy Reconstruction" section to utilize the two 3D virtual models in combination with constructing a 3D virtual model of one or more bones from which a bone graft may be taken (i.e., a donor bone). As will be described in more detail hereafter, the 3D virtual models of the patient's reconstructed and abnormal anatomy are analyzed to generate a 3D virtual model of the bone graft needed for reconstruction. This 3D virtual graft model is compared to the 3D virtual model of the donor bone to access one or more sites on the donor bone from which a bone graft can be excised. After determining the excise location(s), cutting guides and graft placement guides are designed and fabricated for gathering the grafted bone and mounting the grafted bone to the site of reconstruction.

By way of exemplary explanation, the instant system and methods will be described in the context of a facial reconstruction, where the donor bone comprises the fibula. Those skilled in the art should realize that the instant system and methods are applicable to any reconstructive surgical procedure utilizing one or more bone grafts. Moreover, while discussing facial reconstruction and the fibula as the bone donor, those skilled in the art should understand that the exemplary system and methods may be used with donor bones other than the fibula.

As a prefatory step to discussing the exemplary system and methods for use with reconstructive surgical planning and surgical procedures using bone grafts, it is presumed that the patient's abnormal anatomy has been imaged and virtual 3D models of the patient's abnormal and reconstructed anatomy have been generated pursuant to those processes described in the prior "Full Anatomy Reconstruction" section. Consequently, a detailed discussion of utilizing patient images to generate both virtual 3D models of the patient's abnormal and reconstructed anatomy has been omitted in furtherance of brevity.

After virtual 3D models of the patient's abnormal and reconstructed anatomy have been created, the software compares the anatomies and highlights areas of difference. In particular, the areas in common between the virtual 3D models denotes bone that will be retained, whereas areas that differ is indicative of one or more sites for reconstruction. The software extracts from the virtual 3D model of the patient's reconstructed anatomy those areas not in common and isolates these areas as separate 3D virtual models of the intended bone graft. The surgeon or other pre-operative planner may view the virtual 3D bone graft models and use his judgment as to the bone or bones from which the bone grafts might be best excised.

Regardless as to the logic utilized to initially choose a possible bone as a graft candidate, the bone(s) in question is imaged using conventional modalities (X-ray, CT, MRI, etc.). Using the processes described in the prior "Full Anatomy Reconstruction" section, each imaged bone is segmented and a virtual 3D model of the imaged bone is created. This 3D donor bone model is compared to the virtual 3D bone graft model to isolate areas in common. In particular, the software compares the surface contours of the 3D donor bone model with the surface contours of the virtual 3D bone graft model to identify areas in common or having similar curvature. Presuming no areas are in common or similar, the process can be restarted by analyzing another possible donor bone. In contrast, if one or more areas in common or having similar curvature exist in the donor bone, these areas are highlighted on the 3D donor bone model. In particular, the highlighted areas mimic the shape of the virtual 3D bone graft model. If the area in common is judged to be appropriate for excising the bone graft, the software virtually excises the bone graft as a virtual 3D model and applies the bone graft (which has contours specific/unique as to the donor bone) to the virtual 3D model of the patient's abnormal anatomy to verify potential fit and any areas of the patient's abnormal anatomy that may need to be excised as part of the reconstruction. In circumstances where application of the virtual 3D model of the excised bone to the virtual 3D model of the patient's abnormal anatomy results less than satisfactory reconstruction, the process may be restarted at the bone selection point or restarted to excise a different area of bone. But presuming application of the virtual 3D model of the excised bone to the virtual 3D model of the patient's abnormal anatomy results in an appropriate fit, the system moves forward with designing jigs to facilitate excising the bone graft and mounting the bone graft to the patient's residual bone.

In this exemplary embodiment, the system generates and outputs machine code necessary for a rapid prototyping machine, CNC machine, or similar device to fabricate a bone graft cutting guide and a bone graft placement guide. In order to generate the outputs necessary to fabricate the bone graft cutting guide and a bone graft placement guide, the system utilizes the virtual 3D model of the excised bone to the virtual 3D model of the patient's abnormal anatomy.

In particular, the virtual 3D model of the excised bone defines the boundary of a virtual 3D cutting guide. Moreover, in this exemplary context, a portion of the fibula is intended to be excised to provide the bone graft. In order to ensure the appropriate portion of the fibula is excised, the virtual 3D cutting guide includes a window within which a cutting device (saw, cutting drill, etc.) traverses to create the appropriately outlined bone graft. Not only does the virtual 3D cutting guide need to be shaped to create the appropriate bone graft outline, but it also needs to be shaped to ensure placement of the cutting guide on the patient's donor bone is particularized. More specifically, the placement of the cutting guide on the donor bones needs to concurrently ensure the excised bone includes the correct outline shape and also exhibits the correct contours. In this fashion, the underside of the virtual 3D cutting guide is designed to be the "negative" of the surface of the donor bone where the cutting guide will be mounted. Exemplary mounting techniques for securing the cutting guide to the donor bone may include, without limitation, screws, dowels, and pins. In order to accommodate one or more of these mounting techniques or others, the virtual 3D cutting guide is also designed to include one or more through orifices besides the window within which the surgical cutter traverses. After the design of the virtual 3D cutting guide is completed, the system generates and outputs machine code necessary for a rapid prototyping machine, CNC machine, or similar device to fabricate the bone graft cutting guide, which is followed by fabrication of the actual cutting guide.

In addition to the cutting guide, the software also designs one or more bone graft placement guides. The bone graft placement guides are patient-specific and conform to the anatomy of the patient (both donor bone and residual bone to which the donor bone is mounted) to ensure correct placement of the bone graft with respect to the residual bone.

In exemplary form, the bone graft placement guide is configured for a mandible bone reconstructive procedure. In order to design the bone graft placement guides, the software utilizes the virtual 3D model of the excised bone applied to the virtual 3D model of the patient's abnormal anatomy to construct a hybrid model. Using this hybrid model, joints are identified where the bone graft will interface with (and hopefully join via bone growth) the adjacent residual bone. At these joints, depending upon various factors, such as surgeon preference, the system identifies bone graft plate locations and, for each plate, one or more guides to facilitate correct placement and securing of the plates to the bone graft and residual bone.

Customized Trauma Plate Templating and Placement Guides

Referring to FIG. 152, an exemplary system and method for trauma plate templating are depicted graphically in the form of a flow diagram. This system and method, which include a computer and associated software, makes calculations to determine the best fit among a group of template trauma plates in order to reduce future shape changes that may be necessary to fit the trauma plate to match a patient's bone geometry. In exemplary form, the system includes constructing a 3D model of the patient's fractured bone as a unified bone and then forming a template trauma plate to the 3D model to finalize the shape of the trauma plate prior to implantation. In this fashion, the final trauma plate shape is patient-specific and allows for a closer fit to the patient's anatomy, eliminates ambiguity in placement location of the trauma plate, and shortens surgery time. The system can be easily deployed in everyday clinical environments or surgeon's offices.

Referring back to FIG. 152, the initial input to the system is any number of medical image depicting a fractured bone. By way of example, these medical images may be one or more of X-ray, ultrasound, CT, and MRI. The images of the fractured bone are analyzed by human operator to select which bone, among a plurality of possible programmed bones, is fractured. Using the bone selection, the software utilizes the medical image data to form 3D models of the fractured bone components (as previously described with respect to FIG. 127 and its associated description, which is incorporated herein by reference). These 3D bone models are then reduced (i.e., reassembled to form a patchwork bone orienting and locating the 3D bone models as if connected to one another when part of a unified, unfractured bone) to form a 3D patchwork bone model using bone data from a statistical atlas. Likewise, bone data from the statistical atlas is also used in combination the 3D patchwork bone model to morph the 3D patchwork bone model onto a complete, unfractured bone model to generate a complete, 3D bone model (unfractured) of the patient's bone in question, referred to as the reconstructed bone model.

This reconstructed bone model is analyzed by the software to extract longitudinal curves (e.g., midline curves) along the dominant dimension, while the software also extracts cross-sectional curves taken perpendicular to the dominant dimension, in order to extract trauma plate design parameters. From these design parameters, the software calculates which, among a plurality of template trauma plates, most closely resembles the design parameters. These design parameters may include length of the trauma plate, longitudinal curvature of the trauma plate, lateral curvature perpendicular to the longitudinal curvature, lateral length, and fixation locations for bone fasteners that minimize interference with muscle attachment sites and nerve locations, while at the same time ensuring proper mounting and retention of the trauma plate to the fractured bone.

The reconstructed bone model is also utilized to generate a tangible, 3D bone model. In exemplary form, the software is programmed to output the virtual reconstructed bone model as machine code, thereby allowing rapid prototyping of the 3D bone model, either in an additive or subtractive process. For purposes of the instant disclosure, an additive process includes 3D printing where the model is created from a starting blank canvas by the addition of material to form discrete layers or slices of the bone model that, once stacked upon one another by printing successive layers, form the final bone model. In contrast, a subtractive process includes starting with a solid block of material and, using machine code (e.g., CNC code) to machine away material to arrive at a solid bone model. Those skilled in the art will understand that any number of processes may be utilized to fabricate a tangible bone model. Depending upon the process chosen, the software is programmed to convert the 3D virtual model into machine code to facilitate rapid prototyping and construction of the 3D bone model.

Post 3D bone model construction, the template trauma plate may be constructed, machined, or selected based upon the selection of the software as to the trauma plate most closely shaped to conform to the patient's fractured bone. Once at hand, the template trauma plate is fitted to the 3D bone model and further refined by manual bending to conform the trauma plate to the 3D bone model. After sufficient conformity between the trauma plate and bone model, the trauma plate may be considered patient-specific and, post sterilization, is ready for implantation into the patient.

Patient-Specific Hip Cage Templating and Placement Guides

Referring to FIG. 153, an exemplary system and method for hip cage templating and placement guides are depicted graphically in the form of a flow diagram. This system and method, which include a computer and associated software, makes calculations to determine the best fit among a group of template hip cages in order to reduce future shape changes that may be necessary to fit the hip cage to match a patient's bone geometry. In exemplary form, the system includes constructing a 3D model of the patient's hip (as a unified bone if fractured or degenerated) and then forming a template hip cage to the 3D model to finalize the shape of the hip cage prior to implantation. In this fashion, the final hip cage shape and attachment sites are patient-specific and allows for a closer fit to the patient's anatomy, eliminates ambiguity in placement location of the hip cage, and shortens surgery time. The system can be easily deployed in everyday clinical environments or surgeon's offices.

Referring back to FIG. 153, the initial input to the system is any number of medical images depicting the patient's hip (total or partial pelvis). By way of example, these medical images may be one or more of X-ray, ultrasound, CT, and MRI. The images of the hip bone are utilized by the software to construct a 3D virtual bone model of the patient's hip (as previously described with respect to FIGS. 1 and 7 and its associated description, which is incorporated herein by reference). This 3D bone model is then automatically landmarked by the software.

The software utilizes inputs from the statistical atlas (e.g., regions likely to contain a specific landmark) and local geometrical analyses to calculate anatomical landmarks for 3D bone model in comparison to those hip bone models within the statistical atlas. This calculation is specific to each landmark. The approximate shape of the region is known, for example, and the location of the landmark being searched for is known relative to the local shape characteristics. For example, locating the superior margin of the anterior labral sulcus point of the acetabulum is accomplished by refining the search based on the approximate location of superior margin of the anterior labral sulcus points within the statistical atlas. This process is repeated for each landmark in question.

After the anatomical landmarks are automatically calculated for the 3D bone model, the bone model is analyzed by the software to calculate which, among a plurality of template hip cages, most closely fits the anatomical landmarks. In addition to calculating which, among a plurality of hip cages, most closely fits the anatomical landmarks of the patient's hip, the software also calculates the location where the cage will be mounted to the patient's anatomy. Referring back to FIGS. 20 and 21, the associated discussion of which is incorporated herein by reference, the software is operative to determine the location where the cage will be mounted to the patient's anatomy, as well as generate virtual 3D guides that may be utilized to output machine code sufficient to construct a tangible 3D placement guide for the revision cage.

The bone model of the patient's hip is also utilized to generate a tangible, 3D bone model. In exemplary form, the software is programmed to output the virtual 3D bone model as machine code, thereby allowing rapid prototyping of the tangible 3D bone model, either in an additive or subtractive process. For purposes of the instant disclosure, an additive process includes 3D printing where the model is created from a starting blank canvas by the addition of material to form discrete layers or slices of the bone model that, once stacked upon one another by printing successive layers, form the final bone model. In contrast, a subtractive process includes starting with a solid block of material and, using machine code (e.g., CNC code) to machine away material to arrive at a solid bone model. Those skilled in the art will understand that any number of processes may be utilized to fabricate a tangible bone model. Depending upon the process chosen, the software is programmed to convert the 3D virtual model into machine code to facilitate rapid prototyping and construction of the 3D bone model.

Post 3D bone model construction, a template cage may be constructed, machined, or selected based upon the selection of the software as to the cage most closely shaped to conform to the patient's hip. Once at hand, the template cage is fitted to the 3D bone model and further refined by manual bending to conform the cage to the 3D bone model. After sufficient conformity between the cage and bone model, the cage may be considered patient-specific and, post sterilization, is ready for implantation into the patient.

IMU Kinematic Tracking

Referring to FIG. 154, an exemplary system and process overview is depicted for kinematic tracking of bones and soft tissues using IMUs that makes use of a computer and associated software. For example, this kinematic tracking may provide useful information as to patient kinematics for use in preoperative surgical planning. By way of exemplary explanation, the instant system and methods will be described in the context of tracking bone motion and obtaining resulting soft tissue motion from 3D virtual models integrating bones and soft tissue. Those skilled in the art should realize that the instant system and methods are applicable to any bone, soft tissue, or kinematic tracking endeavor. Moreover, while discussing bone and soft tissue kinematic tracking in the context of the knee joint or spine, those skilled in the art should understand that the exemplary system and methods are applicable to joints besides the knee and bones other than vertebrae.

As a prefatory step to discussing the exemplary system and methods for use with bone and soft tissue kinematic tracking, it is presumed that the patient's anatomy (to be tracked) has been imaged (including, but not limited to, X-ray, CT, Mill, and ultrasound) and virtual 3D models of the patient's anatomy have been generated by the software pursuant to those processes described in the prior "Full Anatomy Reconstruction" section, which is incorporated herein by reference. Consequently, a detailed discussion of utilizing patient images to generate virtual 3D models of the patient's anatomy has been omitted in furtherance of brevity.

If soft tissue (e.g., ligaments, tendons, etc) images are available based upon the imaging modality, these images are also included and segmented by the software when the bone(s) is/are segmented to form a virtual 3D model of the patient's anatomy. If soft tissue images are unavailable from the imaging modality, the 3D virtual model of the bone moves on to a patient-specific soft tissue addition process. In particular, a statistical atlas may be utilized for estimating soft tissue locations relative to each bone shape of the 3D bone model.

The 3D bone model (whether or not soft tissue is part of the model) is subjected to an automatic landmarking process carried out by the software. The automatic landmarking process utilizes inputs from the statistical atlas (e.g., regions likely to contain a specific landmark) and local geometrical analyses to calculate anatomical landmarks for each instance of anatomy within the statistical atlas as discussed previously herein. In those instances where soft tissue is absent from the 3D bone model, the anatomical landmarks calculated by the software for the 3D bone model are utilized to provide the most likely locations of soft tissue, as well as the most likely dimensions of the soft tissue, which are both incorporated into the 3D bone model to create a quasi-patient-specific 3D bone and soft tissue model. In either instance, the anatomical landmarks and the 3D bone and soft tissue model are viewable and manipulatable using a user interface for the software (i.e., software interface).

The software interface is communicatively coupled to a visual display that provides information to a user regarding the relative dynamic positions of the patient's bones and soft tissues that comprise the virtual bone and soft tissue model. In order to provide this dynamic visual information, which is updated in real-time as the patient's bones and soft tissue are repositioned, the software interface is also communicatively coupled to any number of IMUs 1002. These IMUs are fixed rigidly to one or more bones corresponding to the bones of the virtual 3D model and track relative rotation of the bones. By way of example, the bones may comprise the tibia and femur in the context of the knee joint or may comprise one or more vertebrae (e.g., the L1 and L5 vertebrae) in the context of the spine. In order to track translation of the bones, additional tracking sensors (such as ultra-wide band) are associated with each IMU (or combined as part of a single device) in order to register the location of each IMU with respect to the corresponding bone it is mounted to. In this fashion, by tracking the tracking sensors dynamically in 3D space and knowing the position of the tracking sensors with respect to the IMUS, as well as the position of each IMU mounted to a corresponding bone, the system is initially able to correlate the dynamic motion of the tracking sensors to the dynamic position of the bones in question. In order to obtain meaningful data from the IMUs, the patient's bones need to be registered with respect to the virtual 3D bone and soft tissue model. In order to accomplish this, the patient's joint or bone is held stationary in a predetermined position that corresponds with a position of the virtual 3D bone model. For instance, the patient's femur and tibia may be straightened so that the lower leg is in line with the upper leg while the 3D virtual bone model also embodies a position where the femur and tibia are longitudinally aligned. Likewise, the patient's femur and tibia may be oriented perpendicular to one another and held in this position while the 3D virtual bone and soft tissue model is oriented to have the femur and tibia perpendicular to one another. Using the UWB tracking sensors, the position of the bones with respect to one another is registered with respect to the virtual 3D bone and soft tissue model, as are the IMUs. I should be noted that, in accordance with the foregoing disclosure, the IMUs are calibrated prior to registration using the exemplary calibration tool 1000 disclosed previously herein.

For instance, in the context of a knee joint where the 3D virtual bone and soft tissue model includes the femur, tibia, and associated soft tissues of the knee joint, the 3D virtual model may take on a position where the femur and tibia lie along a common axis (i.e., common axis pose). In order to register the patient to this common axis pose, the patient is outfitted with the IMUs and tracking sensors (rigidly fixed to the tibia and femur) and assumes a straight leg position that results in the femur and tibia being aligned along a common axis. This position is kept until the software interface confirms that the position of the IMUs and sensors is relatively unchanged and a user of the software interface indicates that the registration pose is being assumed. This process may be repeated for other poses in order to register the 3D virtual model with the IMUs and tracking sensors. Those skilled in the art will understand that the precision of the registration will generally be increased as the number of registration poses increases.

Referring to FIGS. 175 and 176, in the context of the spine where the 3D virtual model includes certain vertebrae of the spine, the 3D virtual model may take on a position where the vertebrae lie along a common axis (i.e., common axis pose) in the case of a patient lying flat on a table or standing upright. In order to register the patient to this common axis pose, the patient is outfitted with the IMUs 1002 and other tracking sensors rigidly fixed in position with respect to the L1 and L5 vertebrae as depicted in FIG. 175, and assumes a neutral upstanding spinal position that correlates with a neutral upstanding spinal position of the 3D virtual model. This position is kept until the software interface confirms that the position of the IMUs and tracking sensors is relatively unchanged and a user of the software interface indicates that the registration pose is being assumed. This process may be repeated for other poses in order to register the 3D virtual model with the IMUs and tracking sensors. Those skilled in the art will understand that the precision of the registration will generally be increased as the number of registration poses increases.

After registration, the patient anatomy may be moved in 3D space and dynamically tracked using the IMUs and tracking sensors so that the movement of the bones and soft tissue appears graphically on the visual display by way of movement of the 3D virtual model (see FIG. 176 in the context of the spine). While the patient moves, the software reads outputs from the IMUs and/or tracking sensors and processes these outputs to convert the outputs into dynamic graphical changes in the 3D model being depicted on the visual display (while keeping track of ligament length, joint pose and articulating surface contact areas, for example). As shown in FIG. 177, when two or more IMUs are utilized to track a patient anatomy (e.g., a bone), the software interface determines the relative orientation of a first IMU with respect to a second IMU as discussed previously herein as each IMU processor is programmed to utilize a sequential Monte Carlo method (SMC) with von Mises-Fisher density algorithm to calculate changes in position of the IMU 1002 based upon inputs from the IMU's gyroscopes, accelerometers, and magnetometers. The previous discussion of the SMC method is incorporated herein by reference.

The motion profile of healthy and pathological lumbar patients differ significantly, such that the out of plane motion is higher for pathological patients. Specifically, healthy and pathological can be differentiated using IMUs by having the patient perform three activities—axial rotation (AR), lateral bending (LB) and flexion-extension (FE). The coefficients for each of the prescribed motions are calculated as:

$$C_{FE} = \frac{A_{AR} + A_{LB}}{A_{FE}}$$

$$C_{LB} = \frac{A_{AR} + A_{FE}}{A_{LB}}$$

$$C_{AR} = \frac{A_{LB} + A_{FE}}{A_{AR}}$$

where $A_M$ represents the sum of the absolute value of angular motion, during motion M, for which C is calculated. FIG. 178 depicts the response of healthy versus pathological patients as measured using the dual IMUs. By using IMUs, the exemplary system allows patient kinematic analysis and quantitative evaluation without the need for more expensive and intrusive tracking systems.

FIGS. 155 and 174 depict an exemplary visual display (i.e., user interface) operatively coupled to the software interface. As depicted in exemplary form in FIG. 155, a distal femur is shown interfacing with a proximal tibia (and also shown in a phantom proximal fibula). The visual display reflects the software interface's dynamic updating to show how positions of the respective bones are changing in real-time as the patient's lower leg is repositioned with respect to the upper leg. In the context of FIG. 174, the software is also able to calculate predicted load distribution upon the proximal tibia based upon kinematic data. In other words, in the context of a knee joint, the software tracks the movement of the distal femur and proximal tibia and records the frequency by which certain portions of the tibia surface are contacted by the distal femur through a range of motion of the knee joint. Based upon the frequency of contact between areas of the femur and tibia, the software is operative to generate color gradients reflective of the contact distribution so that areas in darker red are contacted the most frequent, whereas areas in blue are contacted the least, with gradients of shades between red and blue (including orange, yellow, green, and aqua) indicating areas of contact between the most and least frequent. By way of further example, the software interface also highlights locations of soft tissue deformity as well as tracking anatomical axes through this range of motion, such as those shown in FIGS. 160-162.

For example, as shown in FIGS. 156-158, the software utilizes the location of soft tissue attachment sites stored in the statistical bone atlas to approximate the attachment sites and, based upon the kinematic movements of the tracked bones (in this case a femur and tibia), incorporates soft tissue data as part of the virtual models. More specifically, the software interface is communicatively coupled to a kinematic database and an anatomical database (e.g., a statistical bone atlas). Data from the two databases having been previously correlated (to link kinematic motion of bones with respect to one another with the locations of soft tissue attachment sites) allows the software to concurrently display anatomical data and kinematic data. Accordingly, the software is operative to include a ligament construction or reconstruction feature, as shown in FIG. 159, so that ligaments may be shown coupled to the bones. Likewise, the software interface tracks and records the motion of the bone and ligament model to show how the ligaments are stretched dynamically as the patient's bones are moved through a range of motion in a time lapsed sense as shown in FIG. 160. This range of motion data provides clearer images in comparison to fluoroscopy and also avoids subjecting the patient is harmful radiation.

Referencing FIGS. 164-172, the visual representation of the 3D virtual bone and soft tissue model moving dynamically has particular applicability for a clinician performing diagnosis and pre-operative planning. For instance, the clinician may perform various tests on a knee joint, such as the drawer test, to view movement of the bone and soft tissue across a range of motion. This kinematic tracking information may be imported into a surgical planning interface, for example, to restrict resection plans that may violate the ligament lengths obtained from the kinematic data. Kinematic data may also be used for real time quantification of various knee tests (e.g., Oxford knee score) or for the creation of novel quantifiable knee scoring systems using statistical pattern recognition or machine learning techniques. In sum, the clinician testing may be used for more accurate pre-operative and post-operative evaluations when alternatives, such as fluoroscopy, may be more costly and more detrimental to patient wellness.

Referring to FIG. 173, an exemplary IMU holster is depicted. The holster is fixedly mounted to a pair of ratchet straps. The ratchet straps are configured to circumscribe the anatomy in question, such as a distal femur, and be cinched down to inhibit significant repositioning of the holster with respect to the anatomy in question. The holster also includes a IMU package well that is sized to receive an IMU package. When the IMU package is positioned within the well, the well is dimensioned to disallow significant movement of the IMU package with respect to the holster when a repositionable lock engages the opposing end of the IMU package. In this fashion, the IMU package can be fixed to the holster or removed from the holster by manipulating the lock.

In exemplary form, the IMU package includes at least one IMU 1002 and an associated power supply, IMU processor, and a wireless transmitter, in addition to a power on-off switch. In this fashion. The IMU package is a self-contained item that is able to be coupled to the holster when in use to track a patient's bone(s) and then removed from the holster. In the context of reuse and sterilization, the IMU holster may be reusable or disposable, while the IMU package is intended for re-use. Nevertheless, in certain instances, it may be more economical for the IMU package to be disposable.

In addition to pre-operative and post-operative evaluation, the instant system and methods may be useful for intraoperative evaluations. For the patient-specific resection plan, a custom cutting guide is created from the plan and the patient bone data.

Surgical Navigation using IMUs for TKA

Referring to FIG. 181, an alternate exemplary system and process are depicted for using one or more inertial measurement units (IMUs) to facilitate surgical navigation to accurately position a tibial component during a total knee arthroplasty (TKA) procedure. The initial steps of utilizing patient images (whether X-ray, CT, MRI, etc.) and performing segmentation or registration to arrive at virtual templates of the patient's anatomy and appropriate implant size, shape, and placement parallels that previously described with reference to FIGS. 87, 88, 90-92. What differs somewhat are the modules and processes utilized downstream from the virtual templating module.

Downstream from the virtual templating module is an initialization model generation module. Similar to the previously discussed jig generation module, this module also receives template data and associated planning parameters (i.e., the shape and placement of a patient-specific tibial implant is known with respect to the patient's residual tibia, as well as the shape and placement of a patient-specific femoral implant with respect to the patient's residual femur). Using this patient-specific information, the initialization model generation module fabricates a 3D virtual model of an initialization device for the patient's native distal femur and a 3D virtual model of an initialization device for the proximal tibia. In other words, the 3D model of the femoral initialization device is created as a "negative" of a particular anatomical surface of the patient's distal femur so that the tangible initialization device precisely matches the patient's distal femur. Similarly, the 3D model of the tibial initialization device is created as a "negative" of the anatomical surface of the patient's proximal tibia so that the tangible initialization device precisely matches the patient's residual tibia at only a single location and single orientation. In addition to generating these initialization devices, the initialization model generation module also generates machine codes necessary for a rapid prototyping machine, CNC machine, or similar device to fabricate the tangible femoral initialization device and tibial initialization device. The tangible femoral initialization device and tibial initialization device are fabricated and mounted to (or formed concurrently or integrally with) or integral with surgical navigation tools configured to have at least one IMU 1002.

Each IMU 1002 is capable of reporting orientation and translational data and are combined with (e.g., mounted to) one or more surgical tools to assist in surgical navigation to place the femoral component and the tibial component during a TKA procedure. Each IMU 1002 is communicatively coupled (wired or wireless) to a software system that receives output data from the IMU indicating relative velocity and time that allows the software to calculate the IMU's current position and orientation, or the IMU 1002 calculates and sends the position and orientation of the surgical instrument, which will be discussed in more detail hereafter, the position and orientation of the surgical instrument associated with the IMU. In this exemplary description, each IMU 1002 includes three gyroscopes, three accelerometers, and three Hall-effect magnetometers (set of three, tri-axial gyroscopes, accelerometers, magnetometers) that may be integrated into a single circuit board or comprised of separate boards of one or more sensors (e.g., gyroscope, accelerometer, magnetometer) in order to output data concerning three directions perpendicular to one another (e.g., X, Y, Z directions). In this manner, each IMU 1002 is operative to generate 21 voltage or numerical outputs from the three gyroscopes, three accelerometers, and three Hall-effect magnetometers. In exemplary form, each IMU 1002 includes a sensor board and a processing board, with a sensor board including an integrated sensing module consisting of a three accelerometers, three gyroscopic sensors and three magnetometers (LSM9DS, ST-Microelectronics) and two integrated sensing modules consisting of three accelerometers, and three magnetometers (LSM303, ST-Microelectronics). In particular, the IMUs 1002 each include angular momentum sensors measuring rotational changes in space for at least three axes: pitch (up and down), yaw (left and right) and roll (clockwise or counter-clockwise rotation). More specifically, each integrated sensing module consisting magnetometer is positioned at a different location on the circuit board, with each magnetometer assigned to output a voltage proportional to the applied magnetic field and also sense polarity direction of a magnetic field at a point in space for each of the three directions within a three dimensional coordinate system. For example, the first magnetometer outputs voltage proportional to the applied magnetic field and polarity direction of the magnetic field in the X-direction, Y-direction, and Z-direction at a first location, while the second magnetometer outputs voltage proportional to the applied magnetic field and polarity direction of the magnetic field in the X-direction, Y-direction, and Z-direction at a second location, and the third magnetometer outputs voltage proportional to the applied magnetic field and polarity direction of the magnetic field in the X-direction, Y-direction, and Z-direction at a third location. By using these three sets of magnetometers, the heading orientation of the IMU may be determined in addition to detection of local magnetic field fluctuation. Each magnetometer uses the magnetic field as reference and determines the orientation deviation from magnetic north. But the local magnetic field can, however, be distorted by ferrous or magnetic material, commonly referred to as hard and soft iron distortion. Soft iron distortion examples are materials that have low magnetic permeability, such as carbon steel, stainless steel, etc. Hard iron distortion is caused by permanent magnets. These distortions create a non-uniform field (see FIGS. Calibration 1-3), which affects the accuracy of the algorithm used to process the magnetometer outputs and resolve the heading orientation. Consequently, as discuss in more detail hereafter, a calibration algorithm is utilized to calibrate the magnetometers to restore uniformity in the detected magnetic field. Each IMU 1002 may be powered by a replaceable or rechargeable energy storage device such as, without limitation, a CR2032 coin cell battery and a 200 mAh rechargeable Li ion battery.

The integrated sensing modules in IMU 1002 may include a configurable signal conditioning circuit and analog to digital converter (ADC), which produces the numerical outputs for the sensors. The IMU 1002 may use sensors with voltage outputs, where an external signal conditioning circuit, which may be an offset amplifier that is configured to condition sensor outputs to an input range of a multi-channel 24 bit analog-to-digital converter (ADC) (ADS1258, Texas Instrument). The IMU 1002 further includes an integrated processing module that includes a microcontroller and a wireless transmitting module (CC2541, Texas Instrument). Alternatively, the IMU 1002 may use separate low power microcontroller (MSP430F2274, Texas Instrument) as the processor and a compact wireless transmitting module (A2500R24A, Anaren) for communication. The processor may be integrated as part of each IMU 1002 or separate from each IMU, but communicatively coupled thereto. This processor may be Bluetooth compatible and provide for wired or wireless communication with respect to the gyroscopes, accelerometers, and magnetometers, as well as provide for wired or wireless communication between the processor and a signal receiver.

Each IMU 1002 is communicatively coupled to a signal receiver, which uses a pre-determined device identification number to process the received data from multiple IMUs. The data rate is approximately 100 Hz for a single IMU and decreases as more IMUs join the shared network. The software of the signal receiver receives signals from the IMUs 1002 in real-time and continually calculates the IMU's current position based upon the received IMU data. Specifically, the acceleration measurements output from the IMU are integrated with respect to time to calculate the current velocity of the IMU in each of the three axes. The calculated velocity for each axis is integrated over time to calculate the current position. But in order to obtain useful positional data, a frame of reference must be established, which includes calibrating each IMU.

Prior to utilizing the IMUs 1002 for surgical navigation, the IMUs are calibrated pursuant to the calibration disclosure previously discussed herein and consequently incorporated herein by reference. Moreover, each IMU processor is programmed to utilize a sequential Monte Carlo method (SMC) with von Mises-Fisher density algorithm to calculate changes in position of the IMU 1002 based upon inputs from the IMU's gyroscopes, accelerometers, and magnetometers.

Subsequent to calibration, as shown in FIG. 181, the IMUs 1002 may be registered to the anatomy in question. In this case, the IMUs are registered to the proximal tibia and the distal femur. In order to register the IMUs 1002 to the proximal tibia, a first IMU is mounted to a proximal tibia positioning tool having an interior surface that matches the exterior of a portion of the proximal tibia in only a single location and orientation. Once positioned in this unique location and orientation, the proximal tibia positioning tool is mounted to the proximal tibia, in exemplary form using surgical screws. A second IMU is fixedly mounted to a rotational navigation tool, which is positioned on top of a resected proximal tibia. When the rotational navigation tool is correctly oriented and rotationally positioned on the patient's proximal resected tibia, the orientation of the second IMU 1002 relative to the first IMU is known. An operator indicates to the software system that first IMU is in its correct position and then the software uses the outputs from both IMUs to establish the position of the second IMU. This position of the second IMU is compared to a previously determined surgical plan to determine if the orientation and rotational alignment of the rotational navigation tool is correct with respect to the surgical plan. If so, the rotational navigation tool is utilized to drill one or more holes into the proximal tibia for later alignment of the permanent tibial component of the TKA. If the rotational alignment is awry, the software and visual display provides feedback to the surgeon to facilitate proper surgical navigation of the navigational tool with respect to the proximal tibia.

In exemplary form, the software program provides a graphical user interface for a surgeon that displays virtual models of the patient's proximal tibia and a virtual model of the rotational navigation tool (the virtual model of the patient's tibia having already been completed pursuant to the virtual templating step, and the virtual model of the rotational navigation tool having been previously loaded into the system for the particular rotational navigation tool that may be utilized), and updates the orientation of the tibia and rotational navigation tool in real time via the graphical user interface providing position and orientation information to the surgeon. Rather than using a graphical user interface, the instant system may include surgical devices having indicator lights indicating to the surgeon whether the rotational navigation tool is correctly oriented and, if not, what direction(s) the rotational navigation tool needs to be repositioned to correctly orient the navigation tool consistent with the pre-operative planning. After orientation and location of the rotational navigation tool have been achieved, the surgeon may drill one or more holes into the proximal femur in preparation of implanting the proximal tibial component of the TKA. An analogous rotational navigation tool and set of IMUs may be used, along with an analogous process for registration, with the software system to assist with placement of the distal femoral component during the TKA.

Those skilled in the art are familiar with conventional mandible bone plates and, accordingly, a detailed discussion of general designs of mandible bone plates has been omitted in furtherance of brevity. What the present system and methods accomplish, unlike conventional systems and methods, is the formation of patient-specific bone plates and placement guides that account for the shape of both the residual bone and the bone graft. In particular, for each bone plate location identified (either automatically or manually), the system designed a virtual 3D bone plate and associated placement guide. Each virtual 3D bone plate and guide model is overlaid with respect to the hybrid 3D model (including bone graft and patient residual bone in their reconstructed location) to ensure the underside of each virtual 3D bone plate and guide model is the negative of the underlying bone, whether that comprises the bone graft or the residual bone. In this manner, the virtual 3D bone plate and guide model work together to ensure proper placement of the bone plate and corresponding engagement between the bone plate, bone graft, and residual bone. Exemplary mounting techniques for securing a bone plate to a bone graft and residual bone may include, without limitation, screws, dowels, and pins. In order to accommodate one or more of these mounting techniques or others, each virtual 3D bone plate and placement guide includes one or more through orifices. After the design of each virtual 3D bone plate and guide is completed, the system generates and outputs machine code necessary for a rapid prototyping machine, CNC machine, or similar device to fabricate each 3D bone plate and guide, which is followed by fabrication of the actual bone plate and guide.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A method of registering inertial measurement units in an operating room, the method comprising:
   generating a patient-specific point cloud model based upon a scan of a patient;
   registering a template point cloud model with the patient-specific point cloud model, the registering comprising a first registration, and a second registration, the first registration comprising
      extracting features from the template point cloud model and the patient-specific point cloud model from different scale spaces, and matching the features from the template point cloud model and the patient-specific point cloud model,
the second registration comprising
deforming the template point cloud model to match the patient-specific point cloud model,
generating correspondence vectors from each vertex in the template point cloud model and a plurality of matched vertices in the patient-specific point cloud model,
generating a distance for each of the plurality of matched vertices in the patient-specific point cloud model, and
selecting a single matched vertex in the patient-specific point cloud model for each vertex in the template point cloud model based upon the distances of the plurality of matched vertices;
forming a patient-specific registration tool based upon the patient-specific point cloud model;
mounting a first inertial measurement unit to a patient anatomy;
positioning the patient-specific registration tool against a portion of the patient anatomy, where the positioning of the patient-specific registration tool correctly engages the patient anatomy in only a single position and orientation that is known, and where the patient-specific registration tool includes a second inertial measurement unit mounted thereto in a known position and orientation; and
gathering data from the first and second inertial measurement units while the patient-specific registration tool is stationary with respect to the patient to establish a known location of the second inertial measurement unit with respect to the patient anatomy.

2. The method of claim 1, comprising:
removing the second inertial measurement unit from the patient-specific registration tool after establishment of the known location; and,
mounting the second inertial measurement unit to a first surgical instrument.

3. The method of claim 2, wherein the second inertial measurement unit is mounted to the first surgical instrument in a known location and orientation.

4. The method of claim 2, comprising:
displaying a virtual model of the patient anatomy and a virtual model of the first surgical instrument; and
updating an orientation and a position of the virtual model of the patient anatomy with respect to the virtual model of the first surgical instrument in real time.

5. The method of claim 2, comprising displaying, on the first surgical instrument, information about an orientation of the first surgical instrument with respect to a preoperative plan.

6. The method of claim 2, comprising displaying, on the first surgical instrument, information about how to correct an orientation of the first surgical instrument based upon a preoperative plan.

7. The method of claim 2, wherein the patient-specific registration tool including a head, and a stem extending from the head and configured to be received within an intramedullary canal cavity of the patient anatomy at only the single position and orientation that is known.

8. The method of claim 7, comprising removing the second inertial measurement unit from the first surgical instrument and mounting the second inertial measurement unit to a second surgical instrument.

9. The method of claim 1, wherein the patient-specific registration tool includes a cavity that is configured to receive a projection of the patient anatomy at only the single position and orientation that is known.

10. The method of claim 1, wherein the patient anatomy comprises a bone.

11. The method of claim 1, wherein the registering of the template point cloud model comprises iteratively aligning the template point cloud model and the patient-specific point cloud model.

12. A method of registering inertial measurement units in an operating room, the method comprising:
generating a patient-specific point cloud model based upon a scan of a patient;
registering a template point cloud model with the patient-specific point cloud model, the registering comprising a first registration, and a second registration, the first registration comprising
extracting features from the template point cloud model and the patient-specific point cloud model from different scale spaces, and
matching the features from the template point cloud model and the patient-specific point cloud model,
the second registration comprising
deforming surface vertexes of the template point cloud model to match surface vertexes of the patient-specific point cloud model,
generating correspondence vectors from each vertex in the template point cloud model and a plurality of matched vertices in the patient-specific point cloud model,
generating a distance for each of the plurality of matched vertices in the patient-specific point cloud model, and
selecting a single matched vertex in the patient-specific point cloud model for each vertex in the template point cloud model based upon the distances of the plurality of matched vertices;
forming a patient-specific registration tool based upon the registered template point cloud model;
mounting a first inertial measurement unit to a patient bone;
positioning the patient-specific registration tool against a portion of the patient bone, where the positioning of the patient-specific registration tool correctly engages the patient bone in only a single position and orientation that is known, and where the patient-specific registration tool includes a second inertial measurement unit mounted thereto in a known position and orientation; and
gathering data from the first and second inertial measurement units while the patient-specific registration tool is stationary with respect to the patient to establish a known location of the second inertial measurement unit with respect to the patient bone.

13. The method of claim 12, comprising:
removing the second inertial measurement unit from the patient-specific registration tool after establishment of the known location; and,
mounting the second inertial measurement unit to a first surgical instrument.

14. The method of claim 12, wherein the registering of the template point cloud model comprises iteratively aligning the template point cloud model and the patient-specific point cloud model.

15. The method of claim 12, wherein the deforming of the surface vertexes comprises deforming vertexes of a same class from a plurality of different vertex classes.

16. The method of claim 15, wherein the plurality of different vertex classes comprises a scale space feature vertex class, a normal scale feature vertex class, and a non-feature vertex class.

\* \* \* \* \*